US012762520B2

(12) United States Patent
Bull et al.

(10) Patent No.: US 12,762,520 B2
(45) **Date of Patent: *Oct. 13, 2026**

(54) SYSTEMS AND METHODS FOR ALLOCATING RESOURCES VIA INFORMATION TECHNOLOGY INFRASTRUCTURE

(71) Applicant: Alegeus Technologies, LLC, Boston, MA (US)

(72) Inventors: John Bull, Nashua, NH (US); Christopher Rodkey, Beverly, MA (US)

(73) Assignee: Alegeus Technologies, LLC, Boston, MA (US)

(*) Notice: Subject to any disclaimer, the term of this patent is extended or adjusted under 35 U.S.C. 154(b) by 159 days.

This patent is subject to a terminal disclaimer.

(21) Appl. No.: 18/901,716

(22) Filed: Sep. 30, 2024

(65) Prior Publication Data

US 2025/0021951 A1 Jan. 16, 2025

Related U.S. Application Data

(63) Continuation of application No. 18/815,146, filed on Aug. 26, 2024, now Pat. No. 12,182,778, which is a (Continued)

(51) Int. Cl.

*G06Q 20/10* (2012.01)
*G06Q 20/22* (2012.01)

(Continued)

(52) U.S. Cl.

CPC ........... *G06Q 20/10* (2013.01); *G06Q 20/227* (2013.01); *G06Q 20/367* (2013.01);

(Continued)

(58) Field of Classification Search

CPC ...... G06Q 20/10; G06Q 20/367; G06Q 40/02; G06Q 20/227; G06Q 20/405

(Continued)

(56) References Cited

U.S. PATENT DOCUMENTS 5,930,759 A 7/1999 Moore et al.
6,000,608 A 12/1999 Dorf (Continued)

FOREIGN PATENT DOCUMENTS

CA 2589769 A1 6/2006
CA 2653488 A1 7/2010

(Continued)

OTHER PUBLICATIONS

Notice of Allowance on U.S. Appl. No. 19/254,700 dated Jan. 16, 2026.

(Continued)

*Primary Examiner* — Jason S Tiedeman
(74) *Attorney, Agent, or Firm* — Foley & Lardner LLP

(57) ABSTRACT

A system to allocate resources via information technology infrastructure is described. A server includes processors to provide to a plurality of devices, an electronic benefits account transaction application programming interface ("API") configured to receive transaction requests from a plurality of heterogeneous electronic funding sources. The server can receive a request to initiate a single transaction to fund an electronics benefit account. The server can transmit data in an alert format indicating a denial of the single request responsive to a comparison of a value to one or more threshold limits.

43 Claims, 31 Drawing Sheets

Related U.S. Application Data continuation of application No. 18/215,750, filed on Jun. 28, 2023, now Pat. No. 12,217,226, which is a continuation of application No. 17/843,142, filed on Jun. 17, 2022, now Pat. No. 11,727,370, which is a continuation of application No. 16/728,707, filed on Dec. 27, 2019, now Pat. No. 11,367,058, which is a continuation of application No. 15/237,340, filed on Aug. 15, 2016, now Pat. No. 10,521,778.

(60) Provisional application No. 62/268,219, filed on Dec. 16, 2015.

(51) Int. Cl.
*G06Q 20/36* (2012.01)
*G06Q 20/40* (2012.01)
*G06Q 40/02* (2023.01)
*G16H 10/00* (2018.01)

(52) U.S. Cl.
CPC ........... *G06Q 20/405* (2013.01); *G06Q 40/02* (2013.01); *G16H 10/00* (2018.01)

(58) Field of Classification Search
USPC ..................................................... 705/2, 3, 4
See application file for complete search history.

(56) References Cited

U.S. PATENT DOCUMENTS

| | | | | |
|---|---|---|---|---|
| 6,108,641 | A | 8/2000 | Kenna et al. | |
| 6,185,545 | B1 | 2/2001 | Resnick et al. | |
| 6,513,838 | B2 | 2/2003 | Poehler | |
| 6,816,090 | B2 | 11/2004 | Teckchandani et al. | |
| 6,820,058 | B2 | 11/2004 | Wood et al. | |
| 6,880,079 | B2 | 4/2005 | Kefford et al. | |
| 6,985,720 | B2 | 1/2006 | Qu et al. | |
| 7,116,985 | B2 | 10/2006 | Wilson et al. | |
| 7,151,932 | B2 | 12/2006 | Major | |
| 7,174,302 | B2 | 2/2007 | Patricelli et al. | |
| 7,197,468 | B1 | 3/2007 | Patricelli et al. | |
| 7,346,522 | B1 | 3/2008 | Baylor et al. | |
| 7,380,707 | B1 | 6/2008 | Fredman | |
| 7,444,291 | B1 | 10/2008 | Prasad et al. | |
| 7,464,859 | B1 * | 12/2008 | Hawkins | G06Q 40/00 235/382 |
| 7,529,700 | B1 | 5/2009 | Kessler | |
| 7,594,611 | B1 | 9/2009 | Arrington, III | |
| 7,617,114 | B1 * | 11/2009 | Tooke, III | G16H 40/20 705/2 |
| 7,661,586 | B2 | 2/2010 | Robbins et al. | |
| 7,680,679 | B1 | 3/2010 | Patricelli et al. | |
| 7,711,660 | B1 | 5/2010 | Gentile et al. | |
| 7,757,944 | B2 | 7/2010 | Cline et al. | |
| 7,857,205 | B2 | 12/2010 | Hoffman et al. | |
| 7,866,548 | B2 * | 1/2011 | Reed | G06Q 20/04 235/380 |
| 8,005,687 | B1 | 8/2011 | Pederson et al. | |
| 8,019,627 | B2 | 9/2011 | Baylor et al. | |
| 8,047,430 | B2 | 11/2011 | Hoffman et al. | |
| 8,086,530 | B2 | 12/2011 | Resnick et al. | |
| 8,099,303 | B1 | 1/2012 | Battaglia et al. | |
| 8,195,482 | B2 | 6/2012 | Baylor et al. | |
| 8,204,768 | B1 | 6/2012 | Grinberg | |
| 8,214,230 | B1 | 7/2012 | Dipiero et al. | |
| 8,219,420 | B1 | 7/2012 | Heffley et al. | |
| 8,234,214 | B2 | 7/2012 | Templeton | |
| 8,275,652 | B2 | 9/2012 | Hafeman et al. | |
| 8,352,367 | B2 | 1/2013 | Templeton | |
| 8,364,498 | B2 | 1/2013 | Sohr et al. | |
| 8,386,384 | B2 | 2/2013 | Templeton | |
| 8,392,310 | B1 | 3/2013 | Praisner et al. | |
| 8,527,298 | B2 | 9/2013 | Baylor et al. | |
| 8,595,031 | B1 | 11/2013 | Heffley et al. | |
| 8,595,135 | B2 | 11/2013 | Templeton | |
| 8,639,629 | B1 | 1/2014 | Hoffman | |
| 8,660,861 | B2 | 2/2014 | Chun et al. | |
| 8,682,690 | B2 | 3/2014 | Pederson et al. | |
| 8,738,405 | B2 | 5/2014 | Rourk | |
| 8,768,838 | B1 | 7/2014 | Hoffman | |
| 8,788,281 | B1 | 7/2014 | Pletz et al. | |
| 8,799,007 | B2 | 8/2014 | Boyle | |
| 8,930,217 | B2 | 1/2015 | Feinschreiber et al. | |
| 8,939,356 | B2 | 1/2015 | Pourfallah et al. | |
| 8,959,619 | B2 | 2/2015 | Sanft et al. | |
| 8,965,798 | B1 | 2/2015 | Mackrell et al. | |
| 9,311,672 | B2 | 4/2016 | Hochstatter et al. | |
| 9,633,174 | B2 | 4/2017 | Nichols | |
| 9,760,871 | B1 * | 9/2017 | Pourfallah | G06Q 10/10 |
| 10,002,366 | B2 | 6/2018 | Beyer | |
| 10,032,217 | B2 | 7/2018 | Roberts et al. | |
| 10,127,359 | B2 | 11/2018 | Blue | |
| 10,180,777 | B2 | 1/2019 | Blue | |
| 10,333,707 | B1 | 6/2019 | Pathak et al. | |
| 10,354,233 | B2 | 7/2019 | Murphy | |
| 10,380,586 | B2 | 8/2019 | Haulotte et al. | |
| 10,510,265 | B2 | 12/2019 | Jiao et al. | |
| 10,546,339 | B2 | 1/2020 | Jiao et al. | |
| 10,580,531 | B2 | 3/2020 | Jiao et al. | |
| 10,629,293 | B2 | 4/2020 | Jiao et al. | |
| 10,636,525 | B2 | 4/2020 | Jiao et al. | |
| 10,650,474 | B2 | 5/2020 | Jiao et al. | |
| 10,672,519 | B2 | 6/2020 | Jiao et al. | |
| 10,692,153 | B2 | 6/2020 | Obee et al. | |
| 10,929,935 | B1 | 2/2021 | Frankenfield et al. | |
| 10,930,378 | B2 | 2/2021 | Jiao et al. | |
| 10,978,189 | B2 | 4/2021 | White et al. | |
| 11,164,154 | B2 | 11/2021 | Roberts et al. | |
| 11,170,351 | B1 | 11/2021 | Kurani et al. | |
| 11,348,096 | B2 | 5/2022 | Roberts et al. | |
| 11,393,043 | B2 | 7/2022 | Bhavsar et al. | |
| 11,704,742 | B2 | 7/2023 | Frankenfield et al. | |
| 11,720,975 | B2 | 8/2023 | Srikanta et al. | |
| 11,861,717 | B2 | 1/2024 | Sitler et al. | |
| 2002/0087444 | A1 | 7/2002 | Dipiero et al. | |
| 2002/0147678 | A1 | 10/2002 | Drunsic | |
| 2003/0061153 | A1 | 3/2003 | Birdsong et al. | |
| 2004/0006490 | A1 | 1/2004 | Gingrich et al. | |
| 2004/0073465 | A1 | 4/2004 | Wilson | |
| 2004/0249745 | A1 | 12/2004 | Baaren | |
| 2005/0018820 | A1 | 1/2005 | Chaddha et al. | |
| 2005/0033677 | A1 | 2/2005 | Birdsong et al. | |
| 2005/0080692 | A1 * | 4/2005 | Padam | G06Q 40/12 705/30 |
| 2005/0086075 | A1 | 4/2005 | Kaehler et al. | |
| 2005/0121511 | A1 | 6/2005 | Robbins et al. | |
| 2005/0177050 | A1 | 8/2005 | Cohen | |
| 2005/0187800 | A1 | 8/2005 | Luftig | |
| 2005/0187870 | A1 | 8/2005 | Grear et al. | |
| 2005/0240473 | A1 | 10/2005 | Ayers et al. | |
| 2005/0288964 | A1 | 12/2005 | Lutzen et al. | |
| 2006/0036523 | A1 | 2/2006 | Stover et al. | |
| 2006/0064380 | A1 | 3/2006 | Zukerman | |
| 2006/0113376 | A1 | 6/2006 | Reed et al. | |
| 2006/0149670 | A1 | 7/2006 | Nguyen et al. | |
| 2006/0212378 | A1 | 9/2006 | Hoffman et al. | |
| 2007/0000999 | A1 | 1/2007 | Kubo et al. | |
| 2007/0005402 | A1 * | 1/2007 | Kennedy | G06Q 40/08 705/3 |
| 2007/0005403 | A1 * | 1/2007 | Kennedy | G16H 40/20 705/3 |
| 2007/0007335 | A1 | 1/2007 | Cracchiolo et al. | |
| 2007/0027727 | A1 | 2/2007 | Cochrane | |
| 2007/0094115 | A1 | 4/2007 | Inman et al. | |
| 2007/0130042 | A1 | 6/2007 | Dryden | |
| 2007/0150414 | A1 | 6/2007 | Templeton | |
| 2007/0179813 | A1 | 8/2007 | Darling | |
| 2007/0194108 | A1 * | 8/2007 | Kalappa | G06Q 40/00 235/381 |
| 2007/0203757 | A1 | 8/2007 | Dibiasi et al. | |
| 2007/0233525 | A1 | 10/2007 | Boyle | |
| 2008/0027753 | A1 | 1/2008 | Dean | |

(56) References Cited

U.S. PATENT DOCUMENTS

2008/0033750 A1* 2/2008 Burriss .................. G06Q 10/10 705/2
2008/0086416 A1 4/2008 Alias et al.
2008/0097903 A1 4/2008 Boyle
2008/0162348 A1* 7/2008 Lee ...................... G06Q 20/363 705/44
2008/0183505 A1 7/2008 Brown
2008/0183627 A1* 7/2008 Harrison ................ G06Q 20/02 705/67
2008/0215472 A1 9/2008 Brown
2008/0228641 A1 9/2008 Fredman
2008/0300916 A1 12/2008 Parkinson et al.
2008/0306765 A1 12/2008 Daniels et al.
2009/0048954 A1 2/2009 Blackburn et al.
2009/0055225 A1 2/2009 Russell
2009/0106148 A1 4/2009 Prada
2009/0164352 A1 6/2009 Sorbe et al.
2009/0171852 A1* 7/2009 Taylor .................. G06Q 20/027 705/79
2009/0192904 A1 7/2009 Patterson et al.
2009/0272796 A1 11/2009 Ong
2010/0010901 A1* 1/2010 Marshall ................ G06Q 20/20 705/17
2010/0010909 A1 1/2010 Marshall et al.
2010/0057621 A1* 3/2010 Faith .................. G06Q 20/3829 705/71
2010/0094663 A1 4/2010 Spriggs
2010/0116882 A9* 5/2010 Harrison ................ G06Q 20/20 235/381
2010/0145737 A1 6/2010 Joao
2010/0145810 A1* 6/2010 Pourfallah ............. G06Q 30/06 705/17
2010/0145848 A1 6/2010 Robbins et al.
2010/0145855 A1 6/2010 Fordyce et al.
2010/0185461 A1 7/2010 Broeska et al.
2010/0241535 A1 9/2010 Nightengale et al.
2010/0262538 A1 10/2010 Rosenberger
2010/0332247 A1 12/2010 Spriggs
2011/0004494 A1 1/2011 Denny et al.
2011/0029434 A1 2/2011 Templeton
2011/0035240 A1* 2/2011 Joao ................... G06Q 20/3276 235/379
2011/0071854 A1 3/2011 Medeiros et al.
2011/0173083 A1 7/2011 Reed et al.
2012/0041084 A1 2/2012 Du et al.
2012/0047073 A1 2/2012 Hoffman et al.
2012/0197658 A1 8/2012 Spriggs
2012/0215605 A1 8/2012 Gardner et al.
2012/0239417 A1 9/2012 Pourfallah et al.
2012/0253852 A1 10/2012 Pourfallah et al.
2013/0191475 A1 7/2013 Partovi
2013/0204638 A1 8/2013 Barson et al.
2013/0212021 A1 8/2013 Kingston et al.
2013/0275279 A1* 10/2013 Raymond ............ G06Q 40/125 705/30
2013/0282608 A1 10/2013 Raymond et al.
2013/0290963 A1 10/2013 Simske et al.
2013/0346100 A1 12/2013 Darling et al.
2014/0019352 A1* 1/2014 Shrivastava ......... G06Q 20/326 705/41
2014/0122095 A1 5/2014 Devine
2014/0142964 A1 5/2014 Lang et al.
2014/0149292 A1* 5/2014 Kunz ..................... G06Q 40/00 705/44
2014/0200909 A1 7/2014 Felix et al.
2014/0229203 A1 8/2014 Dean et al.
2014/0279474 A1* 9/2014 Evans .................... G06Q 20/40 705/41
2014/0279638 A1 9/2014 Raymond et al.
2014/0282715 A1 9/2014 Yang et al.
2014/0297307 A1 10/2014 Pletz et al.
2014/0304010 A1* 10/2014 Kennedy ................ G06Q 40/08 705/4
2014/0344141 A1 11/2014 Cook
2014/0379361 A1* 12/2014 Mahadkar .............. G06Q 40/08 705/2
2015/0066811 A1 3/2015 Legare et al.
2015/0134515 A1 5/2015 Cosgray
2015/0134517 A1 5/2015 Cosgray
2015/0154365 A1 6/2015 Darling et al.
2015/0178454 A1 6/2015 Brown
2015/0199657 A1 7/2015 Castinado et al.
2015/0228029 A1 8/2015 Licata et al.
2015/0278464 A1 10/2015 Darling et al.
2015/0332227 A1 11/2015 Cosgray
2016/0063445 A1 3/2016 Feinschreiber et al.
2016/0125362 A1 5/2016 Dziuba et al.
2016/0125373 A1 5/2016 Chevlin et al.
2016/0148317 A1 5/2016 Benway et al.
2016/0314471 A1 10/2016 Gerber et al.
2017/0053274 A1 2/2017 Strom
2017/0098193 A1 4/2017 Roberts et al.
2017/0185724 A1 6/2017 Darling
2017/0185725 A1 6/2017 Darling
2017/0351823 A1 12/2017 Darling et al.
2017/0352098 A1 12/2017 Roberts et al.
2018/0018647 A1 1/2018 Fredman et al.
2018/0322570 A1 11/2018 Roberts et al.
2020/0027547 A1 1/2020 Darling
2020/0104935 A1 4/2020 Schmitt et al.
2021/0110351 A1 4/2021 Wang et al.
2022/0164816 A1 5/2022 Darling
2022/0344058 A1 10/2022 Jiao et al.
2022/0391874 A1 12/2022 Pezewski et al.
2023/0085859 A1 3/2023 Carroll et al.
2023/0206196 A1 6/2023 Mac Manus et al.
2023/0214837 A1 7/2023 Wyper et al.
2023/0306526 A1 9/2023 Frankenfield et al.
2023/0351517 A1 11/2023 Russell et al.
2024/0037647 A1 2/2024 Roberts et al.
2024/0078245 A1 3/2024 Foley et al.

FOREIGN PATENT DOCUMENTS

WO WO-2005/036363 A1 4/2005
WO WO-2007/143599 A2 12/2007
WO WO-2011/085352 A1 7/2011
WO WO-2012/122065 A1 9/2012
WO WO-2014/153136 A2 9/2014
WO WO-2015/070152 A1 5/2015
WO WO-2015/123540 A1 8/2015
WO WO-2016/034996 A1 3/2016
WO WO-2016/077781 A1 5/2016
WO WO-2016/145183 A1 9/2016
WO WO-2018/057798 A1 3/2018

OTHER PUBLICATIONS

Non-Final Office Action on U.S. Appl. No. 18/185,668 dated Sep. 25, 2025.
Advisory Action on U.S. Appl. No. 15/237,333 dated Feb. 24, 2020.
Final Office Action on U.S. Appl. No. 11/364,514, dated Mar. 26, 2015.
Final Office Action on U.S. Appl. No. 14/751,876, dated Jan. 18, 2018.
Final Office Action on U.S. Appl. No. 14/751,876, dated Dec. 4, 2018.
Final Office Action on U.S. Appl. No. 14/805,522 dated Apr. 15, 2020.
Final Office Action on U.S. Appl. No. 14/805,522 dated Jan. 10, 2019.
Final Office Action on U.S. Appl. No. 14/805,522 dated Mar. 16, 2021.
Final Office Action on U.S. Appl. No. 15/237,333 dated Jan. 29, 2021.
Final Office Action on U.S. Appl. No. 15/237,333 dated Mar. 3, 2022.
Final Office Action on U.S. Appl. No. 15/237,333 dated Nov. 19, 2019.
Final Office Action on U.S. Appl. No. 17/334,061 dated Mar. 29, 2023.

(56) References Cited

OTHER PUBLICATIONS

Gogou, V., et al., “A smart card network in health care services,” Proceedings of the 22nd Annual International Conference of the IEEE Engineering in Medicine and Biology Society (Cat. No. 00CH37143), Chicago, IL, USA, 2000, pp. 559-561 vol. 1, DOI: 10.1109/IEMBS (Year: 2000).
Non-Final Office Action for U.S. Appl. No. 15/237,340, dated May 17, 2019.
Non-Final Office Action on U.S. Appl. No. 14/751,876, dated Aug. 9, 2017.
Non-Final Office Action on U.S. Appl. No. 14/751,876, dated May 25, 2018.
Non-Final Office Action on U.S. Appl. No. 14/805,522 dated Jun. 13, 2018.
Non-Final Office Action on U.S. Appl. No. 14/805,522 dated Sep. 16, 2020.
Non-Final Office Action on U.S. Appl. No. 14/805,522 dated Sep. 30, 2019.
Non-Final Office Action on U.S. Appl. No. 15/237,333 dated Apr. 19, 2019.
Non-Final Office Action on U.S. Appl. No. 15/237,333 dated Sep. 24, 2020.
Non-Final Office Action on U.S. Appl. No. 15/237,333 dated Sep. 29, 2021.
Non-Final Office Action on U.S. Appl. No. 16/533,161 dated Sep. 25, 2020.
Non-Final Office Action on U.S. Appl. No. 17/334,061 dated Nov. 4, 2022.
Non-Final Office Action on U.S. Appl. No. 18/185,668 dated Apr. 1, 2024.
Non-Final Office Action on U.S. Appl. No. 18/185,668 dated Sep. 26, 2023.
Notice of Allowance on U.S. Appl. No. 17/843,142 dated Mar. 29, 2023.
Notice of Allowance on U.S. Appl. No. 14/751,876 dated May 20, 2019.
Notice of Allowance on U.S. Appl. No. 14/805,522 dated Oct. 6, 2021.
Notice of Allowance on U.S. Appl. No. 15/237,340, dated Sep. 3, 2019.
Notice of Allowance on U.S. Appl. No. 16/533,161 dated Feb. 11, 2021.
Notice of Allowance on U.S. Appl. No. 16/728,707 dated Feb. 25, 2022.
Notice of Allowance on U.S. Appl. No. 17/334,061 dated Jul. 14, 2023.
Notice of Allowance on U.S. Appl. No. 17/665,159 dated Dec. 8, 2022.
Notice of Allowance on U.S. Appl. No. 18/215,750 dated May 10, 2024.
Notice of Allowance on U.S. Appl. No. 18/215,750 dated Oct. 11, 2024.
Notice of Allowance on U.S. Appl. No. 18/815,146 dated Nov. 14, 2024.
Final Office Action on U.S. Appl. No. 18/185,668 dated Feb. 28, 2025.

* cited by examiner

SYSTEMS AND METHODS FOR ALLOCATING RESOURCES VIA INFORMATION TECHNOLOGY INFRASTRUCTURE

CROSS-REFERENCE TO RELATED APPLICATIONS

This application claims the benefit of priority under 35 U.S.C. § 120 as a continuation of U.S. patent application Ser. No. 18/815,146, filed Aug. 26, 2024, which claims the benefit of priority under 35 U.S.C. § 120 as a continuation of U.S. patent application Ser. No. 18/215,750, filed Jun. 28, 2023, which claims the benefit of priority under 35 U.S.C. § 120 as a continuation of U.S. patent application Ser. No. 17/843,142, filed Jun. 17, 2022, which claims the benefit of priority under 35 U.S.C. § 120 as a continuation of U.S. patent application Ser. No. 16/728,707, filed Dec. 27, 2019, which claims the benefit of priority under 35 U.S.C. § 120 as a continuation of U.S. patent application Ser. No. 15/237,340, filed Aug. 15, 2016, which claims the benefit of priority under 35 U.S.C. § 119 to Provisional Patent Application No. 62/268,219, filed Dec. 16, 2015, all of which are incorporated herein by reference in entirety.

FIELD OF THE DISCLOSURE

The present solution is generally directed to managing electronic transaction portals connected to heterogeneous electronic funding sources for funding electronic benefits accounts. In particular, the present solution can manage the electronic transaction portal to prevent electronic transactions from exceeding an IRS contribution threshold limit of the electronic benefit account.

BACKGROUND OF THE DISCLOSURE

Companies or health insurance providers can establish electronic benefits accounts such as flexible spending accounts for individuals such as employees or subscribers, which can provide a tax advantage. The individual can transfer or allocate funds to contribute to the flexible spending account. The individuals can purchase qualifying items at a merchant using funds in their flexible spending account in order take advantage of tax savings. As individuals increasingly utilize flexible spending accounts, it can be challenging for the individuals to manage complex electronic transactions involved in contributing to the flexible spending account from a plurality of heterogeneous electronic funding sources without exceeding IRS contribution threshold limits.

BRIEF SUMMARY OF THE DISCLOSURE

The systems and methods of the present solution are directed to the technical problems and challenges of implementing the functionality of resource allocation in electronic transaction portal based technology and platforms. Existing resource allocation based technologies and platforms do not effectively and efficiently make use of the computing and network resources deployed for electronic transaction portals. Without implementing such functionality, existing electronic transaction portal based technologies and platforms have the problems of excessive server-client requests and responses, processing delays, increase bandwidth usage, or erroneous resource allocations.

The systems and methods of the present solution are directed to the improvement of the performance and operation of the electronic transaction portal based technology and platform and computing and networking resource used by such electronic transaction portals. In some aspects, the present solution improves and enhances the implemented functionality of the electronic transaction portal based technology and platform implemented on, integrated with and inherently tied to the processor, memory, network and computing resources of one or more computing devices. In some aspects, the present solution more effectively performs the functionality of the electronic transaction portal technology and platform thereby making and causing more effective use of the computing and networking resources to achieve the improved functionality of the present solution. The same computing and network resources used by such electronic transaction portal technology and platform will provide increased and improved functionality with implementation of the present solution.

In some aspects, the present solution more efficiently uses the computing and networking resources to implement the improved functionality of the electronic transaction based technology and platform. For example, systems and methods of the present solution are directed to allocating resources via information technology infrastructure. Systems and methods of the present solution can manage electronic transaction portals connected to heterogeneous electronic funding sources for funding electronic benefits accounts. Systems and methods of the present solution can manage the electronic transaction portal to prevent single electronic benefits account transactions from exceeding threshold limits for contributions. Systems and methods of the present solution are directed to conducting electronic transactions using a multi-purse debit card. Systems and methods of the present solution can use a multi-purse transaction system that maintains an electronic account having multiple purses, such as an electronic benefits account and an electronic reimbursement account.

Systems and methods of the present solution can adjudicate a single claim against the electronic benefits account (e.g., determine that the single claim is approved for reimbursing an electronic account by an amount of expenditures associated with the electronic transaction). An electronic account can be maintained by a server and include a database in memory or a storage device. The electronic account can include sub structures or fields. The electronic account can include multiple purses that are configured with one or more rules, parameters, restrictions, or policies. For example, the electronic account can include a first purse that is configured for benefits as an electronic benefits account purse. A purse configured for benefits can refer to a purse that is configured for transactions made using a tax benefit account such as a flexible spending account ("FSA"), Dependent Care Account ("DCA"), Transport Account (e.g., for parking or monthly passes). In some embodiments, the FSA, DCA, and Transport Account can be further separated into sub-purses within the electronic benefits account purse of the electronic account. A flexible spending account, or flexible spending arrangement, can refer to a tax-advantaged financial account that can be set up through a cafeteria plan of an employer and used to set aside a portion of earnings to pay for qualified expenses as established in the cafeteria plan. Types of FSA can include medical expense FSA, health FSA, health savings account (HSA), health reimbursement account (HRA), health reimbursement plan (HRP), etc. Qualified expenses can include, for example, medical expenses, dependent care, dental expenses, vision expenses, parking, monthly passes, etc. An FSA can be tax-advantaged because funds deducted from an employee's account and transferred to the FSA is not subject to payroll taxes, resulting in payroll tax savings.

A computing device can initiate, instruct, cause, or make an electronic transaction to transfer funds to an electronic benefits account, or an entity such as server of an employer or an insurance administrator. In some cases, a financial institution can manually, periodically, and/or automatically initiate, instruct, cause, or make the electronic transaction. The transaction can be associated with information such as an FSA account identifier, time stamp, entity identifier, and transaction amount. This information can be provided in real-time to a transaction repository. The electronic transaction portal can receive electronic transaction requests from a plurality of electronic client devices corresponding to a heterogeneous plurality of electronic funding sources. The electronic funding sources can include an automatic clearinghouse ("ACH"), individual checking, bill pay, and savings accounts, credit card accounts, employer payroll (e.g., for funding cafeteria, FSA, etc.), and other electronic funding sources. The heterogeneous electronic funding sources can be provided custom electronic benefits account transaction application programming interfaces to facilitate enforcement of a single transaction request from one of the electronic funding sources. The electronic transaction portal can transfer funds, such as when the electronic transaction request is generated based on transaction types such as point of sale transactions, manual transactions, and deposit transactions. The electronic transaction portal can maintain daily net general ledger files using enforcement rules, and transmit instructions to an electronic entity (e.g., a server) of the relevant financial institution that causes the financial institution server to transfer funds internally.

When multiple heterogeneous electronic funding sources initiate electronic funding transactions, the electronic funding transactions might all post to the electronic benefits account, even if the electronic funding transactions exceed a threshold limit for the electronic benefits account, requiring a participant associated with the electronic benefits account to withdraw excess contributions or later engage in complex tax management procedures. The present solution is configured to apply enforcement rules executed by a transaction enforcement portal system, on a single transaction basis, to prevent the contribution threshold limit from being exceeded even when multiple transactions are received from a plurality of heterogeneous electronic funding sources. The present solution provides the transaction enforcement portal system that receives indications of electronic transaction requests and executes enforcement rules based on the electronic transaction requests in order to deny transaction requests that would otherwise cause the threshold limit to be exceeded.

For example, if a participant initiates a single electronic transaction request to transfer funds to a flexible spending account (e.g., an HSA) from an electronic checking account, the present solution can receive the electronic transaction request, and parse the request to identify a transaction amount and the flexible spending account. The present solution can determine whether authorizing the transaction would cause a threshold limit (e.g., an IRS-established threshold limit) for contributions to the flexible spending account to be exceeded, before the transaction is posted to the flexible spending account. The present solution can prevent threshold limits to be exceeded in real-time, overcoming difficulties caused when the participant is not aware that the threshold limit is exceeded until the transaction is posted, often several days after the transaction is requested, at which point complex reimbursement procedures may be required to avoid tax penalties.

A client device can initiate the electronic transaction responsive to receiving input via a user interface, at an entity such as a merchant, pharmacy, retail store, medical supply store, or other entity that provides goods or services that are deemed to be qualified expenses in accordance with the tax benefit account or FSA. The transaction can occur via a point-of-sale terminal or device (e.g., checkout device, electronic point of sale device or other device that includes hardware and software to facilitate a transaction) configured to receive financial transaction information via a user interface (e.g., via a user interface configured to receive information from a debit card, pin number, mobile payment device, near field communication-enabled device, mobile telecommunications device) and communicate with one or more servers or databases to authenticate the financial transaction information, identify a corresponding FSA of the participant, and initiate or facilitate the transfer of funds from the FSA to the entity. The transaction can be associated with information such as an FSA account identifier, time stamp, entity identifier, and transaction amount. This information can be provided in real-time to a transaction repository.

When participants submit claims for reimbursement from their FSA, HRA or other benefit account, the present solution provides a real time credit to their electronic reimbursement account when the claim is approved for reimbursement. The present solution provides real time adjudication of the single claim. By adjudicating the single claim, the present solution improves over batch processed claims that might not be processed until several hours, days, weeks, or months after the electronic transaction occurs. The present solution provides a real time notification via electronic mail or electronic messaging of the real time credit to the electronic reimbursement account, and can explain in real time that the reimbursed amount is now available for unrestricted spending at any merchant. The present solution uses one or more policy or logic engines to authorize transactions, such as by authorizing transactions based on a merchant category code ("MCC"), a goods and services code, a health care provider code, or other policy codes, to determine that the single claim against the electronic benefits account is approved for an amount of expenditures qualifying under the electronic benefits account.

For example, if the participant has $100 in their FSA which is setup for Medical, Rx, Vision and Dental purchases, and the participant swipes their card at a vision provider for $75, the system makes a determination based on a policy to select an FSA from which to deduct funds. If the card is swiped at a restaurant and the participant has an electronic reimbursement account on the card, the system can deduct funds from a reimbursement purse. If the participant performs a transaction for a qualified expense that exceeds the amount of funds in the participant's FSA, the system can use the FSA funds plus an amount from the reimbursement purse. Participants can text a code such as "BAL" to a system of the present solution to receive a current balance in one or more electronic accounts/purses, including the electronic reimbursement account, or call to obtain balances for all accounts through an interactive voice response, as well as view the balance through a mobile application or online portal. Participants can text a code such as "CLAIM" to the present solution to receive a status of the adjudication of the single claim.

At least one aspect of the present solution is directed to a system to manage resource allocation via an information technology infrastructure. The system can include a server including one or more processors configured to provide to a plurality of devices corresponding to a plurality of heterogeneous electronic funding sources, an electronic benefits account transaction application programming interface ("API") configured to receive transaction requests from the plurality of heterogeneous electronic funding sources, and configured to receive, via the electronic benefits account transaction API, from a first device of the plurality of devices corresponding to a first electronic funding source of the plurality of heterogeneous electronic transaction sources, a first one or more packets comprising a request to initiate a single electronic benefits account transaction to fund an electronic benefits account. The request can identify a transaction destination, a transaction code, a transaction amount and an identifier identifying the first electronic funding source. The server can include an enforcement engine configured on an executed by the server. The enforcement engine is executed to determine the transaction code maps to one of a current year or a previous year. The enforcement engine is executed to perform a lookup in an electronic transaction queue of the electronic benefits account maintained in memory by the server to identify an in-process transaction amount and a reportable contribution amount. The enforcement engine is executed to generate a value by combining the transaction amount, the in-process transaction amount and the reportable contribution amount identified from the electronic transaction queue of the electronic benefits account maintained in memory by the server. The value can indicate a virtual transaction balance. The enforcement engine is executed to compare the value with a threshold limit for the one of the current year or the previous year mapped to the transaction code to determine that the value exceeds the threshold limit. The enforcement engine is executed to select an alert format configured for an interface corresponding to the first electronic funding source. The enforcement engine is executed to transmit, via a network to the first device, one or more packets carrying data in the alert format indicating a denial of the single electronic benefits account transaction request responsive to the comparison and the transaction code mapping to the one of the current year or the previous year. The one or more packets can be configured to indicate to the first device termination of the single electronic benefits account transaction initiated by the request to prevent exceeding the threshold limit established for the electronic benefits account.

In some embodiments, the enforcement engine is further configured to identify using a profile database stored in memory, that the first electronic funding source enforces electronic benefits account limits, and determine, responsive to identifying that the first electronic funding source enforces electronic benefits account limits, the transaction code maps to one of the current year or the previous year.

In some embodiments, the enforcement engine is further configured to determine an enforcement rule based on the single electronic benefits account transaction request, and identify the threshold limit based on the enforcement rule.

In some embodiments, the enforcement engine is further configured to generate the value by summing the transaction amount, the in-process transaction amount and the reportable contribution amount identified.

In some embodiments, the enforcement engine is further configured to select the threshold limit based on a predetermined threshold limit configured for the electronic funding source.

In some embodiments, the enforcement engine is further configured to receive the request to initiate a single electronic benefits account transaction, the request initiated by a remote device that is remote to the first device and configured with authentication credentials to access the first device.

In some embodiments, the enforcement engine is further configured to generate an alert in the alert format that includes instructions to terminate the single electronic benefits account transaction initiated by the request to prevent exceeding the threshold limit established for the electronic benefits account.

In some embodiments, the enforcement engine is further configured to establish a bidirectional communication channel with the first device, the bidirectional communication channel configured to transfer requests and instructions to terminate transactions.

In some embodiments, the enforcement engine is further configured to transmit, via the network to the first device, the response packets indicating the denial of the single electronic benefits account transaction request within a predetermined time interval from receiving the single electronic benefits account request.

In some embodiments, the enforcement engine is further configured to determine that the electronic funding source corresponds to a funded payroll deposit, select the alert format corresponding to the funded payroll deposit, the alert format comprising a first field for the instructions to deny the single electronic benefits account transaction and a second field for a reason code, generate an alert in the alert format that includes instructions to terminate the single electronic benefits account transaction and a reason code, and transmit the one or more response packets carrying the alert.

In some embodiments, the enforcement engine is further configured to access a profile database to determine that the electronic funding source corresponds to a non-payroll deposit, select the alert format for the instructions to terminate the single electronic benefits account transaction corresponding to the non-payroll deposit, the alert format including a first field for a reason code, and a second field for instructions to exclude the transaction from the in-process transaction amount, generate an alert in the alert format that includes instructions to terminate the single electronic benefits account transaction, the reason code, the instructions to exclude the transaction from the in-process transaction amount, and transmit the one or more response packets carrying the alert.

In some embodiments, the enforcement engine is further configured to receive a second one or more packets comprising a second request to initiate a second single electronic benefits account transaction to fund the electronic benefits account, the second request including a second data structure identifying the transaction destination, the transaction code, a second transaction amount and the first electronic funding source, generate a second value by combining the second transaction amount, the in-process transaction amount and the reportable contribution amount identified from the electronic transaction queue of the electronic benefits account maintained in memory by the server, the second value different from the value, determine the second value is less than the threshold limit based on a comparison of the second value with the threshold limit, and generate, responsive to the second value being less than the threshold limit, second response packets to authorize the second single electronic benefits account transaction.

Another aspect of the present solution is directed to a method of managing resources via information technology infrastructure. A server including one or more processor provides, to a plurality of devices corresponding to a plurality of heterogeneous electronic funding sources, an electronic benefits account transaction application programming interface ("API") configured to receive transaction requests from the plurality of heterogeneous electronic funding sources. The server receives via the electronic benefits account transaction API, from a first device of the plurality of devices corresponding to a first electronic funding source of the plurality of heterogeneous electronic transaction sources, a first one or more packets comprising a request to initiate a single electronic benefits account transaction to fund an electronic benefits account, the request identifying a transaction destination, a transaction code, a transaction amount and an identifier identifying the first electronic funding source. The server executes an enforcement engine to determine that the transaction code maps to one of a current year or a previous year. The executes the enforcement engine to perform a lookup in an electronic transaction queue of the electronic benefits account maintained in memory by the server to identify an in-process transaction amount and a reportable contribution amount. The server executes the enforcement engine to generate a value by combining the transaction amount, the in-process transaction amount and the reportable contribution amount identified from the electronic transaction queue of the electronic benefits account maintained in memory by the server, setting generated value to indicate a virtual transaction balance. The server executes the enforcement engine to compare the value with a threshold limit for the one of the current year or the previous year mapped to the transaction code to determine that the value exceeds the threshold limit based on the comparison. The server executes the enforcement engine to select an alert format configured for an interface corresponding to the first electronic funding source. The server executes the enforcement engine to transmit, via a network to the first device, one or more response packets carrying data in the alert format indicating a denial of the single electronic benefits account transaction request responsive to the comparison and the transaction code mapping to the one of the current year or the previous year, the one or more packets configured to indicate to the first device termination of the single electronic benefits account transaction initiated by the request to prevent exceeding the threshold limit established for the electronic benefits account.

In some embodiments, the server executes the enforcement engine to identify, using a profile database stored in memory, that the first electronic funding source enforces electronic benefits account limits, and determine responsive to identifying that the first electronic funding source enforces electronic benefits account limits, the transaction code maps to one of the current year or the previous year.

In some embodiments, the server executes the enforcement engine to determine an enforcement rule based on the single electronic benefits account transaction request, and identify the threshold limit based on the enforcement rule.

In some embodiments, the server executes the enforcement engine to generate the value by summing the transaction amount, the in-process transaction amount and the reportable contribution amount identified.

In some embodiments, the server executes the enforcement engine to select the threshold limit based on a predetermined threshold limit configured for the electronic funding source.

In some embodiments, the server executes the enforcement engine to receive the request to initiate a single electronic benefits account transaction, the request initiated by a remote device that is remote to the first device and configured with authentication credentials to access the first device.

In some embodiments, the server executes the enforcement engine to generate an alert in the alert format that includes instructions to terminate the single electronic benefits account transaction initiated by the request to prevent exceeding the threshold limit established for the electronic benefits account, and transmit the alert to the first device to cause the first device to terminate the transaction, the transaction initiated by a remote device remote to the first device.

In some embodiments, the server executes the enforcement engine to transmit, via the network to the first device, the response packets indicating the denial of the single electronic benefits account transaction request within a predetermined time interval from receiving the single electronic benefits account request.

At least one aspect of the present solution is directed to a system for conducting electronic transactions via a computer network. The system can include a communication interface of a server having one or more processors to receive a request to adjudicate a single claim against an electronic benefits account. The system can include a policy engine executed by the one or more processors of the server to determine, responsive to the communication interface receiving the request to adjudicate the single claim, that the single claim against the electronic benefits account is approved for an amount of expenditures qualifying under the electronic benefits account. The policy engine is executed to identify, via a configuration of the electronic benefits account maintained by the server, a reimbursement policy of the electronic benefits account specifying an ordered list of account destinations for benefits account reimbursements. The electronic reimbursement account is configured to allow transactions for non-qualifying benefits account expenditures. The policy engine executed to update the electronic reimbursement account maintained by the server with a value corresponding to a credit for the approved amount for the single claim. The system can include a notification engine executed by the server to generate, responsive to the request adjudicated by the server and the update by the policy engine of the electronic reimbursement account with the value corresponding to the credit for the approved amount for the single claim, a notification identifying the update to the electronic reimbursement account corresponding to the credit. The notification engine is executed to transmit, via the computer network to a device of the electronic benefits account, a first one or more packets carrying data indicating the notification of the credit.

In some embodiments, the server is further configured to determine a balance of the electronic reimbursement account, the balance including the value used to update the electronic reimbursement account prior to transmission of the first one or more packets carrying data indicating the notification of the credit. The server can be further configured to transmit the first one or more packets responsive to determining the balance includes the value.

In some embodiments, the server is further configured to receive a second one or more packets carrying the request to adjudicate the single claim against the electronic benefits account, the request comprising a request data structure having a first field indicating a merchant ID, a second field indicating a total amount of expenditures, and a third field indicating the electronic benefits account. The server can be further configured to parse the second one or more packets to identify the electronic benefits account indicated via the third field. The server can be further configured to perform, with the identification of the electronic benefits account, a lookup in a benefits account policy database maintained in memory by the server. The server can be further configured to retrieve, responsive to the lookup, an electronic benefits account policy corresponding to the single claim against the electronic benefits account. The server can be further configured to generate, responsive to application of the electronic benefits account policy using the merchant ID and the total amount of expenditures, the indication that the single claim against the electronic benefits account is approved for the amount of expenditures qualifying under the electronic benefits account.

In some embodiments, the server is further configured to determine the amount of expenditures qualifying under the electronic benefits account is different from the total amount of expenditures.

In some embodiments, the server is further configured to receive, via the computer network, a second one or more packets carrying a request to adjudicate the single claim against the electronic benefits account, the request comprising a request data structure having a first field indicating a merchant ID, a second field indicating a total amount of expenditures, and a third field indicating the electronic benefits account. The server can be further configured to transmit the first one or more packets carrying data indicating the notification of the transferred credit within a predetermined time interval of receiving the second one or more packets.

In some embodiments, the server is further configured to receive a second one or more packets generated by a merchant device to conduct an electronic transaction at a merchant, the second one or more packets carrying data identifying a merchant category of the merchant, the electronic benefits account maintained and configured on the server, and a total monetary amount of the electronic transaction. The server can be further configured to transmit the first one or more packets carrying data indicating the notification of the transferred credit within a predetermined time interval of receiving the second one or more packets.

In some embodiments, the server is further configured to receive a second one or more packets generated by a merchant device to conduct an electronic transaction at a merchant, the second one or more packets carrying data identifying a merchant category of the merchant, the electronic benefits account maintained and configured on the server, and a total monetary amount of the electronic transaction. The server can be further configured to initiate a claim adjudication process responsive to receiving the second one or more packets. The server can be further configured generate, responsive to initiating the single claim adjudication process, a second notification of the initiation. The server can be further configured to transmit, prior to transmission of the first one or more packets, a third one or more packets carrying data indicating the second notification of the initiation.

In some embodiments, the server is further configured to transmit the first one or more packets carrying data indicating the notification and the third one or more packets carrying data indicating the second notification with a predetermined time interval.

In some embodiments, the server is further configured to retrieve, responsive to transmission of the instructions including the value to update the electronic reimbursement account, an electronic report template configured for the electronic benefits account. The server can be further configured generate the notification using the electronic report template to include a balance of the electronic reimbursement account subsequent to updating the electronic reimbursement account with the credit. The server can be further configured to transmit, to the device, the first one or more packets carrying data indicating the notification via at least one of a Short Message Service protocol or an electronic mail protocol.

In some embodiments, the server is further configured to perform a lookup in a profile database of the electronic benefits account to identify the device configured to receive notifications for the electronic benefits account. The server can be further configured to retrieve, from the profile database, a unique identifier for the device and a notification mode, the notification mode including at least one of a Short Message Service protocol or an electronic mail protocol. The server can be further configured to configure the first one or more packets carrying data indicating the notification based on the notification mode.

Another aspect of the present solution is directed to a method of managing electronic transactions via a computer network. A communication interface of a server receives a request to adjudicate a single claim against an electronic benefits account. The server can include one or more processors. A policy engine executed by the server determines, responsive to the communication interface receiving the request to adjudicate the single claim, that the single claim against the electronic benefits account is approved for an amount of expenditures qualifying under the electronic benefits account. The policy engine identifies, via a configuration of the electronic benefits account maintained by the server, a reimbursement policy of the electronic benefits account specifying an ordered list of account destinations for benefits account reimbursements. The policy engine determines, via application of the reimbursement policy to the single claim, an electronic reimbursement account as a destination for a benefits account reimbursement, the electronic reimbursement account configured to allow transactions for non-qualifying benefits account expenditures. The server transmits instructions to update the electronic reimbursement account maintained by the server with a value corresponding to a credit for the approved amount for the single claim. The server generates, responsive to the request adjudicated by the server and transmitting the instructions to update the electronic reimbursement account with the credit of the single claim, a notification identifying the update to the electronic reimbursement account corresponding to the credit of the single claim. The server transmits, via the computer network to a device of the electronic benefits account, a first one or more packets carrying data indicating the notification of the credit.

In some embodiments, the server determines a balance of the electronic reimbursement account. The balance can include the value used to update the electronic reimbursement account. The server can determine the balance prior to transmitting the first one or more packets carrying data indicating the notification of the credit. In some embodiments, the server transmits the first one or more packets responsive to determining the balance includes the value.

In some embodiments, the policy engine receives, via the computer network, a second one or more packets carrying the request to adjudicate the single claim against the electronic benefits account, the request comprising a request data structure having a first field indicating a merchant ID, a second field indicating a total amount of expenditures, and a third field indicating the electronic benefits account. The policy engine can the second one or more packets to identify the electronic benefits account indicated via the third field.

The policy engine can perform a lookup in a benefits account policy database maintained in memory by the server using the identification of the electronic benefits account. The policy engine can retrieve, responsive to the lookup, a benefits account policy corresponding to the single claim against the electronic benefits account. The server can generate, responsive to application of the electronic benefits account policy using the merchant ID and the total amount of expenditures, the indication that the single claim against the electronic benefits account is approved for the amount of expenditures qualifying under the electronic benefits account.

In some embodiments, the server determines the amount of expenditures qualifying under the electronic benefits account is different from the total amount of expenditures.

In some embodiments, the server receives, via the computer network, a second one or more packets carrying a request to adjudicate the single claim against the electronic benefits account, the request comprising a request data structure having a first field indicating a merchant ID, a second field indicating a total amount of expenditures, and a third field indicating the electronic benefits account. The server can transmit the first one or more packets carrying data indicating the notification of the transferred credit within a predetermined time interval of receiving the second one or more packets.

In some embodiments, the server receives a second one or more packets generated by a merchant device to conduct an electronic transaction at a merchant, the second one or more packets carrying data identifying a merchant category of the merchant, the electronic benefits account maintained and configured on the server, and a total monetary amount of the electronic transaction. The server can transmit the first one or more packets carrying data indicating the notification of the transferred credit within a predetermined time interval of receiving the second one or more packets.

In some embodiments, the server can receive a second one or more packets generated by a merchant device to conduct an electronic transaction at a merchant, the second one or more packets carrying data identifying a merchant category of the merchant, the electronic benefits account maintained and configured on the server, and a total monetary amount of the electronic transaction. The server can initiate a claim adjudication process responsive to receiving the second one or more packets. The server can generate, responsive to initiating the single claim adjudication process, a second notification of the initiation. The server can transmit, prior to transmission of the first one or more packets, a third one or more packets carrying data indicating the second notification of the initiation.

In some embodiments, the server can transmit the first one or more packets carrying data indicating the notification and the third one or more packets carrying data indicating the second notification with a predetermined time interval.

In some embodiments, the server can retrieve, responsive to transmitting the instructions including the value to update the electronic reimbursement account, an electronic report template configured for the electronic benefits account. The server can generate the notification using the electronic report template to include a balance of the electronic reimbursement account subsequent to updating the electronic reimbursement account with the credit. The server can transmit, to the device, the first one or more packets carrying data indicating the notification via at least one of a Short Message Service protocol or an electronic mail protocol.

In some embodiments, the server can perform a lookup in a profile database of the electronic benefits account to identify the device configured to receive notifications for the electronic benefits account. The server can retrieve, from the profile database, a unique identifier for the device and a notification mode, the notification mode including at least one of a Short Message Service protocol or an electronic mail protocol. The server can configure the first one or more packets carrying data indicating the notification based on the notification mode.

At least one aspect of the present solution is directed to a method of managing electronic transactions via a computer network. A communications interface of a server receives a first one or more data packets via a network protocol. The server can include one or more processors. The first one or more data packets can be generated by a first device at a first merchant to conduct a first electronic transaction at the first merchant. The first one or more data packets can include first header information and first payload information carrying data. The first one or more data packets can carry data identifying a first merchant category of the first merchant, an electronic account maintained and configured on the server, and a first monetary amount of the first electronic transaction. A policy engine executing on the one or more processors of the server selects a first purse of a plurality of purses allocated to the electronic account maintained by the server based on a first policy applied to the data. The first purse can be configured as a purse with funds exempt from payroll tax deductions to be used to conduct approved transactions. The server obtains the first monetary amount of the first electronic transaction from the first purse of the electronic account. The policy engine applies a second policy to the data to determine a reimbursement amount based on the first monetary amount of the transaction. The server electronically provides, via the computer network, the reimbursement amount to a second purse of the electronic account. The second purse can be different from the first purse.

In some embodiments, the server selects the first purse based on the first policy applied to the first merchant category. In some embodiments, the server provides a real-time notification of the reimbursement amount responsive to transferring the reimbursement amount to the second purse of the electronic account. In some embodiments, the policy engine determines that the first purse of the electronic purse is configured for prescription purchases. The server can select the first purse responsive to determining that the first merchant is a prescription provider based on the first merchant category.

In some embodiments, the server receives a second one or more data packets generated by a second device at a second merchant to conduct a second electronic transaction at the second merchant. The second one or more data packets can carry second data indicating a second merchant category of the second merchant, the electronic account, and a second monetary amount of the second electronic transaction. The policy engine can use the first policy to select the second purse of the electronic account based on the second merchant category. The server can provide an indication to use the second account for at least a portion of the secondary monetary amount. In some embodiments, the server can select the first account for a first portion of the second monetary amount based on the second merchant category matching the first account. The server can select the second account for a second portion of the second monetary amount based on an available balance in the first account being less than the second monetary amount of the second transaction.

In some embodiments, the server can select the second purse responsive to determining that the first purse is not configured for the second merchant category of the second merchant. In some embodiments, the server can map, using the first policy, the first merchant to the first purse based on the first merchant category and a first configuration of the first purse. The server can use the first policy to map the second merchant to the second purse based on the second merchant category and a second configuration of the second purse.

In some embodiments, the server can retrieve, from a policy repository stored in memory, the second policy using an identifier of the electronic account. In some embodiments, the server can access a data record in memory for the electronic account. The data record can include a first available amount and a first configuration for the first purse, and a second available amount and a second configuration for the second purse. The server can determine, based on the first available amount and the first configuration, to use the first purse for the first electronic transaction. The server can determine, based on the first available amount and the first configuration, not to use the second purse for the first electronic transaction. The server can determine, based on the first configuration, not to use the first purse for a second electronic transaction. The server can determine, based on the second available amount and the second configuration, to use the second purse for the second electronic transaction.

In some embodiments, the server can receive a request from a client device for information about the electronic account. The server can authenticate the request from the client device using credentials associated with the request. The server can access a data record in memory for the electronic account. The data record can include a first available amount for the first purse, and a second available amount for the second purse. The server can provide for display on the client device a report indicating the first available amount and the second available amount.

In some embodiments, the server can receive the request via a Short Message Service protocol from the client device. The client device can be a mobile telecommunications device. The server can provide the report via at least one of the Short Message Service protocol or an electronic mail protocol.

Another aspect of the present solution is directed to a system to conduct electronic transactions via a computer network. The system can include a server having one or more processors and a communication interface. The system can include a policy engine and a transaction engine. The communications interface receives, via a network protocol, a first one or more data packets generated by a first device at a first merchant to conduct a first electronic transaction at the first merchant. The first one or more data packets carry data identifying a first merchant category of the first merchant, an electronic account, and a first monetary amount of the first electronic transaction. The policy engine selects a first purse of a plurality of purses allocated to the electronic account maintained by the server based on a first policy applied to the data. The first purse can be configured as a purse with funds exempt from payroll tax deductions to be used to conduct approved transactions. The transaction engine obtains the first monetary amount of the first electronic transaction from the first purse of the electronic account. The policy engine applies a second policy to the data to determine a reimbursement amount based on the first monetary amount of the transaction. The transaction engine provides, via a network, the reimbursement amount to a second purse of the electronic account, the second purse different from the first purse.

In some embodiments, the server provides a real-time notification of the reimbursement amount responsive to transferring the reimbursement amount to the second purse of the electronic account. In some embodiments, the server determines that the first purse of the electronic purse is configured for prescription purchases. The server can select the first purse responsive to determining that the first merchant is a prescription provider based on the first merchant category.

In some embodiments, the server receives a second one or more data packets generated by a second device at a second merchant to conduct a second electronic transaction at the second merchant. The second one or more data packets carry second data indicating a second merchant category of the second merchant, the electronic account, and a second monetary amount of the second electronic transaction. The server can use the first policy to select the second purse of the electronic account based on the second merchant category. The server can provide an indication to use the second account for at least a portion of the secondary monetary amount.

In some embodiments, the server can select the second purse responsive to determining that the first purse is not configured for the second merchant category of the second merchant. In some embodiments, the server can use the first policy to map the first merchant to the first purse based on the first merchant category and a first configuration of the first purse. The server can use the first policy to map the second merchant to the second purse based on the second merchant category and a second configuration of the second purse.

In some embodiments, the server can access a data record in memory for the electronic account. The data record can include a first available amount and a first configuration for the first purse, and a second available amount and a second configuration for the second purse. The server can determine, based on the first available amount and the first configuration, to use the first purse for the first electronic transaction. The server can determine, based on the first available amount and the first configuration, not to use the second purse for the first electronic transaction. The server can determine, based on the first configuration, not to use the first purse for a second electronic transaction. The server can determine, based on the second available amount and the second configuration, to use the second purse for the second electronic transaction.

In some embodiments, the server can receive a request from a client device for information about the electronic account. The server can authenticate the request from the client device using credentials associated with the request. The server can access a data record in memory for the electronic account. The data record can include a first available amount for the first purse, and a second available amount for the second purse. The server can provide, for display on the client device, a report indicating the first available amount and the second available amount.

At least one aspect of the present solution is directed to a system to manage information technology infrastructure. The system can include a device including one or more processors, the device configured with a tool that interfaces with a plurality of administrator devices remote from the device, the plurality of administrator devices each configured to administer one or more tax benefit accounts corresponding to one or more participants. The tool is executed to receive, via a network, an identifier of an administrator of an administrator device of the plurality of administrator devices. The tool is executed to retrieve, from an administrator profile data structure stored in memory, an administrator profile corresponding to the identifier. An administrator matching engine of the tool is executed to identify one or more administrator profiles stored in the administrator profile data structure of one or more different administrators. The administrator matching engine is executed to determine, based on a parameter matching technique, from the one or more identified administrator profiles, a similarity metric between the administrator profile and each of the identified one or more administrator profiles. The administrator matching engine is executed to identify the one or more administrator profiles having the similarity metric satisfying a predetermined threshold. A report generator of the tool is executed to instantiate a dynamic report interface to render for display via the administrator device, an electronic report indicating a first value of a first performance metric of the administrator based on the administrator profile and a second value of the first performance metric based on the identified one or more administrator profiles. The tool is executed to provide, via the dynamic report interface, the electronic report for display via the administrator device.

In some embodiments, the tool is further configured to receive, via the network from the administrator device, a parameter of the administrator profile, the parameter including at least one of an account opening fee, a minimum operating balance, a monthly fee, an annual fee, an electronic fund access type, or an interest rate.

In some embodiments, the tool is further configured to generate the administrator profile with parameters received from the administrator device, the administrator device configured to receive data from a plurality of participant devices corresponding to the one or more tax benefit accounts configured using the administrator profile.

In some embodiments, the tool is further configured to train, via a machine learning technique, an administrator profile model using a plurality of administrator profiles, and input a parameter of the administrator profile into the administrator profile model to determine the first value of the first performance metric.

In some embodiments, the tool is further configured to aggregate a plurality of administrator profiles corresponding to the plurality of administrator devices, and store the plurality of administrator profiles in the administrator profile data structure in memory.

In some embodiments, the tool is further configured to render the electronic report indicating the first value of the first performance metric based on a number of participants of the administrator during a time interval, and the second value of the first performance metric based on the number of customers of the identified one or more administrators.

In some embodiments, the tool is further configured to receive, via the instance of the dynamic report interface, an indication from the administrator device to adjust the time interval, and manipulate the first value of the first performance metric and the second value of the first performance metric indicated in the rendered electronic report responsive to the indication to adjust the time interval.

In some embodiments, the tool is further configured to receive, via the instance of the dynamic report interface, a filter criterion, use the filter criterion to identify a subset of the one or more administrator profiles stored in the administrator profile data structure, generate a third value of the first performance metric based on the subset of the one or more administrator profiles, render, via the dynamic report interface, the electronic report to indicate the first value of the first performance metric and the third value of the first performance metric, and remove the second value of the first performance metric from the rendered electronic report, the second value of the first performance metric being different from the third value of the first performance metric.

In some embodiments, the tool is further configured to receive an update to the administrator profile after the electronic report is rendered, generate a third value of the first performance metric based on the update to the administrator profile, and render, via the dynamic report interface, the electronic report to include the third value of the first performance metric and remove the first value of the first performance metric.

In some embodiments, the tool is further configured to render the electronic report for display on the administrator device via the dynamic report interface, and receive, from the administrator device via the dynamic report interface, an indication to manipulate the electronic report.

Another aspect of the present solution is directed to a method of managing information technology infrastructure. A tool executed by one or more processors of a device that interfaces with a plurality of administrator devices remote from the device receives, via a network, an identifier of an administrator of an administrator device of a plurality of administrator devices, the plurality of administrator devices each configured to administer one or more tax benefit accounts corresponding to one or more participants. The tool retrieves from an administrator profile data structure stored in memory, an administrator profile corresponding to the identifier. The tool executes an administrator matching engine to identify, based on a parameter matching technique, one or more administrator profiles of one or more different administrators stored in the administrator profile data structure. The tool determines, based on the parameter matching technique from the one or more identified administrator profiles, a similarity metric between the administrator profile and each of the one or more administrator profiles. The tool identifies the one or more administrator profiles having the similarity metric satisfying a similarity threshold. The tool executes a report generator to generate an instance of a dynamic report interface to render for display via the administrator device, an electronic report indicating a first value of a first performance metric of the administrator based on the administrator profile and a second value of a first performance metric based on the identified one or more administrator profiles. The tool provides, via the dynamic report interface, the electronic report for display via the administrator device.

In some embodiments, the tool receives, via the network from the administrator device, a parameter of the administrator profile, the parameter including at least one of an account opening fee, a minimum operating balance, a monthly fee, an annual fee, an electronic fund access type, or an interest rate.

In some embodiments, the tool generates the administrator profile with parameters received from the administrator device, the administrator device configured to receive data from a plurality of participant devices corresponding to the one or more tax benefit accounts configured using the administrator profile.

In some embodiments, the tool trains, via a machine learning technique, an administrator profile model using a plurality of administrator profiles, and determines the first value of a first performance metric based on an output from the administrator profile model responsive to a parameter of the administrator profile input into the administrator profile model.

In some embodiments, the tool aggregates a plurality of administrator profiles corresponding to the plurality of administrator devices, and stores the plurality of administrator profiles in the administrator profile data structure in memory.

In some embodiments, the tool renders the electronic report indicating the first value of a first performance metric based on a number of participants of the administrator during a time interval, and the second value of a first performance metric based on the number of customers of the identified one or more administrators.

In some embodiments, the tool receives, via the instance of the dynamic report interface, an indication from the administrator device to adjust the time interval, and manipulates the first value of a first performance metric and the second value of a first performance metric indicated in the rendered electronic report responsive to the indication to adjust the time interval.

In some embodiments, the tool receives, via the instance of the dynamic report interface, a filter criterion, uses the filter criterion to identify a subset of the one or more administrator profiles stored in the administrator profile data structure, generates a third value of a first performance metric based on the subset of the one or more administrator profiles, renders via the dynamic report interface, the electronic report to indicate the first value of a first performance metric and the third value of a first performance metric, and removes the second value of a first performance metric from the rendered electronic report, the second value of a first performance metric different from the third value of a first performance metric.

In some embodiments, the tool receives an update to the administrator profile after the electronic report is rendered, generates a third value of the first performance metric based on the update to the administrator profile, and renders via the dynamic report interface, the electronic report to include the third value of the first performance metric and remove the first value of the first performance metric.

In some embodiments, the tool renders the electronic report for display on the administrator device via the dynamic report interface, and receives from the administrator device via the dynamic report interface, an indication to manipulate the electronic report.

At least one aspect of the present solution is directed to a system to allocate resources using an information technology infrastructure. The system can include a communication interface executed by one or more processors of a server and configured to receive financial data indicating a financial snapshot of a participant of a client device and health data of the participant to predict lifetime healthcare expenses of the participant. The system can include a forecast engine executed by the server. The forecast engine is executed to generate a multi-dimensional feature vector of the participant based on the received financial data and the health data of the participant. The forecast engine is executed to identify a healthcare expense prediction model to predict the future healthcare expenses of the participant, the healthcare expense prediction model generated by the server using financial data and health data of a plurality of participants. The forecast engine is executed to determine from the identified healthcare expense prediction model using the multi-dimensional feature vector of the participant, the predicted lifetime healthcare expenses of the participant. The forecast engine is executed to identify lifetime non-healthcare expenses of the participant. The forecast engine is executed to perform a lookup in a database to identify a healthcare tax benefit account of the participant to provide funds towards the predicted lifetime healthcare expenses of the participant and a non-healthcare tax benefit account of the participant to provide funds towards lifetime non-healthcare expenses of the participant. The forecast engine is executed to determine, based on the predicted lifetime healthcare expenses of the participant, a first amount of funds to allocate per time period to the healthcare tax benefit account. The forecast engine is executed to determine, based on the lifetime non-healthcare expenses of the participant, a second amount of funds to allocate per time period to the non-healthcare tax benefit account. The communication interface is executed to provide, for presentation via an interactive user interface, the first amount of funds to allocate to the healthcare tax benefit account and the second amount of funds to allocate to the non-healthcare tax benefit account, the interactive user interface including a control object configured to i) receive an input to adjust the first amount, and ii) responsive to receiving the input to adjust the first amount, updating a total amount of funds projected to be allocated to the healthcare tax benefit account.

In some embodiments, the server generates the interactive user interface with an electronic survey comprising one or more input elements, the interactive user interface configured to receive the financial data and the health data.

In some embodiments, the server generates the interactive user interface with a countdown timer set to a predetermined time interval, initiates the countdown timer responsive to enabling the interactive user interface to receive the financial data and the health data, and disables input via the interactive user interface responsive to expiration of the countdown timer.

In some embodiments, the server generates the multi-dimensional feature vector comprising a first feature indicating demographic information, a second feature indicating a healthcare spend amount, a third feature indicating a health savings account contribution amount, and a fourth feature indicating a health preference.

In some embodiments, the server can include a machine learning engine, and the machine learning engine is executed to train the healthcare expense prediction model with the financial data and the health data of the plurality of participants.

In some embodiments, the server inputs the multi-dimensional feature vector into the healthcare expense prediction model to output the predicted lifetime healthcare expenses of the participant, the predicted lifetime healthcare expenses of the participant based on data associated with similar participants used to generate the healthcare expense prediction model.

In some embodiments, the server determines the first amount of funds to allocate per time period to the healthcare tax benefit account using a first feature indicating demographic information, a second feature indicating a healthcare spend amount, a third feature indicating a health savings account contribution amount, and a fourth feature indicating a health preference In some embodiments, the server determines the second amount of funds to allocate per time period to the non-healthcare tax benefit account using a first feature indicating demographic information, a second feature indicating a non-healthcare spend amount, and a third feature indicating a non-health retirement account contribution amount.

In some embodiments, the server determines a first allocation priority associated with the healthcare tax benefit account, and determines a second allocation priority associated with the non-healthcare tax benefit account, the second allocation priority less than the first allocation priority.

In some embodiments, the server determines the first amount of funds to allocate to the healthcare tax benefit account based on the first allocation priority, the second allocation priority, and the healthcare expense prediction model.

Another aspect of the present solution is directed to a method of allocating resources using an information technology infrastructure. A server including one or more processors receives financial data indicating a financial snapshot of a participant of a client device and health data of the participant to predict lifetime healthcare expenses of the participant. The server generates a multi-dimensional feature vector of the participant based on the received financial data and the health data of the participant. The server identifies a healthcare expense prediction model to predict the future healthcare expenses of the participant, the healthcare expense prediction model generated by the server using financial data and health data of a plurality of participants. The server determines from the identified healthcare expense prediction model using the multi-dimensional feature vector of the participant, the predicted lifetime healthcare expenses of the participant. The server identifies lifetime non-healthcare expenses of the participant. The server performs a lookup in a database to identify a healthcare tax benefit account of the participant to provide funds towards the predicted lifetime healthcare expenses of the participant and a non-healthcare tax benefit account of the participant to provide funds towards lifetime non-healthcare expenses of the participant. The server determines, based on the predicted lifetime healthcare expenses of the participant, a first amount of funds to allocate per time period to the healthcare tax benefit account. The server determines, based on the lifetime non-healthcare expenses of the participant, a second amount of funds to allocate per time period to the non-healthcare tax benefit account. The server provides, for presentation via an interactive user interface, the first amount of funds to allocate to the healthcare tax benefit account and the second amount of funds to allocate to the non-healthcare tax benefit account, the interactive user interface including a control object configured to i) receive an input to adjust the first amount, and ii) responsive to receiving the input to adjust the first amount, updating a total amount of funds projected to be allocated to the healthcare tax benefit account.

In some embodiments, the server generates the interactive user interface with an electronic survey comprising one or more input elements, the interactive user interface configured to receive the financial data and the health data.

In some embodiments, the server generates the interactive user interface with a countdown timer set to a predetermined time interval, initiates the countdown timer responsive to enabling the interactive user interface to receive the financial data and the health data, and disables input via the interactive user interface responsive to expiration of the countdown timer.

In some embodiments, the server generates the multi-dimensional feature vector comprising a first feature indicating demographic information, a second feature indicating a healthcare spend amount, a third feature indicating a health savings account contribution amount, and a fourth feature indicating a health preference.

In some embodiments, the server can include a machine learning engine, and the machine learning engine is executed to train the healthcare expense prediction model with the financial data and the health data of the plurality of participants.

In some embodiments, the server inputs the multi-dimensional feature vector into the healthcare expense prediction model to output the predicted lifetime healthcare expenses of the participant, the predicted lifetime healthcare expenses of the participant based on data associated with similar participants used to generate the healthcare expense prediction model.

In some embodiments, the server determines the first amount of funds to allocate per time period to the healthcare tax benefit account using a first feature indicating demographic information, a second feature indicating a healthcare spend amount, a third feature indicating a health savings account contribution amount, and a fourth feature indicating a health preference In some embodiments, the server determines the second amount of funds to allocate per time period to the non-healthcare tax benefit account using a first feature indicating demographic information, a second feature indicating a non-healthcare spend amount, and a third feature indicating a non-health retirement account contribution amount.

In some embodiments, the server determines a first allocation priority associated with the healthcare tax benefit account, and determines a second allocation priority associated with the non-healthcare tax benefit account, the second allocation priority less than the first allocation priority.

In some embodiments, the server determines the first amount of funds to allocate to the healthcare tax benefit account based on the first allocation priority, the second allocation priority, and the healthcare expense prediction model.

At least one aspect of the present solution is directed to a system to manage information technology infrastructure. The system can include a device including one or more processors, the device configured with a tool that interfaces with a plurality of administrator devices remote from the device, the plurality of administrator devices each configured to administer one or more tax benefit accounts corresponding to one or more participants. The tool is executed to receive, via a network, an identifier of an administrator of an administrator device of the plurality of administrator devices. The tool is executed to retrieve, from an administrator profile data structure stored in memory, an administrator profile corresponding to the identifier. An administrator matching engine of the tool is executed to identify one or more administrator profiles stored in the administrator profile data structure of one or more different administrators. The administrator matching engine is executed to determine, based on a parameter matching technique, from the one or more identified administrator profiles, a similarity metric between the administrator profile and each of the identified one or more administrator profiles. The administrator matching engine is executed to identify the one or more administrator profiles having the similarity metric satisfying a predetermined threshold. A report generator of the tool is executed to instantiate a dynamic report interface to render for display via the administrator device, an electronic report indicating a first value of a first performance metric of the administrator based on the administrator profile and a second value of the first performance metric based on the identified one or more administrator profiles. The tool is executed to provide, via the dynamic report interface, the electronic report for display via the administrator device.

In some embodiments, the tool is further configured to receive, via the network from the administrator device, a parameter of the administrator profile, the parameter including at least one of an account opening fee, a minimum operating balance, a monthly fee, an annual fee, an electronic fund access type, or an interest rate.

In some embodiments, the tool is further configured to generate the administrator profile with parameters received from the administrator device, the administrator device configured to receive data from a plurality of participant devices corresponding to the one or more tax benefit accounts configured using the administrator profile.

In some embodiments, the tool is further configured to train, via a machine learning technique, an administrator profile model using a plurality of administrator profiles, and input a parameter of the administrator profile into the administrator profile model to determine the first value of the first performance metric.

In some embodiments, the tool is further configured to aggregate a plurality of administrator profiles corresponding to the plurality of administrator devices, and store the plurality of administrator profiles in the administrator profile data structure in memory.

In some embodiments, the tool is further configured to render the electronic report indicating the first value of the first performance metric based on a number of participants of the administrator during a time interval, and the second value of the first performance metric based on the number of customers of the identified one or more administrators.

In some embodiments, the tool is further configured to receive, via the instance of the dynamic report interface, an indication from the administrator device to adjust the time interval, and manipulate the first value of the first performance metric and the second value of the first performance metric indicated in the rendered electronic report responsive to the indication to adjust the time interval.

In some embodiments, the tool is further configured to receive, via the instance of the dynamic report interface, a filter criterion, use the filter criterion to identify a subset of the one or more administrator profiles stored in the administrator profile data structure, generate a third value of the first performance metric based on the subset of the one or more administrator profiles, render, via the dynamic report interface, the electronic report to indicate the first value of the first performance metric and the third value of the first performance metric, and remove the second value of the first performance metric from the rendered electronic report, the second value of the first performance metric being different from the third value of the first performance metric.

In some embodiments, the tool is further configured to receive an update to the administrator profile after the electronic report is rendered, generate a third value of the first performance metric based on the update to the administrator profile, and render, via the dynamic report interface, the electronic report to include the third value of the first performance metric and remove the first value of the first performance metric.

In some embodiments, the tool is further configured to render the electronic report for display on the administrator device via the dynamic report interface, and receive, from the administrator device via the dynamic report interface, an indication to manipulate the electronic report.

At least one aspect of the present disclosure is directed to a system to reduce resource consumption via information technology infrastructure. The system can include one or more servers with one or more processors and memory. The system can include a communications interface, a forecast engine, and a notification engine executed by one or more servers. In some embodiments, the communications interface can receive one or more data packets including data indicating a healthcare transaction event corresponding to a participant of a plurality of participants of a healthcare management platform. The forecast engine can select a healthcare trend model to provide healthcare related recommendations to the plurality of participants of the healthcare management platform maintained by the server. The healthcare trend model can be trained by the server using previously received data packets including data indicating healthcare transaction events corresponding to the plurality of participants of the healthcare management platform. The notification engine can perform a lookup in a recommendation data structure using an identifier of the selected healthcare trend model to identify a plurality of healthcare related recommendations linked with the selected healthcare trend model. The notification engine can determine a correlation coefficient between each of the plurality of healthcare related recommendations and the selected healthcare trend model. The notification engine can select, based on a rank of each correlation coefficient, a highest ranking healthcare related recommendation of the plurality of healthcare related recommendations. The notification engine can retrieve, responsive to the selection of the highest ranking healthcare related recommendation, a notification template from a notification data structure that maps to the highest ranking healthcare related recommendation. The notification engine can generate, using the notification template, a notification corresponding to the highest ranking healthcare related recommendation. The notification engine can generate a request to deliver the notification corresponding to the highest ranking healthcare related recommendation at a destination address of a computing device of the participant. The notification engine can transmit the notification to the computing device of the participant responsive to the request. The notification engine can transmit the notification to the computing device via a communication channel established between the server and the computing device.

The healthcare transaction events can include one or more of a claim payment, a card denial, a password change, or a received deposit. In some embodiments, the healthcare transaction event can include a denial. The server can be further configured to retrieve a denial healthcare trend model responsive to the healthcare transaction event including the denial. The server can be further configured to select, based on the denial healthcare trend model, a denial recommendation that includes a recommended processing configuration. The server can select the denial recommendation responsive to a processing configuration that resulted in the denial healthcare transaction event. In some cases, the server can select a denial recommendation that includes a recommended resource allocation responsive to determining that an insufficient amount of resources resulted in the denial healthcare transaction event. In some cases, the server can select a denial recommendation that includes an ordered list including at least one qualifying item and at least one non-qualifying item responsive to determining that the denial healthcare transaction event resulted from a transaction including one or more qualifying items and one or more non-qualifying items.

In some embodiments, the server can categorize the healthcare transaction event into a first category selected from a plurality of categories. The server can determine, from the healthcare trend model, that a metric of the first category meets or exceeds a threshold for the first category. The server can select, responsive to the determination of the metric meeting or exceeding the threshold, the highest ranking healthcare related recommendation.

In some embodiments, the server can generate a first vector based on the healthcare transaction event and one or more healthcare transaction events of the participants. The server can identify a second vector for each of a plurality of healthcare transaction events. The server can determine for each of the plurality of healthcare transaction events, a distance between the first vector and the second vector. The server can identify a minimum distance from the determined distance for each of the plurality of healthcare transaction events. The server can select the healthcare trend model corresponding to the minimum distance.

In some embodiments, the server can categorize the healthcare transaction event into a first category selected from a plurality of categories. The server can determine, from the healthcare trend model, that a metric of the first category is below a threshold. The server can select, responsive to the determination of the metric below the threshold, the highest ranking healthcare related recommendation.

In some embodiments, the system can include the healthcare management platform. The healthcare management platform can receive electronic healthcare transactions. The healthcare management platform can process the electronic healthcare transaction to cause healthcare transaction events. The healthcare management platform can store the healthcare transaction events in a database.

In some embodiments, the server can receive the previously received data packets from a device of an administrator remote from the server via an administrator interface rendered by the server on the device of the administrator.

Another aspect of the present disclosure is directed to a method of reducing resource consumption via information technology infrastructure. In some embodiments, the method can include the server receiving, via a communications interface, one or more data packets including data indicating a healthcare transaction event corresponding to a participant of a plurality of participants of a healthcare management platform. The method can include the server identifying a healthcare trend model to provide healthcare related recommendations to the plurality of participants of the healthcare management platform maintained by the server. The healthcare trend model can be trained by the server using previously received data packets including data indicating healthcare transaction events corresponding to the plurality of participants of the healthcare management platform. The method can include the server performing a lookup in a recommendation data structure using an identifier of the selected healthcare trend model to identify a plurality of healthcare related recommendations linked with the selected healthcare trend model. The method can include the server determining a correlation coefficient between each of the plurality of healthcare related recommendations and the selected healthcare trend model. The method can include the server selecting, based on a rank of each correlation coefficient, a highest ranking healthcare related recommendation of the plurality of healthcare related recommendations. The method can include the server retrieving a notification template from a notification data structure that maps to the highest ranking healthcare related recommendation. The server can retrieve the notification template responsive to selecting the highest ranking healthcare related recommendation. The method can include the server configuring a notification engine with the notification template to generate a notification corresponding to the highest ranking healthcare related recommendation. The method can include the notification engine of the server generating a request to deliver the notification corresponding to the highest ranking healthcare related recommendation at a destination address of a computing device of the participant. The method can include the server transmitting the notification to the computing device of the participant. The server can transmit the notification responsive to the request and via a communication channel established between the server and the computing device.

In some embodiments, the method can include the server retrieving a denial healthcare trend model responsive to the healthcare transaction event including a denial. The method can include the server selecting, based on the denial healthcare trend model, a denial recommendation that includes a recommended processing configuration. The server can select the denial healthcare trend model responsive to a processing configuration that resulted in the denial healthcare transaction event. In some embodiments, the method can include the the server selecting, based on the denial healthcare trend model, a denial recommendation comprising a recommended resource allocation responsive to determining that an insufficient amount of resources resulted in the denial healthcare transaction event. In some embodiments, the method can include the server selecting, based on the denial healthcare trend model, a denial recommendation that includes an ordered list. The ordered list can include at least one qualifying item and at least one non-qualifying item. The server can select the denial recommendation with the ordered list responsive to determining that the denial healthcare transaction event resulted from a transaction including one or more qualifying items and one or more non-qualifying items.

In some embodiments, the method includes the server categorizing the healthcare transaction event into a first category selected from a plurality of categories. The method can include the server determining, from the healthcare trend model, that a metric of the first category meets or exceeds a threshold for the first category. The method can include the server selecting, responsive to determining the metric meeting or exceeding the threshold, the highest ranking healthcare related recommendation.

In some embodiments, the method includes the server generating a first vector based on the healthcare transaction event and one or more healthcare transaction events of the participants. The method can include the server identifying a second vector for each of a plurality of healthcare transaction events. The method can include the server determining, for each of the plurality of healthcare transaction events, a distance vector between the first vector and the second vector. The method can include the server identifying a minimum distance vector from the determined distance vector for each of the plurality of healthcare transaction events. The method can include the server selecting the healthcare trend model corresponding to the minimum distance vector.

In some embodiments, the method can include the server categorizing the healthcare transaction event into a first category selected from a plurality of categories. The method can include the server determining, from the healthcare trend model, that a metric of the first category falls below a threshold. The method can include the server selecting, responsive to determining that the metric falls below the threshold, the highest ranking healthcare related recommendation.

In some embodiments, the method can include the healthcare management platform receiving electronic healthcare transactions. The method can include the healthcare management platform processing the electronic healthcare transaction to cause healthcare transaction events. The method can include the healthcare management platform storing, in a database, the healthcare transaction events. In some embodiments, the healthcare transaction events can include one or more of a claim payment, a card denial, a password change, or a received deposit. In some embodiments, the method includes the server receiving the previously received data packets from a device of an administrator remote from the server via an administrator interface rendered by the server on the device of the administrator.

BRIEF DESCRIPTION OF THE DRAWINGS

The foregoing and other objects, aspects, features, and advantages of the disclosure will become more apparent and better understood by referring to the following description taken in conjunction with the accompanying drawings, in which.

Figure 1A:
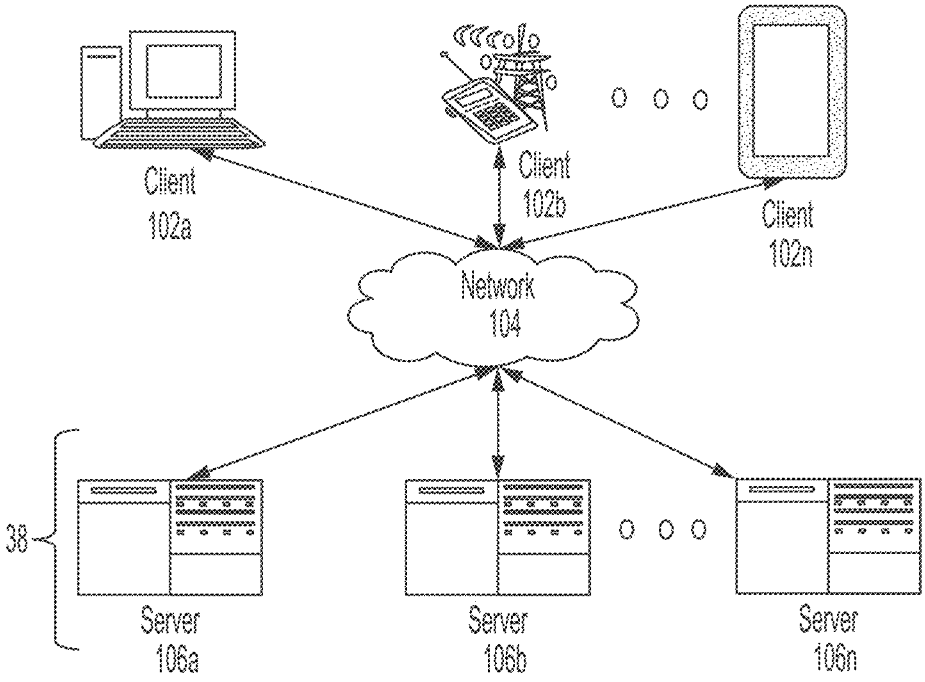
FIG. 1A is a block diagram depicting an embodiment of a network environment comprising client device in communication with server device.

The features and advantages of the present invention will become more apparent from the detailed description set forth below when taken in conjunction with the drawings, in which like reference characters identify corresponding elements throughout. In the drawings, like reference numbers generally indicate identical, functionally similar, or structurally similar elements.

DETAILED DESCRIPTION

For purposes of reading the description of the various embodiments below, the following descriptions of the sections of the specification and their respective contents can be helpful:

- Section A describes a network environment and computing environment which can be useful for practicing embodiments described herein.
- Section B describes embodiments of systems and methods for conducting electronic transactions.
- Section C describes embodiments of systems and methods for using a multi-purse card and providing notifications relating to the electronic transactions.
- Section D describes embodiments of systems and methods for managing electronic transactions using a transaction portal.
- Section E describes embodiments of systems and methods for managing information technology infrastructure using an administrator matching and report generating system.
- Section F describes embodiments of systems and methods for allocating resources using a predictive resource allocating system.
- Section G describes embodiments of systems and methods for reducing resource consumption via information technology infrastructure.

A. Computing and Network Environment

Prior to discussing specific embodiments of the present solution, it can be helpful to describe aspects of the operating environment as well as associated system components (e.g., hardware elements) in connection with the methods and systems described herein. Referring to FIG. 1A, an embodiment of a network environment is depicted. In brief overview, the network environment includes one or more clients 102*a*-102*n* (also generally referred to as local machine(s) 102, client(s) 102, client node(s) 102, client machine(s) 102, client computer(s) 102, client device(s) 102, endpoint(s) 102, or endpoint node(s) 102) in communication with one or more servers 106*a*-106*n* (also generally referred to as server(s) 106, node 106, or remote machine(s) 106) via one or more networks 104. In some embodiments, a client 102 has the capacity to function as both a client node seeking access to resources provided by a server and as a server providing access to hosted resources for other clients 102*a*-102*n*.

Although FIG. 1A shows a network 104 between the clients 102 and the servers 106, the clients 102 and the servers 106 can be on the same network 104. In some embodiments, there are multiple networks 104 between the clients 102 and the servers 106. In one of these embodiments, a network 104' (not shown) can be a private network and a network 104 can be a public network. In another of these embodiments, a network 104 can be a private network and a network 104' a public network. In still another of these embodiments, networks 104 and 104' can both be private networks.

The network 104 can be connected via wired or wireless links. Wired links can include Digital Subscriber Line (DSL), coaxial cable lines, or optical fiber lines. The wireless links can include BLUETOOTH, Wi-Fi, Worldwide Interoperability for Microwave Access (WiMAX), an infrared channel or satellite band. The wireless links can also include any cellular network standards used to communicate among mobile devices, including standards that qualify as 1G, 2G, 3G, or 4G. The network standards can qualify as one or more generation of mobile telecommunication standards by fulfilling a specification or standards such as the specifications maintained by International Telecommunication Union. The 3G standards, for example, can correspond to the International Mobile Telecommunications-2000 (IMT-2000) specification, and the 4G standards can correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards can use various channel access methods e.g. FDMA, TDMA, CDMA, or SDMA. In some embodiments, different types of data can be transmitted via different links and standards. In other embodiments, the same types of data can be transmitted via different links and standards.

The network 104 can be any type and/or form of network. The geographical scope of the network 104 can vary widely and the network 104 can be a body area network (BAN), a personal area network (PAN), a local-area network (LAN), e.g. Intranet, a metropolitan area network (MAN), a wide area network (WAN), or the Internet. The topology of the network 104 can be of any form and can include, e.g., any of the following: point-to-point, bus, star, ring, mesh, or tree. The network 104 can be an overlay network which is virtual and sits on top of one or more layers of other networks 104'. The network 104 can be of any such network topology as known to those ordinarily skilled in the art capable of supporting the operations described herein. The network 104 can utilize different techniques and layers or stacks of protocols, including, e.g., the Ethernet protocol, the internet protocol suite (TCP/IP), the ATM (Asynchronous Transfer Mode) technique, the SONET (Synchronous Optical Networking) protocol, or the SDH (Synchronous Digital Hierarchy) protocol. The TCP/IP internet protocol suite can include application layer, transport layer, internet layer (including, e.g., IPv6), or the link layer. The network 104 can be a type of a broadcast network, a telecommunications network, a data communication network, or a computer network.

In some embodiments, the system can include multiple, logically-grouped servers 106. In one of these embodiments, the logical group of servers can be referred to as a server farm 38 or a machine farm 38. In another of these embodiments, the servers 106 can be geographically dispersed. In other embodiments, a machine farm 38 can be administered as a single entity. In still other embodiments, the machine farm 38 includes a plurality of machine farms 38. The servers 106 within each machine farm 38 can be heterogeneous-one or more of the servers 106 or machines 106 can operate according to one type of operating system platform (e.g., WINDOWS NT, manufactured by Microsoft Corp. of Redmond, Washington), while one or more of the other servers 106 can operate on according to another type of operating system platform (e.g., Unix, Linux, or Mac OS X).

In one embodiment, servers 106 in the machine farm 38 can be stored in high-density rack systems, along with associated storage systems, and located in an enterprise data center. In this embodiment, consolidating the servers 106 in this way can improve system manageability, data security, the physical security of the system, and system performance by locating servers 106 and high performance storage systems on localized high performance networks. Centralizing the servers 106 and storage systems and coupling them with advanced system management tools allows more efficient use of server resources.

The servers 106 of each machine farm 38 do not need to be physically proximate to another server 106 in the same machine farm 38. Thus, the group of servers 106 logically grouped as a machine farm 38 can be interconnected using a wide-area network (WAN) connection or a metropolitan-area network (MAN) connection. For example, a machine farm 38 can include servers 106 physically located in different continents or different regions of a continent, country, state, city, campus, or room. Data transmission speeds between servers 106 in the machine farm 38 can be increased if the servers 106 are connected using a local-area network (LAN) connection or some form of direct connection. Additionally, a heterogeneous machine farm 38 can include one or more servers 106 operating according to a type of operating system, while one or more other servers 106 execute one or more types of hypervisors rather than operating systems. In these embodiments, hypervisors can be used to emulate virtual hardware, partition physical hardware, virtualize physical hardware, and execute virtual machines that provide access to computing environments, allowing multiple operating systems to run concurrently on a host computer. Native hypervisors can run directly on the host computer. Hypervisors can include VMware ESX/ESXi, manufactured by VMWare, Inc., of Palo Alto, California; the Xen hypervisor, an open source product whose development is overseen by Citrix Systems, Inc.; the HYPER-V hypervisors provided by Microsoft or others. Hosted hypervisors can run within an operating system on a second software level. Examples of hosted hypervisors can include VMware Workstation and VIRTUALBOX.

Management of the machine farm 38 can be de-centralized. For example, one or more servers 106 can comprise components, subsystems and modules to support one or more management services for the machine farm 38. In one of these embodiments, one or more servers 106 provide functionality for management of dynamic data, including techniques for handling failover, data replication, and increasing the robustness of the machine farm 38. Each server 106 can communicate with a persistent store and, in some embodiments, with a dynamic store.

Server 106 can be a file server, application server, web server, proxy server, appliance, network appliance, gateway, gateway server, virtualization server, deployment server, SSL VPN server, or firewall. In one embodiment, the server 106 can be referred to as a remote machine or a node. In another embodiment, a plurality of nodes 290 can be in the path between any two communicating servers.

Figure 1B:
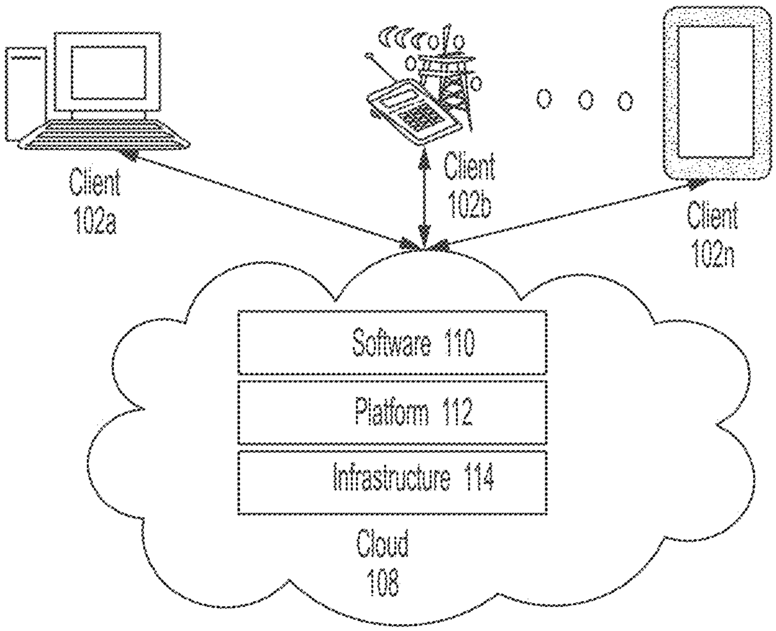
FIG. 1B is a block diagram depicting a cloud computing environment comprising a client device in communication with cloud service providers.

Referring to FIG. 1B, a cloud computing environment is depicted. A cloud computing environment can provide client 102 with one or more resources provided by a network environment. The cloud computing environment can include one or more clients 102*a*-102*n*, in communication with the cloud 108 over one or more networks 104. Clients 102 can include, e.g., thick clients, thin clients, and zero clients. A thick client can provide at least some functionality even when disconnected from the cloud 108 or servers 106. A thin client or a zero client can depend on the connection to the cloud 108 or server 106 to provide functionality. A zero client can depend on the cloud 108 or other networks 104 or servers 106 to retrieve operating system data for the client device. The cloud 108 can include back end platforms, e.g., servers 106, storage, server farms or data centers.

The cloud 108 can be public, private, or hybrid. Public clouds can include public servers 106 that are maintained by third parties to the clients 102 or the owners of the clients. The servers 106 can be located off-site in remote geographical locations as disclosed above or otherwise. Public clouds can be connected to the servers 106 over a public network. Private clouds can include private servers 106 that are physically maintained by clients 102 or owners of clients. Private clouds can be connected to the servers 106 over a private network 104. Hybrid clouds 108 can include both the private and public networks 104 and servers 106.

The cloud 108 can also include a cloud based delivery, e.g. Software as a Service (SaaS) 110, Platform as a Service (PaaS) 112, and Infrastructure as a Service (IaaS) 114. IaaS can refer to a user renting the use of infrastructure resources that are needed during a specified time period. IaaS providers can offer storage, networking, servers or virtualization resources from large pools, allowing the users to quickly scale up by accessing more resources as needed. Examples of IaaS can include infrastructure and services (e.g., EG-32) provided by OVH HOSTING of Montreal, Quebec, Canada, AMAZON WEB SERVICES provided by Amazon.com, Inc., of Seattle, Washington, RACKSPACE CLOUD provided by Rackspace US, Inc., of San Antonio, Texas, Google Compute Engine provided by Google Inc. of Mountain View, California, or RIGHTSCALE provided by RightScale, Inc., of Santa Barbara, California. PaaS providers can offer functionality provided by IaaS, including, e.g., storage, networking, servers or virtualization, as well as additional resources such as, e.g., the operating system, middleware, or runtime resources. Examples of PaaS include WINDOWS AZURE provided by Microsoft Corporation of Redmond, Washington, Google App Engine provided by Google Inc., and HEROKU provided by Heroku, Inc. of San Francisco, California. SaaS providers can offer the resources that PaaS provides, including storage, networking, servers, virtualization, operating system, middleware, or runtime resources. In some embodiments, SaaS providers can offer additional resources including, e.g., data and application resources. Examples of SaaS include GOOGLE APPS provided by Google Inc., SALESFORCE provided by Salesforce.com Inc. of San Francisco, California, or OFFICE 365 provided by Microsoft Corporation. Examples of SaaS can also include data storage providers, e.g. DROPBOX provided by Dropbox, Inc. of San Francisco, California, Microsoft SKYDRIVE provided by Microsoft Corporation, Google Drive provided by Google Inc., or Apple ICLOUD provided by Apple Inc. of Cupertino, California.

Clients 102 can access IaaS resources with one or more IaaS standards, including, e.g., Amazon Elastic Compute Cloud (EC2), Open Cloud Computing Interface (OCCI), Cloud Infrastructure Management Interface (CIMI), or OpenStack standards. Some IaaS standards can allow clients access to resources over HTTP, and can use Representational State Transfer (REST) protocol or Simple Object Access Protocol (SOAP). Clients 102 can access PaaS resources with different PaaS interfaces. Some PaaS interfaces use HTTP packages, standard Java APIs, JavaMail API, Java Data Objects (JDO), Java Persistence API (JPA), Python APIs, web integration APIs for different programming languages including, e.g., Rack for Ruby, WSGI for Python, or PSGI for Perl, or other APIs that can be built on REST, HTTP, XML, or other protocols. Clients 102 can access SaaS resources through the use of web-based user interfaces, provided by a web browser (e.g. GOOGLE CHROME, Microsoft INTERNET EXPLORER, or Mozilla Firefox provided by Mozilla Foundation of Mountain View, California). Clients 102 can also access SaaS resources through smartphone or tablet applications, including, e.g., Salesforce Sales Cloud, or Google Drive app. Clients 102 can also access SaaS resources through the client operating system, including, e.g., Windows file system for DROPBOX.

In some embodiments, access to IaaS, PaaS, or SaaS resources can be authenticated. For example, a server or authentication server can authenticate a user via security certificates, HTTPS, or API keys. API keys can include various encryption standards such as, e.g., Advanced Encryption Standard (AES). Data resources can be sent over Transport Layer Security (TLS) or Secure Sockets Layer (SSL).

Figure 1C:
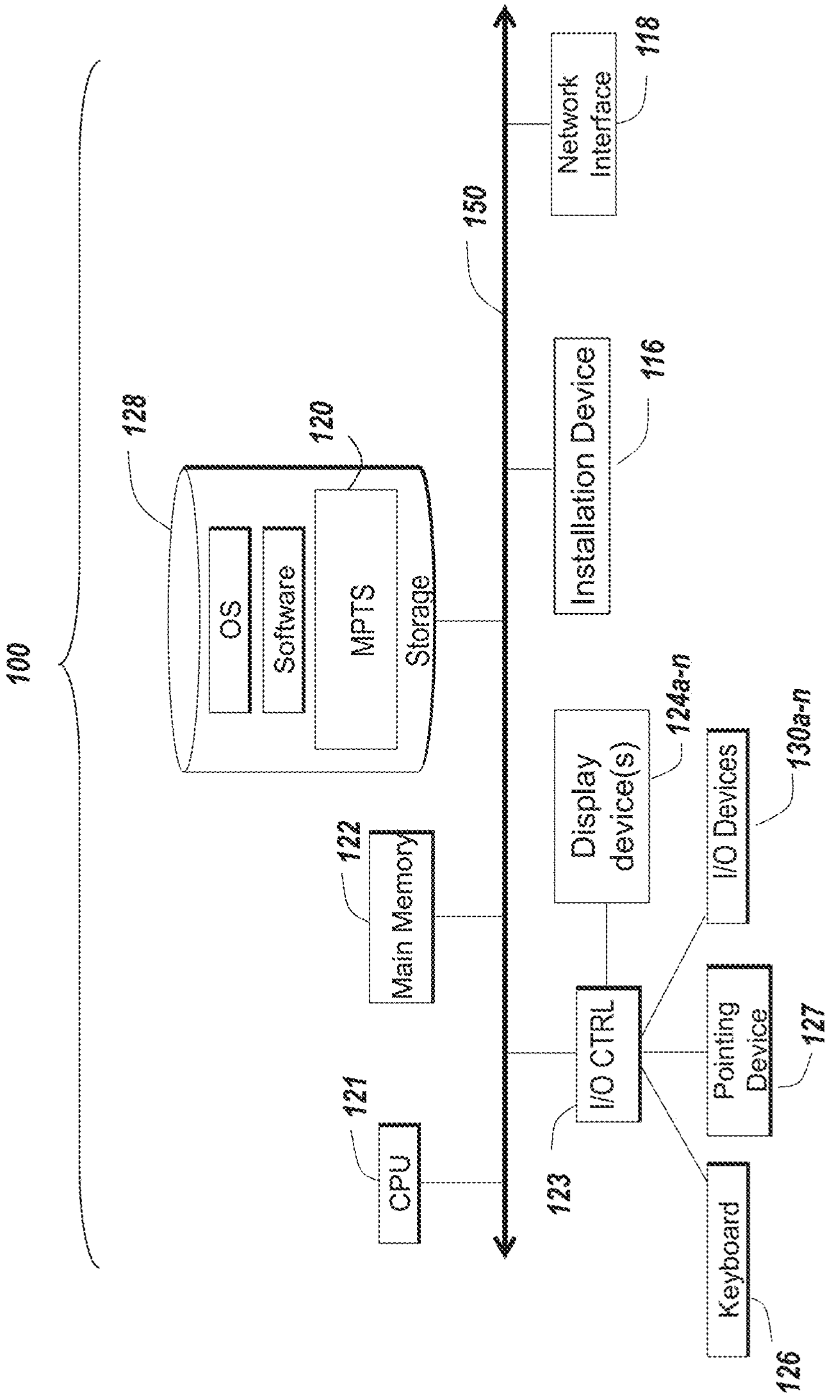
FIGS. 1C and 1D are block diagrams depicting embodiments of computing devices useful in connection with the methods and systems described herein.
Figure 1D:
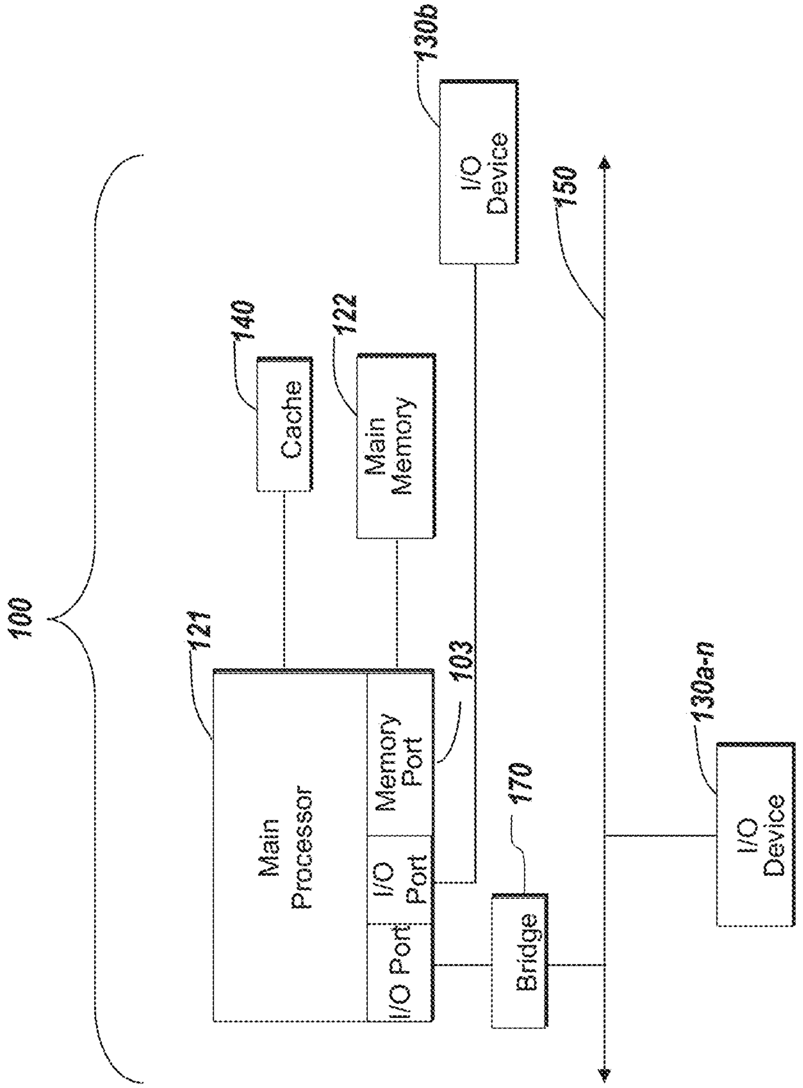

The client 102 and server 106 can be deployed as and/or executed on any type and form of computing device, e.g. a computer, network device or appliance capable of communicating on any type and form of network and performing the operations described herein. FIGS. 1C and 1D depict block diagrams of a computing device 100 useful for practicing an embodiment of the client 102 or a server 106. As shown in FIGS. 1C and 1D, each computing device 100 includes a central processing unit 121, and a main memory unit 122. As shown in FIG. 1C, a computing device 100 can include a storage device 128, an installation device 116, a network interface 118, an I/O controller 123, display devices 124*a*-124*n*, a keyboard 126 and a pointing device 127, e.g. a mouse. The storage device 128 can include, without limitation, an operating system, software, and a software of a multi-purse transaction system (MPTS) 120. As shown in FIG. 1D, each computing device 100 can also include additional optional elements, e.g. a memory port 103, a bridge 170, one or more input/output devices 130*a*-130*n* (generally referred to using reference numeral 130), and a cache memory 140 in communication with the central processing unit 121.

The central processing unit 121 is any logic circuitry that responds to and processes instructions fetched from the main memory unit 122. In many embodiments, the central processing unit 121 is provided by a microprocessor unit, e.g.: those manufactured by Intel Corporation of Mountain View, California; those manufactured by Motorola Corporation of Schaumburg, Illinois; the ARM processor and TEGRA system on a chip (SoC) manufactured by Nvidia of Santa Clara, California; the POWER7 processor, those manufactured by International Business Machines of White Plains, New York; or those manufactured by Advanced Micro Devices of Sunnyvale, California. The computing device 100 can be based on any of these processors, or any other processor capable of operating as described herein. The central processing unit 121 can utilize instruction level parallelism, thread level parallelism, different levels of cache, and multi-core processors. A multi-core processor can include two or more processing units on a single computing component. Examples of multi-core processors include the AMD PHENOM IIX2, INTEL CORE i5 and INTEL CORE i7.

Main memory unit 122 can include one or more memory chips capable of storing data and allowing any storage location to be directly accessed by the microprocessor 121.

Main memory unit 122 can be volatile and faster than storage 128 memory. Main memory units 122 can be Dynamic random access memory (DRAM) or any variants, including static random access memory (SRAM), Burst SRAM or SynchBurst SRAM (BSRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Single Data Rate Synchronous DRAM (SDR SDRAM), Double Data Rate SDRAM (DDR SDRAM), Direct Rambus DRAM (DRDRAM), or Extreme Data Rate DRAM (XDR DRAM). In some embodiments, the main memory 122 or the storage 128 can be non-volatile; e.g., non-volatile read access memory (NVRAM), flash memory non-volatile static RAM (nvSRAM), Ferroelectric RAM (FeRAM), Magnetoresistive RAM (MRAM), Phase-change memory (PRAM), conductive-bridging RAM (CBRAM), Silicon-Oxide-Nitride-Oxide-Silicon (SONOS), Resistive RAM (RRAM), Racetrack, Nano-RAM (NRAM), or Millipede memory. The main memory 122 can be based on any of the above described memory chips, or any other available memory chips capable of operating as described herein. In the embodiment shown in FIG. 1C, the processor 121 communicates with main memory 122 via a system bus 150 (described in more detail below). FIG. 1D depicts an embodiment of a computing device 100 in which the processor communicates directly with main memory 122 via a memory port 103. For example, in FIG. 1D the main memory 122 can be DRDRAM.

FIG. 1D depicts an embodiment in which the main processor 121 communicates directly with cache memory 140 via a secondary bus, sometimes referred to as a backside bus. In other embodiments, the main processor 121 communicates with cache memory 140 using the system bus 150. Cache memory 140 typically has a faster response time than main memory 122 and is typically provided by SRAM, BSRAM, or EDRAM. In the embodiment shown in FIG. 1D, the processor 121 communicates with various I/O devices 130 via a local system bus 150. Various buses can be used to connect the central processing unit 121 to any of the I/O devices 130, including a PCI bus, a PCI-X bus, or a PCI-Express bus, or a NuBus. For embodiments in which the I/O device is a video display 124, the processor 121 can use an Advanced Graphics Port (AGP) to communicate with the display 124 or the I/O controller 123 for the display 124. FIG. 1D depicts an embodiment of a computer 100 in which the main processor 121 communicates directly with I/O device 130*b* or other processors 121' via HYPERTRANSPORT, RAPIDIO, or INFINIBAND communications technology. FIG. 1D also depicts an embodiment in which local busses and direct communication are mixed: the processor 121 communicates with I/O device 130*a* using a local interconnect bus while communicating with I/O device 130*b* directly.

A wide variety of I/O devices 130*a*-130*n* can be present in the computing device 100. Input devices can include keyboards, mice, trackpads, trackballs, touchpads, touch mice, multi-touch touchpads and touch mice, microphones, multi-array microphones, drawing tablets, cameras, single-lens reflex camera (SLR), digital SLR (DSLR), CMOS sensors, accelerometers, infrared optical sensors, pressure sensors, magnetometer sensors, angular rate sensors, depth sensors, proximity sensors, ambient light sensors, gyroscopic sensors, or other sensors. Output devices can include video displays, graphical displays, speakers, headphones, inkjet printers, laser printers, and 3D printers.

Devices 130*a*-130*n* can include a combination of multiple input or output devices, including, e.g., Microsoft KINECT, Nintendo Wiimote for the WII, Nintendo WII U GAMEPAD, or Apple IPHONE. Some devices 130*a*-130*n* allow gesture recognition inputs through combining some of the inputs and outputs. Some devices 130*a*-130*n* provides for facial recognition which can be utilized as an input for different purposes including authentication and other commands. Some devices 130*a*-130*n* provides for voice recognition and inputs, including, e.g., Microsoft KINECT, SIRI for IPHONE by Apple, Google Now or Google Voice Search.

Additional devices 130*a*-130*n* have both input and output capabilities, including, e.g., haptic feedback devices, touchscreen displays, or multi-touch displays. Touchscreen, multi-touch displays, touchpads, touch mice, or other touch sensing devices can use different technologies to sense touch, including, e.g., capacitive, surface capacitive, projected capacitive touch (PCT), in-cell capacitive, resistive, infrared, waveguide, dispersive signal touch (DST), in-cell optical, surface acoustic wave (SAW), bending wave touch (BWT), or force-based sensing technologies. Some multi-touch devices can allow two or more contact points with the surface, allowing advanced functionality including, e.g., pinch, spread, rotate, scroll, or other gestures. Some touchscreen devices, including, e.g., Microsoft PIXELSENSE or Multi-Touch Collaboration Wall, can have larger surfaces, such as on a table-top or on a wall, and can also interact with other electronic devices. Some I/O devices 130*a*-130*n*, display devices 124*a*-124*n* or group of devices can be augment reality devices. The I/O devices can be controlled by an I/O controller 123 as shown in FIG. 1C. The I/O controller can control one or more I/O devices, such as, e.g., a keyboard 126 and a pointing device 127, e.g., a mouse or optical pen. Furthermore, an I/O device can also provide storage and/or an installation medium 116 for the computing device 100. In still other embodiments, the computing device 100 can provide USB connections (not shown) to receive handheld USB storage devices. In further embodiments, an I/O device 130 can be a bridge between the system bus 150 and an external communication bus, e.g. a USB bus, a SCSI bus, a Fire Wire bus, an Ethernet bus, a Gigabit Ethernet bus, a Fibre Channel bus, or a Thunderbolt bus.

In some embodiments, display devices 124*a*-124*n* can be connected to I/O controller 123. Display devices can include, e.g., liquid crystal displays (LCD), thin film transistor LCD (TFT-LCD), blue phase LCD, electronic papers (e-ink) displays, flexile displays, light emitting diode displays (LED), digital light processing (DLP) displays, liquid crystal on silicon (LCOS) displays, organic light-emitting diode (OLED) displays, active-matrix organic light-emitting diode (AMOLED) displays, liquid crystal laser displays, time-multiplexed optical shutter (TMOS) displays, or 3D displays. Examples of 3D displays can use, e.g. stereoscopy, polarization filters, active shutters, or autostereoscopy. Display devices 124*a*-124*n* can also be a head-mounted display (HMD). In some embodiments, display devices 124*a*-124*n* or the corresponding I/O controllers 123 can be controlled through or have hardware support for OPENGL or DIRECTX API or other graphics libraries.

In some embodiments, the computing device 100 can include or connect to multiple display devices 124*a*-124*n*, which each can be of the same or different type and/or form. As such, any of the I/O devices 130*a*-130*n* and/or the I/O controller 123 can include any type and/or form of suitable hardware, software, or combination of hardware and software to support, enable or provide for the connection and use of multiple display devices 124*a*-124*n* by the computing device 100. For example, the computing device 100 can include any type and/or form of video adapter, video card, driver, and/or library to interface, communicate, connect or otherwise use the display devices 124*a*-124*n*. In one embodiment, a video adapter can include multiple connectors to interface to multiple display devices 124*a*-124*n*. In other embodiments, the computing device 100 can include multiple video adapters, with each video adapter connected to one or more of the display devices 124*a*-124*n*. In some embodiments, any portion of the operating system of the computing device 100 can be configured for using multiple displays 124*a*-124*n*. In other embodiments, one or more of the display devices 124*a*-124*n* can be provided by one or more other computing devices 100*a* or 100*b* connected to the computing device 100, via the network 104. In some embodiments software can be designed and constructed to use another computer's display device as a second display device 124*a* for the computing device 100. For example, in one embodiment, an Apple iPad can connect to a computing device 100 and use the display of the device 100 as an additional display screen that can be used as an extended desktop. One ordinarily skilled in the art will recognize and appreciate the various ways and embodiments that a computing device 100 can be configured to have multiple display devices 124*a*-124*n*.

Referring again to FIG. 1C, the computing device 100 can comprise a storage device 128 (e.g. one or more hard disk drives or redundant arrays of independent disks) for storing an operating system or other related software, and for storing application software programs such as any program related to the software 120 for the multi-purse transaction system. Examples of storage device 128 include, e.g., hard disk drive (HDD); optical drive including CD drive, DVD drive, or BLU-RAY drive; solid-state drive (SSD); USB flash drive; or any other device suitable for storing data. Some storage devices can include multiple volatile and non-volatile memories, including, e.g., solid state hybrid drives that combine hard disks with solid state cache. Some storage device 128 can be non-volatile, mutable, or read-only. Some storage device 128 can be internal and connect to the computing device 100 via a bus 150. Some storage device 128 can be external and connect to the computing device 100 via a I/O device 130 that provides an external bus. Some storage device 128 can connect to the computing device 100 via the network interface 118 over a network 104, including, e.g., the Remote Disk for MACBOOK AIR by Apple. Some client devices 100 may not require a non-volatile storage device 128 and can be thin clients or zero clients 102. Some storage device 128 can also be used as an installation device 116, and can be suitable for installing software and programs. Additionally, the operating system and the software can be run from a bootable medium, for example, a bootable CD, e.g. KNOPPIX, a bootable CD for GNU/Linux that is available as a GNU/Linux distribution from knoppix.net.

Client device 100 can also install software or application from an application distribution platform. Examples of application distribution platforms include the App Store for iOS provided by Apple, Inc., the Mac App Store provided by Apple, Inc., GOOGLE PLAY for Android OS provided by Google Inc., Chrome Webstore for CHROME OS provided by Google Inc., and Amazon Appstore for Android OS and KINDLE FIRE provided by Amazon.com, Inc. An application distribution platform can facilitate installation of software on a client device 102. An application distribution platform can include a repository of applications on a server 106 or a cloud 108, which the clients 102*a*-102*n* can access over a network 104. An application distribution platform can include application developed and provided by various developers. A user of a client device 102 can select, purchase and/or download an application via the application distribution platform.

Furthermore, the computing device 100 can include a network interface 118 to interface to the network 104 through a variety of connections including, but not limited to, standard telephone lines LAN or WAN links (e.g., 802.11, T1, T3, Gigabit Ethernet, Infiniband), broadband connections (e.g., ISDN, Frame Relay, ATM, Gigabit Ethernet, Ethernet-over-SONET, ADSL, VDSL, BPON, GPON, fiber optical including FiOS), wireless connections, or some combination of any or all of the above. Connections can be established using a variety of communication protocols (e.g., TCP/IP, Ethernet, ARCNET, SONET, SDH, Fiber Distributed Data Interface (FDDI), IEEE 802.11a/b/g/n/ac CDMA, GSM, WiMax and direct asynchronous connections). In one embodiment, the computing device 100 communicates with other computing devices 100' via any type and/or form of gateway or tunneling protocol e.g. Secure Socket Layer (SSL) or Transport Layer Security (TLS), or the Citrix Gateway Protocol manufactured by Citrix Systems, Inc. of Ft. Lauderdale, Florida. The network interface 118 can comprise a built-in network adapter, network interface card, PCMCIA network card, EXPRESSCARD network card, card bus network adapter, wireless network adapter, USB network adapter, modem or any other device suitable for interfacing the computing device 100 to any type of network capable of communication and performing the operations described herein.

A computing device 100 of the sort depicted in FIGS. 1B and 1C can operate under the control of an operating system, which controls scheduling of tasks and access to system resources. The computing device 100 can be running any operating system such as any of the versions of the MICROSOFT WINDOWS operating systems, the different releases of the Unix and Linux operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 2000, WINDOWS Server 2012, WINDOWS CE, WINDOWS Phone, WINDOWS XP, WINDOWS VISTA, and WINDOWS 7, WINDOWS RT, and WINDOWS 8 all of which are manufactured by Microsoft Corporation of Redmond, Washington; MAC OS and iOS, manufactured by Apple, Inc. of Cupertino, California; and Linux, a freely-available operating system, e.g. Linux Mint distribution ("distro") or Ubuntu, distributed by Canonical Ltd. of London, United Kingdom; or Unix or other Unix-like derivative operating systems; and Android, designed by Google, of Mountain View, California, among others. Some operating systems, including, e.g., the CHROME OS by Google, can be used on zero clients or thin clients, including, e.g., CHROMEBOOKS.

The computer system 100 can be any workstation, telephone, desktop computer, laptop or notebook computer, netbook, ULTRABOOK, tablet, server, handheld computer, mobile telephone, smartphone or other portable telecommunications device, media playing device, a gaming system, mobile computing device, or any other type and/or form of computing, telecommunications or media device that is capable of communication. The computer system 100 has sufficient processor power and memory capacity to perform the operations described herein. In some embodiments, the computing device 100 can have different processors, operating systems, and input devices consistent with the device. The Samsung GALAXY smartphones, e.g., operate under the control of Android operating system developed by Google, Inc. GALAXY smartphones receive input via a touch interface.

In some embodiments, the computing device 100 is a gaming system. For example, the computer system 100 can comprise a PLAYSTATION 3, or PERSONAL PLAYSTATION PORTABLE (PSP), or a PLAYSTATION VITA device manufactured by the Sony Corporation of Tokyo, Japan, a NINTENDO DS, NINTENDO 3DS, NINTENDO WII, or a NINTENDO WII U device manufactured by Nintendo Co., Ltd., of Kyoto, Japan, an XBOX 360 device manufactured by the Microsoft Corporation of Redmond, Washington.

In some embodiments, the computing device 100 is a digital audio player such as the Apple IPOD, IPOD Touch, and IPOD NANO lines of devices, manufactured by Apple Computer of Cupertino, California. Some digital audio players can have other functionality, including, e.g., a gaming system or any functionality made available by an application from a digital application distribution platform. For example, the IPOD Touch can access the Apple App Store. In some embodiments, the computing device 100 is a portable media player or digital audio player supporting file formats including, but not limited to, MP3, WAV, M4A/AAC, WMA Protected AAC, AIFF, Audible audiobook, Apple Lossless audio file formats and .mov, .m4v, and .mp4 MPEG-4 (H.264/MPEG-4 AVC) video file formats.

In some embodiments, the computing device 100 is a tablet e.g. the IPAD line of devices by Apple; GALAXY TAB family of devices by Samsung; or KINDLE FIRE, by Amazon.com, Inc. of Seattle, Washington. In other embodiments, the computing device 100 is an eBook reader, e.g. the KINDLE family of devices by Amazon.com, or NOOK family of devices by Barnes & Noble, Inc. of New York City, New York.

In some embodiments, the communications device 102 includes a combination of devices, e.g. a smartphone combined with a digital audio player or portable media player. For example, one of these embodiments is a smartphone, e.g. the IPHONE family of smartphones manufactured by Apple, Inc.; a Samsung GALAXY family of smartphones manufactured by Samsung, Inc.; or a Motorola DROID family of smartphones. In yet another embodiment, the communications device 102 is a laptop or desktop computer equipped with a web browser and a microphone and speaker system, e.g. a telephony headset. In these embodiments, the communications devices 102 are web-enabled and can receive and initiate phone calls. In some embodiments, a laptop or desktop computer is also equipped with a webcam or other video capture device that enables video chat and video call.

In some embodiments, the status of one or more machines 102, 106 in the network 104 are monitored, generally as part of network management. In one of these embodiments, the status of a machine can include an identification of load information (e.g., the number of processes on the machine, CPU and memory utilization), of port information (e.g., the number of available communication ports and the port addresses), or of session status (e.g., the duration and type of processes, and whether a process is active or idle). In another of these embodiments, this information can be identified by a plurality of metrics, and the plurality of metrics can be applied at least in part towards decisions in load distribution, network traffic management, and network failure recovery as well as any aspects of operations of the present solution described herein. Aspects of the operating environments and components described above will become apparent in the context of the systems and methods disclosed herein.

B. Multi-Purse Transaction System

Systems and methods of the present solution are directed to conducting electronic transactions via a computer network. Systems and methods of the present solution can use a multi-purse transaction system that maintains an electronic account having multiple purses. An electronic account can be maintained by a server and be included in a database in memory or a storage device. The electronic account can include sub structures or fields. The electronic account can include multiple purses that are configured with one or more rules, parameters, restrictions, or policies. For example, the electronic account can include a first purse that is configured as a benefits purse. A purse configured for benefits can refer to a purse that is configured for transactions made using a tax benefit account such as a flexible spending account ("FSA"), Dependent Care Account ("DCA"), Transport Account (e.g., for parking or monthly passes). In some embodiments, the FSA, DCA, and Transport Account can be further separated into sub-purses within the benefits purse of the electronic account. A flexible spending account, or flexible spending arrangement, can refer to a tax-advantaged financial account that can be set up through a cafeteria plan of an employer and used to set aside a portion of earnings to pay for qualified expenses as established in the cafeteria plan. Types of FSA can include medical expense FSA, health FSA, health savings account (HSA), health reimbursement account (HRA), health reimbursement plan (HRP), etc. Qualified expenses can include, for example, medical expenses, dependent care, dental expenses, vision expenses, parking, monthly passes, etc. An FSA can be tax-advantaged because funds deducted from an employee's account and transferred to the FSA is not subject to payroll taxes, resulting in payroll tax savings.

A user can make the transaction at an entity such as a merchant, pharmacy, retail store, medical supply store, or other entity that provides goods or services that are deemed to be qualified expenses in accordance with the tax benefit account or FSA. The transaction can occur via a point-of-sale terminal or device (e.g., checkout device, electronic point of sale device or other device that includes hardware and software to facilitate a transaction) configured to receive financial transaction information from the user (e.g., via a debit card, pin number, mobile payment device, near field communication-enabled device, mobile telecommunications device) and communicate with one or more servers or databases to authenticate the financial transaction information, identify a corresponding FSA of the user, and initiate or facilitate the transfer of funds from the FSA to the entity. The transaction can include or be associated with information such as an FSA account identifier, time stamp, entity identifier, and transaction amount. This information can be provided in real-time to a transaction repository.

When participants submit claims for reimbursement from their FSA, HRA or other benefit account, the present solution provides a real time credit to their multi-purse debit card when the claim is approved for reimbursement. The present solution provides a notification via electronic mail or electronic messaging explaining that the reimbursed amount is now available for unrestricted spending at any merchant. The present solution uses one or more policy or logic engines to authorize transactions based on a merchant category code ("MCC") to determine from which of the accounts on the electronic multi-purse card, commonly called purses, are eligible to pay for the transaction.

For example, if the participant has $100 in their FSA which is setup for Medical, Rx, Vision and Dental purchases, and the participant swipes their card at a vision provider for $75, the system makes a determination based on a policy to select an FSA from which to detect funds. If the card is swiped at a restaurant and the participant has a Reimbursement Purse on the card, the system can deduct funds from a reimbursement purse. If the participant has a transaction that exceeds the FSA for a qualified expense, the system can use the FSA funds plus an amount from the reimbursement purse. Participants can text a code such as "BAL" to the present solution to receive a current balance in one or more accounts/purses, including the reimbursement purse, or call to obtain balances for all accounts through an interactive voice response, as well as view the balance through a mobile application or online portal.

Figure 2:
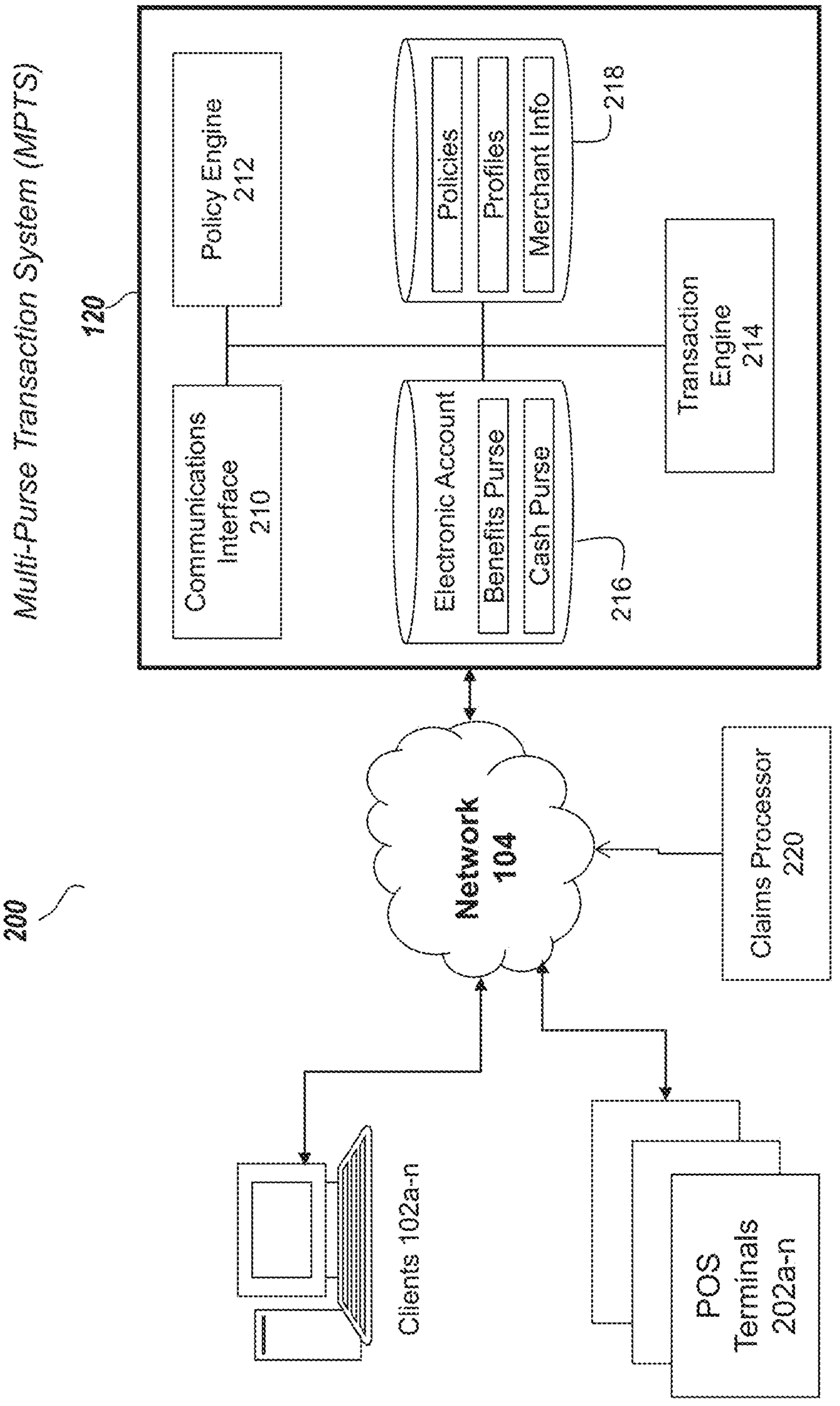
FIG. 2 is a block diagram depicting an embodiment of a system for conducting electronic transactions via a computer network.

Referring now to FIG. 2, a block diagram depicting an embodiment of a system 200 comprising a multi-purse transaction system (MPTS) is shown. In brief overview, the system 200 includes a multi-purse transaction system 120 ("MPTS") that can receive and/or transmit data via a network 104 with clients 102*a-n* and POS terminals 202*a-n*. The system 200 can include or interact with one or more clients 102*a-n* (or client device 102), and one or more point-of-sale (POS) terminals 202*a-n* (or POS terminal 202). The MPTS 120 can include a communications interface 210 that is configured with one or more communications ports, application programming interfaces, network protocols (e.g., TCP/IP), authentication protocols, or security protocols (e.g., SSL). The MPTS 120 can include a policy engine 212 that selects a purse of an electronic account including multiple purses to use to conduct a transaction. The MPTS 120 can include a transaction engine 214 that obtains funds from one or more accounts or purses and transfers the funds to one or more accounts or purses or merchants. The MPTS 120 can include one or more databases or data structure that store information to facilitate the systems and methods of the present solution, such as database 216 and database 218. The database 216 (or electronic account) can include an electronic account maintained or configured on the MPTS 120 that includes one or more purses, such as a benefits purse and a cash purse. The database 218 can include one or more policies in a policy repository, user profiles, or merchant information.

The system 120, communications interface 120, policy engine 212, and transaction engine 214 can each include one or more processing units or other logic devices such as programmable logic array engines, modules, or circuitry designed and constructed to facilitate managing security on a network infrastructure. The MPTS 120 can include the components 100 shown in FIG. 1C or FIG. 1D, or be configured to operate as a service in cloud 108. The MPTS can include or interact with one or more servers 106*a-n* and clients 102*a-n*.

In some embodiments, the MPTS 120 can employ a multitier architecture such as a client-server architecture in which presentation, application processing, and data management functions are logically or physically separated. The presentation tier, or front-end, can include the communications interface 210 that serves static content or dynamic content to be rendered by the client 102 (e.g., by a web browser executing on client 102). The presentation tier or web server 210 can interact or communicate with the application tier to obtain data to provide to the client 102 or POS terminals 202*a-n*. The application tier can include the policy engine 212 and transaction engine 214 that controls the system's functionality and performs additional processing or analysis on data. The application tier can interact with the data tier to obtain the transaction data. The data tier can include data persistence mechanisms (database servers, file shares, etc.) and the data access layer that encapsulates the persistence mechanisms and exposes the data. The data tier can include databases 216 and 218. The data tier can include an application programming interface (API) to the application tier. The databases 216 or 218 can include stored procedures (e.g., SQL statements) that perform tasks with respect the stored data.

In further detail, and in some embodiments, the MPTS 120 includes a communications interface 210. The communications interface 210 can execute on one or more processors of a server. The communications interface 210 can include one or more communications ports and be configured with one or more network protocols. Communications ports can include, e.g., network ports, Ethernet ports, WAN ports, I/O ports, or software ports. The communication port can be configured with a network protocol such as Transport Layer Protocols such as TCP/IP or UDP that are configured to receive and process data packets received via a computer network. The port can include or be associated with an IP address of a host and a protocol type of the communication.

In some embodiments, the communications interface 210 can receive data packets. The data packets can be generated by a first device at a first merchant to conduct a first electronic transaction at the first merchant. The first device can refer to a POS terminal such as POS terminal 202*a*. A point of sale terminal 202 ("POS") is the place where a retail transaction is completed. The POS terminal 202 is the point at which a customer of the entity or merchant makes a payment to the merchant in exchange for goods or services. At the point of sale the merchant can calculate the amount owed by the customer and provide options for the customer to make payment. The merchant can also issue a receipt for the transaction.

The POS terminal 202 can include hardware and software. Merchants can utilize weighing scales, scanners, electronic and manual cash registers, EFTPOS terminals, touch screens and any other wide variety of hardware and software available for use with POS terminal 202. For example, a pharmacy can use software to customize the item or service sold when a customer has a special medication request.

The POS terminal 202 can include advanced features to cater to different functionality, such as inventory management, CRM, financials, warehousing, flexible spending account transactions, etc., all built into the POS software. The point of sale terminal 202 can be configured to conduct a transactions using a debit card, multipurse card, Bluetooth, near field communications, smartphone, smartwatch, mobile telecommunications computing device, wearable communications, RFID, etc.

The communications interface 210 can receive data packets generated by the POS Terminal 202*a* responsive to conducting an electronic transaction. The data packets can include header information and payload information. Multiple data packets can be strung together in a sequence. The header information can refer to TCP/IP headers that include fields such as source port, destination port, sequence number, acknowledgment number, window size, etc. The payload information of the data packet can include information related to the transaction, merchant, or customer. The system 120 can receive the data packet with header information and payload information and process the packets to obtain information for further processing. The payload can include data identifying a first merchant category of the first merchant, an electronic account, and a monetary amount of the electronic transaction.

The data packets can carry data identifying a merchant or merchant category of the merchant. In some embodiments, the data carried by the data packets include a merchant category code or identifier (e.g., dental, medical, etc.). In some embodiments, the data identified a merchant, and the system 120 determined a merchant category based on the identification of the merchant by, for example, using a merchant to merchant category mapping or lookup table stored in database 218.

The data packets (e.g., payload of the data packets) can further identify an electronic account maintained and configured on the server. The electronic account can be maintained and configured in a database 216. The electronic account can correspond to a user and have a unique identifier. The unique identifier can include numbers, letters, characters, symbols, etc. The electronic account can be associated with the customer making the transaction at the merchant. The POS terminal 202*a* can receive or determine the electronic account identifier via a card swipe or other communication technique employed at the POS terminal 202*a*, which the POS 202*a* can then convey to the system 120.

The communications interface 210 can further receive data packets (e.g., payload information) identifying a first monetary amount of the first electronic transaction. The monetary amount can be for the purchase of goods or services made at the merchant. The monetary amount of the transaction can refer to the amount of funds in consideration for goods or services obtained from the entity or merchant. The merchant or entity can refer to the entity at which a point-of-sale terminal or device used to make the transaction is located or with which the terminal is associated. The monetary amount can be in any currency (e.g., United States dollars) or units. The monetary amount can be further tied to a category, such as medical services.

In some embodiments, the POS terminal 202 can generate multiple data packets for a single transaction. The multiple data packets can each include a header and a payload. The header can indicate that the multiple data packets are to be grouped together for routing, transmission or processing purposes.

In some embodiments, the system 120 includes a policy engine 212. The policy engine 212 can execute on one or more processors of a server. The policy engine 212 can receive, retrieve, or otherwise obtain or access some or all of the data carried by the data packets. The policy engine 212 can receive, retrieve, or otherwise obtain or access policies, such as policies stored in database 218. The policy engine 212 can apply the policy to the data to select a purse of the electronic account.

The policy engine 212 can use or apply a policy that includes one or more techniques, algorithms, heuristics, or procedures. The policy can include decision points and utilize parameters or criteria. The policy can be based on criteria or rules that are established by an administrator of the MPTS 120 or another entity. The policy can facilitate determining which purse of the multipurse electronic account to use to transfer funds.

In some embodiments, the policy can be based on a merchant category. The policy can be based on a merchant category code ("MCC"). The MCC can refer to a code (e.g., a four-digit number) that can be assigned to a business by an entity, such as a credit card company or the MPTS. This code can be used to classify the merchant by a business type, or type of goods or services provided.

For example, the policy can be: if merchant category corresponds to (or equals or maps to or is) medical, then use benefits purse. In another example, the policy can be: if merchant category corresponds to dental, then use benefits purse. In another example, the policy can be: if merchant category maps to qualified benefits category, then use benefits purse. In some embodiments, the electronic account can include a benefits purse that is preconfigured with merchant categories that map to qualified or approved categories, such as categories for funds exempt from payroll tax can be used to conduct a transaction.

In some embodiments, the policy can include multiple criteria. For example, the policy can include: if merchant category corresponds to (or equals or maps to or is) medical or dental or vision or parking, then use benefits purse. In some embodiments, the policy can be a negative policy. For example, the policy can include: if merchant category does not equal medical or dental or vision, then use cash purse. In some embodiments, the policy can include an action to take when the policy is not satisfied. For example, if merchant category corresponds to medical or dental or vision or parking, then use benefits purse; otherwise, use cash purse. In some embodiments, a single policy can include multiple policies. In some embodiments, the system 120 can use process multiple policies before identifying a policy that is satisfied.

In some embodiments, the policy engine 212 can select a sub-purse using the policy. The sub-purse can refer to a purse within a benefits purse. For example, the benefits purse can include multiple purses, such as an FSA purse, HRA purse, HAS purse, DCA purse, or Transport Purse. Thus, the policy engine 212 can use a policy that can select the benefits purse and a benefits sub-purse based on a merchant identifier or merchant category. For example, the policy can be: if merchant category corresponds to parking, then select Purse{Benefits].SubPurse{Transport}.

In some embodiments, the policy engine 212 can use a policy that includes monetary amount thresholds. For example, a merchant category can correspond to an approved benefits purse. However, the approved benefits purse can include a threshold that limits a monetary amount of a transaction. For example, the benefits purse can be configured with a parking sub-purse with a monetary amount threshold. The monetary amount threshold can be for a time period, such as a month, quarter, year, week, or other time interval. For example, the transport or parking sub-purse can be approved for $200 per month for transactions made at merchants that correspond to merchant category transport or parking. Thus, the policy can include criteria such as merchant category, transaction amount, and time interval. For example: if merchant category corresponds to transport and if transaction amount less than or equal to approved transaction amount for time interval, then use transport sub-purse.

In some embodiments, the policy engine 212 can obtain funds for a single transaction at a merchant from multiple purses of the electronic account. For example, a benefits purse can be configured with a monetary amount limit or threshold for a merchant category. The policy engine can then determine, using the policy, to select the cash purse for the remaining monetary amount. For example, for a transaction of a first transaction amount made at a medical provider, the policy can include: if merchant category corresponds to medical, then select benefits purse for funds up to medical amount threshold; if transaction amount is greater than medical amount threshold, then select cash purse for remaining amount, where remaining amount is transaction amount minus medical amount threshold.

In some cases, where the amount thresholds are based on a time interval, the system 120 can determine the amount using historical transaction information stored in a database 216 or 218. For example, the electronic account 216 can include transaction information with time stamps for one or more purses. Similarly, profiles stored in database 218 can include a user's profile which can include transaction information.

Thus, and in some embodiments, the first policy can refer to one or more policies that are used to determine or select one or more purses from which funds are to be obtained or withdrawn to complete a transaction conducted at a merchant.

In some embodiments, the policy engine 212 can apply a second policy directed to additional factors after using a first policy. The policy engine 212 can select the second policy responsive to or based on the first policy. The second policy can be associated with a monetary amount, transaction amount, or reimbursement amount. The policy engine 212 can use the second policy to determine a reimbursement amount. The policy engine 212 can use a reimbursement policy. The reimbursement policy can be applied to the data that identifies the transaction amount, merchant category, and electronic account. The reimbursement policy can be selected based on an insurance policy tied to or associated with the electronic account. The electronic account can include a unique identifier that maps to or corresponds to a type of insurance policy or reimbursement policy. The reimbursement or insurance policy (e.g., second policy) can be established by an administrator of the system 120, an employer of the user/customer conducting the transaction, or another entity. Using this reimbursement policy, the policy engine 212 can determine a reimbursement amount. For example, if the transaction amount for the medical service was $100, the policy engine 212 can determine that 80% of the transaction is covered by insurance. The system 120 can initially deduct $100 from the benefits purse of the electronic account in accordance with the first policy. Thereafter, applying the second policy, the system 120 can determine to credit or reimburse the electronic account $80.

Responsive to determining the reimbursement amount, the policy engine 212 can further select a second purse of the electronic account for the reimbursement. The second purse can be different from the first purse. For example, the second purse can be a cash purse without the same restrictions as the benefits purse. The cash purse or reimbursement purse can be configured for use for any type of transaction, including, e.g., food or entertainment.

In some embodiments, the second policy refers to a policy the policy engine 212 can use to select a purse for the reimbursement amount that is different from the first purse selected using the first policy. For example, the first purse selected using the first policy can be a benefits purse that can have restrictions. The restrictions on the benefits purse can refer to restrictions on what types of goods or services funds in the benefits can be used. However, the electronic account can include an additional purse that may not be configured with such restrictions. The additional purse can be referred to as a reimbursement purse or cash purse. The cash purse can be stored on the electronic account in database 216.

The second policy used by the policy engine 212 and obtained from database 218 to determine a reimbursement amount can include rules, parameters, criteria or thresholds. For example, the reimbursement policy can include: if merchant category corresponds to medical, then reimburse 80% of transaction amount. In another example, the policy can include: if merchant category corresponds to medical, then reimburse 80% of transaction amount, but do not reimburse more than reimbursement limit. The reimbursement limit can be on a per transaction basis, or a time interval basis. For example, the reimbursement limit can refer to the maximum reimbursement amount for a time interval, such as a month, quarter, year or other time interval. The reimbursement limit can be a global limit across all benefits purses, or can be specific for each benefits subpurse (e.g., a first limit for HRA, a second limit for DCA, a third limit for FSA, etc.).

In some embodiments, the policy engine 212 can receive an indication from a claims processor 220 external to the system 120 via network 104. In some embodiments, the system 120 or policy engine 212 is configured with the claims processor 220 or configured to interface with the claims processor 220 via communications interface 210. The claims processor 220 can process an insurance claim to determine a reimbursement amount. The claims processor 220 can be configured to use one or more policies or rules to process the insurance claim and determine a reimbursement amount. The policies can be based on a type of insurance coverage associated with a user of the electronic account. The claims processor 220 can automatically receive the insurance claim responsive to a user conducting a transaction using the multipurse card connected with the electronic account. The claims processor 220 can obtain, via database 216 or 218, policies, profiles and merchant information to adjudicate the claim. The claims processor 220 can adjudicate the claim, determine a reimbursement amount, and provide an indication to the system 120 regarding the reimbursement amount. The indication can identify the electronic account, user identifier, time, original transaction amount, reimbursement policy, or reimbursement amount.

The system 120, upon receiving the indication of the reimbursement amount from the claims processor 220, can select a second policy to determine to which purse of the multipurse electronic account to transfer the reimbursement amount. The policy engine 212 can retrieve the second policy from the database 218. The second policy include, for example, the following: if transaction corresponds to reimbursement, then select cash purse of the electronic account. The cash purse may not have the same restrictions as the benefits purse.

The system 120 can include a transaction engine 214. The transaction engine 214 can receive information or instructions from the policy engine 212 regarding a transaction, and conduct the transaction. The transaction engine 214 can obtain merchant information from database 218 and electronic account information from 216 to perform the transaction. The transaction can include electronically transferring funds from a first account to a second account. The first account can be an electronic account, and the second account can be an account of a merchant (such as a financial account). In some cases, the transaction engine 214 can facilitate a transfer of funds between an electronic account of a claims processor 220 and the electronic account 216. The transaction engine 214 can receive account identifiers, transaction amounts, credentials, authentication information, etc. The transaction engine 214 can conduct the transaction via communications interface 210, thereby using the network protocols, security protocols and other components or interfaces provided by the communications interface 210.

In some embodiments, upon completing the transaction via the transaction engine 214, the system 120 can provide, via the communications interface 210, a real-time notification of the reimbursement amount to account holder of the electronic account including the cash purse that received the reimbursement amount. The communications interface 210 can be configured to provide the notification via an electronic mail protocol, Simple Messaging Service protocol, notification or prompt on a mobile telecommunications devices (e.g., a smartphone, tablet, smartwatch, wearable telecommunications device, laptop computer, desktop computer, etc.). The notification can be in real-time, which can refer to providing the notification soon after completion of the transaction (e.g., within 1 minute, within 5 minutes, within 30 seconds). In some embodiments, the notifications can include status information regarding the reimbursement transaction (e.g., processing reimbursement, reimbursement approved, reimbursement denied, reimbursement submitted for transfer, transferring reimbursement, or reimbursement complete).

In some embodiments, the system 120 (e.g., via communication interface 210), receives a request for account information from a client device 102 associated with an electronic account maintained or configured on the system 120. The request for information can include information about a balance of the electronic account, available purses, balance of an individual purse, status of a reimbursement, policies associated with purses, or transaction history. The request can further include authentication information or credentials associated with the request. The authentication information can include network security credentials, such as security certificates or tokens. The authentication information can further include a username, password, two-tier authentication information (e.g., date of birth, cell phone number, verification code sent via text message to cell phone number in profile associated with electronic account). The request can be from a client device such as a smartphone. The request can be sent using a text messaging protocol such as SMS. The system 120 can authenticate a request sent via SMS based on the cell phone number of the device sending the SMS request, and matching the cell phone number with corresponding number stored in profile in database 218 for the electronic account.

Responsive to authenticating or otherwise approving the request, the system 120 can access a data record in database 216 for the electronic account to generate a report with the requested information, or generate a standard report, or generate another preconfigured report. The report can identify the account holder information, available purses, benefits purses, reimbursement purse, subpurses, and available amounts for each purse. The report can further identify a transaction history for the electronic account or each subpurse thereof. The report can further identify or indicate if one or more purses have reached a maximum limit. The report can further include a forecast based on current/previous transaction history that indicates whether the user can likely deplete available resources or exceed maximum limits based on current spending for a time interval.

Figure 3:
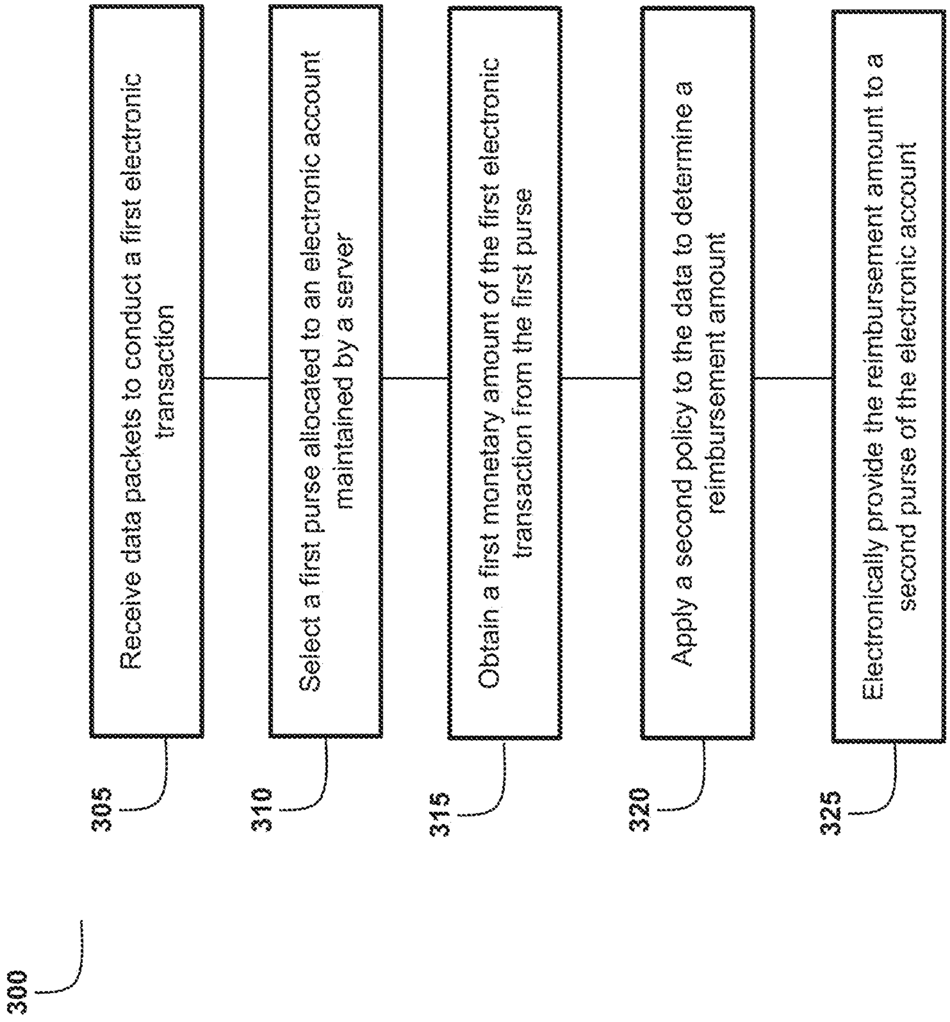
FIG. 3 is a flow diagram depicting an embodiment of a method of conducting electronic transactions.

Referring now to FIG. 3, a flow diagram depicting an embodiment of a method of conducting an electronic transaction is shown. The method can be performed by system 200, MPTS 120, or one or more component thereof. In brief overview, at step 305, a server of a multipurse transaction system receives data packets to conduct a first electronic transaction.

At step 310, the server selects a first purse allocated to an electronic account maintained by the server. At step 315, the server obtains a first monetary amount of the first electronic transaction from the first purse. At step 320, the server applies a second policy to the data to determine a reimbursement amount. At step 325, the server electronically provides the reimbursement amount to a second purse of the electronic account.

Still referring to FIG. 3, and in further detail, a server of a multipurse transaction system receives data packets to conduct a first electronic transaction at step 305. The data packets can be received via a computer network using a networking protocol. The data packets can be generated by a device at a merchant, such as a Point-of-Sale Terminal. The data packets can include header information and payload information. The header information can include, e.g., TCP header information that can facilitate the routing and transmission of the data packet. The payload information can include data related to, describing, defining, associated with or otherwise about the transaction occurring between the POS terminal, merchant, or customer.

The server can parse, process, or otherwise identify, from the header information or payload information from the one or more data packets, information about the transaction. The system can identify the first merchant (e.g., a name of a merchant, location of the merchant, unique identifier of the first merchant) or merchant category of the first merchant. In the event the data packets do not include a merchant category, the server can determine a merchant category based on a merchant identifier. In some embodiments, where the server fails to determine a merchant category, the server can default to using a cash purse that is approved for any time of transaction (e.g., where the merchant category in the data packets does not correspond to a policy in the policy repository). The data packets can also carry data (e.g., via payload information) identifying an electronic account maintained and configured on the server, and a monetary amount of the electronic transaction. The server can receive data packets for multiple transactions, where each transaction is associated with a merchant or merchant category and transaction amount. The data packets can further include (e.g., within the payload information) an electronic account associated with a multipurse card swiped at a POS of a merchant conducting the transaction. The multipurse card can be a plastic card (e.g., debit card or debit card with a magnetic strip or RFID), or be an electronic card stored on a telecommunications device which transmits an electronic account identifier corresponding to the electronic card via a wireless technology (e.g., Bluetooth, or NFC). The POS can generate or obtain information that allows the MPTS to conduct the transaction, encapsulate or process the information using a protocol to generate data packets, and transmit the data packets in a secure manner over a network to the MPTS for further processing.

At step 310, the server selects a first purse allocated to an electronic account maintained by the server. The electronic account can include several purses that are of different types or configured for different types of transactions, and the server can select the first purse using a policy. The server can retrieve the policy from a policy repository. The policy can include one or more rules, policies, parameters, criteria, comparisons, or thresholds. This first policy can refer to a policy used to select a purse for withdrawing funds to facilitate completing a transaction conducted a merchant. The policy can be used to select a purse having funds that can be allocated towards a purchase made at the merchant.

In some embodiments, the first policy can take into consideration factors such as merchant category and transaction amount. The first policy can select a purse based on the merchant category. The selected purse can be preconfigured or approved for purchases made at a merchant corresponding to a merchant category (e.g., prescription purchase made at a pharmacy can be approved to use funds from a benefits purse, such as a prescription purse). This purse can be configured as a purse with funds exempt from payroll tax deductions to be used to conduct approved transactions. For example, the server can determine that the first purse of the electronic purse is configured for prescription purchases, and select the first purse responsive to determining that the merchant is a prescription provider based on the first merchant category.

At step 315, the server obtains a first monetary amount of the first electronic transaction from the first purse of the electronic account. In some embodiments, the server can interface with a financial institution to conduct the transfer of funds. For example, the server can include an interface configured for conducting financial transactions over a network.

In some embodiments, the server can use the policy to determine the amount to obtain. For example, the amount to obtain from the first can be different from the transaction amount. The amount to obtain from the first can be less than the transaction amount. The amount to obtain from the first purse can be based on the policy. The policy can indicate that only a certain amount of the total transaction amount is approved to be deducted from the first purse. For example, the policy for a benefits purse such as a transport purse can limit the amount of funds that can be deducted during a time interval (e.g., $200 per month). Accordingly, the server can determine, by applying the first policy, to deduct a portion of the transaction amount from the first purse, and deduct a remaining portion from a different purse of the electronic account, such as a cash purse that may not include the same restriction. In some embodiments, the server can determine that there are not sufficient available funds in the first purse to complete the transaction (e.g., the transaction amount is greater than the available funds in the first purse that is configured as the benefits purse or an approved subpurse thereof). The server can then determine to deduct a remaining amount or the entire transaction amount from a cash purse or be configured with a credit card purse that can allow for a credit card transaction.

At step 320, the server applies a second policy to the data to determine a reimbursement amount. The second policy can refer to a policy that determines an amount of the transaction amount that is to be reimbursed to the electronic account. This second policy can be based on an insurance policy, claim policy, plan information, or benefits information. This second policy can include adjudication an insurance claim. In some embodiments, the MPTS can perform one or more component of the adjudication process or otherwise facilitate the adjudication process. In some embodiments, this claim processing can be done by the MPTS. In some embodiments, the claims processing can be performed in real-time (e.g., within 1 minute, 30 seconds, 5 minutes, 30 minutes of the claim being submitted). In some embodiments, the claims processing can be done by a third-party entity external to the MPTS. In some embodiments, the MPTS can receive an indication of the reimbursement amount, an account identifier with for the source of the funds to be reimbursement (e.g., a financial account of an insurance provider), and an account identifier or electronic account identifier or other user identifier corresponding to a destination for the funds to be reimbursed.

The second policy can include one or more policies that facilitate determining a reimbursement amount or a purse to which the reimbursement amount to be allocated. For example, the reimbursement policy can include: if prescription purchase at qualified merchant category, then reimbursement amount is 70% of the prescription amount. In some embodiments, the reimbursement amount can be an absolute value (e.g., $10, $50). In some embodiments, the reimbursement amount can include a function or formulate that takes into account the type of prescription or merchant category, a reimbursement rate, a type of insurance coverage, a geographic location, a cost of living factor, etc.

In some embodiments, the second policy can include a policy or factor that determines to which account to reimburse the funds. The second policy can select an account with fewer restrictions as compared to a benefits account. The second account can be configured with, in, on, or be part of the electronic account that includes a plurality of accounts maintained or configured on the server. The second account can be a cash purse or reimbursement purse of the electronic account. The second account can have no restrictions on where, when or for what the funds available in the second account can be used. In some embodiments, funds from the second account can be withdrawn as cash. In some embodiments, funds from the second account may not be withdrawn as cash, but can be used at any merchant that can conduct a transaction with the second account.

At step 325, the server electronically provides the reimbursement amount to a second purse of the electronic account. This second purse (or reimbursement purse or cash purse or restriction-free purse) can be different from the first purse, but maintained on or correspond to the same electronic account having the first purse or benefits purse. In some embodiments, the server provides a real-time notification of the reimbursement amount responsive to transferring the reimbursement amount to the first purse of the electronic account. The real-time notification can refer to providing the notification within a time interval of transferring the reimbursement amount to the second purse, or when the reimbursement amount is available for use or withdrawal via the second account. The time interval can refer to as soon as possible, 15 seconds, 30 seconds, 5 minutes, or some other time interval that notifies a user of available funds resulting from a reimbursement made to a purse of the electronic account soon after the funds are available.

In some embodiments, the server can receive one more data packets generated by a second device at a second merchant to conduct a second electronic transaction at the second merchant. The second device can refer to a different point of sale terminal, and the second merchant can be a merchant with a merchant category that does not correspond to a merchant category that is approved to receive funds for purchases from a benefits account. The second one or more data packets can include second header information and second payload information. The second payload information can include data associated with, defining, about or identifying aspects of the second transaction. The server can process the second one or more data packets to identify data from the payload information indicative of the second transaction. This payload information can include information such as a merchant identifier, merchant code, transaction amount, location, or electronic account information. In some embodiments, merchant category corresponds to an item being purchased in the transaction (e.g., soda purchased at a pharmacy). Thus, the merchant category of the transaction may not be approved to receive funds from a benefits account, although the merchant can provide other items that can be approved by the benefits account policy (e.g., prescription medications at a pharmacy vs. cigarettes sold at a pharmacy).

Along with these second data packets, the server can receive an identification of the electronic account, and a monetary amount of the second electronic transaction. The server can retrieve a second policy from a policy repository stored in memory using an identifier of the electronic account. The server can use the policy engine to apply the first policy to determine which purse of the electronic account to select for withdrawing funds to pay for the transaction. In some embodiments, the server determines, using a mapping of merchant category to purse configuration or purse policy, that the merchant category is not approved to receive funds from a benefits purse (e.g., the category may not correspond to any of the benefits subpurses, including medical, vision, dental, transport), and, instead, selects the cash purse for the transaction. The server can then instruct a transaction engine to obtain funds for this transaction from a cash purse that may not have restrictions based on merchant category or can be otherwise approved for providing funds for the transaction with the second merchant. For example, the server can select the second purse responsive to determining that the first purse is not configured for the second merchant category of the second merchant.

In some embodiments, merchant category can refer to a merchant category code ("MCC"). Table 1 is an example mapping of merchant categories to purses in accordance with an embodiment:

TABLE 1

Example mapping of merchant categories to purses in accordance with an embodiment.

| MCC | Merchant Category | Purse |
|---|---|---|
| 8099 | Medical Services | Benefits Purse |
| 8062 | Hospitals | Benefits Purse |
| 8042 | Optometrists | Benefits Purse |
| 7832 | Motion Picture Theaters | Cash Purse |
| 7922 | Theatrical Ticket Agencies | Cash Purse |

For example, the server can analyze the amount of available funds in one or more purses of the electronic account in order to select one or more purses to conduct a transaction. For example, multiple purses can be approved or qualify for a transaction based on a merchant code (e.g., both a benefits purse and a cash purse). In some embodiments, a first purse can have a higher priority than a second purse, which can cause the server to select the first purse for funds prior to selecting the second purse.

If multiple accounts are approved based on a merchant category, the server can determine an available amount in each purse. For example, the server can access a data record in memory for the electronic account. The data record can indicate a first available amount and a first configuration for the first purse (e.g., as a benefits purse with $100), and a second available amount and a second configuration for the second purse (e.g., a cash purse with $500). The server can determine, based on the first available amount and the first configuration, to use the first purse for the first electronic transaction. For example, the first electronic transaction can be $100 for prescriptions medications. Further, the server can determine based on the first available amount and the first configuration, not to use the second purse for the first electronic transaction. For example, the first purse can have a higher priority because it has greater restrictions than the second purse, and the transaction parameters satisfies the policy and restrictions of the first purse.

Thereafter, the server can receive an indication of a second transaction. The server can receive a second one or more data packets with second header information and second payload information. The second payload information can include data about the second transaction. The server can parse or otherwise process the second one or more data packets to identify the second payload information and data about the second transaction. Using information about the second transaction, such as a merchant identifier, merchant code, or amount of the second transaction, the server can determine, based on the first configuration of the first purse, not to use the first purse for the second electronic transaction. For example, the second transaction can be for $30 for movie tickets which may not be approved for a benefits purse based on a MCC. Further, the server can determine, based on the second available amount and the second configuration, to use the second purse for the second electronic transaction. For example, the second purse can be a cash purse that is approved for any type of MCC, and the cash purse has sufficient funds for the transaction.

C. Multi-Purse Transaction and Notification System

The systems and methods of the present solution are directed to the technical problems and challenges of implementing the functionality of conducting a multi-purse transaction of an electronic transaction based technology and platform. Existing electronic transaction based technologies and platforms do not effectively and efficiently make use of the computing and network resources deployed for multi-purse transaction based technologies and platforms to include such functionality. Without implementing such functionality, existing electronic transaction based technologies and platforms have the problems of excessive server-client requests and responses, processing delays, increase bandwidth usage, or erroneous transactions.

The systems and methods of the present solution are directed to the improvement of the performance and operation of the electronic transaction based technology and platform and computing and networking resource used by such electronic transaction based technology and platform. In some aspects, the present solution improves and enhances the implemented functionality of the electronic transaction based technology and platform implemented on, integrated with and inherently tied to the processor, memory, network and computing resources of one or more computing devices. In some aspects, the present solution more effectively performs the functionality of the electronic transaction based technology and platform thereby making and causing more effective use of the computing and networking resources to achieve the improved functionality of the present solution. The same computing and network resources used by such electronic transaction based technology and platform will provide increased and improved functionality with implementation of the present solution.

In some aspects, the present solution more efficiently uses the computing and networking resources to implement the improved functionality of the electronic transaction based technology and platform. For example, systems and methods of the present solution can use a multi-purse transaction system that maintains an electronic account having multiple purses, such as an electronic benefits account and an electronic reimbursement account. Systems and methods of the present solution can adjudicate a single claim against the electronic benefits account (e.g., determine that the single claim is approved for reimbursing an electronic account by an amount of expenditures associated with the electronic transaction) and provide notifications relating to such claims. An electronic account can be maintained by a server and include a database in memory or a storage device. The electronic account can include sub structures or fields. The electronic account can include multiple purses that are configured with one or more rules, parameters, restrictions, or policies. For example, the electronic account can include a first purse that is configured for benefits as an electronic benefits account purse. A purse configured for benefits can refer to a purse that is configured for transactions made using a tax benefit account such as a flexible spending account ("FSA"), Dependent Care Account ("DCA"), Transport Account (e.g., for parking or monthly passes). In some embodiments, the FSA, DCA, and Transport Account can be further separated into sub-purses within the electronic benefits account purse of the electronic account. A flexible spending account, or flexible spending arrangement, can refer to a tax-advantaged financial account that can be set up through a cafeteria plan of an employer and used to set aside a portion of earnings to pay for qualified expenses as established in the cafeteria plan. Types of FSA can include medical expense FSA, health FSA, health savings account (HSA), health reimbursement account (HRA), health reimbursement plan (HRP), etc. Qualified expenses can include, for example, medical expenses, dependent care, dental expenses, vision expenses, parking, monthly passes, etc. An FSA can be tax-advantaged because funds deducted from an employee's account and transferred to the FSA is not subject to payroll taxes, resulting in payroll tax savings.

A user can make the transaction at an entity such as a merchant, pharmacy, retail store, medical supply store, or other entity that provides goods or services that are deemed to be qualified expenses in accordance with the tax benefit account or FSA. The transaction can occur via a point-of-sale terminal or device (e.g., checkout device, electronic point of sale device or other device that includes hardware and software to facilitate a transaction) configured to receive financial transaction information from the user (e.g., via a debit card, pin number, mobile payment device, near field communication-enabled device, mobile telecommunications device) and communicate with one or more servers or databases to authenticate the financial transaction information, identify a corresponding FSA of the user, and initiate or facilitate the transfer of funds from the FSA to the entity. The transaction can be associated with information such as an FSA account identifier, time stamp, entity identifier, and transaction amount. This information can be provided in real-time to a transaction repository.

When participants submit claims for reimbursement from their FSA, HRA or other benefit account, the present solution provides a real time credit to their electronic reimbursement account when the claim is approved for reimbursement. The present solution provides real time adjudication of the single claim. By adjudicating the single claim, the present solution improves over batch processed claims that cannot be processed until several hours, days, weeks, or months after the electronic transaction occurs. The present solution provides a real time notification via electronic mail or electronic messaging of the real time credit to the electronic reimbursement account, and can explain in real time that the reimbursed amount is now available for unrestricted spending at any merchant. The present solution uses one or more policy or logic engines to authorize transactions, such as by authorizing transactions based on a merchant category code ("MCC"), a goods and services code, a health care provider code, or other policy codes, to determine that the single claim against the electronic benefits account is approved for an amount of expenditures qualifying under the electronic benefits account.

For example, if the participant has $100 in their FSA which is setup for Medical, Rx, Vision and Dental purchases, and the participant swipes their card at a vision provider for $75, the system makes a determination based on a policy to select an FSA from which to deduct funds. If the card is swiped at a restaurant and the participant has an electronic reimbursement account on the card, the system can deduct funds from a reimbursement purse. If the participant has a transaction that exceeds the FSA for a qualified expense, the system can use the FSA funds plus an amount from the reimbursement purse. Participants can text a code such as "BAL" to the present solution to receive a current balance in one or more electronic accounts/purses, including the electronic reimbursement account, or call to obtain balances for all accounts through an interactive voice response, as well as view the balance through a mobile application or online portal. Participants can text a code such as "CLAIM" to the present solution to receive a status of the adjudication of the single claim.

Figure 4:
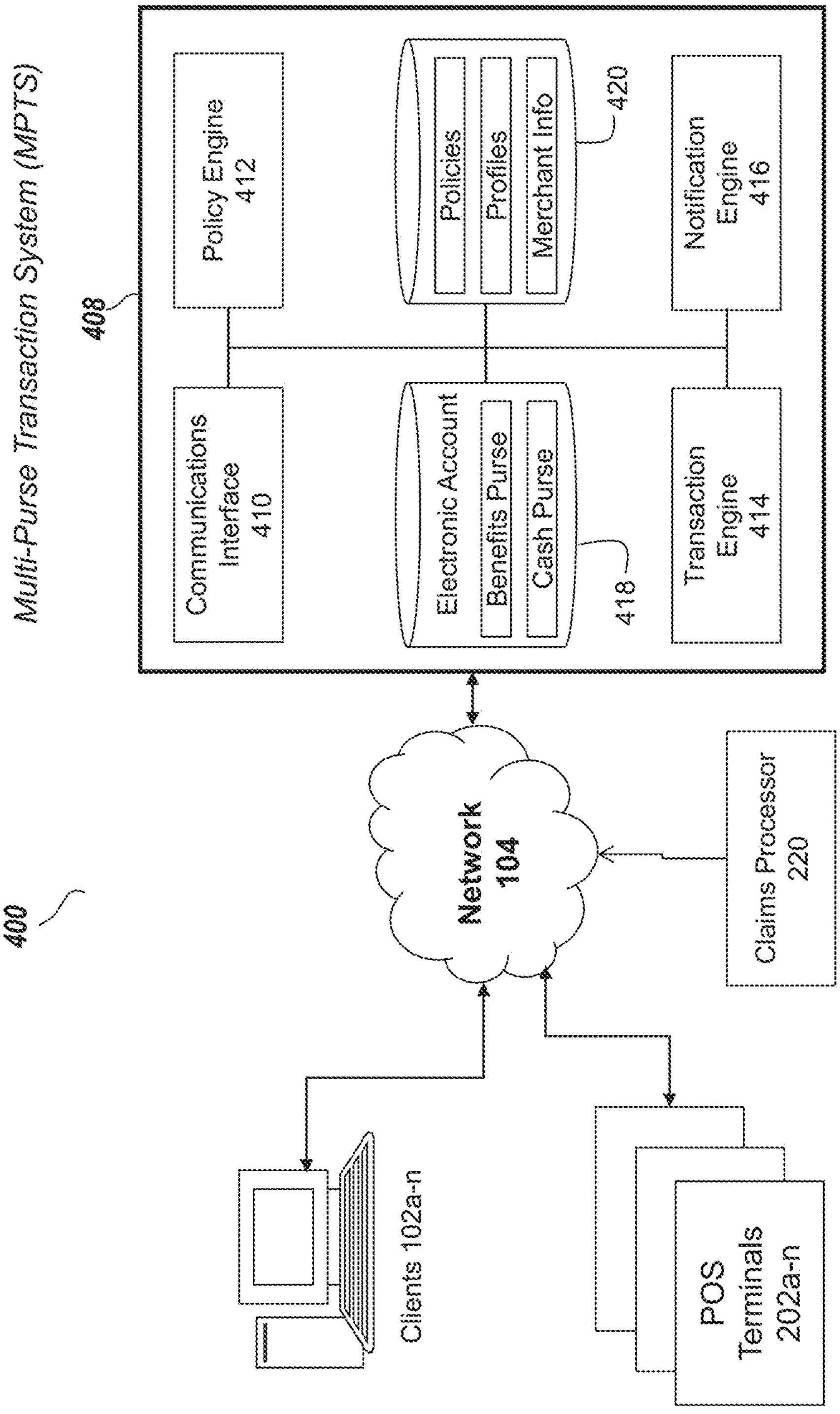
FIG. 4 is a block diagram depicting an embodiment of a system for conducting electronic transactions via a computer network.

Referring now to FIG. 4, a block diagram depicting an embodiment of a system 400 comprising a multi-purse transaction system (MPTS) is shown. In brief overview, the system 400 includes a multi-purse transaction system 408 ("MPTS"). The MPTS 408 can include the MPTS 120 depicted in FIG. 2, or one or more components or modules depicted in FIG. 2, and can perform the functions of the MPTS 120. The MPTS 408 can receive and/or transmit data via a network 104 with clients 102*a-n* and POS terminals 202*a-n*. The system 400 can include or interact with one or more clients 102*a-n* (or client device 102), and one or more point-of-sale (POS) terminals 202*a-n* (or POS terminal 202).

The MPTS 408 can include a communications interface 410. The communications interface 410 can include the communications interface 210 depicted in FIG. 2, or one or more components or modules depicted in FIG. 2, and can perform the functions of the communications interface 210. The communications interface 410 is configured with one or more communications ports, application programming interfaces, network protocols (e.g., TCP/IP), authentication protocols, or security protocols (e.g., SSL). The communications interface 410 can receive a request to adjudicate a single claim against an electronic benefits account.

The MPTS 408 can include a policy engine 412. The policy engine 412 can include the policy engine 212 depicted in FIG. 2, or one or components or modules depicted in FIG. 2, and can perform the functions of the policy engine 212. The policy engine 412 determines, responsive to the communications interface 410 receiving the request to adjudicate the single claim, that the single claim against the electronic benefits account is approved for an amount of expenditures qualifying under the electronic benefits account.

In some aspects, the policy engine 412 comprises an innovative, non-conventional or non-routine implementation. In some aspects, the policy engine 412 is implemented to address the technical problems and challenges of prior systems not deploying the present solution. In some aspects, the policy engine 412 is implemented to make or cause more effective and efficient use of computing and networking resources. For example, the policy engine 412 can cause more effective and efficient use of computing and network resources by reducing the number of processing cycles, memory or network bandwidth used to adjudicate the single claim against the electronic benefits account. The policy engine 412 can provide an improved or faster result by integrating or interfacing with one or more of the communication interface 410, electronic account 416, database 420, transaction engine 414, notification engine 416 or claims processor 220 to perform the adjudication of the single claim.

The MPTS 408 can include a transaction engine 414. The transaction engine 414 can include the transaction engine 212 depicted in FIG. 2, or one or more components or modules depicted in FIG. 2, and can perform the functions of the transaction engine 214. The transaction engine 414 obtains electronic data representing funds from one or more electronic accounts or purses and transfers the funds to one or more accounts or purses or merchants.

In some aspects, the transaction engine 414 comprises an innovative, non-conventional or non-routine implementation. In some aspects, the transaction engine 414 is implemented to address the technical problems and challenges of prior systems not deploying the present solution. In some aspects, the transaction engine 414 is implemented to make or cause more effective and efficient use of computing and networking resources. For example, the transaction engine 414 can cause more effective and efficient use of computing and network resources by reducing the number of processing cycles, memory or network bandwidth used to obtain electronic data regarding funds from one or more electronic accounts or purses to conduct a transfer. The transaction engine 414 can provide an improved system by integrating or interfacing with the communication interface 410, electronic account 416, database 420, policy engine 412, notification engine 416 or claims processor 220 to perform the transfer.

The MPTS 408 can include one or more databases or data structures that store information to facilitate the systems and methods of the present solution, such as database 418 and database 420. The database 418 can include the database 216, or one or more components or modules depicted in FIG. 2, and can perform the functions of the database 216. The database 418 (or electronic account) can include an electronic account maintained on or configured on the MPTS 408 that includes one or more purses, such as a benefits purse and a cash purse. The database 418 can include a profile database of the electronic benefits account. The profile database can include an entry corresponding to a device configured to receive notifications for the electronic benefits account. The entry can include a unique identifier for the device and a notification mode including at least one of a Short Messaging Service (SMS) protocol or an electronic mail protocol. The database 420 can include one or more policies in a policy repository, user profiles, or merchant information. The user profiles can include biographical information associated with users, identifiers for clients 102 or other devices associated with users, security credentials associated with users, transaction histories, etc. In some embodiments, the user profile can include contact information such as an electronic mail protocol, a mobile telephone number, an SMS protocol, a landline telephone number, or a postal address associated with users.

The MPTS 408 can include a notification engine 416. The notification engine 416 can be configured to generate notifications and transmit the notifications to devices of electronic benefits accounts. In some aspects, the notification engine 416 comprises an innovative, non-conventional or non-routine implementation. In some aspects, the notification engine 416 is implemented to address the technical problems and challenges of prior systems not deploying the present solution. In some aspects, the notification engine 416 is implemented to make or cause more effective and efficient use of computing and networking resources. For example, the notification engine 416 can cause more effective and efficient use of computing and network resources by reducing the number of processing cycles, memory or network bandwidth used to generate notification and transmit the notifications to devices of electronic benefits accounts. The notification engine 416 can provide an improved or faster notification by integrating or interfacing with the communication interface 410, electronic account 416, database 420, policy engine 412, policy engine 412 or claims processor 220 to perform the notification.

The MPTS 408, communications interface 410, policy engine 412, transaction engine 414, and notification engine 416 can each include one or more processing units or other logic devices such as programmable logic array engines, modules, or circuitry designed and constructed to facilitate managing security on a network infrastructure. The MPTS 408 can include the components 100 shown in FIG. 1C or FIG. 1D, or be configured to operate as a service in cloud 108. The MPTS 408 can include or interact with one or more servers 106*a-n* and clients 102*a-n*.

In some embodiments, the MPTS 408 can employ a multitier architecture such as a client-server architecture in which presentation, application processing, and data management functions are logically or physically separated. The presentation tier, or front-end, can include the communications interface 410 that serves static content or dynamic content to be rendered by the client 102 (e.g., by a web browser executing on client 102). The presentation tier or web server 210 can interact or communicate with the application tier to obtain data to provide to the client 102 or POS terminals 202*a-n*. The application tier can include the policy engine 412, transaction engine 414, and notification engine 416 that controls the system's functionality and performs additional processing or analysis on data. The application tier can interact with the data tier to obtain the transaction data. The data tier can include data persistence mechanisms (database servers, file shares, etc.) and the data access layer that encapsulates the persistence mechanisms and exposes the data. The data tier can include databases 418 and 408. The data tier can include an application programming interface (API) to the application tier. The databases 418 or 408 can include stored procedures (e.g., SQL statements) that perform tasks with respect the stored data.

In further detail, and in some embodiments, the MPTS 408 includes a communications interface 410. The communications interface 410 can execute on one or more processors of a server. The communications interface 410 can include one or more communications ports and be configured with one or more network protocols. Communications ports can include, e.g., network ports, Ethernet ports, WAN ports, I/O ports, or software ports. The communication port can be configured with a network protocol such as Transport Layer Protocols such as TCP/IP or UDP that are configured to receive and process data packets received via a computer network. The port can include or be associated with an IP address of a host and a protocol type of the communication.

In some embodiments, the communication interface 410 can receive data packets. The data packets can be generated by a device at a merchant to conduct an electronic transaction at the merchant. The device can refer to a point of sale terminal ("POS terminal") such as POS terminal 202*a*. In some embodiments, the POS terminal 202 is the device at which a retail transaction is initiated. The POS terminal 202 is the point at which a customer of the entity or merchant makes a payment to the merchant in exchange for goods or services. At the point of sale the merchant can calculate the amount owed by the customer and provide options for the customer to make payment. The merchant can also issue a receipt for the transaction.

The POS terminal 202 can include hardware and software. Merchants can utilize weighing scales, scanners, electronic and manual cash registers, EFTPOS terminals, touch screens and any other wide variety of hardware and software available for use with POS terminal 202. For example, a pharmacy can use software to customize the item or service sold when a customer has a special medication request.

The POS terminal 202 can include advanced features to cater to different functionality, such as inventory management, CRM, financials, warehousing, flexible spending account transactions, etc., all built into the POS software. The POS terminal 202 can be configured to conduct a transactions using a debit card, multipurse card, Bluetooth, near field communications, smartphone, smartwatch, mobile telecommunications computing device, wearable communications, RFID, etc.

The communications interface 410 can receive data packets generated by the POS terminal 202*a* responsive to an electronic transaction resulting in transmission of a request to adjudicate a single claim against an electronic benefits account. In some embodiments, the request to adjudicate a single claim against the electronic benefits account is transmitted responsive to a user swiping a payment card at the POS terminal. The payment card can include identifying information that can be used to identify an account identifier of the electronic benefit account against which to adjudicate the claim. The data packets can include header information and payload information. Multiple data packets can be strung together in a sequence. The header information can refer to TCP/IP headers that include fields such as source port, destination port, sequence number, acknowledge number, window size, etc. The payload information of the data packet can include information related to the electronic transaction, the request to adjudicate a single claim, the merchant, or the customer. The MPTS 408 can receive the data packet with header information and payload information and process the packets to obtain information for further processing. The payload can include data identifying the POS terminal 202*a* at which the electronic transaction occurred, the merchant providing the POS terminal 202*a*, a merchant category of the merchant, financial information associated with the user performing the electronic transaction (e.g., via a card swipe or other communication technique used to perform the electronic transaction), an amount of expenditures of the electronic transaction, and other information facilitating adjudication of the single claim. The data packets (e.g., via the payload) can include the request to adjudicate the single claim. The request can specify the electronic benefits account for adjudication. The request can specify information for identifying a policy for performing the adjudication. The payload can include data identifying a merchant category of the merchant, an electronic benefits account, and a monetary amount of the electronic transaction.

The data packets can carry data identifying a merchant or merchant category of the merchant. In some embodiments, the data carried by the data packets include a merchant category code or identifier (e.g., dental, medical, etc.). In some embodiments, the data identifies a merchant, and the MPTS 408 determines a merchant category based on the identification of the merchant by, for example, using a merchant to merchant category mapping or lookup table stored in database 420. In some embodiments, the data packets carrying the request to adjudicate the single claim against the electronic benefits account include a data structure having a first field indicating a merchant identifier, a second field indicating a total amount of expenditures, and a third field indicating the electronics benefit account. In some embodiments, the data packets are generated by a merchant device (e.g., a client device 102 of a merchant) to conduct an electronic transaction at the merchant, and the data packets carry data identifying a merchant category of the merchant, the electronic benefits account maintained and configured on the MPTS 408, and a total monetary amount of the electronic transaction.

The data packets (e.g., payload of the data packets) can further identify an electronic account maintained and configured on the server. The electronic account can be maintained and configured in a database 418. The electronic account can correspond to a user and have a unique identifier. The unique identifier can include numbers, letters, characters, symbols, etc. The electronic account can be associated with the customer making the transaction at the merchant. The POS terminal 202*a* can receive or determine the electronic account identifier via a card swipe or other communication technique employed at the POS terminal 202*a*, which the POS 202*a* can then convey to the MPTS 408.

The communications interface 410 can further receive data packets (e.g., payload information) identifying a monetary amount of the electronic transaction, such as a total amount of expenditures. The monetary amount can be for the purchase of goods or services made at the merchant. The monetary amount of the transaction can refer to the amount of funds in consideration for goods or services obtained from the entity or merchant. The merchant or entity can refer to the entity at which a point-of-sale terminal or device used to make the transaction is located or with which the terminal is associated. The monetary amount can be in any currency (e.g., United States dollars) or units. The monetary amount can be further tied to a category, such as medical services.

In some embodiments, the POS terminal 202 can generate multiple data packets for a single transaction. The multiple data packets can each include a header and a payload. The header can indicate that the multiple data packets are to be grouped together for routing, transmission or processing purposes.

The MPTS 408 can be configured to authenticate communications and transactions. In some embodiments, the communications interface 410 receives communications such as the request to adjudicate the single claim. The request can include security credential such as a security certificate or security token. The security credential can be associated with a user or a merchant. The MPTS 408 can be configured to extract the security credential from the request, and authenticate the request by comparing the security credential against a known or verified security credential. For example, the user profiles and/or merchant information stored in database 420 can include known or verified security credentials for comparison with the security credential of the request. In some embodiments, the MPTS 408 receives the request to adjudicate the single claim via the communications interface 410, extracts a security credential from the request, analyzes the extracted security credential to identify a user, queries the database 420 for a verified security credential stored with a user profile corresponding to the identified user, compares the extracted security credential to the verified security credential, and authenticates the request based on the extracted security credential matching the verified security credential. In some embodiments, the MPTS 408 analyzes the extracted security credential to identify a merchant, queries the database 420 for a verified security credential stored with merchant information corresponding to the identified merchant, compares the extracted security credential to the verified security credential, and authenticates the request based on the extracted security credential matching the verified security credential.

In some embodiments, the MPTS 408 includes a policy engine 412. The policy engine 412 can execute on one or more processors of a server, such as a server of the MPTS 408. The policy engine 412 can receive, retrieve, or otherwise obtain or access some or all of the data carried by the data packets. The policy engine 412 can receive, retrieve, or otherwise obtain or access policies, such as policies maintained in database 420. The policy engine 412 can determine that the single claim against the electronic benefits account is approved for an amount of expenditures qualifying under the electronic benefits account, responsive to the communication interface 210 receiving the request to adjudicate the single claim.

The MPTS 408 can initiate a claim adjudication process responsive to receiving the data packets, such as by causing the policy engine 412 to execute policies maintained in the database 420. The MPTS 408 can cause the policy engine 412 to identify a policy maintained in the database 420 to apply to the single claim to adjudicate the single claim based on information extracted from the received data packets. The MPTS 408 can cause the policy engine 412 to determine that a remote policy is required based on information extracted from the received data packets, and the MPTS 408 can request the remote policy by transmitting one or more data packets carrying a policy request to a remote server, such as a server of an insurance administrator or an employer. The policy request can cause the remote server to transmit the requested remote policy to the MPTS 408. For example, the policy engine 412 can determine that the received data packets indicate a new insurance administrator or employer for which a policy is not yet maintained in the database 420.

The policy engine 412 can identify a reimbursement policy of the electronic benefits account specifying an ordered list of account destinations for benefits account reimbursements via a configuration of the electronic benefits account maintained by the server, such as a server of the MPTS 408. The ordered list of account destinations can include or refer to a set of electronic account identifiers or electronic account types that are in a sequence of priority. For example, each electronic account identifier or electronic account type can be associated with, correspond to, or configured with a priority. The priority can include a numeric value, score, text, symbol, or other indicator of a rank, preference, selection technique, selection protocol, or sequence. In some embodiments, the ordered list of account destinations includes at least one of: an electronic reimbursement account maintained by the MPTS 408, such as a cash purse maintained in the database 418; an electronic reimbursement account maintained in a server by an entity remote from the MPTS 408, such as a server of a financial institution, of an insurance administrator, or of an employer; a payroll account, such as a payroll account having direct deposit information for electronically transferring credits to the payroll account; or another account that can be credited by sending (e.g., mailing to a postal address) a check to the account. The electronic reimbursement account can include a tax benefit account, which may or may not include an HSA, an FSA, a checking account, a savings account, or other electronic accounts that can receive funds electronically. The ordered list can prioritize the electronic reimbursement account maintained by the MPTS 408 as a first-highest priority account destination; an electronic reimbursement account maintained remote from the MPTS 408 as a second-highest priority account destination; a payroll account having direct deposit information as a third-highest priority account destination; and another account requiring a check to be mailed as a fourth-highest priority account destination. Any other combination of account priorities are contemplated. In some embodiments, the MPTS 408 specifies a default ordered list. In some embodiments, a user associated with the request to adjudicate the single claim can specify the ordered list. In some embodiments, an insurance administrator or an employer can specify the ordered list. The MPTS 408 can be configured to receive the ordered list from client devices 102 of the user, the insurance administrator, or the employer.

The policy engine 412 can determine an electronic reimbursement account as a destination for a benefits account reimbursement via application of the reimbursement policy to the single claim. The electronic reimbursement account can be configured to allow transactions for non-qualifying benefits. For example, the electronic reimbursement account can be configured to be credited based on transactions that would otherwise not qualify under a policy applied during adjudication. The policy engine 412 can update the electronic reimbursement account maintained by the server with a value corresponding to a credit for the approved amount for the single claim.

The policy engine 412 can use or apply a policy that includes one or more techniques, algorithms, heuristics, rules or procedures. The policy can include decision points and utilize parameters or criteria. The policy can be based on criteria or rules that are established by an administrator of the MPTS 408 or another entity. The policy can facilitate determining whether the single claim against the electronic benefits account is approved for an amount of expenditures qualifying under the electronic benefits account.

The policy can be retrieved from a variety of entities, such as client devices 102 or servers associated with an insurance administrator, an employer, a financial institution (e.g., a bank administering or otherwise maintaining an electronic reimbursement account or a payroll account configured for direct deposit), or the claims processor 222. The insurance administrator can establish or otherwise maintain the electronic benefits account. The employer can at least partially pay for or otherwise subsidize an insurance plan associated with the policy. In some embodiments, the policy defines a maximum amount of expenditures for all goods and services. For example, the policy can set maximum expenditures for a billing cycle, such as a monthly billing cycle, an annual billing cycle, or a billing cycle of another length of time. The maximum amount of expenditures can be prorated for billing cycles less than a year in length, based on a standardized annual amount of expenditures, such as when a user activates the electronic benefits account at a time other than a typical enrollment time for the annual billing cycle.

In some embodiments, the policy defines purchase type categories. Purchase type categories can be exclusive or overlap for various goods and services. For example, healthcare related expenditures can fall within a first category, and cafeteria expenditures can fall within a second category. Healthcare related expenditures can include services provided by a healthcare provider, goods purchased at a pharmacy, goods purchased based on a prescription.

In some embodiments, the policy can be to select the highest priority account destination for the reimbursement. The policy can be to select the highest priority account destination available for receiving funds electronically for reimbursement. The policy can be to select the highest priority account destination associated with the electronic benefits account used to adjudicate the single claim. For example, an insurance administrator or employer can provide both an electronic benefits account and an electronic reimbursement account to a particular user, or an electronics benefit account and an electronic reimbursement account can be otherwise associated with or linked to one another, and the policy can select the highest priority account destination associated with or linked to the electronics benefit account.

In some embodiments, the policy can be based on a merchant category. The policy can be based on a merchant category code ("MCC"). The MCC can refer to a code (e.g., a four-digit number) that can be assigned to a business by an entity, such as a credit card company or the MPTS 408. This code can be used to classify the merchant by a business type, or type of goods or services provided.

For example, the policy can be: if merchant category corresponds to (or equals or maps to or is) medical, then use benefits purse. In another example, the policy can be: if merchant category corresponds to dental, then use benefits purse. In another example, the policy can be: if merchant category maps to qualified benefits category, then use benefits purse. In some embodiments, the electronic account can include a benefits purse that is preconfigured with merchant categories that map to qualified or approved categories, such as categories for funds exempt from payroll tax can be used to conduct a transaction.

In some embodiments, the policy defines geographical requirements for expenditures. For example, expenditures can be approved only if they take place within a particular country, state, county, city, or other geographical region. Expenditures can be approved only if they take place within a certain distance of a home location of the user.

In some embodiments, the policy defines a variety of approval levels for expenditures. For example, a first approval level for expenditures can automatically approve expenditures without further review. A second approval level for expenditures can approve expenditures following review by an administrator of the benefits account. A third approval level for expenditures can approve expenditures following confirmation received from the user. For example, after the MPTS 408 receives the request to adjudicate the single claim via the communications interface 410, the MPTS 408 can transmit a request for confirmation to the client device 102, and approve the expenditure responsive to receiving the confirmation.

In some embodiments, the MPTS 408 can process multiple policies before identifying a policy that is satisfied. For example, the policy can include geographic guidelines and provider guidelines, such that expenditures are approved for goods and services purchased within a geographical region from certain providers or merchants. The policy can prioritize guidelines. For example, the policy can include both geographic guidelines and merchant category guidelines, with merchant category guidelines having a higher priority such that expenditures at approved merchants are always approved independent of geographic location.

In some embodiments, the policy can include multiple criteria. For example, the policy can include: if merchant category corresponds to (or equals or maps to or is) medical or dental or vision or parking, then approve the expenditure.

In some embodiments, the policy can include an action to take when the policy is not satisfied. For example, when the policy is not satisfied, the policy can include generating a notification by the notification engine 416 and transmitting the notification to the client device 102*a* via the communications interface 410, the notification indicating that the policy is not satisfied. The action can include transmitting a request for more information and preventing the transaction engine 414 or the policy engine 412 from performing further actions until the request for more information is satisfied.

In some embodiments, the policy engine 412 can use a policy that includes monetary amount thresholds. For example, a merchant category can correspond to an approved benefits purse. However, the approved benefits purse can include a threshold that limits a monetary amount of a transaction. For example, the benefits purse can be configured with a parking sub-purse with a monetary amount threshold. The monetary amount threshold can be for a time period, such as a month, quarter, year, week, or other time interval. For example, the transport or parking sub-purse can be approved for $200 per month for transactions made at merchants that correspond to merchant category transport or parking. Thus, the policy can include criteria such as merchant category, transaction amount, and time interval. For example: if merchant category corresponds to transport and if transaction amount less than or equal to approved transaction amount for time interval, then use transport sub-purse.

In some embodiments, the policy engine 412 can apply a second policy directed to additional factors after using a first policy. The policy engine 412 can select the second policy responsive to or based on the first policy. The second policy can be associated with a monetary amount, transaction amount, or reimbursement amount. The policy engine 412 can use the second policy to determine a reimbursement amount. The policy engine 412 can use a reimbursement policy. The reimbursement policy can be applied to the data that identifies the transaction amount, merchant category, and electronic account. The reimbursement policy can be selected based on an insurance policy tied to or associated with the electronic account. The electronic account can include a unique identifier that maps to or corresponds to a type of insurance policy or reimbursement policy. The reimbursement or insurance policy (e.g., second policy) can be established by an administrator of the MPTS 408, an employer of the user/customer conducting the electronic transaction, or another entity. Using this reimbursement policy, the policy engine 412 can determine a reimbursement amount for the electronic transaction. For example, if electronic the transaction amount for the medical service was $100, the policy engine 412 can determine that 80% of the transaction is covered by insurance. The MPTS 408 can initially deduct $100 from the benefits purse of the electronic account in accordance with the first policy. Thereafter, applying the second policy using the policy engine 412 to adjudicate the single claim for the electronic transaction, the MPTS 120 can determine to credit or reimburse the electronic account $80.

In some embodiments, the policy engine 412 can receive an indication from a claims processor 220 external to the MPTS 408 via the network 104. In some embodiments, the MPTS 408 or the policy engine 412 is configured with the claims processor 220 or configured to interface with the claims processor 220 via communications interface 410. The claims processor 220 can process an insurance claim to determine a reimbursement amount. The claims processor 220 can be configured to use one or more policies or rules to process the insurance claim and determine a reimbursement amount. The policies can be based on a type of insurance coverage associated with a user of the electronic account. The claims processor 220 can automatically receive the insurance claim responsive to a user conducting a transaction using the multipurse card connected with the electronic account. The claims processor 220 can obtain, via database 418 or 420, policies, profiles and merchant information to adjudicate the claim. The claims processor 220 can adjudicate the claim, determine a reimbursement amount, and provide an indication to the MPTS 408 regarding the reimbursement amount. The indication can identify the electronic account, user identifier, time, original transaction amount, reimbursement policy, or reimbursement amount.

The MPTS 408 can include a transaction engine 414. The transaction engine 414 can receive information or instructions from the policy engine 412 regarding a transaction, and conduct the transaction. The transaction engine 414 can obtain merchant information from database 420 and electronic account information from database 418 to perform the transaction. The transaction can include electronically transferring funds from a first account to a second account. The first account can be an electronic account, and the second account can be an account of a merchant (such as a financial account). In some cases, the transaction engine 414 can facilitate a transfer of funds between an electronic account of a claims processor 220 and the electronic account 418. The transaction engine 414 can receive account identifiers, transaction amounts, credentials, authentication information, etc. The transaction engine 414 can conduct the transaction via communications interface 410, thereby using the network protocols, security protocols and other components or interfaces provided by the communications interface 410.

For example, the transaction engine 414 can be configured to receive a request from the policy engine 412 to execute a transaction, such as to execute a reimbursement transaction in which the electronic reimbursement account is updated with the value corresponding to the credit for the approved amount for the single claim. The request can include an identifier for the electronic reimbursement account, such as the user profile associated with the electronic reimbursement account. The transaction engine 414 can perform a lookup in the database 220 to retrieve the user profile. The transaction engine 414 can extract an identifier for an electronic source account from which the funds are to be transferred, such as electronic financial account. The transaction engine 414 can transmit a fund request to a server maintaining the electronic financial account, such as a server of a financial institution. The fund request can include an identifier of the electronic financial account, such as a routing number and an account number in the case of funds to be transferred from an electronic checking or savings account, or a credit card number in the case of funds to be transferred from an electronic credit card account. The fund request can cause the electronic financial account to release an amount of funds from the electronic financial account for transfer. The fund request can cause the server maintaining the electronic financial account to release an amount of funds corresponding to the credit for the approved amount for the single claim, and transmit a confirmation to the transaction engine 414 of the release of the amount of funds.

The transaction engine 414 can perform a lookup in the database 218 in which the electronic reimbursement account is maintained, and update the amount of funds in the electronic reimbursement account responsive to receiving the confirmation. In some embodiments, the transaction engine 414 can receive the confirmation, extract the amount of funds from the confirmation, and compare the amount of funds to an expected credit for the approved amount for the single claim.

Responsive to the amount of funds from the confirmation matching the expected credit for the approved amount for the single claim, the transaction engine 414 can update the amount of funds in the electronic reimbursement account, and the transaction engine 414 can generate a confirmation message indicating the successful transfer of funds to be transmitted to the client device 102 via the communications interface 412. Responsive to the amount of funds from the confirmation not matching the expected credit, the transaction engine 414 can transmit an additional fund request to the server maintaining the electronic financial account via the communications interface 412. The additional fund request can include an error message generated by the transaction engine 414 based on the amount of funds from the confirmation not matching the expected credit. The transaction engine 414 can also generate an error message to be transmitted to the client device 102 via the communications interface 412.

The MPTS 408 can include a notification engine 416. The notification engine 416 can be executed on one or more processors of a server. The notification engine 416 can generate a notification, responsive to the request adjudicated by the server and the update by the policy engine 412 of the electronic reimbursement account with the value corresponding to the credit for the approved amount for the single claim, a notification identifying the update to the electronic reimbursement account corresponding to the credit. The notification engine 416 can transmit one or more packets carrying data indicating the notification of the credit to a device of the electronic benefits account, such as a client 102.

In some embodiments, the notification engine 416 can be configured to provide the notification in real-time via the communications interface 410. The communications interface 410 can be configured to provide the notification via an electronic mail protocol, SMS protocol, notification or prompt on a mobile telecommunications devices (e.g., a smartphone, tablet, smartwatch, wearable telecommunications device, laptop computer, desktop computer, etc.). A user profile maintained in the database 420 can include contact information corresponding to the client 102, and the notification engine 416 can be configured to transmit the first one or more packets to the client 102 using the contact information via the communications interface 410. In some embodiments, the user profile can include a priority order associated with multiple contact information, a preferred contact information, and/or an indication of multiple contact information for receiving notifications. For example, the user profile can indicate an electronic mail protocol as a preferred contact information, and the notification engine 416 can be configured to identify the electronic mail protocol as the preferred contact information, and transmit the one or more data packets to the client 102 using the electronic mail protocol via the communications interface 410.

In some embodiments, a profile database of the electronic benefits account, such as a profile database maintained in database 418, includes an entry corresponding to a device configured to receive notifications for the electronic benefits account. The entry includes a unique identifier for the device and a notification mode including at least one of an SMS protocol or an electronic mail protocol. The MPTS 408 can be configured to perform a lookup in the profile database to identify the device configured to receive notifications for the electronic benefits account. The MPTS 408 can be configured to retrieve, from the profile database, the unique identifier for the device and the notification mode, the notification mode including at least one of an SMS protocol or an electronic mail protocol. The MPTS 408 can be configured to configure the first one or more packets carrying the data indicating the notification based on the notification mode. For example, if the notification mode includes an SMS protocol, then the MPTS 408 can be configured to configure the first one or more packets into packets having a file size less than or equal to a maximum file size for an SMS protocol transmission.

The notification can be delivered in real-time. A real-time notification can refer to providing the notification soon after completion of an action by the MPTS 408 (e.g., within 30 seconds, within 1 minute, within 5 minutes). The action resulting in a real-time notification can be an adjudication of a single claim against the electronic benefits account; an application of a reimbursement policy to the single claim; an update of the electronic benefits account with a value corresponding to a credit for the approved amount for the single claim, among others. For example, responsive to the MPTS 408 adjudicating the request and the policy engine 412 updating a purse (e.g., a benefits purse) of the electronic account of database 418, the notification engine 416 can generate a notification identifying the update to the benefits purse of database 418 and cause the notification to be transmitted to the client 102*a* via the communications interface 410.

The notification can be transmitted within a pre-determined time interval of receiving the request to adjudicate the single claim. The predetermined time interval can be a time period after an action, e.g. 10 minutes, 5 minutes, 1 minute, 30 seconds. The action can include receiving the request to adjudicate the single claim, receiving one or more packets generated by a merchant device to conduct an electronic transaction at the merchant, and/or generating the notification of the initiation of the single claim adjudication process. The pre-determined time interval can be set in a configuration file or profile maintained by the MPTS 408 in the database 418 or the database 420, the configuration file or profile corresponding to the electronic benefits account. The pre-determined time interval can be set by an entity remote from the MPTS 408. For example, the MPTS 408 can transmit a time interval request to a remote server of an insurance administrator or an employer. The time interval request can cause the remote server to transmit the configuration file or profile setting the pre-determined time interval to the MPTS 408. The notification engine 416 can process the configuration file or profile to extract the pre-determined time interval in order to transmit the notification within the pre-determined time interval.

In some embodiments, responsive to the action occurring that initiates the pre-determined time interval, the notification engine 416 can generate a placeholder notification to be transmitted to the client device 102 independent of the status of adjudication of the single claim. For example, the placeholder notification can indicate that the claim adjudication process has been initiated. The placeholder notification can indicate that further information is required to complete the claim adjudication process. The notification engine 416 can transmit the placeholder notification prior to expiry of the pre-determined time interval via the communications interface 410 to provide real-time communication of the adjudication process.

In some embodiments, the pre-determined time interval can be based on the type of electronic reimbursement account or an expected time required to update the electronic reimbursement account with the reimbursement. For example, if the electronic reimbursement account can be updated by wire transfer, than the pre-determined time interval can be approximately ten seconds, thirty seconds, one minute, etc. If the electronic reimbursement account can be updated by direct deposit, then the pre-determined time interval can be a time associated with electronic communication between the MPTS 408 and an electronic payroll account, such as ten minutes. The pre-determined time interval can be based on a time required to transfer funds from an electronic bank account associated with an insurance administrator or with an employer to the electronic reimbursement account. The pre-determined time interval can be based on a time required for an indication of the adjudication of the single claim to be received at a remote server in order to cause the funds to be transferred to the electronic reimbursement account.

In some embodiments, the notification can include status information regarding the single claim adjudication (e.g., single claim approved, single claim denied, single claim submitted for transfer, single claim adjudication complete, single claim adjudication incomplete, single claim adjudication pending, or single claim adjudication pending further review). In some embodiments, the notification can include status information regarding the application of the reimbursement policy to the single claim (e.g., processing reimbursement, reimbursement approved, reimbursement denied, reimbursement submitted for transfer, transferring reimbursement, or reimbursement complete). In some embodiments, the notification can include status information regarding the update of the electronic benefits account with the value corresponding to the credit for the approved amount for the single claim (e.g., update complete, processing update, update incomplete, credit complete, processing credit, or credit incomplete). In some embodiments, the notification engine 416 is configured to generate notification of the initiation of the single claim adjudication process, and transmit the notification via the communications interface 410 to the client device 102*a*.

In some embodiments, the notification engine 416 is configured to generate electronic reports regarding the electronic transaction and the update of the electronic reimbursement account. The notification engine 416 can retrieve an electronic report template configured for the electronic benefits account responsive to transmitting the instructions including the value (e.g., a value corresponding to the approved amount for the single claim) to update the electronic reimbursement account. The notification engine 416 can generate the notification using the electronic report template. The notification can include a balance of the electronic reimbursement account subsequent to updating the electronic reimbursement account with the credit. The notification engine 416 can transmit the one or more data packets carrying the notification generated using the electronic report template to the client device 102*a* via the communications interface 410. For example, the communications interface 210 can transmit the one or more data packets via at least one of an SMS protocol or an electronic mail protocol.

In some embodiments, the notification engine 216 is configured to retrieve an electronic report template configured for the electronic benefits account and configured for transmission via a particular transmission protocol. For example, the notification engine 416 can retrieve an SMS-compatible electronic report template configured to be compatible with SMS protocol, such as an electronic report template having a particular character limit and an organization configured to use plain text. The SMS-compatible electronic report template can be configured to prioritize particular notification information, such as a status of the request to adjudicate the single claim, and/or the total amount of expenditures approved. The notification engine 416 can retrieve an electronic mail-compatible electronic report template configured to be compatible with electronic mail protocol, such as an electronic report template using rich text or HTML. In some embodiments, the notification engine 416 can retrieve multiple electronic report templates compatible with multiple transmission protocols, generate multiple notifications using the multiple transmission protocols, and transmit the multiple notifications via the multiple transmission protocols via the communications interface 410.

In some embodiments, the notification engine 416 is configured to transmit an instruction to the client device 102*a* to trigger an application on the client device 102*a* to launch a user interface (e.g., a prompt, a graphical user interface, etc.) or application program interface configured to display the information provided via the electronic report. The notification engine 416 can be configured to generate the notification to include the instruction and the electronic report. The notification engine 416 can be configured to transmit an application configuration request to the client device 102*a* that causes the client device 102*a* to transmit details regarding the user interface, and the notification engine 416 can configure the electronic report based on the received details. The notification engine 416 can be configured to transmit an application program interface to the client device 102*a* in a format configured for use by the client device 102*a*, causing the client device 102*a* to install the application program interface in order to display the electronic report received in the notification. The notification engine 416 can configure the one or more data packets carrying the notification to cause the client device 102*a* to launch the user interface or application program interface in order to display the electronic report included in the notification.

In some embodiments, the MPTS 408 (e.g., via communication interface 410), receives a request for account information from a client device 102 associated with an electronic account maintained or configured on the MPTS 408. The request for information can include information about a balance of the electronic account, available purses, balance of an individual purse, status of an adjudication associated with the account, status of a reimbursement, status of an update notification, policies associated with purses, policies associated with adjudication, or transaction history. The request can further include authentication information or credentials associated with the request. The authentication information can include network security credentials, such as security certificates or tokens. The authentication information can further include a username, password, two-tier authentication information (e.g., date of birth, cell phone number, verification code sent via text message to cell phone number in profile associated with electronic account). The authentication can include credentials depending on a security level associated with the account information requested. For example, a first security level requiring a first item of authentication information can be associated with information such as a balance of the electronic account, and a second security level requiring both a first item of authentication information and a second item of authentication information can be associated with personal identification information of associated with the account, such as a date of birth or social security number associated with the account. The request can be from a client device such as a smartphone. The request can be sent using a text messaging protocol such as SMS. The MPTS 408 can authenticate a request sent via SMS based on the cell phone number of the device sending the SMS request, and matching the cell phone number with a corresponding number maintained in a profile in database 418 for the electronic account.

Responsive to authenticating or otherwise approving the request, the MPTS 408 can access a data record in database 418 for the electronic account to generate a report with the requested information, or generate a standard report, or generate another preconfigured report. The report can identify the account holder information, available purses, benefits purses, reimbursement purse, subpurses, and available amounts for each purse. The report can further identify a transaction history for the electronic account or each subpurse thereof. The report can further identify or indicate if one or more purses have reached a maximum limit. The report can further include a forecast based on current/previous transaction history that indicates whether the user can likely deplete available resources or exceed maximum limits based on current spending for a time interval. The report can further include information associated with adjudication of a single claim, such as an adjudication status, a credit associated with the adjudication, and/or a reimbursement account updated based on the credit associated with the adjudication.

In some embodiments, the MPTS 408 is configured to determine a balance of the electronic reimbursement account maintained in the database 418. The MPTS 408 can determine the balance prior to transmitting the notification of the credit to the electronic reimbursement account via the communications interface 410. The MPTS 408 can determine that the balance includes the value used to update the electronic reimbursement account, and then transmit the one or more data packets carrying data indicating the notification of the credit responsive to determining that the balance includes the value.

In some embodiments, the MPTS 408 is configured to parse data packets carrying the request to adjudicate the single claim in order to process the request. For example, the one or more data packets carrying the request to adjudicate the single claim can include the request data structure including the first field indicating a merchant ID, the second field indicating the total amount of expenditures, and the third field indicating the electronic benefits account (e.g., an electronic benefits account maintained in the database 418 of the MPTS 408). The MPTS 408 can be configured to parse the one or more packets to identify the electronic benefits account indicated by the third field. The MPTS 408 can be configured to perform a lookup in a benefits account policy database maintained by the MPTS 408 in the database 418 to retrieve the electronic benefits account policy corresponding to the single claim against the electronic benefits account. The MPTS 408 can be configured to apply the electronic benefits account policy using the merchant ID and the total amount of expenditures to adjudicate the single claim. Responsive to the application of the electronic benefits account policy, the MPTS 408 can be configured to generate the indication that the single claim against the electronic benefits account policy is approved for the amount of expenditures qualifying under the electronic benefits account.

The MPTS 408 can be further configured to determine that the amount of expenditures qualifying under the electronic benefits account is different from the total amount of expenditures. For example, the MPTS 408 can be configured to use the determination to identify multiple electronic reimbursement accounts, to provide a qualifying amount to a reimbursement account, or to notify a user associated with the electronic benefits account that the amount of expenditures qualifying under the electronic benefits account is different from the total amount of expenditures. The amount of expenditures qualifying under the electronic benefits account can be less than the total amount of expenditures. For example, the policy engine 412 can determine that a maximum amount of expenditures in a particular time period or billing cycle will be exceeded if the total amount of expenditures is reimbursed, and instead an amount less than the total amount of expenditures is to be reimbursed. The policy engine 412 can determine based on a product category or merchant category of the goods or services associated with the electronic transaction that the goods or services qualify for less than a full reimbursement, such as a percentage reimbursement (e.g., 10%, 25%, 50%, 75%, 80%, 90%, etc.). For example, the policy engine 412 can receive the request to adjudicate the single claim and process the request to extract the product category or merchant category. The policy engine 412 can perform a lookup in the reimbursement policy maintained in the database 420 to determine whether the extracted product category or merchant category corresponds to or qualifies for a particular amount of reimbursement, such as percentage reimbursement.

The amount of expenditures qualifying under the electronic benefits account can be different from the total amount of expenditures based on the policy engine 412 determining that the reimbursement policy is not congruent with the goods or services associated with the electronic transaction, such as if a reimbursement policy associated with the electronic benefits account does not correspond to the goods or services. For example, the reimbursement policy can only apply to goods purchased at a pharmacy based on a prescription, and the electronic transaction can be based on a non-prescription purchase at a pharmacy. The policy engine 412 can process the reimbursement policy to retrieve a list of qualifying goods or services. The policy engine 412 can process the reimbursement policy to retrieve a list of non-qualifying goods or services. The request to adjudicate the single claim can include an identifier of the merchant category and an identifier of the goods or services purchased in the electronic transaction. The policy engine 412 can process the identifiers and perform a lookup in the reimbursement policy maintained in the database 420 to determine whether the goods or services purchased in the electronic transaction correspond to qualifying goods or services by comparing the identifiers to merchant categories and goods or services that are located in the list of qualifying goods or services or in the list of non-qualifying goods or services.

In some aspects, the system of the present solutions implements a combination of the communication interface 410, policy engine 412, electronic account 416, database 420, transaction engine 414, notification engine 416 or claims processor 220 in an innovative, non-conventional or non-routine manner. In some aspects, the system of the present solutions integrates the communication interface 410, policy engine 412, electronic account 416, database 420, transaction engine 414, notification engine 416 or claims processor 220 in an innovative, non-conventional or non-routine manner to implement the improved functionality, performance and operation of the present solution. In some aspects, the system of the present solutions integrates the communication interface 410, policy engine 412, electronic account 416, database 420, transaction engine 414, notification engine 416 or claims processor 220 in an innovative, non-conventional and/or non-routine manner to more efficiently and effectively use computing and networking resources. The communication interface 410, policy engine 412, electronic account 416, database 420, transaction engine 414, notification engine 416 or claims processor 220 are integrated in an innovative, nonconventional manner to mitigate, reduce, prevent, or resolve the technical problems of adjudicating a single claim in real-time and notifying a user of the result. The communication interface 410, policy engine 412, electronic account 416, database 420, transaction engine 414, notification engine 416 or claims processor 220 integrated in the innovative, non-conventional manner address at least these technical problems by determining, responsive to the communication interface receiving the request to adjudicate the single claim, that the single claim against the electronic benefits account is approved for an amount of expenditures qualifying under the electronic benefits account; identifying, via a configuration of the electronic benefits account maintained by the server, a reimbursement policy of the electronic benefits account specifying an ordered list of account destinations for benefits account reimbursements; determining, via application of the reimbursement policy to the single claim, an electronic reimbursement account as a destination for a benefits account reimbursement, the electronic reimbursement account configured to allow transactions for non-qualifying benefits account expenditures; updating the electronic reimbursement account maintained by the server with a value corresponding to a credit for the approved amount for the single claim; generating, responsive to the request adjudicated by the server and the update by the policy engine of the electronic reimbursement account with the value corresponding to the credit for the approved amount for the single claim, a notification identifying the update to the electronic reimbursement account corresponding to the credit; and transmitting, via the computer network to a device of the electronic benefits account, a first one or more packets carrying data indicating the notification of the credit.

Figure 5:
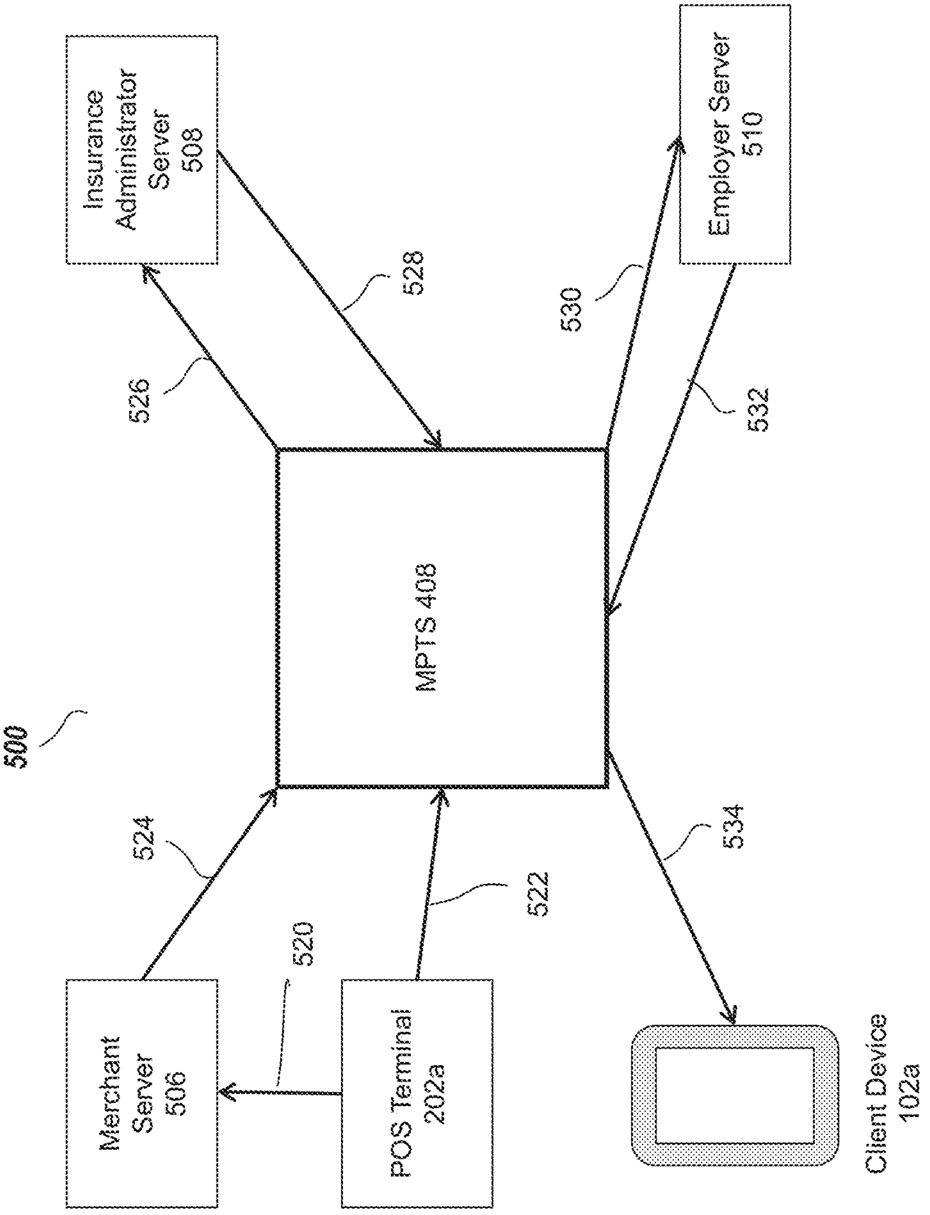
FIG. 5 is a block diagram depicting an embodiment of a system for organizing and communicating data transmissions for conducting electronic transactions via a computer network.

Referring now to FIG. 5, a flow diagram depicting an embodiment of an electronic computer network 500 using the MPTS 408 is shown. The MPTS 408 can include any of the components or modules depicted in FIG. 4, such as the MPTS 120, and can perform the functions of the MPTS 120 and the components or modules depicted in FIG. 4. The electronic computer network 500 illustrates how an electronic transaction is received by the MPTS 408 and used by the MPTS 408 to cause transmission of a notification to the client device 102*a*. The electronic transaction occurs at the POS terminal 202*a*, such as when the participant swipes their card at the POS terminal 202*a*. The electronic computer network 500 is shown to include the MPTS 408 in electronic communication with specific electronic entities including the client device 102*a*, the POS terminal 202*a*, a merchant server 506, an insurance administrator server 508, and an employer server 510.

While FIG. 5 depicts the insurance administrator server 508 and the employer server 510 as being remote from the MPTS 408, in some embodiments, the MPTS 408 can include the insurance administrator server 508 and/or the employer server 510. The MPTS 408 can maintain the insurance administrator server 508 and/or the employer server 510. The MPTS 408 can include local modules of the insurance administrator server 508 and/or the employer server 510 that are maintained by the MPTS 408 and then synchronized or mirrored to the insurance administrator server 508 and/or the employer server 510.

In some embodiments, the MPTS 408 includes interfaces configured to receive and process electronic data transmissions from the electronic entities. Each interface can be configured to authenticate the data transmissions, such as by using security credentials. Each of the electronic entities can also include an interface configured to receive electronic data transmissions from the MPTS 408, and the electronic entity interfaces can be configured to authenticate the data transmissions from the MPTS 408, such as by using security credentials. The MPTS 408 can be configured to transmit interface software to the electronic entities to cause the electronic entities to be compatible with the MPTS 408.

In some embodiments, responsive to the electronic transaction at the POS terminal 202*a*, a request to adjudicate the single claim 520 is received at the MPTS 408 via the merchant server 506 as one or more data packets 524. The MPTS 408 can include a merchant server-facing interface configured to receive the request 520 from the merchant server 506 as the one or more data packets 524, and extract data from the one or more data packets 524 into a format for the MPTS 408 to process. For example, the one or more data packets 524 can carry data identifying a merchant category of the merchant, the electronic benefits account maintained and configured on the MPTS 408, and a total monetary amount of the electronic transaction; the MPTS 408 can parse the one or data packets 524 to extract the carried data. The one or more data packets 524 can include a request data structure having a first field indicating a merchant ID, a second field indicating a total amount of expenditures, and a third field indicating the electronic benefits account. The MPTS 408 can parse the one or more data packets to identify the electronics benefit account indicated via the third field; perform, with the identification of the electronic benefits account, a lookup in the benefits account policy database 420 maintained by the MPTS 408; retrieve, responsive to the lookup, the electronic benefits account policy corresponding to the single claim against the electronic benefits account; and generate, responsive to application of the electronic benefits account policy using the merchant ID and the total amount of expenditures, the indication that the single claim against the electronic benefits account is approved for the amount of expenditures qualifying under the electronic benefits account.

In some embodiments, a request to adjudicate the single claim 522 is received at the MPTS 408 directly from the POS terminal 202*a*. The MPTS 408 can include a POS terminal-facing interface configured to receive the request 522 from the POS terminal 202*a* as one or more data packets, and extract data from the one or more data packets into a format for the MPTS 408 to process.

In some embodiments, responsive to receiving the one or more data packets 524 of the request 520 or the one or more data packets of the request 522, the MPTS 408 executes the policy engine 412 using a policy maintained in the database 420 to determine that the single claim against the electronic benefits account (e.g., an electronic benefits account maintained in the database 418) is approved for an amount of expenditures qualifying under the electronic benefits account. The MPTS 408 can process the one or more data packets 524 (or the one or more data packets of the request 522) to extract information such as identification information associated with a user of the electronic benefits account, transaction information such as identification information associated with the merchant of the merchant server 506, an amount of expenditures associated with the electronic transaction that occurred at the POS terminal 202*a*, a category of the goods or services associated with the expenditures, and other information for adjudicating the single claim. The MPTS 408 can process the extracted information to acquire identification information corresponding to an appropriate policy maintained in the database 420, perform a lookup in the database 420 to access the appropriate policy, and execute the policy engine 412 using the appropriate policy to determine that the single claim against the electronic benefits account is approved for an amount of expenditures qualifying under the electronic benefits account.

In some embodiments, responsive to receiving the one or more data packets 524 of the request 520 or the one or more data packets of the request 522, the MPTS 120 transmits an adjudication request 526 for adjudicating the single claim to an insurance administrator server 508. The adjudication request 526 can be provided as one or more data packets including payload information such as the information extracted from the one or more data packets. The MPTS 408 can include an insurance administrator server-facing interface configured to receive a response 528 to the adjudication request 526 from the insurance administrator server 508. The response 528 can include information specific to an insurance administrator managing the insurance administrator server 508, such as adjudication policies, identification information for electronic benefits accounts administered by the insurance administrator, or reporting requirements of the insurance administrator for reporting expenditure approvals.

The adjudication request 526 can be configured to cause the insurance administrator server 508 to transmit the response 528 to the adjudication request 526. The adjudication request 526 can include a request for the insurance administrator server 508 to adjudicate the single claim, and the response 528 can indicate whether the expenditures of the single claim have been approved, or provide another indication of an adjudication status of the single claim.

The adjudication request 526 can be a request configured to cause the insurance administrator server 508 to transmit a policy with the response 528 so that the MPTS 408 can adjudicate the single claim using the policy engine 412 based on the transmitted policy. The response 528 can be received as one or more data packets, and the MPTS 408 can extract the policy from the response 528 and update the policies maintained in database 420 of the MPTS 408 based on the extracted policy. The MPTS 408 can compare the extracted policy from the response 528 to the policies maintained in the database 420, verify a version status of the extracted policy against a similar policy maintained in the database 420 (e.g., a similar policy having a matching version history), and update the policy maintained in the database 420 responsive to determining that the policy engine maintained in the database 420 is out of date.

In some embodiments, responsive to receiving the one or more data packets 524 of the request 520 or the one or more data packets of the request 522, the MPTS 408 transmits an adjudication request 530 for adjudicating the single claim to an employer server 510. The adjudication request 530 can be provided as one or more data packets including payload information such as the information extracted from the one or more data packets. The MPTS 408 can include an employer server-facing interface configured to receive a response 532 to the adjudication request 530 from the employer server 508. The response 532 can include information specific to an employer funding managing the employer server 510, such as adjudication policies, identification information for electronic benefits accounts funded or otherwise administered by the employer, tax information, or reporting requirements of the employer for reporting expenditure approvals.

The adjudication request 526 can be configured to cause the insurance administrator server 508 to transmit the response 528 to the adjudication request 526. The adjudication request 526 can include a request for the insurance administrator server 508 to adjudicate the single claim, and the response 528 can indicate whether the expenditures of the single claim have been approved, or provide another indication of an adjudication status of the single claim.

The adjudication request 530 can be a request configured to cause the employer server 510 to transmit a policy with the response 532 so that the MPTS 408 can adjudicate the single claim using the policy engine 412 based on the transmitted policy. The response 532 can be received as one or more data packets, and the MPTS 408 can extract the policy from the response 532 and update the policies maintained in database 420 of the MPTS 408 based on the extracted policy. The MPTS 408 can compare the extracted policy from the response 532 to the policies maintained in the database 420, verify a version status of the extracted policy against a similar policy maintained in the database 420 (e.g., a similar policy having a matching version history), and update the policy maintained in the database 420 responsive to determining that the policy engine maintained in the database 420 is out of date.

In some embodiments, responsive to receiving a response 528 or 532 indicating that the single claim against the electronic benefits account is approved, or responsive to the policy engine 412 determining that the single claim against the electronic benefits account is approved, the policy engine 412 is executed to identify, via a configuration of the electronics benefit account maintained by the MPTS 408, the reimbursement policy of the electronic benefits account specifying an ordered list of account destinations for benefits account reimbursements. The policy engine 412 can be executed to determine, via application of the reimbursement policy to the single claim, an electronic benefits account maintained in database 418 as a destination for a benefits account reimbursement, the electronic reimbursement account configured to allow transactions for non-qualifying benefits account expenditures. The policy engine 412 can be executed to update the electronic reimbursement account maintained by the MPTS 408 with a value corresponding to a credit for the approved amount of the single claim.

In some embodiments, the MPTS 408 is configured to generate a notification identifying the update to the electronic reimbursement account maintained by the MPTS 408 corresponding to the credit, and transmit, via the electronic computer network 500, one or more notification data packets 534 carrying data indicating the notification of the credit to the client device 102*a*. The MPTS 408 can be configured to transmit the one or more notification data packets 534 to the client device 102*a* via the communications interface 510.

In some embodiments, the MPTS 408 is configured to perform a lookup in the database 420 for a contact protocol for the user associated with the electronic reimbursement account, identify the appropriate contact protocol for the user, and transmit the one or more notification data packets 534 to the client device 102*a* using the appropriate contact protocol for the user. The MPTS 408 can perform the lookup by querying the user profiles maintained in the database 420 for the contact protocol based on a user identity extracted from the request for adjudication of the single claim 522 or the one or more data packets 524. The MPTS 408 can identify an electronic mail protocol as an appropriate contact protocol for the user, and transmit the one or more notification data packets 534 to the client device 102*a* using an electronic mail address of the electronic mail protocol associated with the client device 102*a*. The MPTS 408 can be configured to transmit the one or more notification data packets 534 to the client device 102*a* in real time. The MPTS 520 can be configured to transmit the one or more notification data packets 534 to the client device 102*a* within a predetermined time interval of receiving data transmissions such as the request 522, the one or more data packets 524, the response 528, or the response 532.

Figure 6:
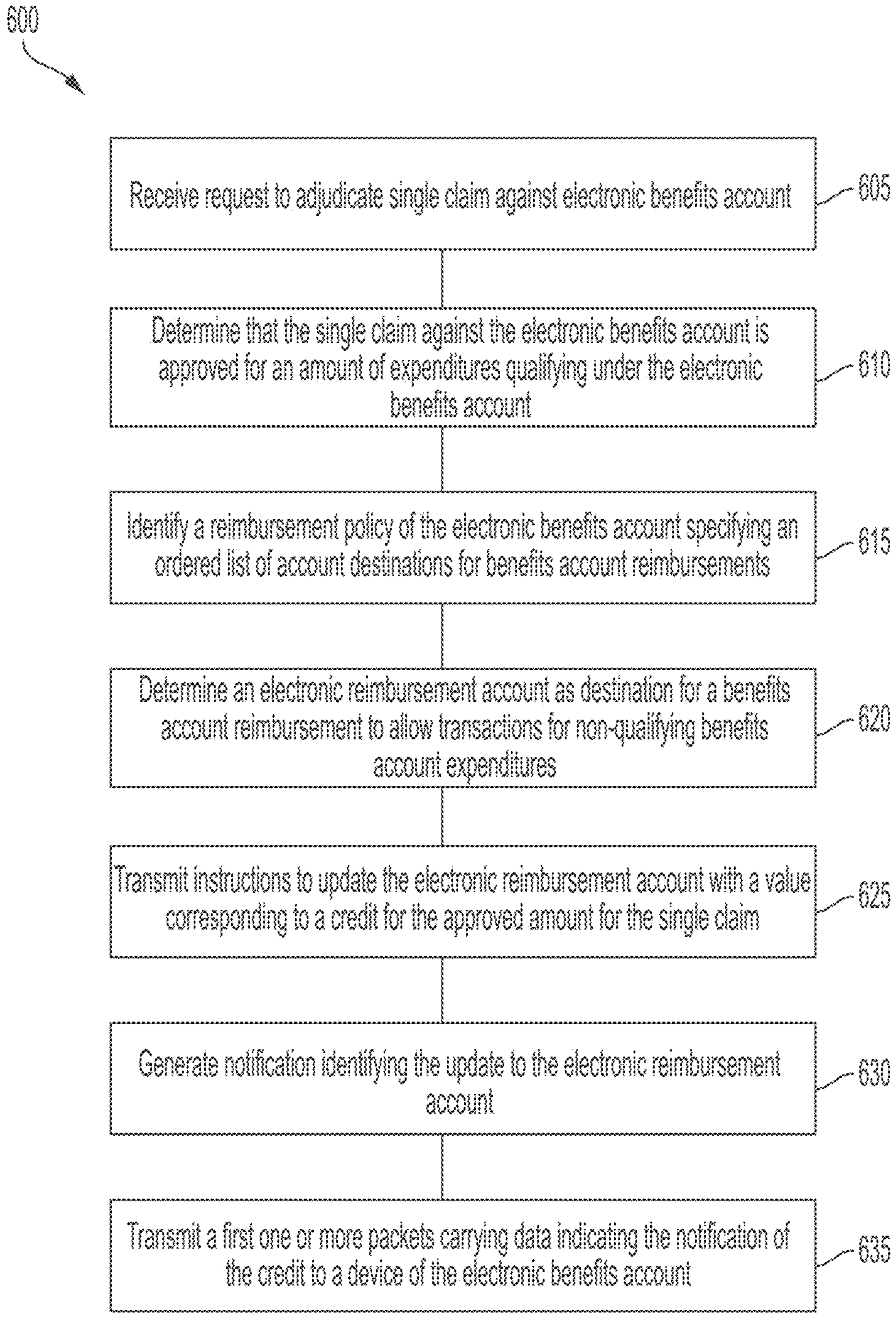
FIG. 6 is a flow diagram depicting an embodiment of a method of conducting electronic transactions.

Referring now to FIG. 6, a flow diagram depicting an embodiment of a method 600 of conducting electronic transactions via a computer network is shown. The method can be performed by one or more component or module of system 400, the MPTS 408, or one or more component or module depicted in FIGS. 1A-1D. In brief overview, at step 605, a server of a multipurse transaction system receives a request to adjudicate a single claim against an electronic benefits account. At step 610, the server determines that the single claim against the electronic benefits account is approved for an amount of expenditures qualifying under the electronic benefits account. At step 615, the server identifies a reimbursement policy of the electronic benefits account specifying an ordered list of account destinations for benefits account reimbursements. At step 620, the server determines an electronic reimbursement account as a destination for a benefits account reimbursement to allow transactions for non-qualifying benefits account expenditures. At step 625, the server transmits instructions to update the electronic reimbursement account with a value corresponding to a credit for the approved amount for the single claim. At step 630, the server generates a notification identifying the update to the electronic reimbursement account. At step 635, the server transmits a first one or more packets carrying data indicating the notification of the credit to a device of the electronic benefits account.

Still referring to FIG. 6, and in further detail, a server of a multipurse transaction system receives a request to adjudicate a single claim against an electronic benefits account at step 605. In some aspects, step 605 comprises an innovative, non-conventional or non-routine way to operate or perform the functionality of the present solution. In some aspects, step 605 is implemented to address the technical problems and challenges of prior systems not deploying the present solution. In some aspects, step 605 is implemented to make or cause more effective and efficient use of computing and networking resources.

The server can include one or more processors. The server can include a communications interface for receiving the request. One or more data packets carrying data indicating the request can be received. The request can be received via a computer network using a networking protocol. The request can be generated by a device at a merchant, such as a POS Terminal. The data packets can include header information and payload information. The header information can include, e.g., TCP header information that can facilitate the routing and transmission of the data packet. The payload information can include data related to, describing, defining, associated with or otherwise about the request to adjudicate the single claim, including information regarding the electronic transaction occurring between the POS terminal, merchant, or customer. The one or more data packets can include data identifying a merchant category of the merchant, an electronic benefits account maintained and configured on the server, and a total monetary amount of the electronic transaction. The one or more data packets can include a request data structure having a request data structure having a first field including a merchant ID, a second field indicating a total amount of expenditures, and a third field indicating the electronic benefits account. The data packets can further include an electronic account associated with a multipurse card swiped at a POS terminal of a merchant conducting the transaction. The multipurse card can be a plastic card (e.g., debit card or debit card with a magnetic stripe or RFID), or be an electronic card stored on a telecommunications device which transmits an electronic account identifier corresponding to the electronic card via a wireless technology (e.g., Bluetooth, or NFC). The POS terminal can generate or obtain information that allows the server to conduct the transaction, encapsulate or process the information using a protocol to generate data packets, and transmit the data packets in a secure manner over a network to the server for further processing. The server can initiate a claim adjudication process responsive to receiving the one or more data packets.

At step 610, the server determines that the single claim against the electronic benefits account is approved for an amount of expenditures qualifying under the electronic benefits account. In some aspects, step 610 comprises an innovative, non-conventional or non-routine way to operate or perform the functionality of the present solution. In some aspects, step 610 is implemented to address the technical problems and challenges of prior systems not deploying the present solution. In some aspects, step 610 is implemented to make or cause more effective and efficient use of computing and networking resources. The server can execute a policy engine maintained by the server to perform the determination. The server can perform the determination responsive to the communication receiving the request to adjudicate the single claim. In some embodiments, the server identifies a merchant category of the merchant from which the request received, and executes the policy engine using a policy applying to the identified merchant category to perform the determination. In some embodiments, the server parses the one or more data packets to identify the electronic benefits account, and performs a lookup in a benefits account policy database maintained by the server using the identification of the electronic benefits account to retrieve a benefits account policy corresponding to the single claim against the electronic benefits account.

The server can parse, process, or otherwise identify, from the header information or payload information of the one or more data packets, information about the request to adjudicate the single claim, including information regarding the electronic transaction occurring between the POS terminal, merchant, or customer. The server can identify the merchant category, the merchant ID, the electronic benefits account, and/or the total amount of expenditures.

At step 615, the server identifies a reimbursement policy of the electronic benefits account specifying an ordered list of account destinations for benefits account reimbursements. In some aspects, step 615 comprises an innovative, non-conventional or non-routine way to operate or perform the functionality of the present solution. In some aspects, step 615 is implemented to address the technical problems and challenges of prior systems not deploying the present solution. In some aspects, step 615 is implemented to make or cause more effective and efficient use of computing and networking resources.

The policy engine of the server can perform the identification via a configuration of the electronic benefits account maintained by the server. The policy engine can parse information regarding the electronic transaction or the request to adjudicate the single claim from the one or more data packets, such an identity of the user of the electronic benefits account, to identify the reimbursement policy. The policy engine can parse the configuration of the electronic benefits account to identify the reimbursement policy associated with the electronic benefits account. For example, the electronic benefits account configuration can include a data structure including a link or association field for associating the electronic benefits account to one or more electronic reimbursement accounts. For example, an insurance administrator or employer can provide both the electronic benefits account and an associated electronic reimbursement account. The ordered list can include one or more account destinations ordered by priority, such as an ordered list specifying that an electronic benefits purse has highest priority for reimbursement, an electronic cash purse has second-highest priority for reimbursement, and a paper check mailed to a postal address has third-highest priority for reimbursement.

At step 620, the server applies the reimbursement policy to the single claim to determine an electronic reimbursement account as a destination for a benefits account reimbursement. In some aspects, step 620 comprises an innovative, non-conventional or non-routine way to operate or perform the functionality of the present solution. In some aspects, step 620 is implemented to address the technical problems and challenges of prior systems not deploying the present solution. In some aspects, step 620 is implemented to make or cause more effective and efficient use of computing and networking resources. The electronic reimbursement account is configured to allow transactions for non-qualifying benefits account expenditures. The policy engine of the server can perform the application and can perform the determination. The policy engine can process the reimbursement policy identified at step 615 to extract an identifier of the electronic reimbursement account that is the destination for the benefits account reimbursement. The policy engine can process the ordered list to identify the highest-priority account destination for reimbursement. The policy engine can process the ordered list to identify the high-priority account destination for reimbursement associated with the electronic benefits account.

At step 625, the server transmits instructions to update the electronic reimbursement account with a value corresponding to a credit for the approved amount for the single claim. In some aspects, step 625 comprises an innovative, non-conventional or non-routine way to operate or perform the functionality of the present solution. In some aspects, step 625 is implemented to address the technical problems and challenges of prior systems not deploying the present solution. In some aspects, step 625 is implemented to make or cause more effective and efficient use of computing and networking resources. The server can maintain the electronic reimbursement account in a database and cause the maintained electronic reimbursement account to be updated. The electronic reimbursement account can be maintained by a remote server such as a financial institution server, an insurance administrator server, or an employer server, and the transmitted instructions can cause the remote server to update the electronic reimbursement account with the value corresponding to the credit for the approved amount.

In some embodiments, the server generates electronic reports regarding the electronic transaction and the update of the electronic reimbursement account. The server can retrieve an electronic report template configured for the electronic benefits account responsive to transmitting the instructions including the value to update the electronic reimbursement account. The server can generate the notification using the electronic report template. The notification can include a balance of the electronic reimbursement account subsequent to updating the electronic reimbursement account with the credit. The server can transmit the one or more data packets carrying the notification generated using the electronic report template to the client device. For example, the server can transmit the one or more data packets via at least one of an SMS protocol or an electronic mail protocol. The notification can cause the client device to launch or execute an interface (e.g., a graphical user interface or prompt) to display an electronic report based on the electronic report template.

In some embodiments, the server retrieves an electronic report template configured for the electronic benefits account and configured for transmission via a particular transmission protocol. For example, the server can retrieve an SMS-compatible electronic report template configured to be compatible with SMS protocol, such as an electronic report template having a particular character limit and an organization configured to use plain text. The SMS-compatible electronic report template can be configured to prioritize particular notification information, such as a status of the request to adjudicate the single claim, and/or the total amount of expenditures approved. The server can retrieve an electronic mail-compatible electronic report template configured to be compatible with electronic mail protocol, such as an electronic report template using rich text or HTML. In some embodiments, the server can retrieve multiple electronic report templates compatible with multiple transmission protocols, generate multiple notifications using the multiple transmission protocols, and transmit the multiple notifications via the multiple transmission protocols.

In some embodiments, the server performs a lookup in a profile database of the electronic benefits account. The lookup identifies the client device configured to receive the notifications for the electronic benefits account. For example, the profile database can include a preferred client device defined by a user of the electronic benefits account. The server retrieves from the profile database a unique identifier for the device and a notification mode. The notification mode includes at least one of an SMS protocol or an electronic mail protocol. The server configures the one or more packets carrying the data indicating the notification based on the notification mode.

At step 630, the server generates a notification identifying the update to the electronic reimbursement account. In some aspects, step 630 comprises an innovative, non-conventional or non-routine way to operate or perform the functionality of the present solution. In some aspects, step 630 is implemented to address the technical problems and challenges of prior systems not deploying the present solution. In some aspects, step 630 is implemented to make or cause more effective and efficient use of computing and networking resources. The notification can include an indication of the electronics benefit account, and indication of the electronic reimbursement account, the value of the credit, an update status indicating whether the update was successful, a report of the adjudication of the single claim, a balance of the electronic reimbursement account, an indication of the electronic transaction, the merchant ID, the POS terminal at which the electronic transaction occurred, and/or the amount of expenditures approved by adjudication of the single claim. In some embodiments, responsive to initiating the claim adjudication process, the sever generates a notification of the initiation.

In some embodiments, responsive to the application of the electronic benefits account policy using the merchant ID and the total amount of expenditures, the server generates the indication that the single claim against the electronic benefits account is approved for the amount of expenditures qualifying under the electronic benefits account. For example, based on the electronic benefits account policy, the server can determine that the merchant falls within an approved network of the electronic benefits account. The server can perform a lookup in a database that can include a list of approved merchants and can include a list of non-approved merchants. The server can compare the merchant ID to the list of approved merchants. Responsive to the merchant ID corresponding to an entry in the list of approved merchants, the server can determine that the merchant is in the approved list. In some embodiments, the server can compare the merchant ID to both the list of approved merchants and the list of non-approved merchants; if the merchant ID does not correspond to an entry in either list, then the server can generate an indication that further information is necessary to adjudicate the single claim. The server can determine that the total amount of expenditures is less than a difference between a current balance of the electronic benefits account and a maximum balance of the electronic benefits account, such that approving the total amount of expenditures will not exceed the maximum balance. For example, the server can process the electronics benefit account to identify the current balance and maximum balance, and compare the sum of the current balance and the total amount of expenditures to the maximum balance to determine that approving the total amount of expenditures will not exceed the maximum balance.

In some embodiments, the server determines that the amount of expenditures qualifying under the electronic benefits account is different from the total amount of expenditures. The server can determine that the amount of expenditures qualifying is different from the total amount of expenditures based on the case that approving the total amount of expenditures would exceed a maximum balance of the electronic benefits account. The server can process the electronic benefits account to identify the current balance and maximum balance, and compare the sum of the current balance and the total amount of expenditures to the maximum balance to determine that approving the total amount of expenditures would exceed the maximum balance. The server can determine that an amount of expenditures qualifying under the electronic benefits account is the amount that would reach the maximum balance without exceeding the maximum balance. The server can be configured to update multiple electronic reimbursement accounts based on expenditures qualifying under the electronic benefits account and also using the electronic reimbursement configured to allow transactions for non-qualifying benefits expenditures. The server can determine that that the maximum amount of expenditures in a particular time period or billing cycle will be exceeded if the total amount of expenditures is reimbursed, and instead the server causes an amount less than the total amount of expenditures to be reimbursed. The server can determine based on a product category or merchant category of the goods or services associated with the electronic transaction that the goods or services qualify for less than a full reimbursement, such as a percentage reimbursement. For example, the server can process the request to adjudicate the single claim to extract the product category or merchant category, and perform a lookup in the database maintaining the reimbursement policy to identify a list of qualifying goods or services and/or a list of qualifying merchants, in which the lists are associated with a less than full reimbursement such as a percentage reimbursement. The server can compare the product category or merchant category to the list of qualifying goods or services or the list of qualifying merchants to determine whether to apply a less than full reimbursement for the request to adjudicate the single claim.

The amount of expenditures qualifying under the electronic benefits account can be different from the total amount of expenditures based on the server determining that the reimbursement policy is not congruent with the goods or services associated with the electronic transaction, such as if a reimbursement policy associated with the electronic benefits account does not correspond to the goods or services. For example, the reimbursement policy can only apply to goods purchased at a pharmacy based on a prescription, and the electronic transaction can be based on a non-prescription purchase at a pharmacy. The server can process the reimbursement policy to retrieve a list of qualifying goods or services. The server can process the reimbursement policy to retrieve a list of non-qualifying goods or services. The request to adjudicate the single claim can include an identifier of the merchant category and an identifier of the goods or services purchased in the electronic transaction. The server can process the identifiers and perform a lookup in the reimbursement policy to determine whether the goods or services purchased in the electronic transaction correspond to qualifying goods or services by comparing the identifiers to merchant categories and goods or services that are located in the list of qualifying goods or services or in the list of non-qualifying goods or services.

At step 635, the server transmits one or more packets carrying data indicating the notification of the credit to a device of the electronic benefits account. In some aspects, step 635 comprises an innovative, non-conventional or non-routine way to operate or perform the functionality of the present solution. In some aspects, step 635 is implemented to address the technical problems and challenges of prior systems not deploying the present solution. In some aspects, step 635 is implemented to make or cause more effective and efficient use of computing and networking resources. The server can transmit the one or more packets in real time. The server can transmit the one or more packets within a predetermined time interval of a preceding action, such as receiving the request to adjudicate the single claim, receiving one or more packets generated by a merchant device to conduct an electronic transaction at the merchant, and/or generating the notification of initiation of the single claim adjudication process.

In some embodiments, prior to transmitting the one or more packets carrying the data indicating the notification of the credit, the server determines a balance of the electronic reimbursement account. For example, the server can process an identifier of the electronic reimbursement account, and perform a lookup in the database maintaining the electronic reimbursement account using the identifier to retrieve the balance of the electronic reimbursement account. The balance includes the value used to update the electronic reimbursement account. The server transmits the one or more data packets responsive to determining that the balance includes the value. Accordingly, the server is able to provide confirmation in the notification that the electronic reimbursement account has been updated with the credit.

In some embodiments, merchant category can refer to a merchant category code ("MCC"). Table 1 is an example mapping of merchant categories to purses in accordance with an embodiment:

TABLE 1

Example mapping of merchant categories to purses in accordance with an embodiment.

| MCC | Merchant Category | Purse |
|---|---|---|
| 8099 | Medical Services | Benefits Purse |
| 8062 | Hospitals | Benefits Purse |
| 8042 | Optometrists | Benefits Purse |
| 7832 | Motion Picture Theaters | Cash Purse |
| 7922 | Theatrical Ticket Agencies | Cash Purse |

In some aspects, the methods of the present solutions implements a combination of steps in an innovative, non-conventional or non-routine manner. In some aspects, the method of the present solution combines the steps of FIG. 6 in an innovative, non-conventional and/or non-routine combination to implement the improved functionality, performance and operation of the present solution. In some aspects, the method 600 of the present solution combines the steps of FIG. 6 in in an innovative, non-conventional or non-routine manner to more efficiently and effectively use computing and networking resources. In some aspects, the method 600 of the present solution provides innovative, non-conventional or non-routine ordered combination of steps.

D. Electronic Transaction Enforcement Portal System

The systems and methods of the present solution are directed to the technical problems and challenges of implementing the functionality of resource allocation in electronic transaction portal based technology and platforms. Existing resource allocation based technologies and platforms do not effectively and efficiently make use of the computing and network resources deployed for electronic transaction portals. Without implementing such functionality, existing electronic transaction portal based technologies and platforms have the problems of excessive server-client requests and responses, processing delays, increase bandwidth usage, or erroneous resource allocations.

The systems and methods of the present solution are directed to the improvement of the performance and operation of the electronic transaction portal based technology and platform and computing and networking resource used by such electronic transaction portals. In some aspects, the present solution improves and enhances the implemented functionality of the electronic transaction portal based technology and platform implemented on, integrated with and inherently tied to the processor, memory, network and computing resources of one or more computing devices. In some aspects, the present solution more effectively performs the functionality of the electronic transaction portal technology and platform thereby making and causing more effective use of the computing and networking resources to achieve the improved functionality of the present solution. The same computing and network resources used by such electronic transaction portal technology and platform will provide increased and improved functionality with implementation of the present solution.

In some aspects, the present solution more efficiently uses the computing and networking resources to implement the improved functionality of the electronic transaction based technology and platform. For example, systems and methods of the present solution are directed to managing or conducting electronic transactions using an electronic transaction portal. Systems and methods of the present solution can manage the electronic transaction portal to prevent single electronic benefits account transactions from exceeding threshold limits for contributions. Systems and methods of the present solution can use a multi-purse transaction system that maintains an electronic account having multiple purses. An electronic account can be maintained by a server and include a database in memory or a storage device. The electronic account can include sub structures or fields. The electronic account can include multiple purses that are configured with one or more rules, parameters, restrictions, or policies. For example, the electronic account can include a first purse that is configured as a benefits a purse. A purse configured for benefits can refer to a purse that is configured for transactions made using a tax benefit account such as a flexible spending account ("FSA"), Dependent Care Account ("DCA"), Transport Account (e.g., for parking or monthly passes). In some embodiments, the FSA, DCA, and Transport Account can be further separated into sub-purses within the benefits purse of the electronic account. A flexible spending account, or flexible spending arrangement, can refer to a tax-advantaged financial account that can be set up through a cafeteria plan of an employer and used to set aside a portion of earnings to pay for qualified expenses as established in the cafeteria plan. Types of FSA can include medical expense FSA, health FSA, health savings account (HSA), health reimbursement account (HRA), health reimbursement plan (HRP), etc. Qualified expenses can include, for example, medical expenses, dependent care, dental expenses, vision expenses, parking, monthly passes, etc. An FSA can be tax-advantaged because funds deducted from an employee's account and transferred to the FSA is not subject to payroll taxes, resulting in payroll tax savings.

A client device can initiate an electronic transaction, responsive to receiving user input via a user interface, to transfer funds to an electronic benefits account, or an entity such as server of an employer, an insurance administrator, or a financial institution can manually, periodically, and/or automatically make the electronic transaction. The transaction can be associated with information such as an FSA account identifier, time stamp, entity identifier, and transaction amount. This information can be provided in real-time to a transaction repository. The electronic transaction portal can receive electronic transaction requests from a plurality of electronic client devices corresponding to a heterogeneous plurality of electronic funding sources. The electronic funding sources can include an automatic clearinghouse ("ACH"), individual checking, bill pay, and savings accounts, credit card accounts, employer payroll (e.g., for funding Roth IRA, cafeteria, FSA, etc.), and other electronic funding sources. The heterogeneous electronic funding sources can be provided custom electronic benefits account transaction application programming interfaces to facilitate enforcement of a single transaction request from one of the electronic funding sources. The electronic transaction portal can transfer funds, such as when the electronic transaction request is generated based on transaction types such as point of sale transactions, manual transactions, and deposit transactions. The electronic transaction portal can maintain daily net general ledger files using enforcement rules, and transmit instructions to an electronic entity (e.g., a server) of the relevant financial institution that causes the financial institution server to transfer funds internally.

When multiple heterogeneous electronic funding sources initiate electronic funding transactions, the electronic funding transactions might all post to the electronic benefits account, even if the electronic funding transactions exceed a threshold limit for the electronic benefits account, requiring a participant associated with the electronic benefits account to withdraw excess contributions or later engage in complex tax management procedures. The present solution is configured to apply enforcement rules executed by a transaction enforcement portal system, on a single transaction basis, in order to prevent the contribution threshold limit from being exceeded even when multiple transactions are received from a plurality of heterogeneous electronic funding sources. The present solution provides the transaction enforcement portal system that receives indications of electronic transaction requests and executes enforcement rules based on the electronic transaction requests in order to deny transaction requests that would otherwise cause the threshold limit to be exceeded.

For example, if a participant initiates a single electronic transaction request to transfer funds to a flexible spending account (e.g., an HSA) from an electronic checking account, the present solution can receive the electronic transaction request, and parse the request to identify a transaction amount and the flexible spending account. The present solution can determine whether authorizing the transaction would cause a threshold limit (e.g., an IRS-established threshold limit) for contributions to the flexible spending account to be exceeded, before the transaction is posted to the flexible spending account. The present solution can prevent threshold limits to be exceeded in real-time, overcoming difficulties caused when the participant is not aware that the threshold limit is exceeded until the transaction is posted, often several days after the transaction is requested, at which point complex reimbursement procedures may be required to avoid tax penalties.

Figure 7:
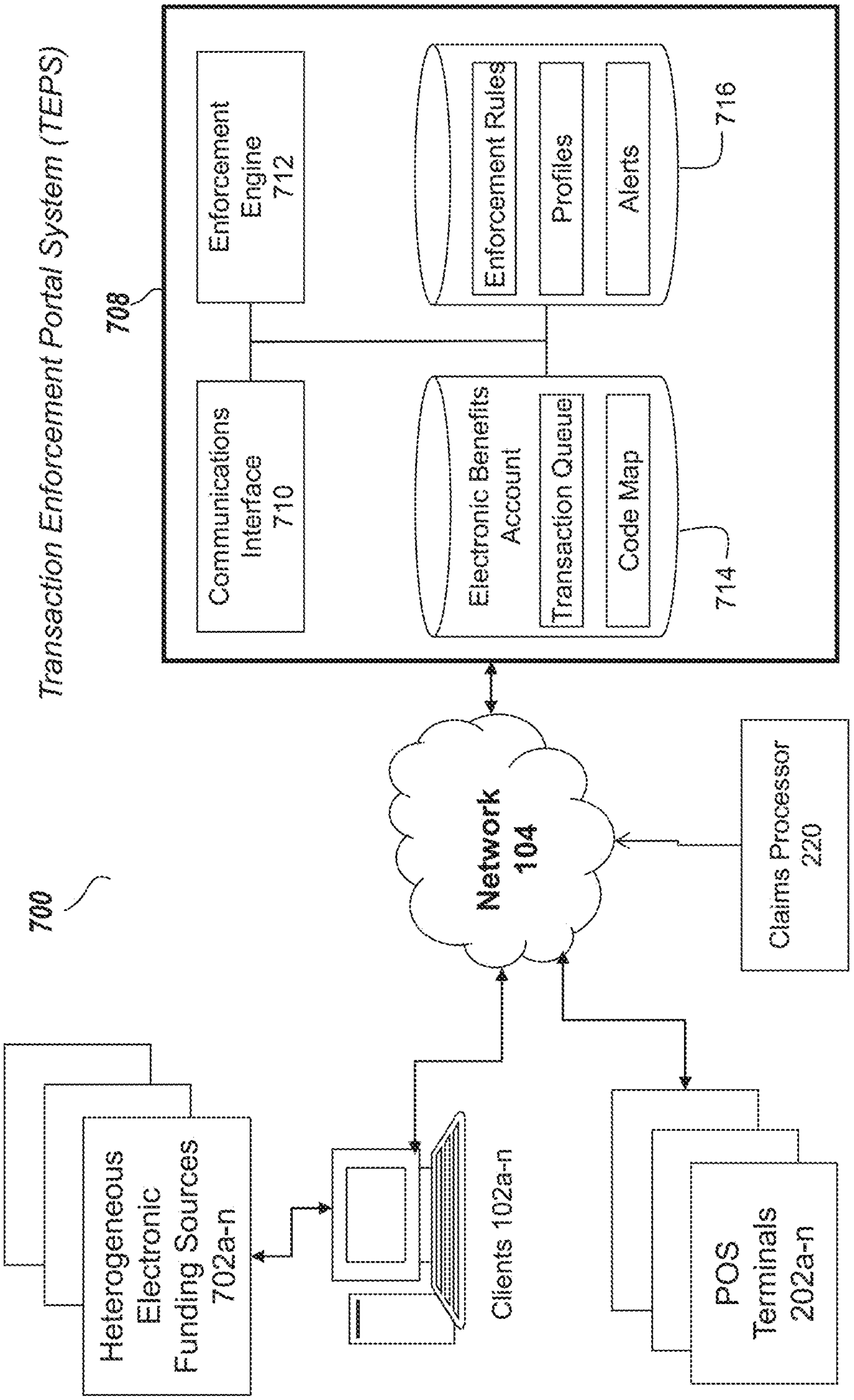
FIG. 7 is a block diagram depicting an embodiment of an electronic transactional portal system for funding electronic benefits accounts.

Referring now to FIG. 7, a block diagram depicting an embodiment of a system 700 comprising a Transaction Enforcement Portal System (TEPS) is shown. In brief overview, the system 700 includes a transaction enforcement portal system 708 ("TEPS") that can receive and/or transmit data via a network 104 with clients 102*a-n* and POS terminals 202*a-n*. The system 700 can include or interact with one or more clients 102*a-n* (or client device 102), and one or more point-of-sale (POS) terminals 202*a-n* (or POS terminal 202). The TEPS 708 can include a communications interface 710 that is configured with one or more communications ports, application programming interfaces, network protocols (e.g., TCP/IP), authentication protocols, or security protocols (e.g., SSL). The TEPS 708 can include an enforcement engine 712 that is configured to prevent an electronic transaction from exceeding an IRS threshold limit for an electronic benefits account. The TEPS 708 can include one or more databases or data structures that store information to facilitate the systems and methods of the present solution, such as database 714 and database 716. The database 714 (or electronic benefits account) can include an electronic account maintained or configured on the TEPS 708 that includes one or more purses, such as a benefits purse and a cash purse. The database 714 can include a transaction queue indicating real-time electronic transactions of the electronic benefits account, and a code map mapping electronic transactions to a point in time, such as a year. The database 716 can include one or more enforcement rules, profiles, or alerts.

The TEPS 708, communications interface 710, and enforcement engine 712 can each include one or more processing units or other logic devices such as programmable logic array engines, modules, or circuitry designed and constructed to facilitate managing security on a network infrastructure. The TEPS 708 can include the components 100 shown in FIG. 1C or FIG. 1D, or be configured to operate as a service in cloud 108. The TEPS 708 can include or interact with one or more servers 106*a-n* and clients 102*a-n*, and can interact with one or more heterogeneous electronic funding sources 702*a-n* via the clients 102*a-n*. Examples of heterogeneous electronic funding sources 702*a-n* can include an ACH, an electronic checking account, an electronic bill pay account, an electronic savings account, an electronic credit card account, or an electronic employer payroll account. In some implementations, two electronic funding sources can be heterogeneous to one another if they are maintained by two separate entities. In some implementations, two electronic funding sources can be heterogeneous to one another if they are administered or managed by two separate business entities. In some implementations, two electronic funding sources can be heterogeneous to one another if they use different data communication channels, transaction types, or payment processing techniques. For example, a wire transfer from a first financial institution and a wire transfer from a second financial institution may be heterogeneous to each other. In another example, a wire transfer from a first financial institution and a deposit from initiated by a mobile application of a user may be heterogeneous to one another.

In some embodiments, the TEPS 708 can employ a multitier architecture such as a client-server architecture in which presentation, application processing, and data management functions are logically or physically separated. The presentation tier, or front-end, can include the communications interface 710 that serves static content or dynamic content to be rendered by the client 102 (e.g., by a web browser executing on client 102). The presentation tier or web server 710 can interact or communicate with the application tier to obtain data to provide to the client 102 or POS terminals 202*a-n*. The application tier can include the transaction engine 712 that controls the system's functionality and performs additional processing or analysis on data. The application tier can interact with the data tier to obtain the transaction data. The data tier can include data persistence mechanisms (database servers, file shares, etc.) and the data access layer that encapsulates the persistence mechanisms and exposes the data. The data tier can include databases 714 and 716. The data tier can include an application programming interface (API) to the application tier. The databases 714 and 716 can include stored procedures (e.g., SQL statements) that perform tasks with respect the stored data.

In further detail, and in some embodiments, the TEPS 708 includes a communications interface 710. In some aspects, the communications interface 710 comprises an innovative, non-conventional or non-routine implementation. In some aspects, the communications interface 710 is implemented to address the technical problems and challenges of prior systems not deploying the present solution. In some aspects, the communications interface 710 is implemented to make or cause more effective and efficient use of computing and networking resources. For example, the communications interface 710 can cause more effective and efficient use of computing and network resources by reducing the number of processing cycles, memory or network bandwidth used to receive requests to adjudicate a single claim. The communications interface 710 can provide an improved adjudication of a single claim by integrating or interfacing with an enforcement engine 712, database 714, database 716, claims processor 220, or POS terminals 202*a-n*, or clients 102*a-n* to receive requests to adjudicate a single claim.

The communications interface 710 can execute on one or more processors of a server. The communications interface 710 can include one or more communications ports and be configured with one or more network protocols. Communications ports can include, e.g., network ports, Ethernet ports, WAN ports, I/O ports, or software ports. The communication port can be configured with a network protocol such as Transport Layer Protocols such as TCP/IP or UDP that are configured to receive and process data packets received via a computer network. The port can include or be associated with an IP address of a host and a protocol type of the communication.

The communications interface 710 can receive data packets. The data packets can be generated by a client device 102*a*. The communications interface 710 can receive data packets generated by the client device 102*a* responsive to an electronic transaction request. The data packets can include header information and payload information. Multiple data packets can be strung together in a sequence. The header information can refer to TCP/IP headers that include fields such as source port, destination port, sequence number, acknowledgment number, window size, etc. The payload information of the data packet can include information related to the transaction, merchant, or customer. The TEPS 708 can receive the data packet with header information and payload information and process the packets to obtain information for further processing. The payload can include data identifying a transaction destination, a transaction code, a transaction amount, and an identifier identifying the electronic funding source.

The transaction request can be configured as one or more data packets carrying data including a transaction destination, a transaction code, a transaction amount, and an identifier identifying the electronic funding source. The transaction destination can include an indication of an electronic benefits account to serve as the destination for transacted funds. The transaction code can include an indication of a date, such as an indication of a year. The transaction amount can include an amount of funds to be transferred as requested, according to user input received at the client device 102*a*, from the electronic funding source to an electronic benefits account. The identifier can include a code or label corresponding to the electronic funding source.

The data packets (e.g., payload of the data packets) can further identify an electronic benefits account maintained and configured on the server. The electronic benefits account can be maintained and configured in a database 714. The electronic benefits account can correspond to a user and have a unique identifier. The unique identifier can include numbers, letters, characters, symbols, etc. The electronic account can be associated with the user making the transaction request at the client device 102*a*.

In some embodiments, the transaction request is configured with authentication or security credentials such as a security certificate or security token. The security credential can be associated with a user, client 102*a*, or electronic funding source 702*a*. The TEPS 708 can be configured to extract the security credential from the transaction request, and authenticate the transaction request by comparing the security credential against a known or verified security credential. For example, the profiles (e.g., user profiles, electronic funding source profiles, electronic benefits account profiles) stored in the database 716 can include known or verified security credentials for comparison with the security credential of the transaction request. In some embodiments, the TEPS 708 receives the transaction request via the communications interface 710, extracts a security credential from the transaction request, analyzes the extracted security credential to identify an entity such as a user, electronic funding source 702*a*, and/or client 102*a*, queries the database 716 for a verified security credential stored with a profile corresponding to the identified entity, and authenticates the request based on the extracted security credential matching the verified security credential.

The communications interface 710 can provide, to the plurality of client devices 102*a-n* corresponding to the plurality of heterogeneous electronic funding sources 702*a-n*, an electronic benefits account application programming interface ("API") configured to receive transaction requests from the plurality of heterogeneous electronic funding sources 702*a-n* via the client devices 102*a-n*. The client 102*a* can establish an electronic connection to the TEPS 708 responsive to receiving input via a user interface of the client 102*a*. The TEPS 708 can receive, via the electronic connection, data packets including an indication of an operating system of the client device 102*a* and an indication of existing applications installed on the client device 102*a*. The TEPS 708 can parse the data packets to use the indication of the operation system and/or the indication of existing applications installed on the client device 102, perform a lookup in a database (e.g., database 716) to identify an appropriate electronic benefits account API for the client device 102*a*, and transmit the appropriate electronic benefits account API to the client device 102*a* via the communications interface 710 in response to determining that the client device 102*a* requires the electronic benefits account API in order for the TEPS 708 to receive an electronic transaction request from the electronic funding source 702*a*. The electronic benefits account API can be configured to match a specific electronic funding source 702*a*. For example, the TEPS 708 can be configured to query the client device 102 for an indication of the specific electronic funding source 702*a*, receive the indication of the specific electronic funding source 702*a* responsive to the query, compare the indication to a list of electronic funding sources stored in a database (e.g., in electronic funding source profiles in database 716), and retrieve an appropriate electronic benefits account API responsive to the comparison for providing to the client device 102*a*.

The communications interface 710 can receive, via the electronic benefits account transaction API, from a first client device 102*a* of the plurality of client devices 102*a-n* corresponding to the plurality of heterogeneous electronic funding sources 702*a-n*, a first one or more data packets including the electronic transaction request to initiate the single electronic benefits account transaction to fund an electronic benefits account. The electronic transaction request can be generated responsive to the first client device 102*a* receiving user input via a user interface, the user input configured to indicate a request that funds be transferred from a first electronic funding source 702*a* to the electronic benefits account to be funded. The one or more data packets can include the request identifying a transaction destination, a transaction code, a transaction amount, and an identifier identifying the first electronic funding source 702*a*.

In some embodiments, the TEPS 708 includes an enforcement engine 712. The enforcement engine 712 can execute on one or more processors of a server. In some aspects, the enforcement engine 712 is implemented to address the technical problems and challenges of prior systems not deploying the present solution. In some aspects, the enforcement engine 712 is implemented to make or cause more effective and efficient use of computing and networking resources. For example, the enforcement engine 712 can cause more effective and efficient use of computing and network resources by reducing the number of processing cycles, memory or network bandwidth used to determine and map transaction codes. The enforcement engine 712 can provide an improved determination and mapping of transaction codes by integrating or interfacing with the communication interface 710, database 714, database 716, claims processor 220, POS terminals 202*a-n*, or clients 102*a-n* to determine and map transaction codes. The enforcement engine 712 can receive, retrieve, or otherwise obtain or access some or all of the data carried by the data packets. The enforcement engine 712 can receive, retrieve, or otherwise obtain or access electronic transaction queues, code maps, enforcement rules, and profiles stored in databases 714, 716.

In some embodiments, the enforcement engine 712 determines that the transaction code of the transaction request maps to one of a current year or a previous year. The enforcement engine 712 can receive the first one or more data packets including the request to initiate the single electronic benefits account transaction. The enforcement engine 712 can parse the first one or more data packets to extract the transaction code.

The enforcement engine 712 can perform a lookup in the code map stored in the database 714 to retrieve a list or other data structure mapping transaction codes to a time reference, such as a year, a current year, a previous year, etc. For example, the database 714 can include a hash table or a hash map that includes an array of data records mapping transaction codes to time references. The enforcement engine 712 can be configured with a hash function that can compute an index into the array of data records from which a value can be determined. For example, the enforcement engine 712 can input into the hash function the transaction codes and determine, via the hash function, an index value. The enforcement engine 712 can use the index value to retrieve, from the hash table or hash map, a data record that includes a time reference. Thus, the enforcement engine 712 can perform a lookup into a hash table using a hash function in order to map the transaction code to a time reference.

In some embodiments, the code map includes a list of transaction codes associated with a current year, a list of transaction codes associated with a previous year, and a list of transaction codes associated with other years. In some embodiments, the transaction code itself is a time reference such as a date or year, and the code map includes a value for a current year, and a value for a previous year. The enforcement engine 712 can then compare the transaction code to the retrieved code map to determine whether the transaction code corresponds to one of a current year or a previous year.

In some embodiments, the enforcement engine 712 can identify using a profile of the electronic benefits account stored in the database 716 that the first electronic funding source 702*a* enforces electronic benefits account limits. For example, the enforcement engine 712 can parse the electronic transaction request to extract the identifier of the first electronic funding source 702*a*, perform a lookup in the database 716 to identify a profile corresponding to the first electronic funding source 702*a*, and retrieve from the profile an indication of whether the first electronic funding source 702*a* enforces electronic benefits account limits. The enforcement engine 712 can determine, responsive to identifying that the first electronic funding source 702*a* enforces electronic benefits account limits, that the transaction code maps to one of the current year or the previous year.

In some embodiments, the enforcement engine 712 can determine an enforcement rule based on the single electronic benefits account transaction request. For example, the enforcement engine 712 can parse the electronic transaction request to extract the transaction destination and/or identifier of the first electronic funding source 702*a*. The enforcement engine 712 can perform a lookup in the database 714 or the database 716 to identify the electronic benefits account associated with the transaction destination, and perform a lookup in the database 716 to identify an enforcement rule associated with the electronic benefits account. The enforcement engine can perform a lookup in the database 714 or the database 716 (e.g., in a profile database) using the identifier of the first electronic funding source 702*a* to retrieve an indicator of an enforcement rule, and perform a lookup in the database 716 to identify the enforcement rule associated with the first electronic funding source 702*a*.

The enforcement engine 712 can identify the threshold limit based on the enforcement rule. The enforcement rules maintained in the database 716 can include a map associating electronic benefits accounts with threshold limits. The enforcement engine 212 can use or apply an enforcement rule that includes one or more techniques, algorithms, heuristics, or procedures. The enforcement rule can include decision points and utilize parameters or criteria. The enforcement rule can be based on criteria or rules that are established by an administrator of the TEPS 708, the heterogeneous electronic funding sources 702*a-n*, electronic employer payroll accounts, insurance entities, or another entity. The enforcement rule can facilitate determining a threshold limit to be applied to the electronic transactions.

For example, the map can associate electronic benefits accounts that are subject to IRS threshold limits with IRS threshold limits. The enforcement rule can include the rule: if transaction code maps to current year, then apply current year threshold limit; else if transaction code maps to previous year, then apply previous year threshold limit; else do not apply limit. The enforcement rule can include the rule: if an age value stored in a user profile for the user associated with the electronics benefits account is less than fifty-five, then the IRS threshold limit includes a family threshold limit value; else (if the age value is greater than or equal to fifty-five) the IRS threshold limit includes a family threshold limit value and a catchup value (e.g., a catchup value allowing for rollover of unused contribution capacity from previous years). The enforcement rule can include the rule: if a participant household type stored in a user profile for the user associated with the electronic benefits account corresponds to "single," then the apply the IRS threshold limit for "single" households; if the participant household type corresponds to "family," then apply the IRS threshold limit for "family" households.

In some embodiments, the enforcement rule can include multiple criteria. For example, the enforcement rule can include: if electronic funding source corresponds to (or equals or maps to or is) employer payroll account or individual checking account or insurance account, then apply IRS threshold limit. In some embodiments, the enforcement rule can be a negative enforcement rule. For example, the enforcement rule can include: if electronic funding source does correspond to employer payroll account or individual checking account or insurance account, then do not apply IRS threshold limit. In some embodiments, the enforcement rule can include an action to take when the enforcement rule is not satisfied. For example, if the electronic funding source corresponds to employer payroll account or individual checking account or insurance account, then apply IRS threshold limit; if not, then post transaction. In some embodiments, a single enforcement can include multiple enforcement rules. In some embodiments, the enforcement engine 712 can use process multiple enforcement rules before identifying an enforcement rule that is satisfied.

In some embodiments, the enforcement engine 712 can be configured to apply the electronic transaction to one of the current year or the previous year depending on the total contribution amount for each year. For example, the enforcement rule can include determining a virtual transaction balance for each of the current year and the previous year, comparing the virtual transaction balance for each of the current year and the previous year, and selecting one of the current year or the previous year for receiving the transaction amount. The enforcement rule can include: if the virtual transaction balance for both the current year and the previous year is less than a threshold limit, then apply the transaction amount to the current year; else if the virtual transaction amount for one of the current year or the previous year is less than a threshold limit, then apply the transaction amount to the one of the current year or the previous year; else do not apply the transaction amount. In some embodiments, the enforcement rule can include applying a partial amount of the transaction amount that will not exceed the threshold limit, such as a partial amount that will cause the virtual transaction balance to equal the threshold limit, or a partial amount that will cause the virtual transaction balance to equal a fraction of the threshold limit (e.g., 50%, 60%, 70%, 80%, 90%, 95%, 99%, etc. of the threshold limit).

In some embodiments, the enforcement engine 712 can parse or perform a lookup in the electronic transaction queue stored in the database 714 to retrieve and identify an in-process transaction amount and a reportable contribution amount. The in-process transaction amount can include a plurality of transactions request amounts for funding the single electronic benefits account that have been received (e.g., received by the TEPS 708) but not yet posted. For example, the in-process transaction amount can include a sum of multiple transaction requests, such as when a client device 102*a* receives user input indicating a request for funds to be transferred from an individual checking account in a first electronic transaction request, and an employer payroll server generates a second transaction request. The in-process transaction amount can include pending transactions that are future dated and not yet sent for processing, and can include processing transactions that have been sent for processing but have not yet posted. The reportable contribution amount can include transactions that have posted to the total amount of the electronic benefits account and thus will count against a threshold limit of the electronic benefits account (e.g., posted transactions that have updated an accumulator that groups or otherwise organizes transactions).

In some embodiments, the enforcement engine 712 generates a value by combining the transaction amount, the in-process transaction amount, and the reportable contribution amount identified from the electronic transaction queue of the electronic benefits account maintained in the database 714. The value can indicate a virtual transaction balance, such as a balance of the electronic benefits account that would occur if all of the transactions of the transaction amount, the in-process transaction amount, and the reportable contribution amount were posted to the electronic benefits account. The enforcement engine 712 can generate the value by summing the transaction amount, the in-process transaction amount, and the reportable contribution amount. The enforcement engine 712 can store the value indicating the virtual transaction balance in a database, such as database 714 maintaining the electronic benefits account, or database 716 maintaining a profile associated with the electronic benefits account. For example, the enforcement engine 712 can generate the value, perform a lookup in the database 716 to identify a profile associated with the electronic benefits account, and store the virtual transaction balance in the profile.

In some embodiments, the enforcement engine 712 can compare the value with a threshold limit for the one of the current year or the previous year mapped to the transaction code to determine that the value exceeds the threshold limit. For example, the enforcement engine 712 can perform a lookup in the database 716 to identify an enforcement rule that includes threshold limits for the one of the current year or the previous year, retrieve the threshold limit for the one of the current year or the previous year mapped to the transaction code, and compare the value to the threshold limit. The enforcement engine 712 can determine that the value exceeds the threshold limit based on the value being greater than the threshold limit.

In some embodiments, the enforcement engine 712 can select the threshold limit based on a predetermined threshold limit configured for the first electronic funding source 702*a*. For example, the enforcement engine 712 can parse the electronic transaction request to extract the identifier of the first electronic funding source 702*a*, perform a lookup in a profile database maintained in the database 716 to retrieve a profile of the first electronic funding source 702*a*, and perform a lookup in the profile to identify the predetermined threshold limit.

Enforcement rules and threshold limits can be received from entities including a claims processor 220, a server of a remote entity such as the electronic funding sources 702*a-n*, and/or a server of an employer, insurance administrator, or financial institution. In some cases, the client 102 can provide the enforcement rule or threshold limit. In some cases, the TEPS 708 can access a central data repository maintained by a third-party server such as an IRS server that stores threshold limits. For example, an employer contributing to the electronic benefits account can establish an enforcement rule and maintain it on a server. The enforcement engine 712 can receive an indication of the electronic benefits account, perform a lookup in the enforcement rules maintained in the database 716, and responsive to determining that the database 716 does not include an appropriate enforcement rule for the electronic benefits account, the enforcement engine 712 can transmit a request for an enforcement rule to the server of the employer, causing the server of the employer to transmit the appropriate enforcement rule to the TEPS 708.

In some embodiments, the enforcement engine 712 can receive the request to initiate the single electronic benefits account transaction from a remote device. The remote device can initiate the request. The remote device that initiates the request can be remote to the first client device 102*a* and configured with authentication credentials to access the first client device 102*a*. For example, the remote device can be a portable electronic device, and the first client device 102*a* can be a server configured to communicate with the portable electronic device and the TEPS 708. The remote device can include an electronic benefits account transaction API configured to receive a single transaction request from an electronic funding source 702*a*. A user of the remote device can interact with a user interface of the remote device to initiate the single transaction request. The remote device can initiate the single transaction request responsive to receiving user input indicating a request to initiate the single transaction request via a user interface. The remote device can transmit the single transaction request as one or more data packets carrying the single transaction request and the authentication credentials. The first client device 102*a* can receive the one or more data packets, extract the authentication credentials, and compare the authentication credentials to corresponding authentication credentials stored on the first client device 102*a* (e.g., authentication credentials stored with an electronic benefits account transaction API) in order to determine whether to authenticate the single transaction request. Responsive to determining to authenticate the single transaction request, the first client device 102*a* can transmit the single transaction request to the TEPS 708. In some embodiments, the stored authentication credentials are maintained by the TEPS 708, and the electronic benefits account transaction API of the first client device 102*a* is configured to receive the single transaction request from the remote device, extract the authentication credentials and transmit only the authentication credentials to the TEPS 708; the TEPS 708 can receive the authentication credentials, compare the authentication credentials to the stored authentication credentials (e.g., by performing a lookup in the database 714 or the database 716 maintaining authentication credentials), and responsive to determining that the extracted authentication credentials match the stored authentication credentials, generate an acknowledgement to transmit to the client device 102*a* causing the client device 102*a* to transmit the single transaction request to the TEPS 708.

In some embodiments, the enforcement engine 712 can apply a second enforcement rule directed to additional factors after using a first enforcement rule. The enforcement engine 712 can select the second enforcement rule responsive to or based on the first enforcement rule. The first enforcement rule can include a map of a transaction code to one of the current year or the previous year, and the second enforcement rule can be a threshold limit for the one of the current year or the previous year.

In some embodiments, the enforcement engine 712 can receive an indication from a claims processor 220 external to the TEPS 708 via network 104. In some embodiments, the TEPS 708 or the enforcement engine 712 is configured with the claims processor 220 or configured to interface with the claims processor 220 via communications interface 710. The claims processor 220 can process an electronic transaction request to determine whether applying an electronic transaction to the electronic benefits account would exceed a threshold limit for the electronic benefits account. The claims processor 220 can be configured to use one or more enforcement rules to process the electronic transaction request. The enforcement rules can be based on a type of insurance coverage associated with a user of the electronic benefits account. The claims processor 220 can automatically receive the electronic transaction request responsive to the client device 102*a* generating the electronic transaction request responsive to user input, or responsive to a server of an employer or insurance administrator generating the electronic transaction request.

The TEPS 708 can receive information or instructions from the enforcement engine 712 regarding an electronic transaction, and conduct the electronic transaction. The TEPS 708 can obtain electronic funding source information and/or electronic benefits account information from the databases 714, 716 to perform the transaction. The transaction can include electronically transferring funds from the electronic funding source 702*a* to the electronic benefits account. The transaction can include memo-posting or hard-posting the electronic transaction. For example, the TEPS 708 can receive instructions to post the electronic transaction, and responsive to receiving the instructions, the TEPS 708 performs a lookup in a profile of the electronic benefits account maintained in the database 716 to identify a financial institution associated with the electronic benefits account in order to transmit instructions to the financial institution to post the transaction, including the value. In some cases, the TEPS 708 can facilitate a transfer of funds between an electronic account of a claims processor 220 and the electronic benefits account maintained in the database 714. The TEPS 708 can receive account identifiers, transaction amounts, credentials, authentication information, etc. The TEPS 708 can conduct the transaction via communications interface 710, thereby using the network protocols, security protocols and other components or interfaces provided by the communications interface 710.

In some embodiments, the TEPS 708 (e.g., via communication interface 710), receives a request for account information from a client device 102*a*. The request for information can include information about a balance of the electronic benefits account (e.g., an in-process transaction amount, a reportable contribution amount, a virtual transaction balance), enforcement rules, or transaction histories. The request can further include authentication information or credentials associated with the request. The authentication information can include network security credentials, such as security certificates or tokens. The authentication information can further include a username, password, two-tier authentication information (e.g., date of birth, cell phone number, verification code sent via text message to cell phone number in profile associated with electronic account). The request can be from a client device such as a smartphone. The request can be sent using a text messaging protocol such as SMS. The TEPS 708 can authenticate a request sent via SMS based on the cell phone number of the device sending the SMS request, and matching the cell phone number with corresponding number stored in a profile in the database 716 for the electronic benefits account.

Responsive to authenticating or otherwise approving the request, the TEPS 708 can access a data record in the database 714 for the electronic benefits account to generate a report with the requested information, or generate a standard report, or generate another preconfigured report. The report can identify the account holder information and balances associated with the electronic benefits account. The report can further identify a transaction history for the electronic benefits account. The report can further identify or indicate if the electronic benefits account has reached or exceeded a threshold limit. The report can further include a forecast based on current/previous transaction history that indicates if and when the threshold limit for a time interval might be reached or exceeded.

In some embodiments, the enforcement engine 712 can select an alert format configured for an interface corresponding the first electronic funding source 702*a*. The enforcement engine 712 can generate an alert in the alert format that includes instructions to terminate the single electronic benefits account transaction initiated by the request to prevent exceeding the threshold limit established for the electronic benefits account. The enforcement engine 712 can perform a lookup in the database 716 maintaining alert formats for alerts based on the identifier of the first electronic funding source 702*a* in order to identify and retrieve the alert format. The alert format can include a variety of fields configured to be read by the first electronic funding source 702*a*. For example, the alert format can includes fields directed to an indication of an approval or denial of the single electronic benefits account transaction request; approval of a partial amount of the transaction amount, an indication of the electronic benefits account, an indication of a user of the electronic benefits account, and an indication of a current or projected balance of the electronic benefits account. The alert format can include fields similar to or directed to information provided by the TEPS 708 in a report responsive to a request for account information from a client device 102*a*. The alert format can include authentication credentials configured to be read by the first electronic funding source 702*a* to authenticate the alert. The alert format can include a field including instructions for terminating or authorizing the request to initiate the single electronic benefits account transaction.

In some embodiments, the enforcement engine 712 can transmit, via the network 104 to the first client device 102*a*, one or more packets carrying data in the alert format indicating a denial of the single electronic benefits account transaction request, responsive to the comparison and the transaction code mapping to the one of the current year or the previous year, the one or more packets configured to indicate to the first client device 102*a* termination of the single electronic benefits account transaction initiated by the request to prevent exceeding the threshold limit established for the electronic benefits account. For example, the enforcement engine 712 can retrieve the alert format, generate the one or more packets carrying the information organized in the selected alert format, and cause the communications interface 710 to transmit the one or more packets to the first client device 102*a*. The enforcement engine 712 can retrieve the information required by the alert format from the electronic transaction request, the database 714, and/or the database 716 to generate the one or more packets of the alert. For example, the enforcement engine can retrieve the identifier of the first electronic funding source 702*a* from the electronic transaction request, the indication of the denial of the electronic transaction request from the database 714 maintaining the electronic benefits account, and the authentication credentials from the profile of the first electronic funding source 702*a* maintained in the database 716, in order to generate the alert as one or more packets carrying this information to be transmitted by the communications interface 710.

The one or more packets can include a reason code or error code indicating a reason or error associated with the denial (or approval, if applicable) of the electronic transaction request. The reason code can be generated by the enforcement engine 712 responsive to the enforcement engine 712 applying an enforcement rule for identifying a threshold limit. The reason code can indicate that the transaction amount of the single electronic transaction request would exceed the threshold limit applied to the electronic benefits account. The reason code can indicate that the transaction amount would exceed the combined IRS family and catchup threshold limit that was applied because the age of the participant was greater than or equal to fifty-five. The reason code can indicate that the electronic benefits account does not segregate threshold limits into coverage tiers (e.g., coverage tiers based on age), and thus the threshold limit used was the combined IRS family and catchup threshold limit. The reason code can indicate that the transaction amount would exceed the IRS family threshold limit that was applied because the age of the participant was less than fifty-five and the household type was "family." The reason code can indicate that the transaction amount would exceed the IRS single threshold limit that was applied because the age of the participant was less than fifty-five and the household type was "single."

The one or more packets can include instructions that cause the electronic benefits account transaction API of the client device 102*a* to reroute the one or more packets to the first electronic funding source 702*a* in order to cause the first electronic funding source 702*a* to terminate the single electronic benefits account transaction. For example, the electronic benefits account transaction API can receive the one or more packets, extract the indication of the denial of the electronic transaction request and the identifier of the first electronic funding source 702*a*, and transmit the one or more packets to the first electronic funding source 702*a*. The one or more packets can include instructions causing the electronic benefits account transaction API to generate instructions causing first electronic funding source 702*a* to terminate the single electronic benefits account transaction. For example, the electronic benefits account transaction API can receive the one or more packets, extract the indication of the denial of the electronic transaction request and the identifier of the first electronic funding source 702*a*, and generate instructions to transmit to the first electronic funding source 702*a* to cause the first electronic funding source 702*a* to terminate the single electronic benefits account transaction.

In some embodiments, the enforcement engine 712 can transmit the alert to the first client device 102*a* to cause the first client device 102*a* to terminate the transaction, when the transaction was initiated by the remote device remote to the first client device 102*a*. For example, a portable electronic device may have initiated the electronic transaction request, responsive to user input, and transmitted the request to the first client device 102*a* which manages the electronic funding source 702*a*; the enforcement engine 712 can identify this chain of command by parsing the electronic transaction request in order to transmit the alert to the first client device 102*a* with instructions causing the first client device 102*a* to terminate the transaction.

In some embodiments, the enforcement engine 712 can establish a bidirectional communication channel with the first client device 102*a*. The enforcement engine 712 can transfer requests and instructions to terminate transactions. For example, the enforcement engine 712 can transmit a request to establish a bidirectional communication channel with the first client device 102*a* to the electronic benefits account transaction API provided to the first client device 102*a*. The enforcement engine 712 can also transmit the bidirectional communication channel request when providing the electronic benefits account transaction API. The request can be configured to cause the client device 102*a* to establish a communication channel with the TEPS 708 and the enforcement engine 712 via the communications interface 710 automatically or responsive to approval received as user input at a user interface, or approval granted by another application of the client device 102*a*. The TEPS 708 can then receive the responsive communication from the client device 102*a*, and retrieve a communication protocol from the database 714 or the database 716 associated with the electronic benefits account transaction API of the client device 102*a* in order to establish the bidirectional communication channel based on the retrieved communication protocol. For example, the bidirectional communication channel can be based on an Internet-based communication channel in which data packets can be regularly transmitted between the client device 102*a* and the TEPS 708.

The communication protocol for establishing the bidirectional communication channel can include authenticating communication between the client device 102*a* and the TEPS 708. For example, the TEPS 708 can retrieve the identifier of the client device 102*a*, perform a lookup in the database 716 to identify authentication credentials associated with the client device 102*a*, transmit the authentication credentials to the client device 102*a*, and responsive to the client device 102*a* authorizing communication based on the authentication credentials, receive a challenge from the client device 102*a*, extract additional authentication credentials from the challenge, perform a lookup in the database 716 to compare the additional authentication credentials to stored authentication credentials, and authorize the bidirectional communication based on the additional authentication credentials matching the stored authentication credentials.

In some embodiments, the enforcement engine 712 can transmit, via the network 104 to the first client device 102*a*, the response packets indicating the denial of the single electronic benefits account transaction request within a predetermined time interval from receiving the single electronic benefits account transaction request. The predetermined time interval can be a time period after an action, e.g. 10 minutes, 5 minutes, 1 minute, 30 seconds. The action can include receiving the electronic transaction request, posting the transaction or denying the transaction, and/or generating the alert including instructions to terminate the single electronic benefits account transaction. The pre-determine time interval can be set in a configuration file or profile maintained by the TEPS 708 in the database 714 or the database 716, the configuration file or profile corresponding to the electronic benefits account. The pre-determined time interval can be set by an entity remote from the TEPS 708. For example, the TEPS 708 can transmit a time interval request to a remote server of an insurance administrator, an employer, or a financial institution. The time interval request can cause the remote server to transmit the configuration file or profile setting the pre-determined time interval to the TEPS 708. The enforcement engine 712 can process the configuration file or profile to extract the pre-determined time interval in order to transmit the notification within the pre-determined time interval.

In some embodiments, responsive to the action occurring that initiates the pre-determined time interval, the enforcement engine 712 can generate a placeholder notification to be transmitted to the first client device 102*a* independent of the status of the electronic transaction request. For example, the placeholder notification can indicate that enforcement of the electronic transaction request has been initiated. The placeholder notification can indicate that further information is required to complete the enforcement of the electronic transaction request. The enforcement engine 712 can transmit the placeholder notification prior to expiry of the pre-determined time interval via the communications interface 210 to provide real-time communication of the adjudication process.

In some embodiments, the pre-determined time interval can be based on the type of electronic benefits account, the type of electronic funding source, or an expected time required to perform transactions with the electronic benefits account or the electronic funding source. For example, if the electronic benefits account or the electronic funding source can perform transactions using wire transfer, than the pre-determined time interval can be approximately ten seconds, thirty seconds, one minute, etc. If the electronic benefits account or the electronic funding source can perform transactions by direct deposit, then the pre-determined time interval can be a time associated with electronic communication between the TEPS 708 and the electronic funding source, such as ten minutes. The pre-determined time interval can be based on a time required to transfer funds from an electronic bank account associated with an insurance administrator or with an employer to the electronic benefits account. The pre-determined time interval can be based on a time required for an indication of the enforcement of the electronic transaction request to be received at a remote server in order to authorize or deny the funds for being transferred to the electronic benefits account.

In some embodiments, the enforcement engine 712 can determine that the electronic funding source 702*a* corresponds to a funded payroll deposit. For example, the enforcement engine 712 can perform a lookup in the profiles maintained in the database 716 based on the identifier of the electronic funding source 702*a* to identify a funding source category and determine if the funding source category corresponds to a funded payroll deposit. The enforcement engine 712 can select an alert format corresponding to the funded payroll deposit, the alert format including a first field for the instructions to deny the single electronic benefits account transaction and a second field for a reason code. For example, the enforcement engine 712 can perform a lookup in the alert formats maintained in the database 716 based on the identified funded payroll deposit to select the alert format. The enforcement engine 712 can then generate the alert in the alert format that includes instructions to terminate the single electronic benefits account transaction and the reason code and transmit the one or more response packets carrying the alert. The reason code can include an indication that the virtual transaction balance exceeds the threshold limit for the electronic benefits account. The reason code can include an indication that the in-process transaction queue and/or the reportable contribution amount exceeds the threshold limit for the electronic benefits account. The reason code can include an indication of excess contribution.

In some embodiments, the enforcement engine 712 can access a profile database to determine that the electronic funding source corresponds to a non-payroll deposit. For example, the enforcement engine 712 can perform a lookup in the profiles maintained in the database 716 based on the identifier of the electronic funding source 702*a* to identify a funding source category and determine if the funding source category corresponds to a non-payroll deposit. The enforcement engine 712 can select the alert format for the instructions to terminate the single electronic benefits account transaction corresponding to the non-payroll deposit, the alert format including a first field for a reason code, and a second field for instructions to exclude the transaction from the in-process transaction amount. The enforcement engine 712 can then generate the alert in the alert format that includes instructions to terminate the single electronic benefits account transaction, the reasons code, and the instructions to exclude the transaction from the in-process transaction amount, and transmit the one or more response packets carrying the alert.

In some embodiments, the enforcement engine 712 is configured to receive a second one or more packets including a second request to initiate a second single electronic benefits account transaction to fund the electronic benefits account. The second request and the enforcement actions performed by the enforcement engine 712 regarding the second request can be similar to the first request and associated enforcement actions. The second request can include a second data structure identifying the transaction destination, the transaction code, a second transaction amount, and the first electronic funding source. The enforcement engine 712 can generate a second value by combining the second transaction amount, the in-process transaction amount, and the reportable contribution amount identified from the electronic transaction queue of the electronic benefits account maintained in the database 714. The second value is different from the value of the first electronic transaction request. The enforcement engine 712 can determine that the second value is less than the threshold limit applied to the first value based on a comparison of the second value with the threshold limit. The enforcement engine can generate, responsive to the second value being less than the threshold limit, second response packets to authorize the second single electronic benefits account transaction. For example, the second response packets can include instructions similar to the response packets denying the first single electronic benefits account transaction, except that the second response packets cause the first client device 102*a* and/or the first electronic funding source 702*a* to authorize and perform the transaction.

In some aspects, the system of the present solutions implements a combination of the communication interface 710, enforcement engine 712, databases 714 or 716, claims processor 220, POS terminals 202*a-n*, or clients 102*a-n* in an innovative, non-conventional or non-routine manner. In some aspects, the system of the present solutions integrates the communication interface 710, enforcement engine 712, databases 714 or 716, claims processor 220, POS terminals 202*a-n*, or clients 102*a-n* in an innovative, non-conventional or non-routine manner to implement the improved functionality, performance and operation of the present solution. In some aspects, the system of the present solutions integrates the communication interface 710, enforcement engine 712, databases 714 or 716, claims processor 220, POS terminals 202*a-n*, or clients 102*a-n* in an innovative, non-conventional and/or non-routine manner to more efficiently and effectively use computing and networking resources. The communication interface 710, enforcement engine 712, databases 714 or 716, claims processor 220, POS terminals 202*a-n*, or clients 102*a-n* are integrated in an innovative, nonconventional manner to mitigate, reduce, prevent, or resolve the technical problems of allocating resources in real-time. The communication interface 710, enforcement engine 712, databases 714 or 716, claims processor 220, POS terminals 202*a-n*, or clients 102*a-n* integrated in the innovative, non-conventional manner address at least these technical problems by providing, to a plurality of devices corresponding to a plurality of heterogeneous electronic funding sources, an electronic benefits account transaction application programming interface ("API") configured to receive transaction requests from the plurality of heterogeneous electronic funding sources; receiving, via the electronic benefits account transaction API, from a first device of the plurality of devices corresponding to a first electronic funding source of the plurality of heterogeneous electronic transaction sources, a first one or more packets comprising a request to initiate a single electronic benefits account transaction to fund an electronic benefits account, the request identifying a transaction destination, a transaction code, a transaction amount and an identifier identifying the first electronic funding source; determining the transaction code maps to one of a current year or a previous year; performing a lookup in an electronic transaction queue of the electronic benefits account maintained in memory by the server to identify an in-process transaction amount and a reportable contribution amount; generating a value by combining the transaction amount, the in-process transaction amount and the reportable contribution amount identified from the electronic transaction queue of the electronic benefits account maintained in memory by the server, the value indicating a virtual transaction balance; comparing the value with a threshold limit for the one of the current year or the previous year mapped to the transaction code to determine that the value exceeds the threshold limit; selecting an alert format configured for an interface corresponding to the first electronic funding source; and transmitting, via a network to the first device, one or more packets carrying data in the alert format indicating a denial of the single electronic benefits account transaction request responsive to the comparison and the transaction code mapping to the one of the current year or the previous year, the one or more packets configured to indicate to the first device termination of the single electronic benefits account transaction initiated by the request to prevent exceeding the threshold limit established for the electronic benefits account.

Figure 8:
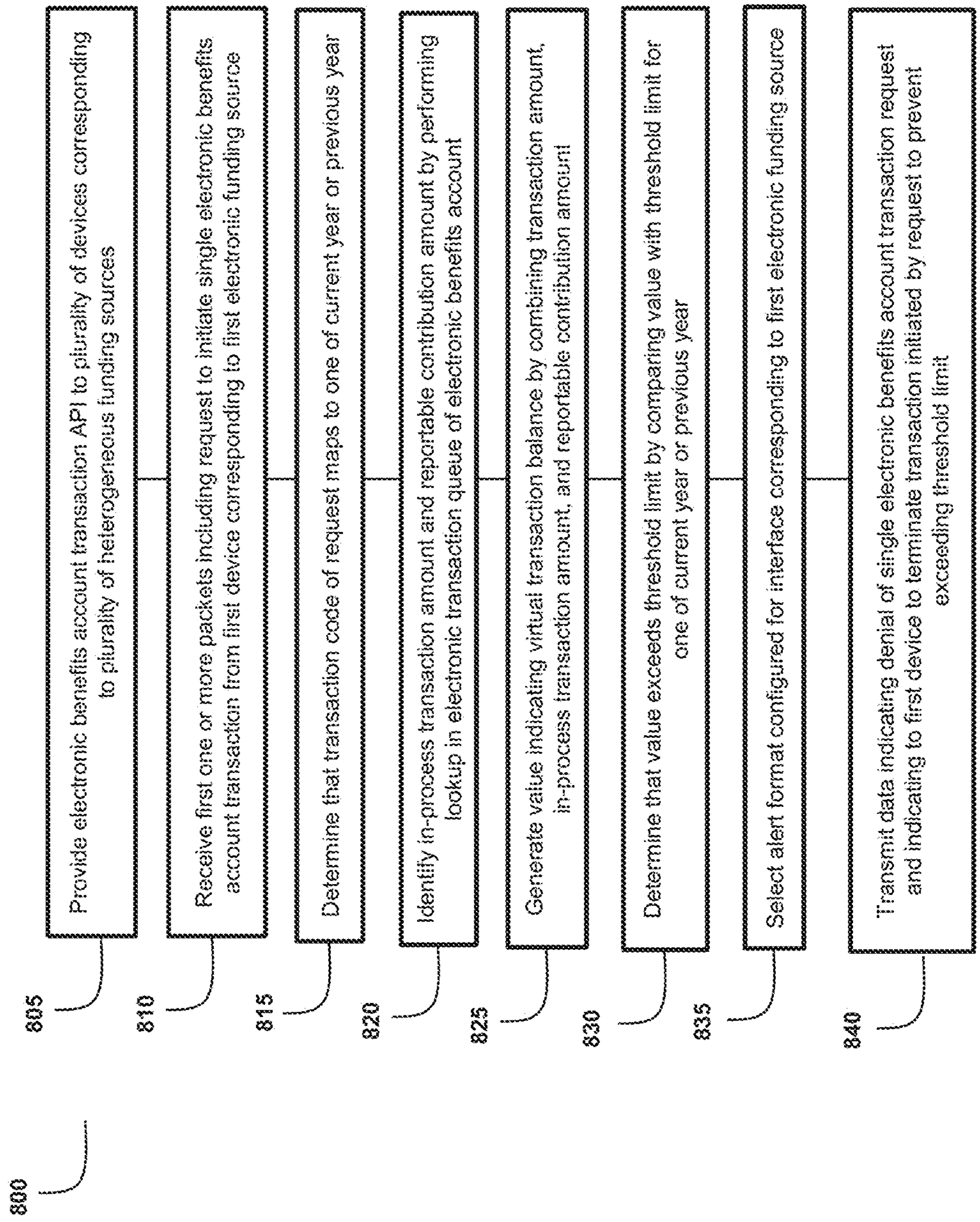
FIG. 8 is a flow diagram depicting an embodiment of a method of operating an electronic transactional portal for funding electronic benefits accounts.

Referring now to FIG. 8, a flow diagram depicting an embodiment of a method of managing an electronic transaction portal is shown. The method can be performed by system 700, TEPS 708, or one or more component thereof. In brief overview, at step 805, a server provides an electronic benefits account transaction API to a plurality of devices corresponding to a plurality of heterogeneous electronic funding sources. At step 810, the server receives a first one or more packets including a request to initiate a single electronic benefits account transaction from a first device corresponding to a first electronic funding source. At step 815, the server determines that a transaction code of the request maps to one of a current year or a previous year. At step 820, the server identifies an in-process transaction amount and a reportable contribution amount by performing a lookup in an electronic transaction queue of the electronic benefits account. At step 825, the server generates a value indicating a virtual transaction balance by combining the transaction amount, the in-process transaction amount, and the reportable contribution amount. At step 835, the server selects an alert format configured for an interface corresponding to the first electronic funding source. At step 840, the server transmits data indicating a denial of the single electronic benefits account transaction request and indicating to the first device to terminate the transaction initiated by the request to prevent exceeding of the threshold limit.

Still referring to FIG. 8, and in further detail, a server of a transaction enforcement portal system provides an electronic benefits account transaction API to a plurality of devices corresponding to a plurality of heterogeneous electronic funding sources at step 805. The server can include one or more processors. The server can include a communications interface for receiving the request. In some aspects, step 805 comprises an innovative, non-conventional or non-routine way to operate or perform the functionality of the present solution. In some aspects, step 805 is implemented to address the technical problems and challenges of prior systems not deploying the present solution. In some aspects, step 805 is implemented to make or cause more effective and efficient use of computing and networking resources.

In some embodiments, one of the devices establishes an electronic connection to the server responsive to user input received at a user interface of the device. Via the electronic connection, the server receives data packets including an indication of an operating system of the device and an indication of existing applications installed on the device. The server parses the data packets to retrieve the indication of the operation system and/or the indication of existing applications installed on the device, performs a lookup in a database to identify an appropriate electronic benefits account API for the device, and transmits the appropriate electronic benefits account API to the device in response to determining that the device requires the electronic benefits account API in order for the server to receive an electronic transaction request from the electronic funding source. The electronic benefits account API can be configured to match a specific electronic funding source. For example, the can query the device for an indication of the specific electronic funding source, receive the indication of the specific electronic funding source responsive to the query, compare the indication to a list of electronic funding sources stored in a database, and retrieve an appropriate electronic benefits account API responsive to the comparison for providing to the device.

The server receives a first one or more data packets including the electronic transaction request to initiate the single electronic benefits account transaction to fund an electronic benefits account via the electronic benefits account transaction API from a first device of the plurality of devices corresponding to the plurality of heterogeneous electronic funding sources at step 810. The request identifies a transaction destination, a transaction code, a transaction amount, and an identifier identifying the first electronic funding source. The device can generate the request responsive to the client device receiving user input at a user interface, which indicates a request for funds to be transferred from a first electronic funding source to the electronic benefits account to be funded. In some aspects, step 810 comprises an innovative, non-conventional or non-routine way to operate or perform the functionality of the present solution. In some aspects, step 810 is implemented to address the technical problems and challenges of prior systems not deploying the present solution. In some aspects, step 810 is implemented to make or cause more effective and efficient use of computing and networking resources.

The server determines that the transaction code maps to one of a current year or a previous year at step 815. The server can perform the determination by executing an enforcement engine. The enforcement engine can execute on one or more processors of the server. The server can receive, retrieve, or otherwise obtain or access electronic transaction queues, code maps, enforcement rules, and profiles stored in databases. The server can receive the first one or more data packets including the request to initiate the single electronic benefits account transaction and parse the first one or more data packets to extract the transaction code. The server can perform a lookup in a code map to retrieve a list or other data structure mapping transaction codes to a time reference, such as a year, a current year, a previous year, etc. In some embodiments, the code map includes a list of transaction codes associated with a current year, a list of transaction codes associated with a previous year, and a list of transaction codes associated with other years. In some embodiments, the transaction code itself is a time reference such as a date or year, and the code map includes a value for a current year, and a value for a previous year. The server can then compare the transaction code to the retrieved code map to determine whether the transaction code corresponds to one of a current year or a previous year.

In some aspects, step 815 comprises an innovative, non-conventional or non-routine way to operate or perform the functionality of the present solution. In some aspects, step 815 is implemented to address the technical problems and challenges of prior systems not deploying the present solution. In some aspects, step 815 is implemented to make or cause more effective and efficient use of computing and networking resources.

In some embodiments, the server identifies, using a profile of the electronic benefits account stored in a database, that the first electronic funding source enforces electronic benefits account limits. For example, the server parses the electronic transaction request to extract the identifier of the first electronic funding source, performs a lookup in the database to identify a profile corresponding to the first electronic funding source, and retrieves from the profile an indication of whether the first electronic funding source enforces electronic benefits account limits. The server can determine, responsive to identifying that the first electronic funding source enforces electronic benefits account limits, that the transaction code maps to one of the current year or the previous year.

In some embodiments, the server determines an enforcement rule based on the single electronic benefits account transaction request. For example, the server parses the electronic transaction request to extract the transaction destination and/or identifier of the first electronic funding source. The server performs a lookup in a database to identify the electronic benefits account associated with the transaction destination, and performs a lookup in the database to identify an enforcement rule associated with the electronic benefits account. The server performs a lookup in a database using the identifier of the first electronic funding source to retrieve an indicator of an enforcement rule, and performs a lookup in a database to identify the enforcement rule associated with the first electronic funding source.

In some embodiments, the server identifies the threshold limit based on the enforcement rule. The enforcement rules maintained in a database can include a map associating electronic benefits accounts with threshold limits. The server can use or apply an enforcement rule that includes one or more techniques, algorithms, heuristics, or procedures. The enforcement rule can include decision points and utilize parameters or criteria. The enforcement rule can be based on criteria or rules that are established by an administrator of the server, the heterogeneous electronic funding sources, electronic employer payroll accounts, insurance entities, or another entity. The enforcement rule can facilitate determining a threshold limit to be applied to the electronic transactions. For example, the map can associate electronic benefits accounts that are subject to IRS threshold limits with IRS threshold limits. The enforcement rule can include the rule: if transaction code maps to current year, then apply current year threshold limit; else if transaction code maps to previous year, then apply previous year threshold limit; else do not apply limit. The enforcement rule can include multiple criteria. For example, the enforcement rule can include: if electronic funding source corresponds to (or equals or maps to or is) employer payroll account or individual checking account or insurance account, then apply IRS threshold limit. The enforcement rule can be a negative enforcement rule. For example, the enforcement rule can include: if electronic funding source does correspond to employer payroll account or individual checking account or insurance account, then do not apply IRS threshold limit. The enforcement rule can include an action to take when the enforcement rule is not satisfied. For example, if the electronic funding source corresponds to employer payroll account or individual checking account or insurance account, then apply IRS threshold limit; if not, then post transaction. A single enforcement can include multiple enforcement rules. The server can use process multiple enforcement rules before identifying an enforcement rule that is satisfied.

In some embodiments, the server applies the electronic transaction to one of the current year or the previous year depending on the total contribution amount for each year. For example, the enforcement rule can include determining a virtual transaction balance for each of the current year and the previous year, comparing the virtual transaction balance for each of the current year and the previous year, and selecting one of the current year or the previous year for receiving the transaction amount. The enforcement rule can include: if the virtual transaction balance for both the current year and the previous year is less than a threshold limit, then apply the transaction amount to the current year; else if the virtual transaction amount for one of the current year or the previous year is less than a threshold limit, then apply the transaction amount to the one of the current year or the previous year; else do not apply the transaction amount. In some embodiments, the enforcement rule can include applying a partial amount of the transaction amount that will not exceed the threshold limit, such as a partial amount that will cause the virtual transaction balance to equal the threshold limit, or a partial amount that will cause the virtual transaction balance to equal a fraction of the threshold limit (e.g., 50%, 60%, 70%, 80%, 90%, 95%, 99%, etc. of the threshold limit).

The server performs a lookup in the electronic transaction queue to identify an in-process transaction amount and a reportable contribution amount at step 820. In some aspects, step 820 comprises an innovative, non-conventional or non-routine way to operate or perform the functionality of the present solution. In some aspects, step 820 is implemented to address the technical problems and challenges of prior systems not deploying the present solution. In some aspects, step 820 is implemented to make or cause more effective and efficient use of computing and networking resources.

The server can execute an enforcement engine to perform the lookup in a database. The in-process transaction amount can include a plurality of transactions request amounts for funding the single electronic benefits account that have been received by the server but not yet posted. For example, the in-process transaction amount can include a sum of multiple transaction requests, such as when a client device receives user input indicating a request for funds to be transferred from an individual checking account in a first electronic transaction request, and an employer payroll generates a second transaction request. The in-process transaction amount can include pending transactions that are future dated and not yet sent for processing, and can include processing transactions that have been sent for processing but have not yet posted. The reportable contribution amount can include transactions that have posted to the total amount of the electronic benefits account and thus will count against a threshold limit of the electronic benefits account.

The server generates a value by combining the transaction amount, the in-process transaction amount, and the reportable contribution amount identified from the electronic transaction queue of the electronic benefits account maintained in a database, setting the generated value to indicate a virtual transaction balance, at step 825. In some aspects, step 825 comprises an innovative, non-conventional or non-routine way to operate or perform the functionality of the present solution. In some aspects, step 825 is implemented to address the technical problems and challenges of prior systems not deploying the present solution. In some aspects, step 825 is implemented to make or cause more effective and efficient use of computing and networking resources.

The server can execute an enforcement engine to perform the generation. The value can indicate a virtual transaction balance, such as a balance of the electronic benefits account that would occur if all of the transactions of the transaction amount, the in-process transaction amount, and the reportable contribution amount were posted to the electronic benefits account. In some embodiments, the server generates the value by summing the transaction amount, the in-process transaction amount, and the reportable contribution amount. The server can store the value indicating the virtual transaction balance in a database maintaining the electronic benefits account, or a database maintaining a profile associated with the electronic benefits account. For example, the server can generate the value, perform a lookup in a database to identify a profile associated with the electronic benefits account, and store the virtual transaction balance in the profile.

The server compares the value with a threshold limit for the one of the current year or the previous year mapped to the transaction code to determine that the value exceeds the threshold limit at step 830. In some aspects, step 830 comprises an innovative, non-conventional or non-routine way to operate or perform the functionality of the present solution. In some aspects, step 830 is implemented to address the technical problems and challenges of prior systems not deploying the present solution. In some aspects, step 830 is implemented to make or cause more effective and efficient use of computing and networking resources.

The server can execute an enforcement engine to perform the comparison. For example, the server can perform a lookup in a database to identify an enforcement rule that includes threshold limits for the one of the current year or the previous year, retrieve the threshold limit for the one of the current year or the previous year mapped to the transaction code, and compare the value to the threshold limit. The server can determine that the value exceeds the threshold limit based on the value being greater than the threshold limit.

In some embodiments, the enforcement engine selects the threshold limit based on a predetermined threshold limit configured for the first electronic funding source. For example, the server can parse the electronic transaction request to extract the identifier of the first electronic funding source, perform a lookup in a profile database maintained in the database to retrieve a profile of the first electronic funding source, and perform a lookup in the profile to identify the predetermined threshold limit.

In some embodiments, the server receives enforcement rules and threshold limits from entities including a claims processor, a server of a remote entity such as the electronic funding sources, and/or a server of an employer, insurance administrator, or financial institution. For example, an employer contributing to the electronic benefits account can establish an enforcement rule and maintain it on a remote employer server. The server can receive an indication of the electronic benefits account, perform a lookup in the enforcement rules maintained in a database, and responsive to determining that the database does not include an appropriate enforcement rule for the electronic benefits account, the server can transmit a request for an enforcement rule to the remote employer server, causing the remote employer server to transmit the appropriate enforcement rule to the server.

In some embodiments, the server receives the request to initiate the single electronic benefits account transaction, and the request is initiated by a remote device that is remote to the first device and configured with authentication credentials to access the first device. For example, the remote device can be a portable electronic device, and the first device can be a client server configured to communicate with the portable electronic device and the server. The remote device can include an electronic benefits account transaction API configured to receive a single transaction request from an electronic funding source. A user of the remote device can interact with a user interface of the remote device to initiate the single transaction request. The remote device can initiate the single transaction request responsive to receiving user input indicating a request to initiate the single transaction request via a user interface. The remote device can transmit the single transaction request as one or more data packets carrying the single transaction request and the authentication credentials. The client server can receive the one or more data packets, extract the authentication credentials, and compare the authentication credentials to corresponding authentication credentials stored on the client server (e.g., authentication credentials stored with an electronic benefits account transaction API) in order to determine whether to authenticate the single transaction request. Responsive to determining to authenticate the single transaction request, the client server can transmit the single transaction request to the server.

In some embodiments, the server maintains the stored authentication credentials, and the electronic benefits account transaction API of the client server receives the single transaction request from the remote device, extracts the authentication credentials and transmits only the authentication credentials to server; the server receives the authentication credentials, compares the authentication credentials to the stored authentication credentials (e.g., by performing a lookup in a database maintaining authentication credentials), and responsive to determining that the extracted authentication credentials match the stored authentication credentials, generates an acknowledgement to transmit to the client server causing the client server to transmit the single transaction request to the server.

In some embodiments, the server applies a second enforcement rule directed to additional factors after using a first enforcement rule. The server selects the second enforcement rule responsive to or based on the first enforcement rule. The first enforcement rule can include a map of a transaction code to one of the current year or the previous year, and the second enforcement rule can be a threshold limit for the one of the current year or the previous year.

In some embodiments, the server receives an indication from a claims processor external to the server via a network. In some embodiments, the server is configured with the claims processor or configured to interface with the claims processor via a communications interface. The claims processor can process an electronic transaction request to determine whether applying an electronic transaction to the electronic benefits account would exceed a threshold limit for the electronic benefits account. The claims processor can be configured to use one or more enforcement rules to process the electronic transaction request. The enforcement rules can be based on a type of insurance coverage associated with a user of the electronic benefits account. The claims processor can automatically receive the electronic transaction request responsive to a client device generating the electronic transaction request responsive to user input, or responsive to a server of an employer or insurance administrator generating the electronic transaction request.

In some embodiments, the server receives information or instructions from an enforcement engine regarding an electronic transaction, and conducts the electronic transaction. The server obtains electronic funding source information and/or electronic benefits account information from a database to perform the transaction. The transaction can include electronically transferring funds from the electronic funding source to the electronic benefits account. The transaction can include memo-posting or hard-posting the electronic transaction. For example, the server can receive instructions to post the electronic transaction, and responsive to receiving the instructions, the server performs a lookup in a profile of the electronic benefits account maintained in a database to identify a financial institution associated with the electronic benefits account in order to transmit instructions to the financial institution to post the transaction, including the value. In some cases, the server facilitates a transfer of funds between an electronic account of a claims processor and the electronic benefits. The server receives account identifiers, transaction amounts, credentials, authentication information, etc. The server conducts the transaction via a communications interface, thereby using the network protocols, security protocols and other components or interfaces provided by the communications interface.

In some embodiments, the server receives a request for account information from a device. The request for information can include information about a balance of the electronic benefits account (e.g., an in-process transaction amount, a reportable contribution amount, a virtual transaction balance), enforcement rules, or transaction histories. The request can further include authentication information or credentials associated with the request. The authentication information can include network security credentials, such as security certificates or tokens. The authentication information can further include a username, password, two-tier authentication information (e.g., date of birth, cell phone number, verification code sent via text message to cell phone number in profile associated with electronic account). The request can be from a device such as a smartphone. The request can be sent using a text messaging protocol such as SMS. The server can authenticate a request sent via SMS based on the cell phone number of the device sending the SMS request, and matching the cell phone number with corresponding number stored in a profile in a database for the electronic benefits account.

Responsive to authenticating or otherwise approving the request, the server can access a data record in a database for the electronic benefits account to generate a report with the requested information, or generate a standard report, or generate another preconfigured report. The report can identify the account holder information and balances associated with the electronic benefits account. The report can further identify a transaction history for the electronic benefits account. The report can further identify or indicate if the electronic benefits account has reached or exceeded a threshold limit. The report can further include a forecast based on current/previous transaction history that indicates if and when the threshold limit for a time interval might be reached or exceeded.

The server selects an alert format configured for an interface corresponding to the first electronic funding source at step 835. In some aspects, step 835 comprises an innovative, non-conventional or non-routine way to operate or perform the functionality of the present solution. In some aspects, step 835 is implemented to address the technical problems and challenges of prior systems not deploying the present solution. In some aspects, step 835 is implemented to make or cause more effective and efficient use of computing and networking resources.

The server can execute an enforcement engine to perform the determination. The server can generate an alert in the alert format that includes instructions to terminate the single electronic benefits account transaction initiated by the request to prevent exceeding the threshold limit established for the electronic benefits account. The server can perform a lookup in a database maintaining alert formats for alerts based on the identifier of the first electronic funding source in order to identify and retrieve the alert format. The alert format can include a variety of fields configured to be read by the first electronic funding source. For example, the alert format can includes fields directed to an indication of an approval or denial of the single electronic benefits account transaction request; approval of a partial amount of the transaction amount, an indication of the electronic benefits account, an indication of a user of the electronic benefits account, and an indication of a current or projected balance of the electronic benefits account. The alert format can include fields similar to or directed to information provided by the server in a report responsive to a request for account information from a device. The alert format can include authentication credentials configured to be read by the first electronic funding source to authenticate the alert. The alert format can include a field including instructions for terminating or authorizing the request to initiate the single electronic benefits account transaction.

The server transmits, via a network to the first device, one or more packets carrying data in the alert format indicating a denial of the single electronic benefits account transaction request, responsive to the comparison and the transaction code mapping to the one of the current year or the previous year, the one or more packets configured to indicate to the first device termination of the single electronic benefits account transaction initiated by the request to prevent exceeding the threshold limit established for the electronic benefits account at step 840. In some aspects, step 840 comprises an innovative, non-conventional or non-routine way to operate or perform the functionality of the present solution. In some aspects, step 840 is implemented to address the technical problems and challenges of prior systems not deploying the present solution. In some aspects, step 840 is implemented to make or cause more effective and efficient use of computing and networking resources.

The server can execute an enforcement engine and a communications interface to perform the transmission. For example, the server can retrieve the alert format, generate the one or more packets carrying the information organized in the selected alert format, and cause a communications interface to transmit the one or more packets to the first device. The server can retrieve the information required by the alert format from the electronic transaction request, and/or a database to generate the one or more packets of the alert. For example, the server can retrieve the identifier of the first electronic funding source from the electronic transaction request, the indication of the denial of the electronic transaction request from a database maintaining the electronic benefits account, and the authentication credentials from the profile of the first electronic funding source maintained in a database, in order to generate the alert as one or more packets carrying this information to be transmitted via a communications interface.

The one or more packets can include a reason code or error code indicating a reason or error associated with the denial (or approval, if applicable) of the electronic transaction request. The reason code can be generated by the server (or an enforcement engine executed by the server) responsive to the server applying an enforcement rule for identifying a threshold limit. The reason code can indicate that the transaction amount of the single electronic transaction request would exceed the threshold limit applied to the electronic benefits account. The reason code can indicate that the transaction amount would exceed the combined IRS family and catchup threshold limit that was applied because the age of the participant was greater than or equal to fifty-five. The reason code can indicate that the electronic benefits account does not segregate threshold limits into coverage tiers (e.g., coverage tiers based on age), and thus the threshold limit used was the combined IRS family and catchup threshold limit. The reason code can indicate that the transaction amount would exceed the IRS family threshold limit that was applied because the age of the participant was less than fifty-five and the household type was "family." The reason code can indicate that the transaction amount would exceed the IRS single threshold limit that was applied because the age of the participant was less than fifty-five and the household type was "single."

The one or more packets can include instructions that cause the electronic benefits account transaction API of the device to reroute the one or more packets to the first electronic funding source in order to cause the first electronic funding source to terminate the single electronic benefits account transaction. For example, the electronic benefits account transaction API can receive the one or more packets, extract the indication of the denial of the electronic transaction request and the identifier of the first electronic funding source, and transmit the one or more packets to the first electronic funding source. The one or more packets can include instructions causing the electronic benefits account transaction API to generate instructions causing first electronic funding source to terminate the single electronic benefits account transaction. For example, the electronic benefits account transaction API can receive the one or more packets, extract the indication of the denial of the electronic transaction request and the identifier of the first electronic funding source, and generate instructions to transmit to the first electronic funding source to cause the first electronic funding source to terminate the single electronic benefits account transaction.

In some embodiments, the server transmits the alert to the first device to cause the first device to terminate the transaction, when the transaction was initiated by the remote device remote to the first client device. For example, a portable electronic device may have initiated the electronic transaction request, responsive to user input, and transmitted the request to the first device which manages the electronic funding source; the server can identify this chain of command by parsing the electronic transaction request in order to transmit the alert to the first client device with instructions causing the first device to terminate the transaction.

In some embodiments, the server establishes a bidirectional communication channel with the first device. The server transfers requests and instructions to terminate transactions. For example, the server can transmit a request to establish a bidirectional communication channel with the first device to the electronic benefits account transaction API provided to the first device. The server can also transmit the bidirectional communication channel request when providing the electronic benefits account transaction API. The request can be configured to cause the device to establish a communication channel via a communications interface automatically or responsive to approval received as user input at a user interface, or approval granted by another application of the device. The server can then receive the responsive communication from the device, and retrieve a communication protocol from a database associated with the electronic benefits account transaction API of the device in order to establish the bidirectional communication channel based on the retrieved communication protocol. For example, the bidirectional communication channel can be based on an Internet-based communication channel in which data packets can be regularly transmitted between the device and the server.

The communication protocol for establishing the bidirectional communication channel can include authenticating communication between the device and the server. For example, the server can retrieve the identifier of the device, perform a lookup in a database to identify authentication credentials associated with the device, transmit the authentication credentials to the device, and responsive to the device authorizing communication based on the authentication credentials, receive a challenge from the device, extract additional authentication credentials from the challenge, perform a lookup in the database to compare the additional authentication credentials to stored authentication credentials, and authorize the bidirectional communication based on the additional authentication credentials matching the stored authentication credentials.

In some embodiments, the server transmits, via a network to the first device, the response packets indicating the denial of the single electronic benefits account transaction request within a predetermined time interval from receiving the single electronic benefits account transaction request. The predetermined time interval can be a time period after an action, e.g. 10 minutes, 5 minutes, 1 minute, 30 seconds. The action can include receiving the electronic transaction request, posting the transaction or denying the transaction, and/or generating the alert including instructions to terminate the single electronic benefits account transaction. The pre-determine time interval can be set in a configuration file or profile maintained by the server in a database, the configuration file or profile corresponding to the electronic benefits account. The pre-determined time interval can be set by an entity remote from the server. For example, the server can transmit a time interval request to a remote server of an insurance administrator, an employer, or a financial institution. The time interval request can cause the remote server to transmit the configuration file or profile setting the pre-determined time interval to the server. The server can process the configuration file or profile to extract the pre-determined time interval in order to transmit the notification within the pre-determined time interval.

In some embodiments, responsive to the action occurring that initiates the pre-determined time interval, the server generates a placeholder notification to be transmitted to the first device independent of the status of the electronic transaction request. For example, the placeholder notification can indicate that enforcement of the electronic transaction request has been initiated. The placeholder notification can indicate that further information is required to complete the enforcement of the electronic transaction request. The server can transmit the placeholder notification prior to expiry of the pre-determined time interval via a communications interface to provide real-time communication of the adjudication process.

In some embodiments, the pre-determined time interval can be based on the type of electronic benefits account, the type of electronic funding source, or an expected time required to perform transactions with the electronic benefits account or the electronic funding source. For example, if the electronic benefits account or the electronic funding source can perform transactions using wire transfer, than the pre-determined time interval can be approximately ten seconds, thirty seconds, one minute, etc. If the electronic benefits account or the electronic funding source can perform transactions by direct deposit, then the pre-determined time interval can be a time associated with electronic communication between the server and the electronic funding source, such as ten minutes. The pre-determined time interval can be based on a time required to transfer funds from an electronic bank account associated with an insurance administrator or with an employer to the electronic benefits account. The pre-determined time interval can be based on a time required for an indication of the enforcement of the electronic transaction request to be received at a remote server in order to authorize or deny the funds for being transferred to the electronic benefits account.

In some embodiments, the server determines that the electronic funding source corresponds to a funded payroll deposit. For example, the enforcement engine can perform a lookup in the profiles maintained in the database based on the identifier of the electronic funding source to identify a funding source category and determine if the funding source category corresponds to a funded payroll deposit. The server can select an alert format corresponding to the funded payroll deposit, the alert format including a first field for the instructions to deny the single electronic benefits account transaction and a second field for a reason code. For example, the server can perform a lookup in the alert formats maintained in a database, based on the identified funded payroll deposit, to select the alert format. The server can then generate the alert in the alert format that includes instructions to terminate the single electronic benefits account transaction and the reason code and transmit the one or more response packets carrying the alert. The reason code can include an indication that the virtual transaction balance exceeds the threshold limit for the electronic benefits account. The reason code can include an indication that the in-process transaction queue and/or the reportable contribution amount exceeds the threshold limit for the electronic benefits account. The reason code can include an indication of excess contribution.

In some embodiments, the server accesses a profile database to determine that the electronic funding source corresponds to a non-payroll deposit. For example, the server can perform a lookup in the profiles maintained in a database based on the identifier of the electronic funding source to identify a funding source category and determine if the funding source category corresponds to a non-payroll deposit. The server can select the alert format for the instructions to terminate the single electronic benefits account transaction corresponding to the non-payroll deposit, the alert format including a first field for a reason code, and a second field for instructions to exclude the transaction from the in-process transaction amount. The server can then generate the alert in the alert format that includes instructions to terminate the single electronic benefits account transaction, the reasons code, and the instructions to exclude the transaction from the in-process transaction amount, and transmit the one or more response packets carrying the alert.

In some embodiments, the server receives a second one or more packets including a second request to initiate a second single electronic benefits account transaction to fund the electronic benefits account. The second request and the enforcement actions performed by the server regarding the second request can be similar to the first request and associated enforcement actions. The second request can include a second data structure identifying the transaction destination, the transaction code, a second transaction amount, and the first electronic funding source. The server can generate a second value by combining the second transaction amount, the in-process transaction amount, and the reportable contribution amount identified from the electronic transaction queue of the electronic benefits account maintained in a database. The second value is different from the value of the first electronic transaction request. The server can determine that the second value is less than the threshold limit applied to the first value based on a comparison of the second value with the threshold limit. The server can generate, responsive to the second value being less than the threshold limit, second response packets to authorize the second single electronic benefits account transaction. For example, the second response packets can include instructions similar to the response packets denying the first single electronic benefits account transaction, except that the second response packets cause the first device and/or the first electronic funding source to authorize and perform the transaction.

In some aspects, the methods of the present solutions implements a combination of steps in an innovative, non-conventional and/or non-routine manner. In some aspects, the method 800 of the present solution combines the steps of FIG. 8 in an innovative, non-conventional and/or non-routine combination to implement the improved functionality, performance and operation of the present solution. In some aspects, the method of the present solution combines the steps of FIG. 8 in in an innovative, non-conventional and/or non-routine manner to more efficiently and effectively use computing and networking resources. In some aspects, the method of the present solution provides innovative, non-conventional and/or non-routine ordered combination of steps.

Referring now to FIGS. 9A-9D, process flow diagrams depicting embodiments of methods of managing an electronic transaction portal are shown. The methods can be performed by system 700, TEPS 708, or one or more components thereof.

Figure 9A:
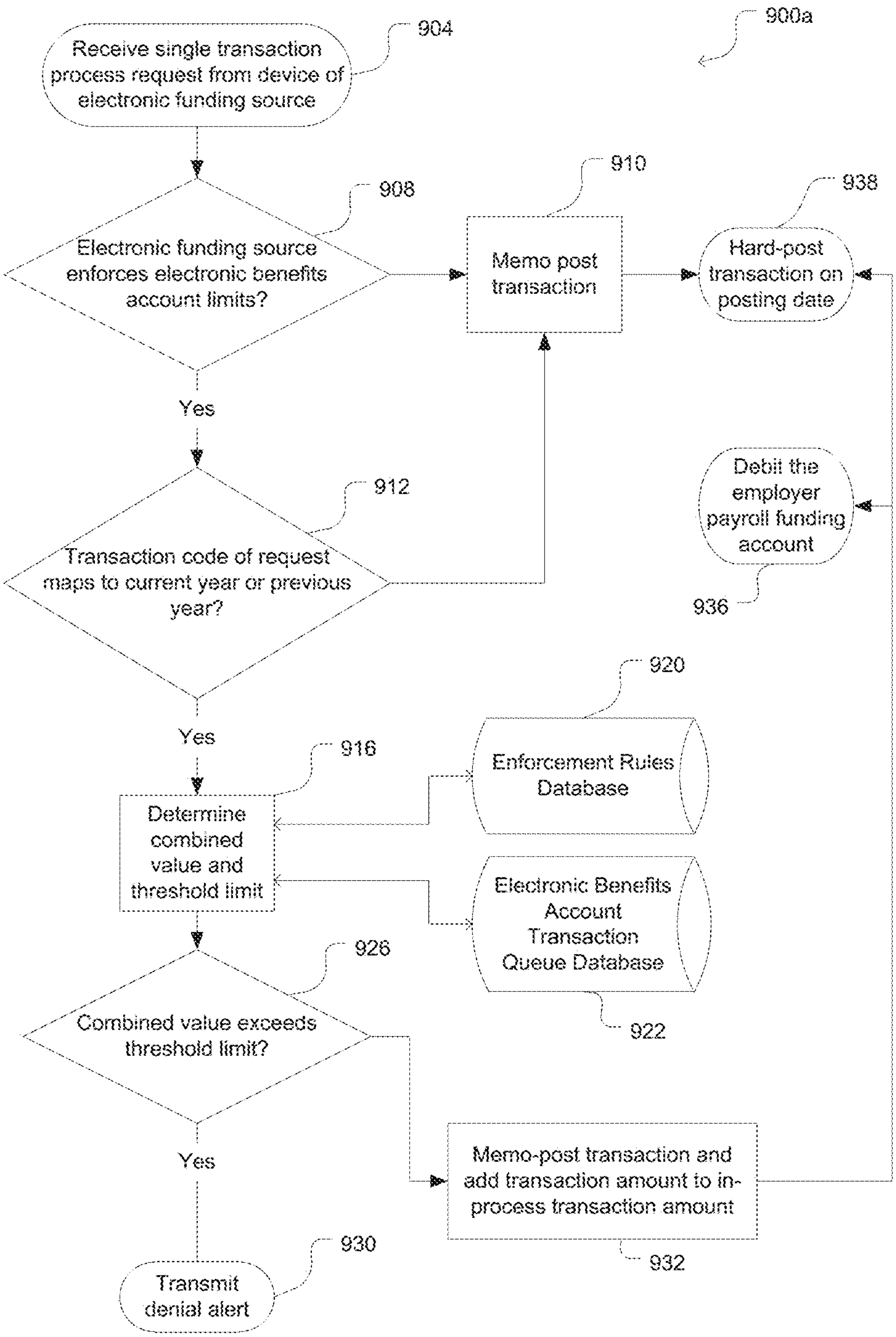
FIGS. 9A-9D are process flow diagrams depicting embodiments of operating an electronic transaction portal for funding electronic benefits accounts.

FIG. 9A illustrates a method 900*a* of managing an electronic transaction portal to receive an electronic transaction request and execute authorization or denial of the electronic transaction request. At 904, a single transaction process request is received at the electronic transaction portal from a device of an electronic funding source. For example, the electronic funding source may be an employer payroll account that regularly deposits funds in an electronic benefits account, such as an HSA, by transferring funds through the electronic transaction portal.

At 908, the electronic transaction portal determines whether the electronic funding source enforces electronic benefits account limits. If the electronic funding source does not enforce electronic benefits account limits, then at 910, the electronic transaction portal memo-posts the transaction.

Responsive to determining that the electronic funding source enforces electronic benefits account limits, at 912, the electronic transaction portal determines whether a transaction code of the electronic transaction request maps to one of a current year or a previous year. The transaction code can be a time reference, such as a date or year. The electronic transaction portal can compare the time reference to the current year and the previous year to identify whether the transaction code maps to one of the current year or the previous year. Responsive to determining that the transaction code does not map to either the current year or the previous year, the electronic transaction portal memo-posts the transaction at 910.

Memo posting can refer to a technique used in a computerized banking environments in which batch processing is employed. Memo posting can represent temporary credit or debit transactions or entries made to an account for which the complete posting to update the balance will be done as part of the end-of-day batch processing. The temporary transaction created as part of the memo-posting will be reversed or removed after the actual transaction is posted in batch processing. For example, a customer receives an electronic credit to an account with current day as effective date. The actual transaction for this entry will be made at the end-of-day in batch posting. In order to access this electronic credit for which the customer is eligible by rules, the bank can creates a temporary “memo” credit to increase the balance available (withdrawal). Later this entry will be removed as part of the end-of-day batch process. In another example, the actual transaction to record a withdrawal using an ATM (automated teller machine) will be posted to accounts in the end-of-day batch. In order to prevent the customer from overdrawing the customer’s account later in the day, the amount of the cash withdrawal is memo-posted as a charge to the customer’s account until the transaction actually posts in the batch update that evening.

Responsive to determining that the transaction code maps to one of the current year or the previous year, the electronic transaction portal determines a combined value and a threshold limit at 916. The electronic transaction portal can perform a lookup in an enforcement rules database 920 to identify a threshold limit from an enforcement rule. The enforcement rules database 920 can be similar or identical to the database 716 depicted in FIG. 7. The electronic transaction portal can perform a lookup in an electronic benefits account transaction queue database 922 to identify an in-process transaction queue and a reportable contribution amount, in order to combine these values with a transaction amount of the electronic transaction request to determine a combined value.

At 926, the electronic transaction portal determines whether the combined value exceeds the threshold limit. Responsive to determining that the combined value does not exceed the threshold limit, the electronic transaction portal authorizes the transaction by memo-posting the transaction and adding the transaction amount to the in-process transaction amount at 932. At 936, the electronic transaction portal can debit an employer payroll funding account, and at 938, the electronic transaction portal can hard-post the transaction on the posting date. Actions 936 and 938 can also be performed responsive to the electronic transaction portal causing a financial institution to act. Action 838 can also be performed responsive to action 910.

At 930, responsive to determining that the combined value exceeds the threshold limit, the electronic transaction portal transmits a denial alert configured to deny the transaction, and thus prevent the threshold limit of the electronic benefits account from being exceeded.

Figure 9B:
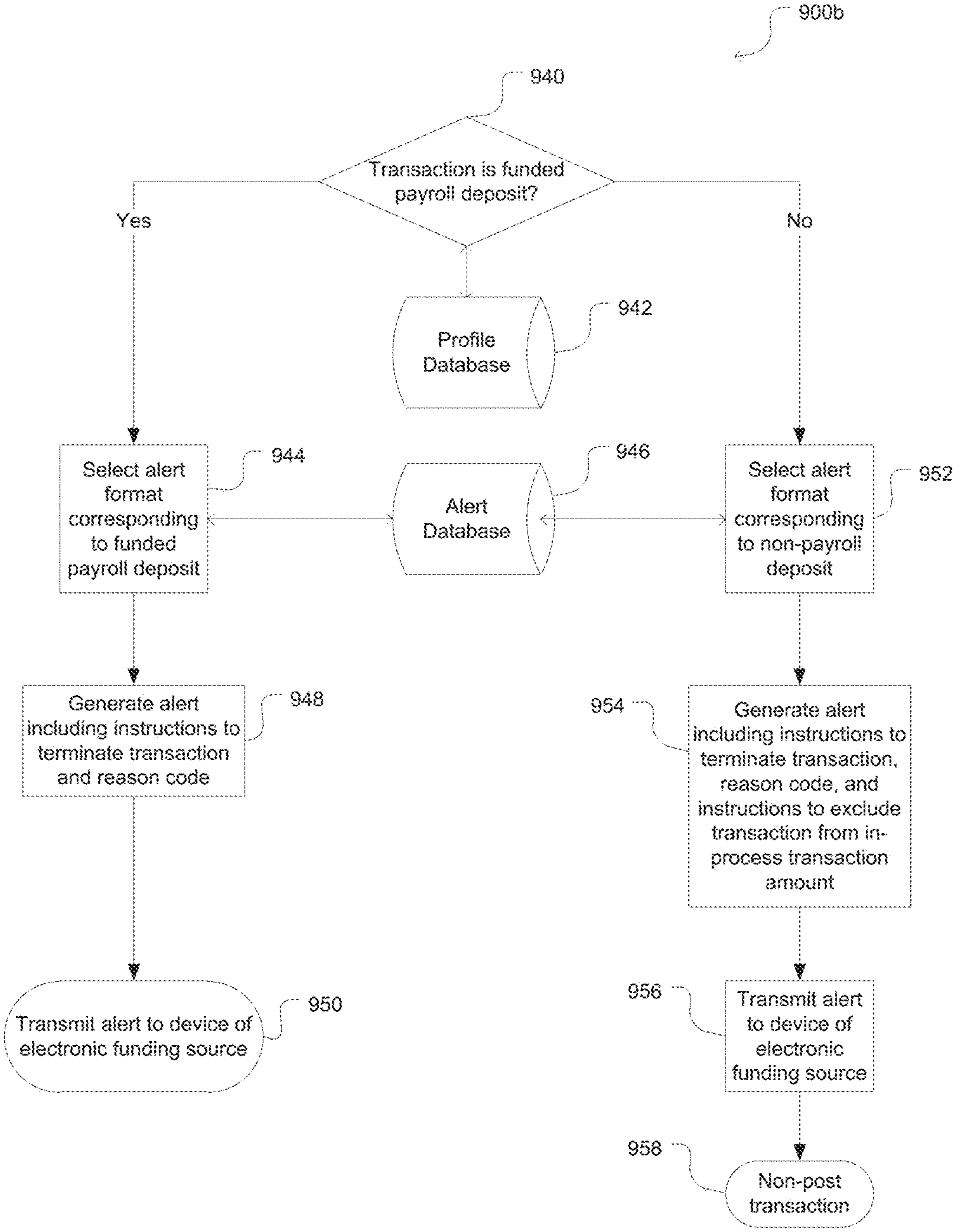

FIG. 9B illustrates a method 900*b* for generating and executing alerts using an electronic transaction portal. Action 930 of FIG. 9A may serve as an input to action 940 of FIG. 9B. At 940, the electronic transaction portal determines whether the transaction indicated by the electronic transaction request is a funded payroll deposit. For example, the electronic transaction portal can extract a funding category of the transaction from the electronic transaction request and perform a lookup in a profile database 942 based on the funding category to identify the funding category of the transaction. The profile database can be similar or identical to the database 716 illustrated in FIG. 7. Responsive to determining whether the transaction is a funded payroll deposit, the electronic transaction portal selects an alert format corresponding to a funded payroll deposit at 944, and selects an alert format corresponding to a non-payroll deposit at 952. The alert format can be selected by performing a lookup in an alert database 946 based on the funding category to identify an appropriate alert format. The alert database 946 can be similar or identical to the database 716 depicted in FIG. 7.

The electronic transaction portal generates an alert using the alert format including instructions to terminate the transaction and a reason code at 948. The electronic transaction portal then transmits the alert to the device of the electronic funding source at 950.

The electronic transaction portal generates an alert including instructions to terminate the transaction, a reason code, an instructions to exclude the transaction from an in-process transaction amount at 954. This can ensure that the transaction does not post in the event that the non-payroll deposit electronic funding source requires additional instructions to prevent the transaction. The electronic transaction portal then transmits the alert to the device of the electronic funding source at 956, and determines not to post the transaction at 958 in order to prevent the transaction from causing the threshold limit for the electronic benefits account to be exceeded. The system can make a determination to not post the transaction, or the system can prevent the transaction from being posted by terminating the transaction.

Figure 9C:
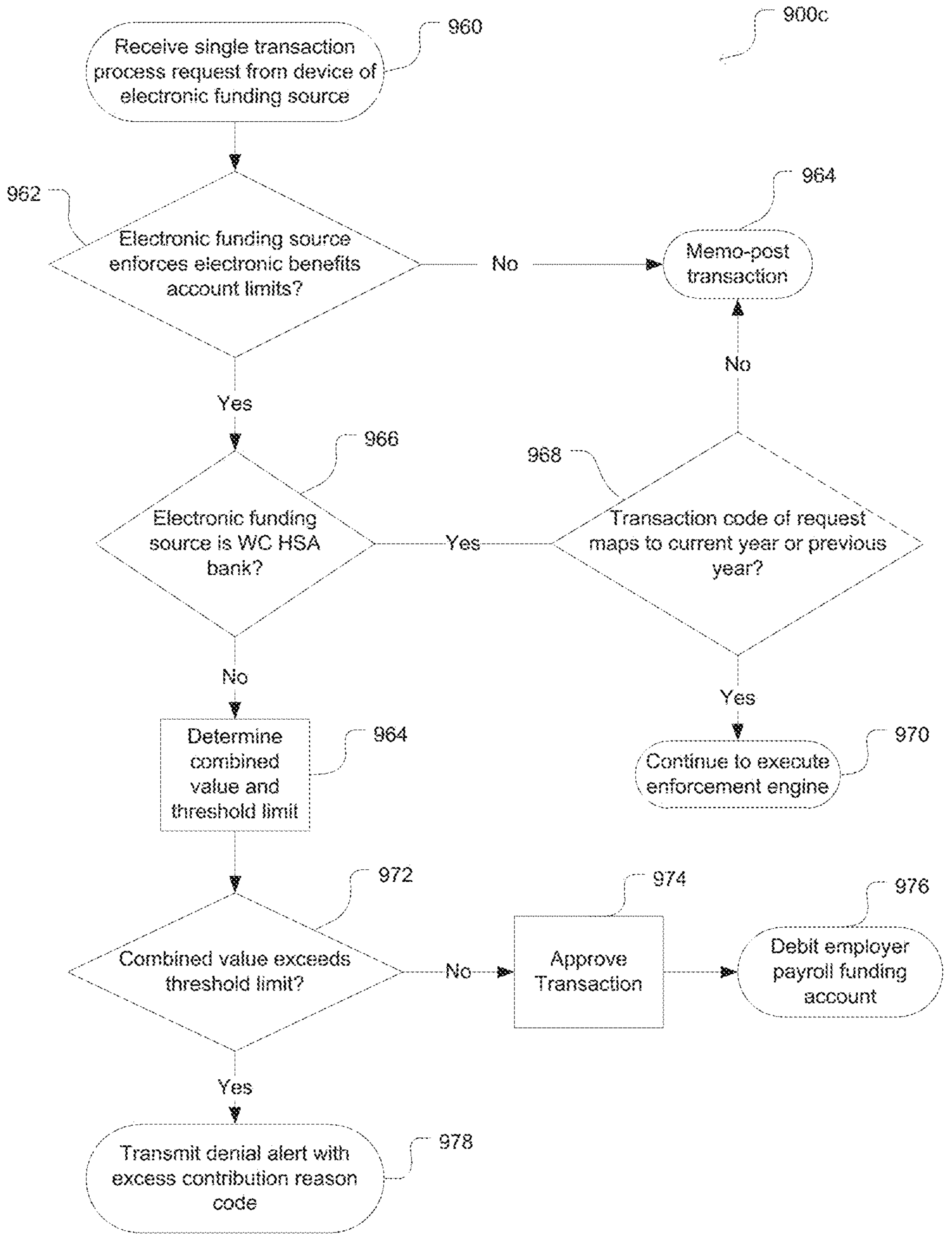

FIG. 9C illustrates a method 900*c* of managing an electronic transaction portal to receive an electronic transaction request and execute authorization or denial of the electronic transaction request. Method 900*c* can be similar to method 900*a*. The electronic transaction portal receives a single transaction process request from a device of an electronic funding source at 960.

The electronic transaction portal determines whether the electronic funding source enforces electronic benefits account limits at 962. Responsive to determining that the electronic funding source does not enforce electronic benefits account limits, the electronic transaction portal memo-posts the transaction at 964.

Responsive to determining that the electronic funding source enforces electronic benefits account limits, the electronic transaction portal determines whether the electronic funding source is a bank for an HSA maintained by the electronic transaction portal at 966, such as an HSA maintained by the WealthCare system provided by Alegeus Technologies (“WC HSA bank”). For example, the electronic transaction portal can extract an identifier of the electronic funding source from the electronic transaction request, and perform a lookup in a profile database based on the identifier to compare the identifier to a list of funding sources to determine whether the electronic funding source is a WC HSA bank.

Responsive to determining that the electronic funding source is not a WC HSA bank, the electronic transaction portal determines the combined value of the transaction, the in-process transaction amount, and the reportable contribution amount at 964, in order to determine whether the combined value exceeds a threshold limit at 972. Responsive to determining that the combined value exceeds the threshold amount, the electronic transaction portal transmits a denial alert with an excess contribution reason code at 978. Responsive to determining that the combined value does not exceed the threshold amount, the electronic transaction portal approves the transaction at 974 and debits an employer payroll funding account at 976.

Responsive to determining that the electronic funding source is a WC HSA bank, the electronic transaction portal determines whether the transaction code of the electronic transaction request maps to one of the current year or previous year at 968. Responsive to determining that the transaction code maps to one of the current year or the previous year, the electronic transaction portal continues to execute the an enforcement engine at 970 (e.g., continues to action 916 of FIG. 9A, etc.). Responsive to determining that the transaction code does not map to one of the current year or the previous year, the electronic transaction portal memo-posts the transaction at 964.

Figure 9D:
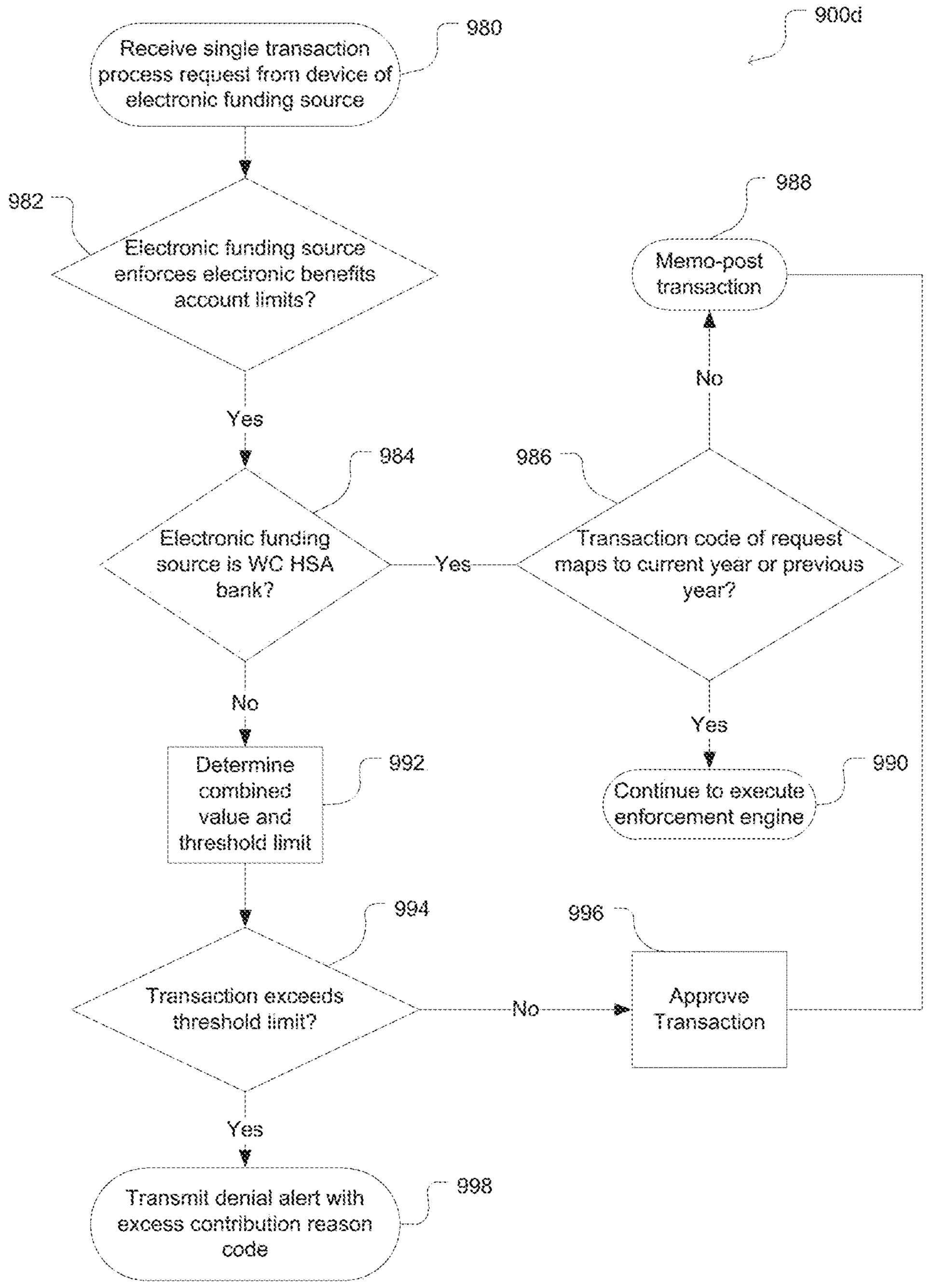

FIG. 9D illustrates a method 900*d* of managing an electronic transaction portal to receive an electronic transaction request and execute authorization or denial of the electronic transaction request. Method 900*c* can be similar to methods 900*a* and 900*b*. The electronic transaction portal receives a single transaction process request from a device of an electronic funding source at 980. The electronic transaction portal determines whether the electronic funding source enforces electronic benefits account limits at 982. Responsive to determining that the electronic funding source does not enforce electronic benefits account limits, the electronic transaction portal memo-posts the transaction at 988.

Responsive to determining that the electronic funding source enforces electronic benefits account limits, the electronic transaction portal determines whether the electronic funding source is a WC HSA bank at 984. For example, the electronic transaction portal can extract an identifier of the electronic funding source from the electronic transaction request, and perform a lookup in a profile database based on the identifier to compare the identifier to a list of funding sources to determine whether the electronic funding source is a WC HSA bank.

Responsive to determining that the electronic funding source is not a WC HSA bank, the electronic transaction portal determines the combined value of the transaction, the in-process transaction amount, and the reportable contribution amount at 992, in order to determine whether the combined value exceeds a threshold limit at 994. Responsive to determining that the combined value exceeds the threshold amount, the electronic transaction portal transmits a denial alert with an excess contribution reason code at 998. Responsive to determining that the combined value does not exceed the threshold amount, the electronic transaction portal approves the transaction at 996 and proceeds to memo-post the transaction at 988.

Responsive to determining that the electronic funding source is a WC HSA bank, the electronic transaction portal determines whether the transaction code of the electronic transaction request maps to one of the current year or previous year at 986. Responsive to determining that the transaction code maps to one of the current year or the previous year, the electronic transaction portal continues to execute the an enforcement engine at 990 (e.g., continues to action 916 of FIG. 9A, etc.). Responsive to determining that the transaction code does not map to one of the current year or the previous year, the electronic transaction portal memo-posts the transaction at 988.

Figure 10A:
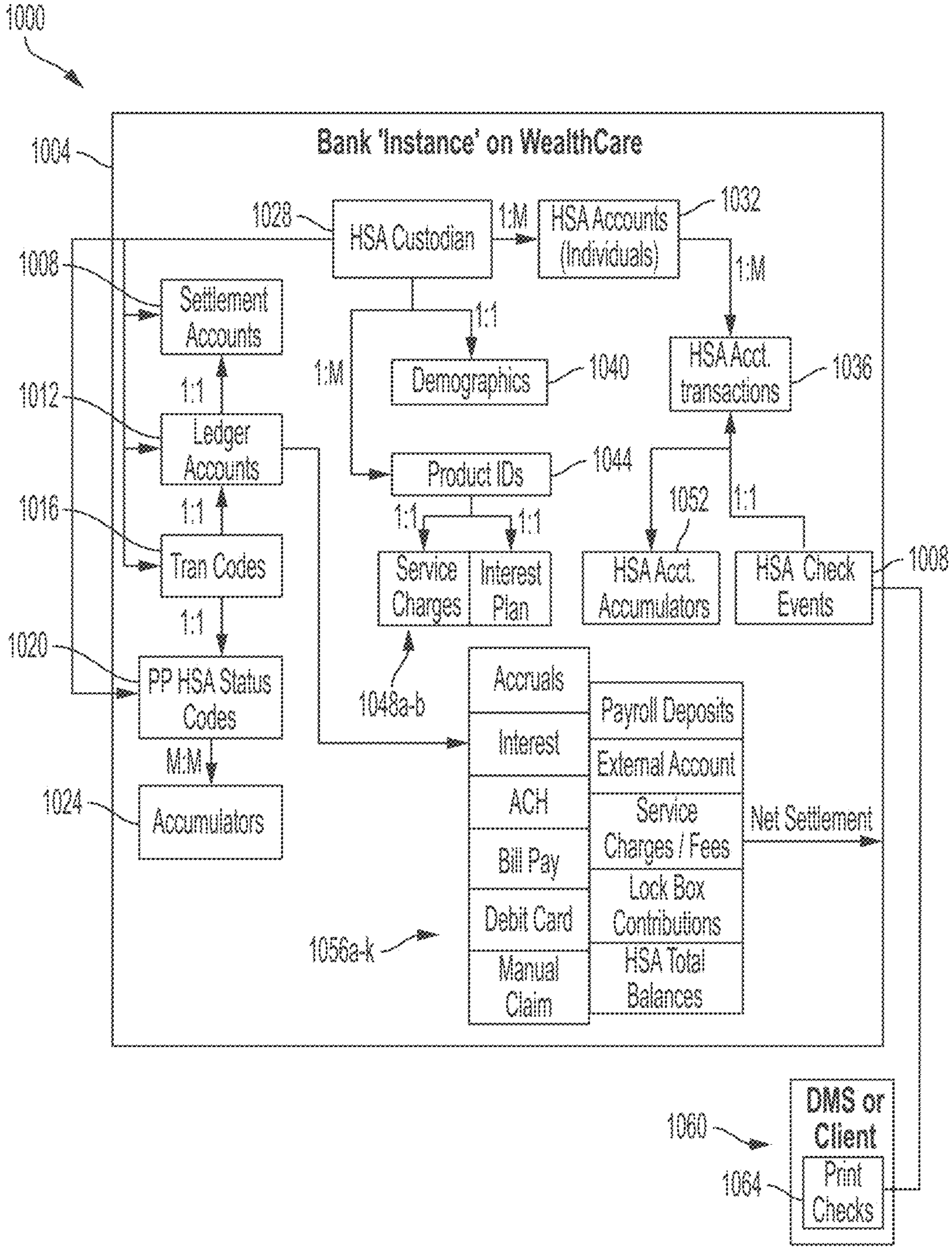
FIGS. 10A-10D are block diagrams depicting embodiments of electronic transaction portal system interfaces for funding electronic benefits accounts.
Figure 10B:
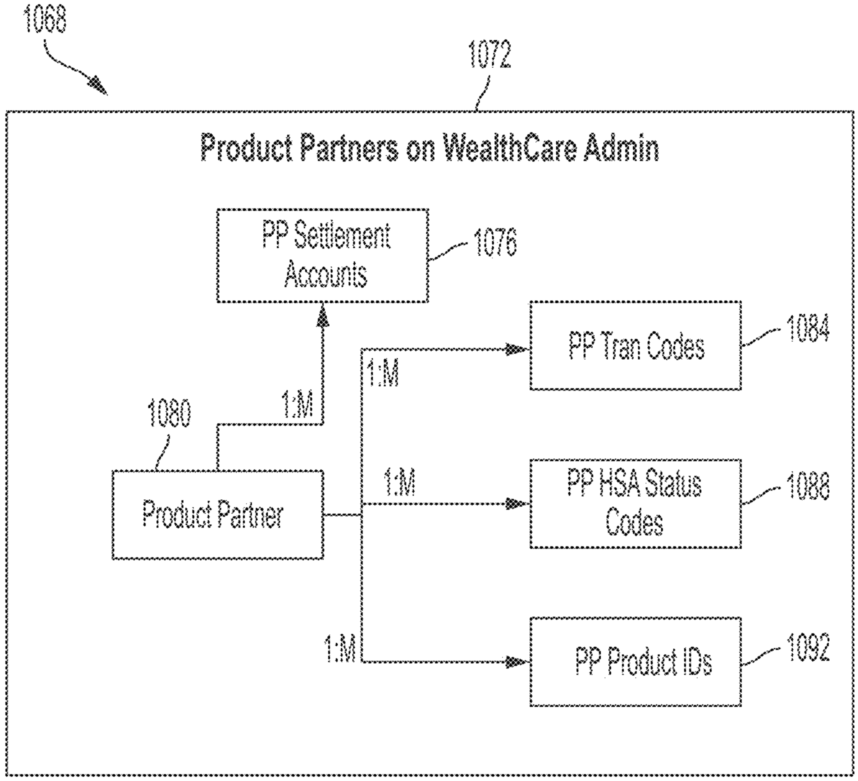
Figure 10C:
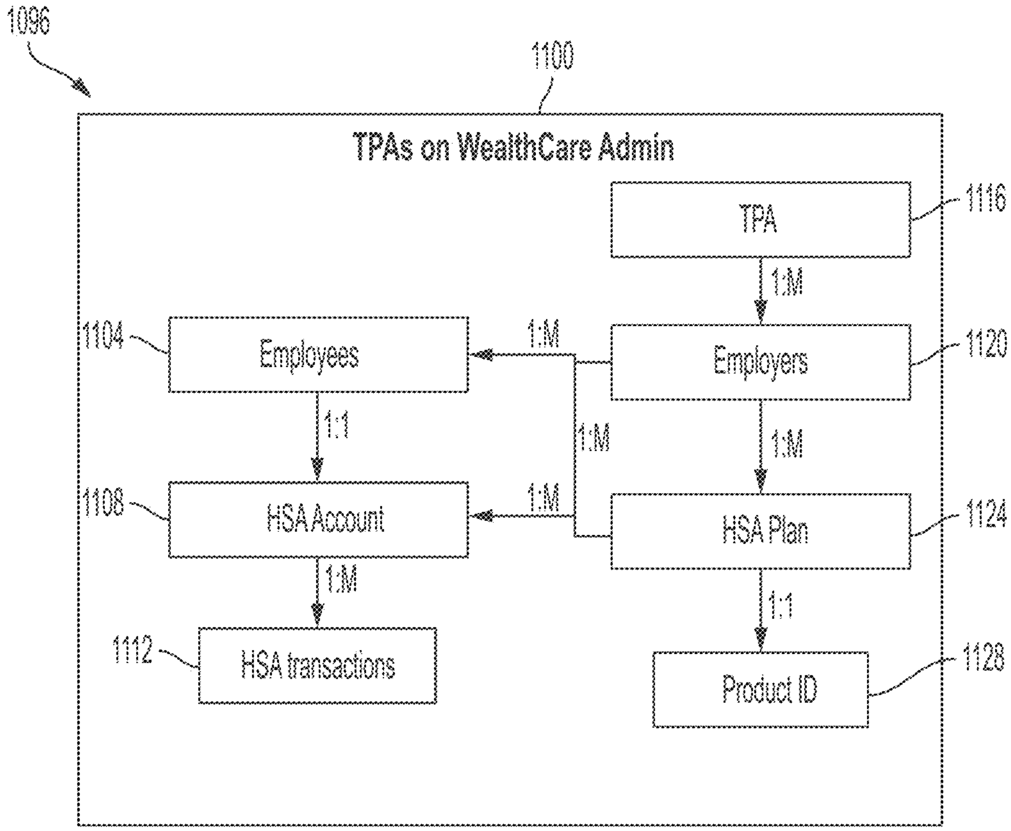
Figure 10D:
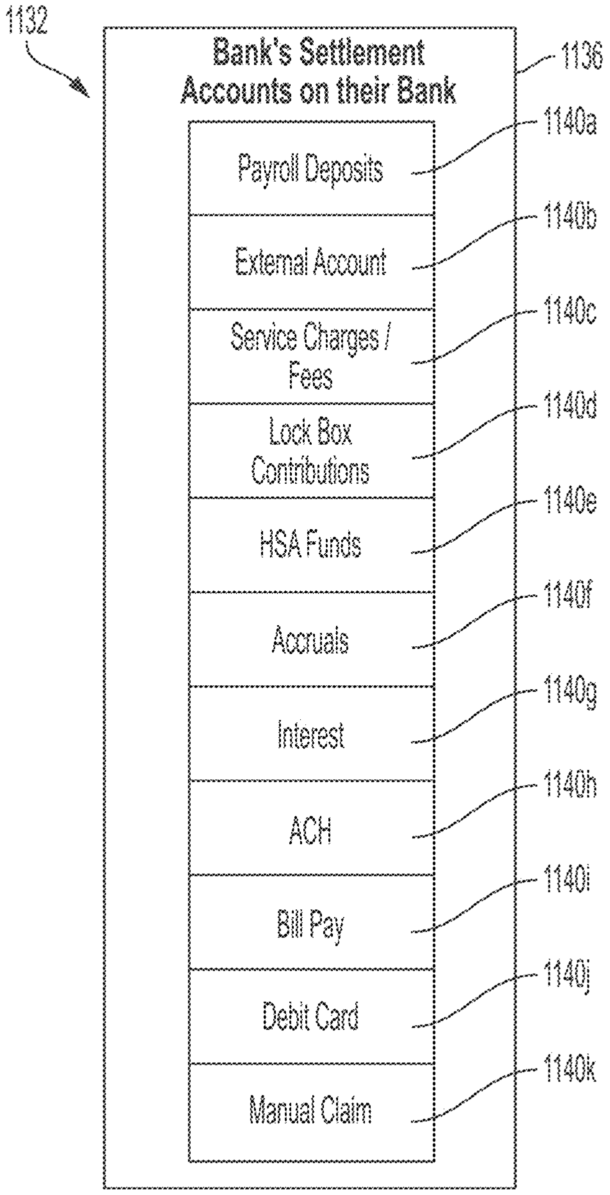

Referring now to FIGS. 10A-10D, block diagrams depicting embodiments of transaction enforcement portal interfaces for managing electronic transaction requests are shown. The interfaces can be executed on a server. The interfaces can include or be executed on system 700, TEPS 708, or one or more components thereof. The interfaces illustrated in FIGS. 10A-10D allow the TEPS 708 to interact with various entities for managing electronic transaction requests, such as servers of insurance administrators, employers, and financial institutions. FIG. 10A illustrates a system 1000 including a bank instance 1004 in which a financial institution entity (e.g., a bank entity) can manage electronic transactions related to electronic benefits accounts and electronic funding transaction requests. FIG. 10B illustrates a system 1068 in which a product partner module 1072 can manage electronic benefits accounts, including updating electronic benefits accounts responsive to electronic transaction requests. FIG. 10C illustrates a system 1096 in which a third party administrator module 1100 can manage electronic benefits accounts, such as for allowing an employer entity to manage electronic benefits accounts provided to employees. FIG. 10D illustrates a system 1132 in which a financial institution entity can manage electronic financial accounts using a bank settlement module 1136, such as via financial modules 1140*a-k*, responsive to a net settlement request. Each of the systems 1000, 1068, 1096, and 1132, and/or the bank instance 1004, the product partner module 1072, the third party administrator module 1100, and the bank settlement module 1136 can include communications interfaces configured to receive and transmit one or more data packets carrying electronic transaction amongst each other, such as for updating relevant databases and modules responsive to adjudication of a request to initiate a single electronic benefits account transaction.

Referring now to FIG. 10A, and in further detail, a system 1000 is shown in which an entity of a financial institution, such as a bank, can interface with the TEPS 708. For example, a bank instance 1004 can be provided on the TEPS 708 as an electronic interface between the TEPS 708 and the bank entity. The bank instance 1004 can be provided as an extension of the TEPS 708 to be executed by a server of the bank entity. The bank instance 1004 allows the bank entity to process electronic transaction requests, The bank instance 1004 includes an HSA custodian 1028 configured to manage transactions between individual HSA accounts 1032 and transaction modules such as settlement accounts module 1008, ledger accounts module 1012, transaction codes module 1016, product partner HSA status codes module 1020, and accumulator module 1024. Responsive to the bank instance 1004 processing an electronic transaction request to transfer funds, the bank instance 1004 can update a settlement account maintained by the settlement accounts module 1008 and a ledger account maintained by the ledger accounts module 1012 corresponding the electronic benefits account, and transmit the transaction amount (if approved) to the accumulators module 1024 in order to update the total amount of funds maintained by the electronic benefits account.

The HSA custodian 1028 can be configured to manage a demographics module 1040 and a products ID module 1044. The demographics module 1040 can store or otherwise maintain demographics data regarding the bank entity. The products ID module 1044 can store or otherwise maintain electronic financial products provided by the bank entity, such as HSA products. The products ID module 1044 can manage service charges module 1048*a* and interest plan module 1048*b*. In some embodiments, the service charges module 1048*a* and interest plan module 1048*b* can allow the bank entity to provide custom financial products. For example, the bank entity can provide an electronic benefits account having a specific service charge per transaction. When the TEPS 708 processes an electronic transaction request, the bank instance 1004 can process an indication of the electronic benefits account associated with the electronic transaction request, identify a product ID based on the electronic benefits account, and perform a lookup in the service charges module 1048*a* in order to identify a service charge to apply with the electronic transaction.

The bank instance 1004 can include an HSA account accumulator module 1052. The HSA account accumulator module 1052 can be similar to or identical to the accumulators module 1024. When the accumulators module 1024 or the HSA account accumulator module 1052 receive an electronic transaction for transferring funds to the electronic benefits account, each module can generate one or more data packets carrying an indication of the transaction amount to transmit to the other module, in order to maintain updated transaction amounts for the electronic benefits account.

In some embodiments, responsive to the TEPS 708 approving an electronic transaction request to fund the electronic benefits account, the HSA account transactions module 1036 can transmit instructions to an HSA check events module 1008 to generate instructions causing a remote entity to generate or print a check. For example, the HSA check events module 1008 can generate instructions including the transaction amount to a remote client device 1060, causing a print checks module 1064 of the remote client device 1060 to receive the instructions, extract the transaction amount from the instructions, and generate or print the check.

In some embodiments, responsive to a transaction causing the ledger accounts module 1012 to update a ledger account associated with an electronic benefits account, the ledger accounts module 1012 can generate one or more data packets carrying an indication of the transaction amount and an indication of a financial product associated with the transaction. The ledger accounts module 1012 can transmit the one or more data packets to one of a bank instance financial module 1056*a-k* configured to store information regarding bank financial products. The bank instance 1004 can be configured to generate one or more data packets carrying a net settlement of one or more bank financial products responsive to the bank instance financial modules 1056*a-k* receiving a transaction indication from the ledger accounts module 1012. For example, the ledger accounts module 1012 can transmit one or more data packets carrying an indication to transfer funds from a payroll deposit account maintained by the payroll deposit module 1056*g* to a debit card maintained by the debit card module 1056*e*. The bank instance financial modules 1056*a-k* can receive the indication of the funds to be transferred, subtract the transaction amount from the payroll deposit account, and add the transaction amount to the debit card account. In some embodiments, the bank instance financial modules 1056*a-k* can generate one or more data packets carrying an indication of the net settlement performed at the bank instance 1004 to be transmitted to a remote server of a financial institution in order to update the remote server regarding the transaction performed.

Referring now to FIG. 10B, and in further detail, a system 1068 is shown in which a product partner can interface with the TEPS 708 to remotely manage electronic transactions for electronic benefits accounts. The system 1068 can be executed on or as part of a server of a remote product partner entity, such as an insurance administrator server. The system 1068 can include a product partner module 1072 configured to communicate with the system 700, the TEPS 708, the bank instance 1004, or components thereof. The product partner module 1072 can include a product partner interface 1080 for communicating with remote entities and managing electronic transactions. The product partner interface 1080 can include a user interface configured to receive user inputs indication electronic transaction requests. The product partner module 1072 can include modules or databases for maintaining information regarding electronic benefits accounts, including product partner transactions codes 1084 (e.g., transaction codes mapping electronic benefits account transactions to one of a current year or a previous year; transaction codes mapping transaction information to human-readable output, etc.); product partner HSA status codes 1088 (e.g., statuses of electronic transactions such as pending, in-process, posted, etc.); and product partner product IDs 1092 (e.g., IDs indicating a type of electronic financial product, such as an FSA, etc.).

Referring now to FIG. 10C, and in further detail, a system 1096 is shown in which a third party administrator (TPA) can interface with the TEPS 708 to remotely manage electronic transactions for electronic benefits accounts. The system 1096 can be executed on or as part of a server of a remote TPA entity, such as an employer administrator server. The system 1096 can include a TPA module 1100 configured to communicate with the system 700, the TEPS 708, the bank instance 1004, the product partner module 1072, or components thereof. The TPA module 1100 can include a TPA interface 1116 configured to manage electronic transactions. The TPA interface 1116 can include a user interface configured to display information maintained by the TPA module 1100 to a user and receive user inputs from a user. The TPA module 1100 can include an employers module 1120 configured to manage information regarding one or more employers. The one or more employers managed by the employers module 1120 can correspond to one or more employees managed by an employees module 1104. Each employee corresponds to one HSA account managed by an HSA account module 1108. Each HSA account managed by the HSA account module 1108 can transmit and receive one or more HSA transactions managed by the HSA transaction module 1112. Each employer managed by the employers module 1120 can provide a plurality of HSA plans managed by an HSA plan module 1124. The TPA module 1100 can store information regarding product IDs for each HSA plan in a product IDs module 1128. The TPA module 1100 can include a communications interface configured to receive and transmit one or more data packets from each of the bank instance 1004 and the product partners module 1072, and components thereof.

Referring now to FIG. 10D, and in further detail, a system 1132 is shown in which a financial institution entity (e.g., a bank entity) can locally manage electronic financial accounts. The system 1132 includes a bank settlement module 1136 including a plurality of financial modules 1140*a*-1140*k*, such as payroll deposits module 1140*a*, external account 1140*b*, service charges/fees module 1140*c*, lock box contributions 1140*d*, HSA funds module 1140*e*, accruals module 1140*f*, interest module 1140*g*, ACH module 1140*h*, bill pay module 1140*i*, debit card module 1140*j*, and manual claim module 1140*k*. Responsive to receiving net settlement requests generated by and transmitted from the bank instance 1004, the bank settlement module 1136 can be caused to process the net settlement request, extract an indication of an electronic financial account associated with the request and a transaction amount, and update the corresponding electronic financial account based on the transaction amount. For example, the bank instance 1004 can transmit a net settlement request including an indication of an electronic benefits account and an interest charge transaction amount to the bank settlement module 1136, causing the bank settlement module 1136 to extract the interest charge transaction amount and update the corresponding electronic benefits account interest charges maintained by the interest module 1140*g*. As such, in some embodiments, the financial modules 1140a-1140k can be configured to mirror the bank instance financial modules 1056a-k shown in FIG. 10A.

The bank instance 1004, the product partners module 1072, and the TPA module 1100 can each include communications interfaces configured to receive and transmit one or more data packets from each other, such as one or more data packets configured to indicate electronic transaction requests, electronic transaction processings, and information regarding electronic benefits accounts. For example, the product partners module 1072 can receive and transmit information regarding settlement accounts with the bank instance 1004, such as for mirroring information stored in the settlement accounts module 1008 and the product partners settlement account module 1076. Similarly, the product partners module 1072 and the TPA module 1100 can receive and transmit information regarding product IDs in order to share and mirror information stored in the product partners ID module 1092 and the product ID module 1128. The TPA module 1100 can receive and transmit information regarding electronic transactions in order to share and mirror information stored in the HSA accounts module 1032 and the HSA account module 1108, and to share and mirror information regarding electronic benefits transactions stored in the HSA account transactions module 1036 and the HSA account transaction module 1112.

In some embodiments, responsive to the TEPS 708 denying an electronic transaction request to transfer funds to an electronic benefits account and generating an alert indicating the denial, the bank instance 1004 can update the HSA account module 1032 and the HSA transactions module 1036 for the electronic benefits account corresponding to the electronic transaction request to indicate that the electronic transaction request was denied. The bank instance 1004 can generate one or more data packets carrying an indication of the electronic benefits account and an indication of the denial to be transmitted to the TPA module 1100. The TPA module 1100 can process the one or more data packets to extract the indications, and perform a lookup in the modules 1108 and 1112 in order to identify corresponding entries for the electronic benefits account to update the modules 1108 and 1112 by writing the transaction denial to the corresponding entries.

In some embodiments, responsive to the TPA module 1100 generating a new HSA plan entry in the HSA plan module 1128, the TPA module 1100 is configured to request a product ID for the new HSA plan. The TPA module 1100 can generate one or more data packets carrying the product ID request including an indication of the HSA plan, and transmit the one or more data packets to the product partners module 1072. The product partners module 1072 can process the one or more data packets to extract the product ID request and the indication of the HSA plan, perform a lookup in the product partners ID module 1092, extract the product ID corresponding the new HSA plan, and generate and transmit one or more data packets including the corresponding product ID to the TPA module 1100.

E. Administrator Matching and Report Generating System (AMRGS)

The systems and methods of the present solution are directed to the technical problems and challenges of implementing the functionality of managing or generating an interface of an electronic transaction based technology and platform. Existing electronic transaction based technologies and platforms do not effectively and efficiently make use of the computing and network resources deployed for interface based technologies and platforms to include such functionality. Without implementing such functionality, existing electronic transaction based technologies and platforms have the problems of excessive server-client requests and responses, processing delays, increase bandwidth usage, or erroneous reports or interfaces.

The systems and methods of the present solution are directed to the improvement of the performance and operation of the electronic transaction based technology and platform and computing and networking resource used by such electronic transaction based technology and platform. In some aspects, the present solution improves and enhances the implemented functionality of the electronic transaction based technology and platform implemented on, integrated with and inherently tied to the processor, memory, network and computing resources of one or more computing devices. In some aspects, the present solution more effectively performs the functionality of the electronic transaction based technology and platform thereby making and causing more effective use of the computing and networking resources to achieve the improved functionality of the present solution. The same computing and network resources used by such electronic transaction based technology and platform will provide increased and improved functionality with implementation of the present solution.

In some aspects, the present solution more efficiently uses the computing and networking resources to implement the improved functionality of the electronic transaction based technology and platform. For example, systems and methods of the present solution can use an administrator matching and report generating system with respect to information regarding electronic accounts, such as an electronic benefits account. Systems and methods of the present solution can generate dynamic reports including multiple performance metrics based on similar administrators.

Administrators that establish or provide electronic tax benefits accounts can utilize backend information technology infrastructure to process, analyze, monitor or manage the electronic tax benefits accounts. An entity managing the backend information technology may have access to data regarding electronics tax benefit accounts across multiple administrators. This data may include the different parameters associated with respective electronic benefits accounts of the different administrators. As examples of parameters, one administrator may have a higher monthly fee compared with another administrator, or may set a higher minimum balance to be maintained compared to another administrator. Some administrators can change parameters associated with their accounts, for example, to increase the number of participants that use their accounts.

The present disclosure provides systems and methods of managing information technology to generate a dynamic interface. The dynamic interface can include a dynamic report based on analyzing peer administrators. For example, the system can provide benchmarking information on a predefined set of administrative indicators and enable administrators to manipulate parameters to compare their performance to similar administrators. The system can further allow an administrator to manipulate the data to further stratify the data on various industry measures and determine how their performance compares with the stratified data.

The system can be configured with an administrator matching technique to identify peer or similar administrators. Peer administrator may refer to administrators having characteristics, features, or parameters that satisfy a matching or similarity criterion or criteria using a matching technique. The matching technique can include a comparison function, a machine learning technique, a statistical technique, correlation techniques or cross-referencing techniques. For example, the matching technique can compare parameters associates with electronic tax benefit accounts between two or more administrators to identify two or more administrators having similar parameters. In some cases, the matching technique can include assigning weights to parameter such that a first parameter may have a higher weight than a second parameter and a third parameter. For example, with this weighting structure, the system can determine that a first administrator is similar to a second administrator if the first parameter with the highest weight matches between the first and second administrators, even though the second and third parameters do not match. In another example, the system may determine that two administrators are not similar because the first parameter with the highest weight does not match, even though the second and third parameters with lower weights do match.

Upon identifying similar administrators using one or more matching techniques, the system can generate a dynamic report. The dynamic report interface can include or be configured on a dashboard. In some cases, the dynamic report interface can be provided or streamed over a data network. The dynamic report interface can be configured to receive data manipulation indications via an input device. For example, the interface can receive indications to manipulate the data for a different time period, based on size of the administrator, geographic location of the administrator (or the administrator's customers), number of years in operation, marketing budget, number of employees, demographics, industry sectors, revenue, profit, expenses, types of electronic accounts, types of transaction configurations, funding sources, interest rate, or any other parameter that facilitates generating a dynamic report.

In an illustrative embodiment, the system can provide payment processing infrastructure and technology to an administrator such as an insurance company. The insurance company can provide various types of insurance (e.g., health, dental, vision, car, property, legal, construction, etc.) to its customers. A customer of the insurance company can include an employer that has employees. The system can enable the insurance company to generate a dynamic report to identify similar administrators and their performance. The insurance company can, for example, set parameters for: opening fee, minimum operating balance, monthly fee, annual fee, investment options, fund access type (e.g., checkbook, debit card). Parameters could also include interest rate, contribution from employer; how invest funds (e.g., investment bank funds, equity investing, mutual funds, or money market accounts).

The dynamic report can indicate a level of performance of the insurance company as well as how the insurance company's level of performance compares or relates to the identified similar administrators. Performance indicators can include, for example, success of investments, number of users, number of employers, percentage of employees per employer using a tax benefit account and amount of contributions. In some cases, the system can aggregate data among multiple similar administrators and display the aggregated data in the dynamic report in an anonymized data format. In some cases, manipulating parameters used to generate the dynamic report can cause the system to re-execute the matching technique and identify a different set of similar administrators based on the new parameters. The system can then regenerate, manipulate, or otherwise update the report provided by the dynamic report interface using the new set of similar administrators.

Figure 11:
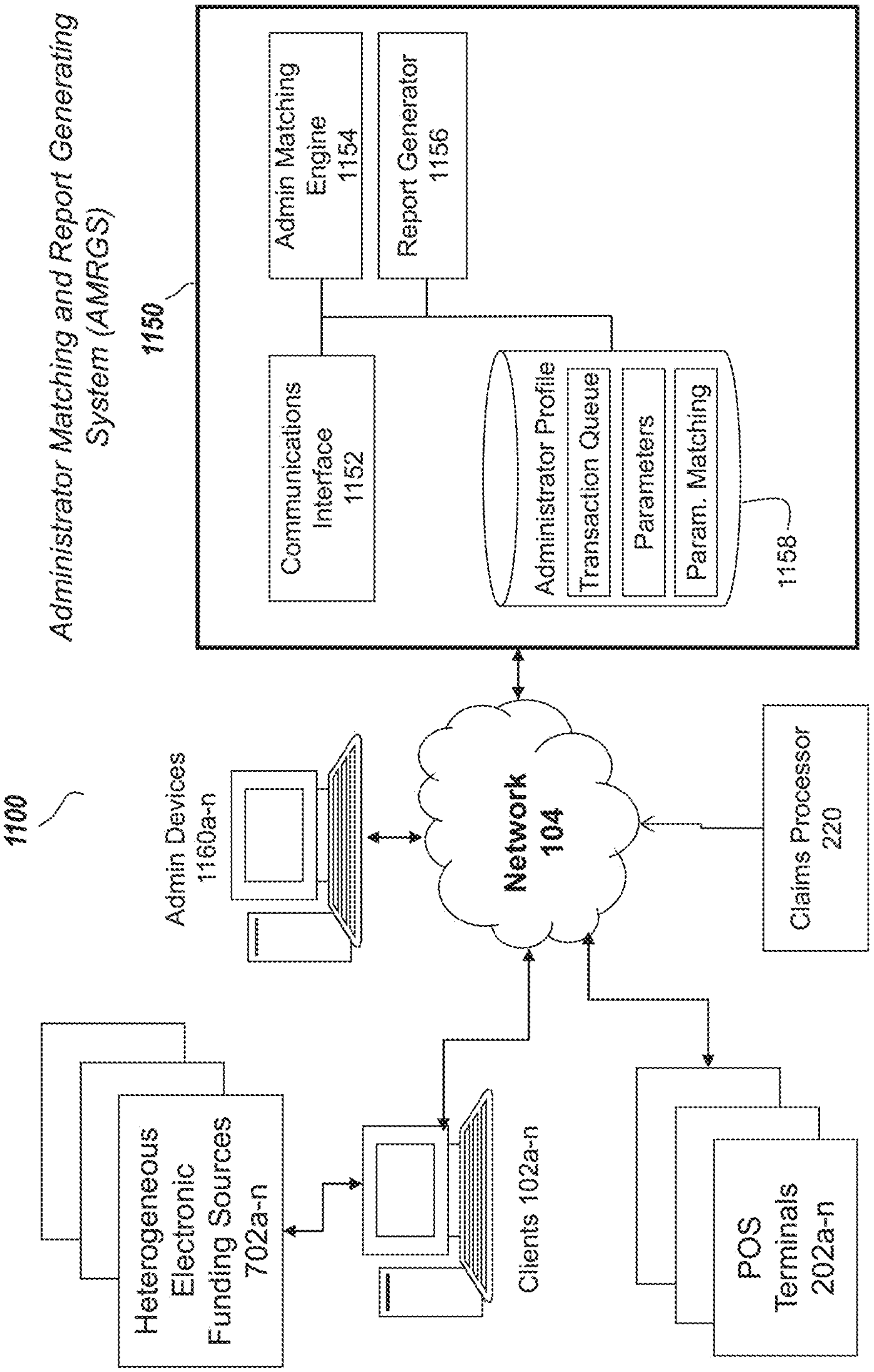
FIG. 11 is a block diagram depicting an embodiment of a system for managing information technology infrastructure.

Referring now to FIG. 11, a block diagram depicting an embodiment of a system for managing information technology infrastructure. In brief overview, and in some embodiments, the system 1100 includes an administrator matching and report generating system 1150 ("AMRGS"). The AMRGS 1150 can include the MPTS 408 depicted in FIG. 4 or the TEPS 708 depicted in FIG. 7, or one or more components, modules or functionality depicted in FIG. 4 or FIG. 7, and can perform the functions of the MPTS 408 or the TEPS 708. The AMRGS 1150 can receive or transmit data via a network 104 with clients 102*a-n*, POS terminals 202*a-n*, and administrator devices 1160*a-n*. The system 1100 can include or interact with one or more clients 102*a-n* (or client device 102), one or more point-of-sale (POS) terminals 202*a-n* (or POS terminal 202), and one or more administrator devices 1160*a-n* (or administrator device 1160).

The AMRGS 1150 can include a communications interface 1152. The communications interface 1152 can include the communications interface 410 depicted in FIG. 4 or the communications interface 710 depicted in FIG. 7, or one or more components or modules depicted in FIG. 4 or FIG. 7, and can perform the functions of the communications interface 210 or the communications interface 710. In some aspects, the communications interface 1152 is implemented to address the technical problems and challenges of prior systems not deploying the present solution. In some aspects, the communications interface 1152 is implemented to make or cause more effective and efficient use of computing and networking resources. For example, the communications interface 1152 can cause more effective and efficient use of computing and network resources by reducing the number of processing cycles, memory or network bandwidth used to generate dynamic interfaces or reports. The communications interface 1152 can provide an improved generation of a dynamic interface or reports by integrating with the admin matching engine 1154, database 1158, report generator 1156, claims processor 220, POS terminals 202*a-n*, or clients 102*a-n* to generate dynamic interfaces or reports.

The communications interface 1152 is configured with one or more communications ports, application programming interfaces, network protocols (e.g., TCP/IP), authentication protocols, or security protocols (e.g., SSL). The communications interface 1152 can receive a request to match an administrator associated with the administrator device 1160 with other administrators similar to the matched administrator. In addition, the communications interface 1152 can receive a request to generate a dynamic report including performance metrics associated with the similar administrators. In some cases, the AMRGS 1150 can generate and process the request to identify similar administrators responsive to receiving a request to generate a report.

The AMRGS 1150 can include a matching engine 1154. The matching engine 1154 can include the policy engine 412 depicted in FIG. 4 or the enforcement engine 712 depicted in FIG. 7, or one or components or modules depicted in FIG. 4 or FIG. 7, and can perform the functions of the policy engine 412 or the enforcement engine 712. The matching engine 1154 identifies, responsive to the communications interface 1152 receiving the request to match an administrator with one or more similar administrators or receiving an identifier of an administrator, one or more administrator profiles that are similar to the administrator requesting the match or sending the identifier. In some aspects, the matching engine 1154 is implemented to address the technical problems and challenges of prior systems not deploying the present solution. In some aspects, the matching engine 1154 is implemented to make or cause more effective and efficient use of computing and networking resources. For example, the matching engine 1154 can cause more effective and efficient use of computing and network resources by reducing the number of processing cycles, memory or network bandwidth used to generate matches. The matching engine 1154 can provide an improved generation of a match by integrating with the communications interface 1152, database 1158, report generator 1156, claims processor 220, POS terminals 202*a-n*, or clients 102*a-n* to generate the match.

The AMRGS 1150 can include a report generator 1156. The report generator 1156 can include the transaction engine 412 depicted in FIG. 4, or one or more components or modules depicted in FIG. 4, and can perform the functions of the transaction engine 414. The report generator 1156 generates a dynamic report including one or more performance metrics associated with the one or more similar administrators identified by the matching engine 1154. The report generator 1156 can generate a dynamic report and transmit one or more data packets carrying data indicating the report to an administrator device 1160 via the communications interface 1152 and the network 104. In some aspects, the report generator 1156 is implemented to address the technical problems and challenges of prior systems not deploying the present solution. In some aspects, the report generator 1156 is implemented to make or cause more effective and efficient use of computing and networking resources. For example, the report generator 1156 can cause more effective and efficient use of computing and network resources by reducing the number of processing cycles, memory or network bandwidth used to generate dynamic interfaces or reports. The report generator 1156 can provide an improved generation of a dynamic interface or reports by integrating with the admin matching engine 1154, database 1158, communications interface 1152, claims processor 220, POS terminals 202*a-n*, or clients 102*a-n* to generate dynamic interfaces or reports.

The AMRGS 1150 can include one or more databases or data structures that store information to facilitate the systems and methods of the present solution, such as database 1158. The database 1158 can include the database 418 or the databases 714 or 716, or one or more components or modules depicted in FIG. 4 or FIG. 7, and can perform the functions of the databases 418, 714, or 716. The database 1158 (or administrator profile) can include an administrator profile associated with an administrator maintained on or configured on the AMRGS 1150 that is associated with one or more parameters and one or more performance metrics. The parameters can include various characteristics and attributes associated with an electronic benefits account, such as, but not limited to, an account opening fee, a minimum operating balance, a monthly fee, an annual fee, an electronic fund access type, an interest rate, or the like. The performance metrics can include various resulting characteristics and attributes associated with an electronic benefits account, such as, but not limited to, percentage or number of participants of an electronic benefits account associated with a given administrator profile, amount of money contributed to an electronic benefits account associated with a given administrator profile, or the like. The database 1158 can include a profile database of the administrators. The profile database can include an entry corresponding to an administrator profile that may point to entries or values in the parameters and performance metrics databases associated with that particular administrator profile. The entry can include a unique identifier for the administrator.

The AMRGS 1150, communications interface 1152, matching engine 1154, and report generator 1156 can each include one or more processing units or other logic devices such as programmable logic array engines, modules, or circuitry designed and constructed to facilitate managing security on a network infrastructure. The AMRGS 1150 can include the components 100 shown in FIG. 1C or FIG. 1D, or be configured to operate as a service in cloud 108. The 1108 can include or interact with one or more servers 106*a-n* and clients 102*a-n*.

In some embodiments, the AMRGS 1150 can employ a multitier architecture such as a client-server architecture in which presentation, application processing, and data management functions are logically or physically separated. The presentation tier, or front-end, can include the communications interface 1152 that serves static content or dynamic content to be rendered by the client 102 or by the administrator device 1160 (e.g., by a web browser executing on client 102 or administrator device 1160). The presentation tier or web server 210 can interact or communicate with the application tier to obtain data to provide to the client 102, POS terminals 202*a-n*, or administrator device 1160. The application tier can include the matching engine 1154 and the report generator 1156 that controls the system's functionality and performs additional processing or analysis on data. The application tier can interact with the data tier to obtain the transaction data. The data tier can include data persistence mechanisms (database servers, file shares, etc.) and the data access layer that encapsulates the persistence mechanisms and exposes the data. The data tier can include database 1158. The data tier can include an application programming interface (API) to the application tier. The database 1158 can include stored procedures (e.g., SQL statements) that perform tasks with respect the stored data.

In further detail, and in some embodiments, the AMRGS 1150 includes a communications interface 1152. The communications interface 410 can execute on one or more processors of a server. The communications interface 1152 can include one or more communications ports and be configured with one or more network protocols. Communications ports can include, e.g., network ports, Ethernet ports, WAN ports, I/O ports, or software ports. The communication port can be configured with a network protocol such as Transport Layer Protocols such as TCP/IP or UDP that are configured to receive and process data packets received via a computer network. The port can include or be associated with an IP address of a host and a protocol type of the communication.

In some embodiments, the communication interface 1110 can receive data packets. The data packets can be generated by a device at an administrator to request matching or a dynamic report. The device can refer to an administrator device ("administrator device") such as administrator device 1160. The administrator device 1160 may monitor data from the various electronic benefits accounts associated with the administrator. The accounts associated with the administrator may be accounts that are managed or maintained by the administrator. The administrator may be a point of contact for customers or participants of the associated accounts. In some embodiments, the client 102, which may correspond to an individual participant of the administrator's electronic benefits account, may access the account and perform a number of actions with respect to the account, such as, fund the account (e.g., via heterogeneous electronic funding sources 702), withdraw from the account, charge the account, and the like. The administrator of the electronic benefits account, as the caretaker of the account, may adjust parameters associated with the account, such as, monthly fees, minimum running balances, etc. At the same time, the AMRGS 1150 may monitor the data, parameters, and performance of the account and store the information under an administrator profile associated with the administrator of the account. The AMRGS 1150 may receive the data associated with the individual participants and their individual accounts from the client's 102 and the parameter data associated with the accounts from the administrator device 1160 via the network 104.

An administrator device 1160 is the place where an administrator may perform various functions of the administrator, for example, functions associated with electronic benefits accounts of the administrator. The administrator device 1160 is the point at an administrator may send requests to the AMRGS 1150 for generating a dynamic report. The administrator device 1160 may also be configured to transmit an identifier associated with the administrator corresponding to the administrator device 1160 for identification by the AMRGS 1150. In some embodiments, the receiving of the identifier initiates the dynamic report generating process.

The administrator device 1160 can include hardware and software. Administrators can utilize scanners, EFTPOS terminals, touch screens and any other wide variety of hardware and software available for use with administrator device 1160. For example, an administrator can use software to make adjustments to parameters associated with their electronic benefits accounts.

The administrator device 1160 can include advanced features to cater to different functionality, such as account participant forecasts and estimates, account simulation, communication with participants of accounts, performing actions associated with individual participant accounts (e.g., freezing an account), collecting data from one or more of the participant accounts, etc., all built into the administrator software. The administrator device 1160 can be configured to execute user-input commands with respect to the electronic benefits accounts of the administrator.

The communications interface 1152 can receive data packets generated by the administrator device 1160 responsive to a user command resulting in transmission of a request to perform administrator matching or generate a dynamic report. The data packets can include header information and payload information. Multiple data packets can be strung together in a sequence. The header information can refer to TCP/IP headers that include fields such as source port, destination port, sequence number, acknowledge number, window size, etc. The payload information of the data packet can include information related to the request, the request to match or generate a report, an identifier of the administrator of the administrator device 1160, parameters associated with the requesting administrator, parameters adjusted by the administrator, and other information facilitating administrator matching and report generation. For example, with respect to the request for administrator matching, the payload information may include an identifier of the administrator sending the request. In response to receiving the identifier, the AMRGS 1150 can access the database 1158 to retrieve the administrator profile corresponding to the identifier, and may further access parameters and performance metrics associated with the retrieved administrator profile. The administrator profile can further include information associated with the administrator, such as, but not limited to, the number of employees or potential participants of electronic benefits accounts under the administrator, a geographic location of the administrator, geographic locations of participants associated with the administrator, size and location of employers associated with the administrator, and other information associated with the administrator. In other embodiments, the payload information of the data packet may include information associated with the requesting administrator. Furthermore, with respect to the request for generation of a dynamic report, the payload information may include an identifier of the administrator sending the request. In response to receiving the identifier, the AMRGS 1150 can access the database 1158 to retrieve the administrator profile corresponding to the identifier, and may further access parameters and performance metrics associated with the retrieved administrator profile. The parameters associated with the accessed administrator profile may include characteristics of the electronic benefits accounts of the administrator, such as, but not limited to, an account opening fee, a minimum operating balance, a monthly fee, an annual fee, an electronic fund access type, or an interest rate. In other embodiments, the payload information of the data packet may include the parameters. For example, a user of the administrator device 1160, instead of relying on the parameters already associated with the stored administrator profile, may modify the administrator parameters to receive a dynamic report based on modified parameters, and send those modified parameters to the AMRGS 1150 as part of the request for generating a dynamic report. The AMRGS 1150 can receive the data packet with header information and payload information and process the packets to obtain information for further processing. The data packets (e.g., via the payload) can include the request to perform matching or generate a dynamic report.

The data packets can carry data identifying an administrator. In some embodiments, the data carried by the data packets include an administrator identifier. The administrator identifier can include strings, characters, numbers, alphanumeric characters, symbols, or other identifiers. In some embodiments, the data identifies a merchant, and the AMRGS 1150 determines an administrator profile based on the identification of the administrator. The AMRGS 1150 can determine the administrator profile by, for example, using an administrator mapping or lookup table stored in database 1158. In some embodiments, the data packets carrying the request to identify matching administrators and generate a dynamic report includes a data structure having a first field indicating an administrator identifier and a second field indicating values of one or more parameters associated with electronic benefits accounts. In some embodiments, the data packets are generated by an administrator device 1160 when requesting matching and a report, and the data packets carry data identifying an administrator profile including information pertaining to the requesting administrator and the parameters.

The data packets (e.g., payload of the data packets) can further identify an administrator profile maintained and configured on the server. The administrator profile can be maintained and configured in a database 1158. The administrator can correspond to an administrator profile and have a unique identifier. The unique identifier can include numbers, letters, characters, symbols, etc. The administrator can be associated with the administrator making the request at the administrator device 1160.

The communications interface 11110 can further receive data packets (e.g., payload information) identifying parameters and values of those parameters pertaining to electronic benefits accounts, such as, but not limited to, an account opening fee, a minimum operating balance, a monthly fee, an annual fee, an electronic fund access type, an interest rate, and the like. In some embodiments, the values of the parameters received at the communications interface via the data packets may be modified or updated at the administrator device. Accordingly, the updated values of the parameters may be received at the AMRGS 1150 via the communications interface for operating on by the matching engine 1154 and the report generator 1156. In such embodiments, the report generator 1156 may output results based on the updated values in real-time, and thus may generate dynamic reports based on updated values of parameters received from the administrator device 1160 in real-time.

In some embodiments, the administrator device 1160 can generate multiple data packets for a single request. The multiple data packets can each include a header and a payload. The header can indicate that the multiple data packets are to be grouped together for routing, transmission, or processing purposes.

The AMRGS 1150 can be configured to authenticate communications and requests. In some embodiments, the communications interface 1152 receives communications such as the request to identify similar or matching administrators and generate a dynamic report. The request can include security credentials such as a security certificate or security token. The security credentials can be associated with an administrator. The AMRGS 1150 can be configured to extract the security credential from the request, and authenticate the request by comparing the security credential against a known or verified security credential. For example, the user profiles or merchant information stored in database 1158 can include known or verified security credentials for comparison with the security credential of the request. In some embodiments, the AMRGS 1150 receives the request to generate a dynamic report via the communications interface 1152, extracts a security credential from the request, analyzes the extracted security credential to identify an administrator, queries the database 1158 for a verified security credential stored with an administrator profile corresponding to the identified administrator, compares the extracted security credential to the verified security credential, and authenticates the request based on the extracted security credential matching the verified security credential. In some embodiments, the AMRGS 1150 analyzes the extracted security credential to identify an administrator, queries the database 1158 for a verified security credential stored with administrator information corresponding to the identified administrator, compares the extracted security credential to the verified security credential, and authenticates the request based on the extracted security credential matching the verified security credential.

In some embodiments, the AMRGS 1150 includes a matching engine 1154. The matching engine 1154 can execute on one or more processors of a server, such as a server of the AMRGS 1150. The matching engine 1154 can receive, retrieve, or otherwise obtain or access some or all of the data carried by the data packets. The matching engine 1154 can receive, retrieve, or otherwise obtain or access administrator profiles, such as administrator profiles maintained in database 1158. The matching engine 1154 can determine one or more administrators that are similar (e.g., based on a similarity metric) or that match the administrator of the administrator device 1160, responsive to the communication interface 1110 receiving the request to generate a dynamic report.

The AMRGS 1150 can initiate, launch, execute or perform a matching process responsive to receiving the data packets, such as by causing the matching engine 1154 to execute matching rules or logic maintained in the database 1158 or maintained in the matching engine 1154 itself. The AMRGS 1150 can cause the matching engine 1154 to identify an administrator profile maintained in the database 1158 identified by an identifier included in the received data packets. The AMRGS 1150 can cause the matching engine 1154 to determine that a remote administrator profile is required based on information extracted from the received data packets, and the AMRGS 1150 can request the remote administrator profile by transmitting one or more data packets carrying an administrator profile request to a remote server, such as a server of an insurance administrator or an employer. The administrator profile request can cause the remote server to transmit the requested remote administrator profile to the AMRGS 1150. For example, the matching engine 1154 can determine that the received data packets indicate a new insurance administrator or employer for which an administrator profile is not yet maintained in the database 1158. In some embodiments, the AMRGS 1150 receives in the data packets, along with the request to generate a dynamic report, the administrator profile of the requesting administrator at administrator device 1160. The administrator profile may include information associated with the administrator, such as, but not limited to, the number of employees or potential participants of electronic benefits accounts under the administrator, a geographic location of the administrator, geographic locations of participants associated with the administrator, size and location of employers associated with the administrator, and other information associated with the administrator.

The matching engine 1154 can use any suitable logic or algorithm as a matching technique for identifying one or more administrator profiles that are similar to the administrator profile associated with the administrator device 1160 requesting a dynamic report. For example, the matching technique can include a comparison function that is a sorting algorithm that reads a list of elements through a single abstract comparison operation (e.g., "less than or equal to" operator or a three-way comparison) that determines which of two elements should occur first in the final sorted list. A requirement may be that the operator obey two of the properties of a total order.

As another example, the matching technique can include a machine learning technique that can learn from and make predictions on data. The machine learning can operate by building a model from example inputs in order to make data-driven predictions or decisions, rather than following strictly static program instructions. In some embodiments, inputs are divided into two or more classes (e.g., similar administrator profiles and not similar administrator profiles), and the learner produces a model that assigns unseen inputs to one (or multi-label classification) or more of these classes.

As another example, the matching technique can include a statistical analysis technique that includes a process or inspecting, cleaning, transforming, and modeling data. The statistical analysis can include one or more steps of data requirements, which identify data necessary as inputs to the analysis based upon requirements of those directing the analysis, data collection, data processing, and modeling and algorithms, which may be applied to the data to identify relationships among the variables, such as correlation and causation. Models may be developed to evaluate a particular variable in the data based on other variable(s) in the data.

As another example, the matching technique can include a correlation technique, which identifies a statistical relationship between two random variables or two sets of data. In some embodiments, measures of correlation to infer a presence or absence of association in a sample of data include one or more of an odds ratio, a risk ratio, an absolute risk reduction, distance correlation, tetrachroic correlation coefficient, mutual information, and the like.

As another example, the matching technique can include a cross-referencing technique. The cross-referencing technique may incorporate a database management system that follows a relational model. The database management system may use a table that has xref as a prefix or suffix to indicate it is a cross-reference table that joins two or more tables together via primary key.

In some embodiments, the matching engine 1154 retrieves the information included in the administrator profile associated with the requesting administrator device 1160, and compares information of the administrator profile with the information of other administrator profiles stored in the database 1158 to determine a similarity metric between the requesting administrator profile and another given administrator profile. After determining a value of a similarity metric between the requesting administrator profile and another administrator profile, the matching engine 1154 may compare the determined value of the similarity metric to a predetermined similarity threshold, and if the similarity metric value meets or exceeds the similarity threshold, then the matching engine 1154 may flag that administrator profile as being similar to the requesting administrator profile. However, if the matching engine 1154 determines that the similarity metric value is below the similarity threshold, then the matching engine 1154 may not flag that administrator profile as being similar to the requesting administrator profile.

In some embodiments, the matching engine 1154 may determine the similarity metric based on the respective similarities of individual parameters included in the information of the administrator profiles (e.g., similarity in number of participants, proximity in locations, etc.). The matching engine 1154 may determine how many of the individual parameters meet or exceed the similarity threshold, and if enough of the individual parameters are sufficiently similar, then the matching engine 1154 may flag that administrator profile as being similar.

In some embodiments, the matching engine 1154 may allocate predetermined weightings to certain parameters of the administrator profiles based on how important some parameters are compared to others for the similarity analysis. For example, the parameter of number of employees or participants of an administrator may be weighted heavier than the parameter of location proximity in the similarity analysis of the matching engine 1154. In some embodiments, the respective weightings associated with individual parameters may be modified at the administrator device 1160 depending on a preference of the administrator associated with the administrator device 1160.

In some embodiments, the matching engine 1154 performs the similarity analysis for each administrator profile in the database 1158 to determine one or more administrator profiles similar to the requesting administrator profile. The one or more similar administrator profiles may be a subset of the total administrator profiles stored in the database 1158. In some embodiments, the matching engine 1154 performs the similarity analysis on a subset of the total administrator profiles. For example, as an initial step, the matching engine 1154 may filter out some of the administrator profiles in the database 1158 that are easily exclude from the analysis, such as an administrator profile that has previously flagged as inactive. In some embodiments, a user at the administrator device 1160 may input a filter, and in response to the received filter information (e.g., via data packets), the matching engine 1154 may exclude administrator profiles from similarity analysis that are excluded due to the filter. For example, a user may input a filter indicating a desire to target administrator profiles that are less than five years old, in which case the matching engine 1154 may perform the similarity analysis only on those administrator profiles that satisfy the filter criteria.

In some embodiments, the matching engine 1154 may output an indication of the results of its similarity analysis and the findings of the one or more similar administrator profiles to the administrator device 1160. The indication may provide a list of the administrators that are determined to be similar to the requesting administrator profile. In some embodiments, the AMRGS 1150 may not provide the list or anonymize the list such that an administrator cannot uniquely identify the similar administrators. For example, the AMRGS 1150 can aggregate the performance data of the identified set of similar administrators to anonymize the data. In some embodiments, the AMRGS 1150 can rename or redact a unique identifier of the similar administrators, and include the false name or a random identifier in the list. In some embodiments, the list of profiles may include a similarity score next to respective administrators for indicating the degree of similarity between the requesting administrator and the listed administrator. The similarity score may be determined by matching engine 1154 based on a matching technique. In some cases, the similarity score may be based on how much a given administrator exceeds the similarity threshold. The listed profiles may be ranked by their respective similarity scores. The similarity score can include a numeric score, word, phrase, color, symbol, grade, percentage or other indicator of similarity. The similarity score can be on a scale or include a range, such as 0 to 10 or 0 to 100, with 0 being least similar and 10 or 100 most similar (or 0 most similar and 10 or 100 least similar). The grade can include A to F, with A indicating most similar and F indicating least similar. In some cases, the numeric score can be on a logarithmic scale.

In some embodiments, the AMRGS 1150 trains an administrator profile model using one or more administrator profiles stored in the database 1158. In some embodiments, the AMRGS 1150 inputs a parameter of an administrator profile into the administrator profile model to determine values of the performance metrics. The AMRGS 1150 may utilize the constantly updated profiles of the stored administrator profiles to extrapolate data and to formulate the model based on the updated profiles. For example, the model can include performance data for various time intervals or time periods, sizes, interest rates, etc. If the administrator sets the time interval from January to October 31, the system can input this time interval into the model to determine the performance (e.g., rate of return on investment or number of customers) during this time interval. In another example, the parameter can be a number of customers, and the system can input this into the model to determine one or more time interval during which this parameter is satisfied, and generate a report indicating the performance (e.g., rate of return on investment) whenever the administrator had this many customers.

In some embodiments, the matching engine 1154, after identifying the one or more similar administrator profiles, can send an indication of the one or more similar profiles to the report generator 1156. The report generator can utilize the one or more similar profiles in generating a dynamic report.

The AMRGS 1150 can include a report generator 1156. The report generator 1156 can execute on one or more processors of a server. The report generator 1156 can generate a dynamic report, responsive to receiving the indication of the one or more similar administrator profiles from the matching engine 1154. The dynamic report may be based on the one or more similar administrator profiles.

The report generator 1156 may access from the database 1158 the performance metrics information corresponding to each of the one or more similar administrator profiles. The performance metrics can include various resulting characteristics and attributes associated with an electronic benefits account, such as, but not limited to, percentage or number of participants or customers of an electronic benefits account associated with a given administrator profile (e.g., during a defined time interval), amount of money contributed to an electronic benefits account associated with a given administrator profile, number of geographic regions in which their customers are located, demographics data associated with customers, number of transactions associated with tax benefit accounts, size of the transactions, frequency of transactions, frequency of funding the tax benefit account, size of contributions, or statistics based on these parameters, performance metrics, or attributes. Values of the performance metrics may vary dependent on the parameters associated with the electronic benefits accounts. For example, an electronic benefits account may include a monthly fee (parameter) with a value of $5 and have a participation percentage (performance metric) with a value of 74%. In another example, an electronic benefits account may include a monthly fee of $10 and have a participation percentage of 86%. Accordingly, due to the lower fee associated with the first account, a higher rate of participation is achieved compared with that of the second account, since lower fees likely encourage participation.

The report generator 1156 may compile the values of the performance metrics of the one or more similar administrator profiles. In some embodiments, the report generator 1156 may average all the values of the similar profiles associated with a performance metric. In some embodiments, the report generator 1156 may simply retrieve the individual values of the performance metric without performing any operations on the values. In some embodiments, the report generator 1156 may perform a weighted average on the values of a performance metric, and assign certain ones of the similar profiles respective weightings. The weightings may be based on particular characteristics of the administrator profiles. For example, ones of the similar profiles that exceed the similarity threshold relatively higher than others may receive a higher weighting than those that barely meet the similarity threshold.

The report generator 1156 can transmit one or more packets carrying data indicating the results of the report generator 1156 to the administrator device 1160 for displaying a dynamic report including the information determined by the report generator 1156. In some embodiments, the dynamic report may also display values of performance metrics associated with the requesting administrator, such that the administrator may compare its performance metrics with those of the one or more similar administrators.

In some embodiments, the report generator 1156 can update the report sent to the administrator device 1160 in real-time in response to an adjusted parameter at the administrator device 1160 and received at the AMRGS 1150. For example, the report generator 1156 may generate a report based on the default parameters associated with the requesting administrator profile. The default parameters may correspond to the actual live parameters that the requesting administrator uses with respect to its electronic benefits accounts. However, in some embodiments, the generated dynamic report at the administrator device 1160 displays the parameters used in the report generator 1156 processes, and the user of the administrator device 1160 may adjust these parameters. In response to an adjusted parameter, the matching engine 1154 may identify a new set of similar administrator profiles and transmit the identification information to the report generator 1156. In response to the new set of similar administrator profiles, the report generator 1156 may retrieve and operate on a new set of values of performance metrics associated with the new set of profiles, and generate a new report based on the new set of performance metric values. This process of dynamic reporting based on administrator adjustments to input parameters may occur in real-time. For example, an administrator may adjust a time interval associated with a number of participants metric of the administrator at the administrator device 1160 (e.g., from 1 year to 2 years), in doing so, the report generator 1156 may determine different values for the various performance metrics and display these updated values via the dynamic report.

In some embodiments, the administrator device 1160 may transmit filter information to the AMRGS 1150 via the dynamic report interface at the device 1160. In response, the AMRGS 1150 may identify a subset of the one or more similar administrator profiles stored in the administrator profile database 1158. Accordingly, the report generator 1156 may generate new values for the performance metric based on the new set of administrator profiles and render the electronic report to indicate the new values of the performance metrics while removing the values associated with the previous set of administrator profiles used before the filter was implemented.

In some embodiments, the report generator 1156 can be configured to provide the dynamic report in real-time via the communications interface 1152. The communications interface 1152 can be configured to provide the report via an electronic mail protocol, SMS protocol, notification or prompt on a mobile telecommunications devices (e.g., a smartphone, tablet, smartwatch, wearable telecommunications device, laptop computer, desktop computer, etc.). An administrator profile maintained in the database 1158 can include other contact information corresponding to the administrator associated with the administrator device 1160, and the report generator 1156 can be configured to transmit the one or more data packets including the report to the administrator using the contact information via the communications interface 1152. In some embodiments, the administrator profile can include a priority order associated with multiple contact information, a preferred contact information, or an indication of multiple contact information for receiving notifications. For example, the administrator profile can indicate an electronic mail protocol as a preferred contact information, and the report generator 1156 can be configured to identify the electronic mail protocol as the preferred contact information, and transmit the one or more data packets to the administrator using the electronic mail protocol via the communications interface 1152.

The report generator 1156 report delivery can be in real-time. A real-time report can refer to providing the notification soon after completion of an action by the AMRGS 1150 (e.g., within 1 minute, within 5 minutes, within 30 seconds). The action resulting in a real-time notification can be the report generator 1156 retrieving the metrics data of the similar profiles; an operation performed by the report generator 1156; an operation performed by the matching engine 1154; receiving adjusted parameters from the administrator device 1160. For example, responsive to the AMRGS 1150 retrieving performance metrics values from the database 1158 and averaging the values, the report generator 1156 can generate a report detailing the results of the operations and cause the report to be transmitted to the administrator device 1160*a* via the communications interface 1152.

The report can be transmitted within a pre-determined time interval of receiving the request for a dynamic report. The predetermined time interval can be a time period after an action, e.g. 10 minutes, 5 minutes, 1 minute, 30 seconds. The action can include receiving the request for a dynamic report, receiving one or more packets generated by the administrator device 1160, or generating the notification of the initiation of the dynamic reporting process. The pre-determined time interval can be set in a configuration file or profile maintained by the AMRGS 1150 in the database 1158. The pre-determined time interval can be set by an entity remote from the AMRGS 1150. For example, the AMRGS 1150 can transmit a time interval request to a remote server of an insurance administrator or an employer. The time interval request can cause the remote server to transmit the configuration file or profile setting the pre-determined time interval to the AMRGS 1150. The report generator 1156 can process the configuration file or profile to extract the pre-determined time interval in order to transmit the report within the pre-determined time interval.

In some embodiments, responsive to the action occurring that initiates the pre-determined time interval, the report generator 1156 can generate a placeholder notification to be transmitted to the administrator device 1160 independent of the status of generating the dynamic report. For example, the placeholder notification can indicate that the report generating process has been initiated. The placeholder notification can indicate that further information is required to complete the report generating process. The report generator 1156 can transmit the placeholder notification prior to expiry of the pre-determined time interval via the communications interface 1152 to provide real-time communication of the reporting process.

In some embodiments, the notification can include status information regarding the report generation (e.g., dynamic report complete, dynamic report incomplete, similar profiles retrieved, performance metrics retrieved, or dynamic report pending). In some embodiments, the notification can include status information regarding the request (e.g., processing request or request processed). In some embodiments, the report generator 1156 is configured to generate notification of the initiation of the report generation process, and transmit the notification via the communications interface 1152 to the administrator device 1160*a*.

In some embodiments, the report generator 1156 can retrieve an electronic report template configured for the reporting the results of the operations of the report generator 1156. The report generator 1156 can generate the notification using the electronic report template. The report generator 1156 can transmit the one or more data packets carrying the results generated using the electronic report template to the administrator device 1160*a* via the communications interface 1152. For example, the communications interface 1152 can transmit the one or more data packets via at least one of an SMS protocol or an electronic mail protocol.

In some embodiments, the report generator 1156 is configured to retrieve an electronic report template configured for transmission via a particular transmission protocol. For example, the report generator 1156 can retrieve an SMS-compatible electronic report template configured to be compatible with SMS protocol, such as an electronic report template having a particular character limit and an organization configured to use plain text. The SMS-compatible electronic report template can be configured to prioritize particular results, such as a value of a prioritized performance metric. The report generator 1156 can retrieve an electronic mail-compatible electronic report template configured to be compatible with electronic mail protocol, such as an electronic report template using rich text or HTML. In some embodiments, the report generator 1156 can retrieve multiple electronic report templates compatible with multiple transmission protocols, generate multiple notifications using the multiple transmission protocols, and transmit the multiple notifications via the multiple transmission protocols via the communications interface 1152.

In some embodiments, the report generator 1156 is configured to transmit an instruction to the administrator device 1160 to trigger an application on the administrator device 1160 to launch a user interface (e.g., a prompt, a graphical user interface, etc.) or application program interface configured to display the information provided via the electronic report. The report generator 1156 can be configured to transmit an application configuration request to the administrator device 1160 that causes the administrator device 1160 to transmit details regarding the user interface, and the report generator 1156 can configure the electronic report based on the received details. The report generator 1156 can be configured to transmit an application program interface to the administrator device 1160 in a format configured for use by the administrator device 1160, causing the administrator device 1160 to install the application program interface in order to display the electronic report received in the notification. The report generator 1156 can configure the one or more data packets carrying the notification to cause the administrator device 1160 to launch the user interface or application program interface in order to display the electronic report.

In some embodiments, the AMRGS 1150 (e.g., via communication interface 1110), receives a request for profile information from an administrator device 1160 associated with an administrator profile on the AMRGS 1150. The request for information can include information about a value of a performance metric for the requesting administrator. The request can further include authentication information or credentials associated with the request. The authentication information can include network security credentials, such as security certificates or tokens. The authentication information can further include a username, password, two-tier authentication information (e.g., verification code sent via text message to phone number in profile associated with administrator). The authentication can include credentials depending on a security level associated with the account information requested. For example, a first security level requiring a first item of authentication information can be associated with information such as a balance of the electronic account, and a second security level requiring both a first item of authentication information and a second item of authentication information can be associated with identification information associated with the profile.

Responsive to authenticating or otherwise approving the request, the AMRGS 1150 can access a data record in database 1158 for the electronic account to generate a report with the requested information, or generate a standard report, or generate another preconfigured report. The report can identify the administrator information, percentage of employees participating in electronic benefits accounts of the administrator, monthly fees of the accounts, and other parameter or performance metric information.

In some aspects, the system of the present solutions implements a combination of the communications interface 1152, matching engine 1154, report generator 1156, database 1158, claims processor 220, POS terminals 202*a-n*, or clients 102*a-n* in an innovative, non-conventional or non-routine manner. In some aspects, the system of the present solutions integrates the communications interface 1152, matching engine 1154, report generator 1156, database 1158, claims processor 220, POS terminals 202*a-n*, or clients 102*a-n* an innovative, non-conventional or non-routine manner to implement the improved functionality, performance and operation of the present solution. In some aspects, the system of the present solutions integrates the communications interface 1152, matching engine 1154, report generator 1156, database 1158, claims processor 220, POS terminals 202*a-n*, or clients 102*a-n* in an innovative, non-conventional and/or non-routine manner to more efficiently and effectively use computing and networking resources. The communications interface 1152, matching engine 1154, report generator 1156, database 1158, claims processor 220, POS terminals 202*a-n*, or clients 102*a-n* are integrated in an innovative, nonconventional manner to mitigate, reduce, prevent, or resolve the technical problems of generating dynamic interfaces or reports. The communications interface 1152, matching engine 1154, report generator 1156, database 1158, claims processor 220, POS terminals 202*a-n*, or clients 102*a-n* are integrated in the innovative, non-conventional manner address at least these technical problems by interfacing with a plurality of administrator devices remote from the device; receiving, via a network, an identifier of an administrator of an administrator device of the plurality of administrator devices; the tool further configured to retrieving, from an administrator profile data structure stored in memory, an administrator profile corresponding to the identifier; identifying one or more administrator profiles stored in the administrator profile data structure of one or more different administrators; determining, based on a parameter matching technique, from the one or more identified administrator profiles, a similarity metric between the administrator profile and each of the identified one or more administrator profiles; identifying the one or more administrator profiles having the similarity metric satisfying a predetermined threshold; instantiating a dynamic report interface to render for display via the administrator device, an electronic report indicating a first value of a first performance metric of the administrator based on the administrator profile and a second value of the first performance metric based on the identified one or more administrator profiles; and providing, via the dynamic report interface, the electronic report for display via the administrator device.

Figure 12A:
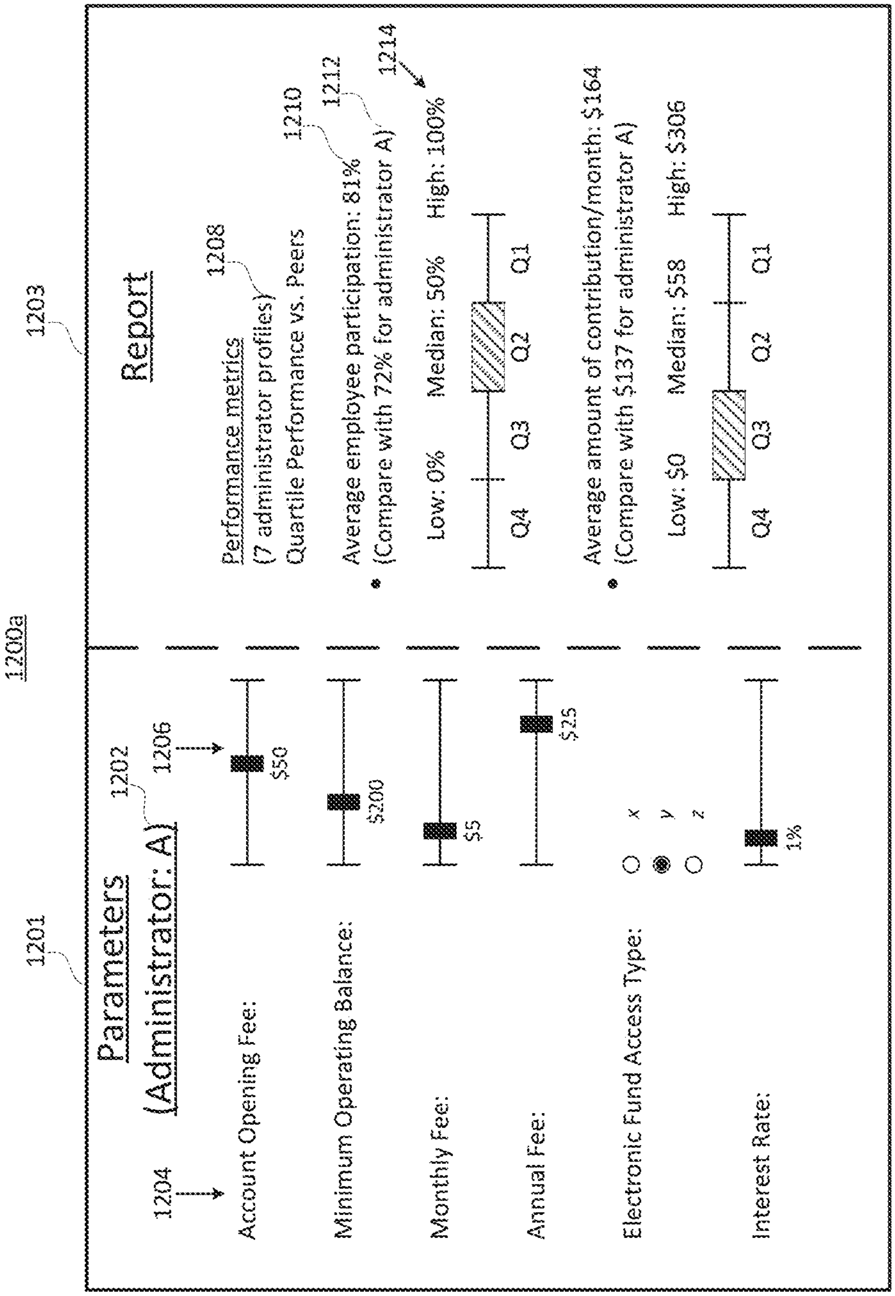
FIGS. 12A and 12B are diagrams depicting a dynamic report interface associated with an administrator matching and report generating system.

Referring now to FIG. 12A, a screenshot 1200*a* of an embodiment of a dynamic report interface for using in conjunction with the AMRGS 1150 is depicted. The dynamic report interface may be displayed at the administrator device 1160 or other computing device via which the administrator requests to access the dynamic report interface. The interface includes an input portion 1201 and an output portion 1203. The input portion includes a requesting administrator field 1202, a parameter column 1204, and a parameter value column 1206. The output portion 1203 includes a similar administrator field 1208, a performance metric field 1210, a requesting administrator performance metric field 1212, and a performance metric display 1214.

In some embodiments, the administrator associated with the administrator device 1160 that requested the dynamic report may be identified in the dynamic report interface 1200*a*. For example, administrator "A" is identified as the requesting administrator of the dynamic report. In some embodiments, the AMRGS 1150 may obtain the information in field 1202 based on the identifier received at the AMRGS 1150. Column 1204 includes a plurality of parameters for input into the dynamic report process. For example, column 1204 may include such parameters as account opening fee, minimum operating balance, monthly fee, electronic fund access type, and interest rate. Each parameter in parameter column 1204 may be associated with a respective value depicted in column 1206. For example, the account opening fee may be associated with $50. In some embodiments, the values in column 1206 may be modified by an administrator and the modified values may be received at the AMRGS 1150. As depicted in FIG. 12A, some of the parameter values in column 1206 are presented with a "slider" interface. The slide interface may allow a user at the administrator device 1160 to interact with the parameter values and adjust the parameter values. In some embodiments, the parameter values may include an interface other than a slider, such as, but not limited to, a dial, an input text box, a selectable list (see "electronic fund access type"), and the like.

In some embodiments, the AMRGS 1150 initially populates and calibrates the interactive parameter value fields to correspond with the default values stored in the database 1158 associated with the requesting administrator profile. For example, administrator "A" may be currently operating its electronic savings account with a $50 account opening fee, a $200 minimum operating balance, etc. As such, the AMRGS 1150 may initially utilize these parameter values in its report generation for display at the dynamic report interface.

Still referring to FIG. 12A, the output portion 1203 may indicate a number of administrator profiles upon which the report is based at the similar administrator field 1208. These administrator profiles may correspond to the administrator profiles determined by the AMRGS 1150 to by sufficiently similar to the requesting administrator profile based on the parameters of the requesting administrator profile. For example, the output portion 1203 indicates that the results of the dynamic report are based on 7 similar administrator profiles. In some embodiments, the dynamic report interface 1200*a* may list by name each of the similar administrator profiles. In some embodiments, the names may not be listed or otherwise hidden from view.

The performance metric field 1210 may indicate a performance metric and a value associated with the performance metric based on the similar administrator profiles. For example, the performance metric field 1210 indicates a performance metric of "average employee participation" of the similar administrator profiles as being "81%". In some embodiments, the dynamic report interface 1200*a* may list each of the respective employee participation rates of the individual similar administrator profiles. In some embodiments, the average is a weighted average. In addition, the output portion may indicate the performance metric value associated with the requesting administrator profile at the requesting administrator performance metric field 1212. For example, the field 1212 indicates that the average employee participation rate for administrator A is 72%. In addition, further information calculated based on the performance metrics of the similar administrator profiles may be depicted at the performance metric display 1214. Any suitable information relating to the performance parameters may be depicted at the field 1214, including, trends over time of the performance metrics, graphical depictions of the performance metric values, forecasts of the values, and the like. For example, dynamic report interface 1200*a* depicts a lowest value (of the similar administrators) performance metric, a median value, and a high value. In addition, the performance metric display 1214 graphically illustrates where administrator A is ranked with respect to the performance metric. For example, administrator A is at the second quartile of the group consisting of the similar administrators. In some embodiments, the information generated in the output portion 1203 is based on the profile of the requesting administrator (in addition to the administrator profiles of the similar administrators).

Figure 12B:
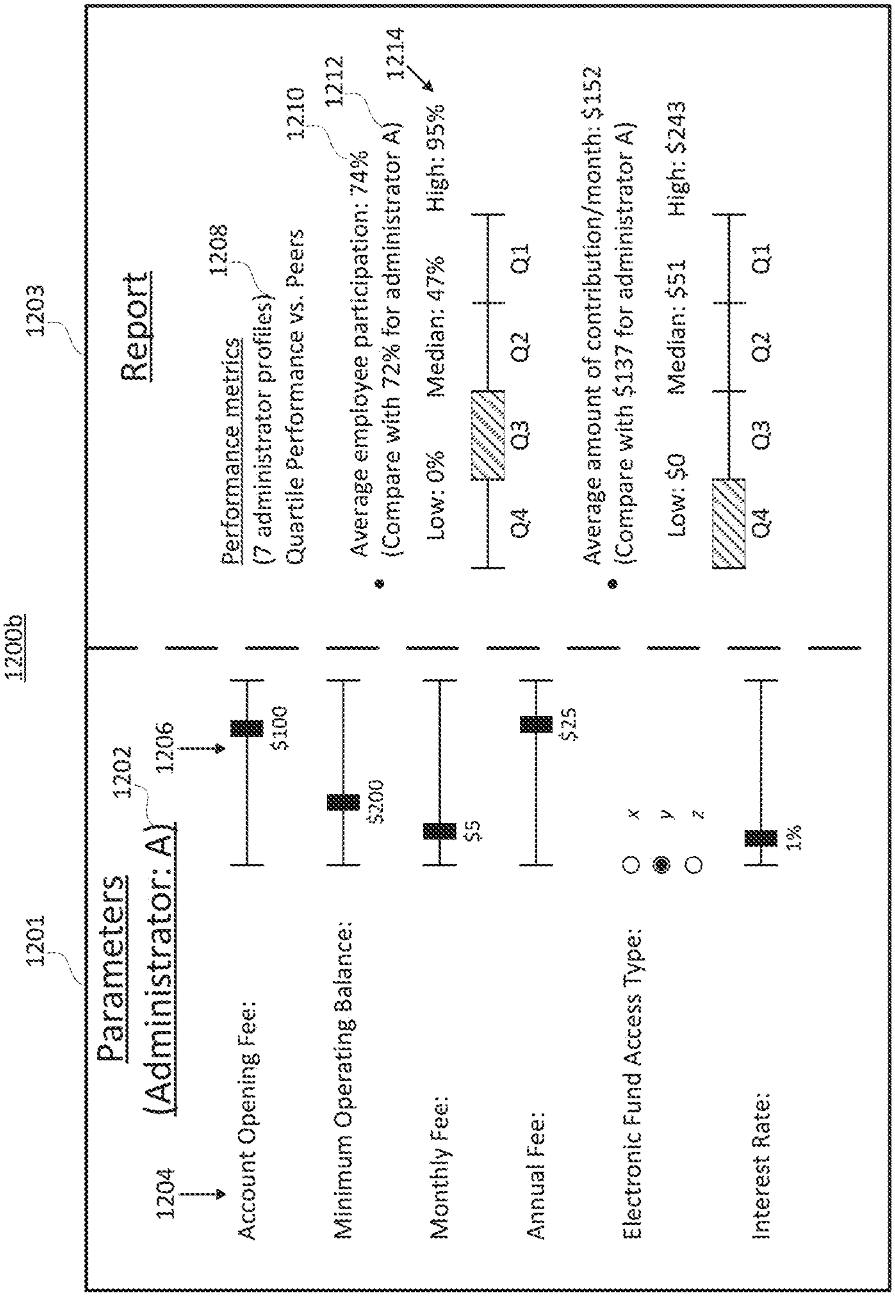

Referring now to FIG. 12B, another screenshot 1200*b* of a dynamic report interface for using in conjunction with the AMRGS 1150 is depicted. The dynamic report interface may be displayed at the administrator device 1160 and is substantially similar to that depicted in FIG. 12A. The screenshot includes the input portion 1201 and the output portion 1203. The input portion includes the requesting administrator field 1202, the parameter column 1204, and the parameter value column 1206. The output portion 1203 includes the similar administrator field 1208, the performance metric field 1210, the requesting administrator performance metric field 1212, and a performance metric display 1214.

FIG. 12B, illustrates a scenario in which one or more of the parameter values under column 1206 is modified. For example, the account opening fee is adjusted from $50 in FIG. 12A to $100 in FIG. 12B. The parameter modification may be performed at the administrator device 1160 by interaction with the dynamic report interface. In response to a parameter modification, the dynamic report interface may output different performance metric values based on the updated set of parameters in the input portion 1201. The performance metric value updates may occur in real-time. For example, after receiving the updated account opening fee parameter value, the AMRGS 1150 may perform the administrator matching or the report generating process, or both, based on the updated parameter value and the other parameter values that have not been modified. After performing operations on the new parameter set, the AMRGS 1150 may report the updated metric values to the administrator device 1160 via the dynamic interface 1200*b*. For example, in response to the change of the account opening fee parameter value from $50 to $100, the average employee participation at field 1210 decreased to 74%, from 81% in FIG. 12A, and the average amount of contribution per month metric value decreased to $152, from $164 in FIG. 12A. In addition, the median and high values in the performance metric display 1214 decreased to 47% and 95%, respectively.

In some embodiments, the AMRGS 1150 may perform updated administrator matching based on the modified parameters. As such, the set of similar administrator profiles on which the performance metric calculations are based, may change, and thus the value of the similar administrator field 1208 may also change depending on how many similar administrator profiles are identified with respect to the updated parameters. For example, when the account opening fee is increased to $100, some administrator profiles may no longer be sufficiently similar to the administrator profile having the changed parameter, and those dissimilar profiles may no longer be used for purposes of the dynamic report. On the other hand, other previously dissimilar administrator profiles may become sufficiently similar due to the updated parameter, and those newly similar administrator profiles may be used in the dynamic report.

Figure 13:
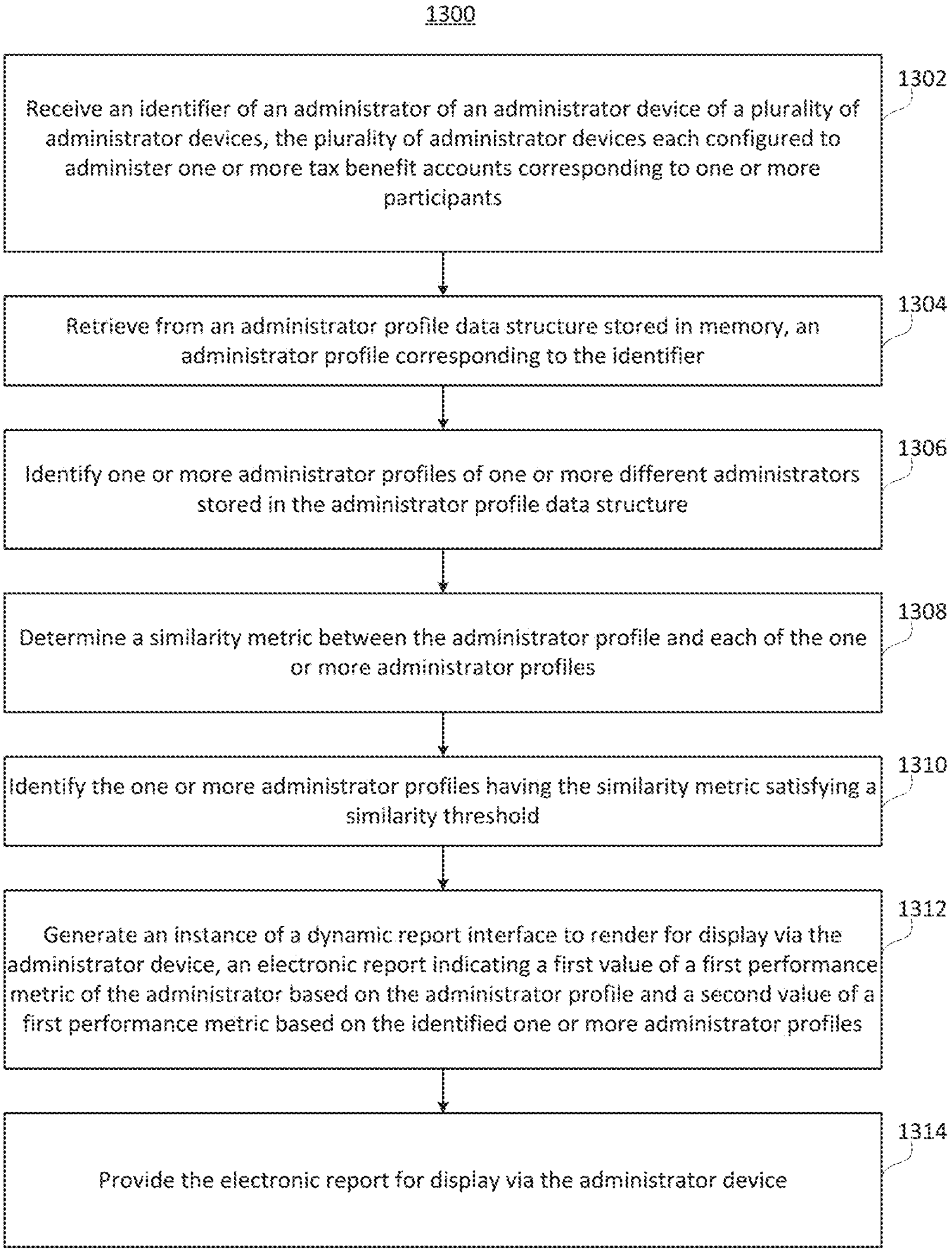
FIG. 13 is a flow diagram depicting an embodiment of a method of managing information technology infrastructure.

Referring now to FIG. 13, a flow diagram depicting an embodiment of a method 1300 of managing information technology infrastructure is shown. The method can be performed by one or more component or module of system 1100, the AMRGS 1150, or one or more component or module depicted in FIGS. 1A-1D. In brief overview, at step 1302, a server of an administrator matching and report generating system receives an identifier of an administrator of an administrator device of a plurality of administrator devices. At step 1304, the server retrieves an administrator profile corresponding to the identifier. At step 1306, the server identifies one or more administrator profiles of one or more different administrators stored in the administrator profile data structure. At step 1308, the server determines a similarity metric between the administrator profile and each of the one or more administrator profiles. At step 1310, the server identifies the one or more administrator profiles having the similarity metric satisfying a similarity threshold. At step 1312, the server generates an instance of a dynamic report interface to render for display, an electronic report indicating a first value of a first performance metric of the administrator based on the administrator profile and a second value of a first performance metric based on the identified one or more administrator profiles. At step 1314, the server provides the electronic report for display via the administrator device.

Still referring to FIG. 13, and in further detail, at step 1302, a server of an administrator matching and report generating system receives an identifier of an administrator of an administrator device of a plurality of administrator devices. In some aspects, step 1302 comprises an innovative, non-conventional or non-routine way to operate or perform the functionality of the present solution. In some aspects, step 1302 is implemented to address the technical problems and challenges of prior systems not deploying the present solution. In some aspects, step 1302 is implemented to make or cause more effective and efficient use of computing and networking resources.

The received identifier can indicate a request for a dynamic report. The server can include one or more processors. The server can include a communications interface for receiving the request. One or more data packets carrying data indicating the request can be received. The request can be received via a computer network using a networking protocol. The request can be generated by a device at an administrator. The data packets can include header information and payload information. The header information can include, e.g., TCP header information that can facilitate the routing and transmission of the data packet. The payload information can include data related to, describing, defining, associated with or otherwise about the request for a dynamic report, including input parameters regarding electronic benefits accounts. The one or more data packets can include data identifying the administrator making the request. The administrator device can generate or obtain information that allows the server to conduct the report generation and profile matching, encapsulate or process the information using a protocol to generate data packets, and transmit the data packets in a secure manner over a network to the server for further processing. The server can initiate a report generating process responsive to receiving the one or more data packets. The server can also receive a parameter of the administrator profile, and the parameter may include at least one of an account opening fee, a minimum operating balance, a monthly fee, an annual fee, an electronic fund access type, or an interest rate.

At step 1304, the server retrieves an administrator profile corresponding to the identifier. In some aspects, step 1304 comprises an innovative, non-conventional or non-routine way to operate or perform the functionality of the present solution. In some aspects, step 1304 is implemented to address the technical problems and challenges of prior systems not deploying the present solution. In some aspects, step 1304 is implemented to make or cause more effective and efficient use of computing and networking resources.

The server can access a database maintained by the server to retrieve the stored administrator profile. The server can perform the retrieving responsive to receiving the identifier. In some embodiments, the server parses the one or more data packets to identify the administrator profile, and performs a lookup in an administrator profile database maintained by the server using the identifier to retrieve. The server can also generate an administrator profile of the requesting administrator with parameters received from the administrator device. The administrator device may be configured to receive data from a plurality of participant devices corresponding to the one or more tax benefit accounts configured using the administrator profile. The server can train (e.g., via a machine learning technique) an administrator profile model using a plurality of administrator profiles. The server can determine the first value of a first performance metric based on an output from the administrator profile model responsive to a parameter of the administrator profile input into the administrator profile model.

At step 1306, the server identifies one or more administrator profiles of one or more different administrators stored in the administrator profile data structure. The server can access the administrator profile database to access or identify the one or more different administrator profiles different from the administrator profile identified in the previous step. The server can perform the identifying responsive to the retrieving. The different administrators may be a subset of the total administrator profiles stored in the database based on a filter received by the server. In some aspects, step 1306 comprises an innovative, non-conventional or non-routine way to operate or perform the functionality of the present solution. In some aspects, step 1306 is implemented to address the technical problems and challenges of prior systems not deploying the present solution. In some aspects, step 1306 is implemented to make or cause more effective and efficient use of computing and networking resources.

At step 1308, the server determines a similarity metric between the administrator profile and each of the one or more administrator profiles. The similarity metric can indicate the degree to which the administrator profile is similar to each of the one or more different administrator profile. The similarity metric may be executed by an administrator matching engine maintained on the server. The similarity metric may be obtained by determining the similarity between individual parameters between the two administrator profiles. In some aspects, step 1308 comprises an innovative, non-conventional or non-routine way to operate or perform the functionality of the present solution. In some aspects, step 1308 is implemented to address the technical problems and challenges of prior systems not deploying the present solution. In some aspects, step 1308 is implemented to make or cause more effective and efficient use of computing and networking resources.

At step 1310, the server identifies the one or more administrator profiles having the similarity metric satisfying a similarity threshold. The server can maintain the similarity thresholds on the database of the server. The similarity threshold may be adjustable, and an indication of adjustment of a similarity threshold may be received at the server. A similarity threshold may be implemented for each individual parameter being compared. The server can determine a subset of the different one or more administrator profiles based on the ones that satisfy the similarity threshold to obtain one or more administrator profile similar to the administrator profile associated with the identifier. In some aspects, step 1310 comprises an innovative, non-conventional or non-routine way to operate or perform the functionality of the present solution. In some aspects, step 1310 is implemented to address the technical problems and challenges of prior systems not deploying the present solution. In some aspects, step 1310 is implemented to make or cause more effective and efficient use of computing and networking resources.

At step 1312, the server generates an instance of a dynamic report interface to render for display, an electronic report indicating a first value of a first performance metric of the administrator based on the administrator profile and a second value of a first performance metric based on the identified one or more administrator profiles. In some aspects, step 1312 comprises an innovative, non-conventional or non-routine way to operate or perform the functionality of the present solution. In some aspects, step 1312 is implemented to address the technical problems and challenges of prior systems not deploying the present solution. In some aspects, step 1312 is implemented to make or cause more effective and efficient use of computing and networking resources.

The dynamic report may be generated at a report generator maintained at the server. The first performance metric may be any resulting characteristic of an electronic benefits account, such as, customer participation percentage. The first value of the first performance metric may correspond to the administrator profile associated with the received identifier. The second value of the first performance metric may be associated with the one or more similar administrator profiles. The second value may be an average of each of the values associated with each similar administrator profile, or may be a weighted average value. The server can render an electronic report indicating the first value of a first performance metric based on a number of participants of the administrator during a time interval, and the second value of the first performance metric based on the number of customers of the identified one or more administrators.

At step 1314, the server provides the electronic report for display via the administrator device. In some aspects, step 1314 comprises an innovative, non-conventional or non-routine way to operate or perform the functionality of the present solution. In some aspects, step 1314 is implemented to address the technical problems and challenges of prior systems not deploying the present solution. In some aspects, step 1314 is implemented to make or cause more effective and efficient use of computing and networking resources.

The server can transmit the one or more packets in real time. The server can transmit the one or more packets within a predetermined time interval of a preceding action, such as receiving the identifier. In some embodiments, the server receives adjustment information regarding the input parameters and updates the dynamic report provided based on the updated parameters in real-time. The server can receive, via the instance of the dynamic report interface, an indication from the administrator device to adjust the time interval. The server can manipulate the first value of a first performance metric and the second value of a first performance metric indicated in the rendered electronic report responsive to the indication to adjust the time interval. The server can receive, via the instance of the dynamic report interface, a filter criterion. The server can use the filter criterion to identify a subset of the one or more administrator profiles stored in the administrator profile data structure. The server can generate a third value of a first performance metric based on the subset of the one or more administrator profiles. The server can render, via the dynamic report interface, the electronic report to indicate the first value of a first performance metric and the third value of a first performance metric. The server can remove the second value of a first performance metric from the rendered electronic report, the second value of a first performance metric different from the third value of a first performance metric. The server can receive an update to the administrator profile after the electronic report is rendered. The server can generate a third value of the first performance metric based on the update to the administrator profile. The server can render via the dynamic report interface, the electronic report to include the third value of the first performance metric and remove the first value of the first performance metric. The server can render the electronic report for display on the administrator device via the dynamic report interface, and receive from the administrator device via the dynamic report interface, an indication to manipulate the electronic report.

In some aspects, the methods of the present solutions implements a combination of steps in an innovative, non-conventional and/or non-routine manner. In some aspects, the method 1300 of the present solution combines the steps of FIG. 13 in an innovative, non-conventional and/or non-routine combination to implement the improved functionality, performance and operation of the present solution. In some aspects, the method of the present solution combines the steps of FIG. 13 in in an innovative, non-conventional and/or non-routine manner to more efficiently and effectively use computing and networking resources. In some aspects, the method of the present solution provides innovative, non-conventional and/or non-routine ordered combination of steps.

F. Predictive Resource Allocating System (PRAS)

The systems and methods of the present solution are directed to the technical problems and challenges of implementing the functionality of resource allocation an electronic transaction based technology and platform. Existing electronic transaction based technologies and platforms do not effectively and efficiently make use of the computing and network resources deployed for electronic transaction based technologies and platforms to include such functionality. Without implementing such functionality, existing electronic transaction based technologies and platforms have the problems of excessive server-client requests and responses, processing delays, increase bandwidth usage, or erroneous or inefficient resource allocation.

The systems and methods of the present solution are directed to the improvement of the performance and operation of the electronic transaction based technology and platform and computing and networking resource used by such electronic transaction based technology and platform. In some aspects, the present solution improves and enhances the implemented functionality of the electronic transaction based technology and platform implemented on, integrated with and inherently tied to the processor, memory, network and computing resources of one or more computing devices. In some aspects, the present solution more effectively performs the functionality of the electronic transaction based technology and platform thereby making and causing more effective use of the computing and networking resources to achieve the improved functionality of the present solution. The same computing and network resources used by such electronic transaction based technology and platform will provide increased and improved functionality with implementation of the present solution.

In some aspects, the present solution more efficiently uses the computing and networking resources to implement the improved functionality of the electronic transaction based technology and platform. For example, systems and methods of the present solution are directed to allocating resources using an information technology infrastructure. Systems and methods of the present solution can determine amounts of funds a participant should allocate to a healthcare tax benefit account to cover predicted lifetime healthcare expenses.

Administrators that establish or provide electronic tax benefits accounts for various participants of those accounts can utilize backend information technology infrastructure to process, analyze, monitor or manage the electronic tax benefits accounts. An entity managing the backend information technology may have access to data regarding electronics tax benefit accounts across multiple administrators. This data may include financial and health information of the various participants across the various administrators, which the entity managing the backend information technology may advantageously utilize to provide unique services.

The present disclosure provides systems and methods of allocating resources using an information technology infrastructure. The interactive interface can include a report based on analyzing the financial and health data of the various participants across multiple administrators. For example, the system can use the data on participants in the system to build various profiles and saving or spending trends for those participants. The system enables existing or new participants to enter information about themselves, into an interactive interface, about their healthcare and retirement savings, income, or spending, and compare that to lifestyle profiles or expense prediction models to forecast the necessary retirement funds needed to fund not only their lifestyle, but their healthcare needs. Additionally the system can profile the economic advantage (e.g., tax advantage) of various retirement vehicles to determine the most beneficial savings approach for the participant (e.g., health savings accounts triple tax benefit vs. 401k vs. Roth IRA vs. other healthcare spending accounts like health retirement accounts and flexible spending accounts).

The system can be configured with a machine learning technique to constantly update and refine expense prediction models. The machine learning technique can be based on new financial and health data of the participants that is continuously received by the system. The system can parse the new information and determine how the data reinforces a predictive model or changes a predictive model. Upon receiving personal financial and health data from a participant seeking to identify how to optimally allocate funds to their electronic benefits accounts, the system can identify a predictive model based on the received information that is most similar to the seeking participant's information, and can then identify future healthcare and non-healthcare costs of the participant based on the identified predictive model. Based on the predicted expenses of the participant, the system can determine the economically optimal (e.g., most tax-advantaged) contribution scheme for the participant to invest in one or more healthcare benefits accounts and one or more non-healthcare benefits accounts (e.g., how much and into which accounts the participant should deposit funds).

Upon determining the optimal contribution plan, the system can generate an interactive interface for displaying the results of the system's calculations to the participant seeking the information. The interactive interface can include or be configured on a dashboard. In some cases, the interface can be provided or streamed over a data network. The interface can be configured to receive data manipulation indications via an input device, and the system can update the calculated results and display the results via the interface in real-time. For example, the interface can receive indications to manipulate the data corresponding to the amount of annual contribution to one or more of the electronic benefits account, the amount already saved in the accounts, health indicators (e.g., a promise to increase exercise activities), financial indicators (e.g., an imminent income raise), or the like.

In an illustrative embodiment, the system can provide payment processing infrastructure and technology to a plurality of administrators such as multiple insurance companies. The insurance companies can provide various types of insurance (e.g., health, dental, vision, car, property, legal, construction, etc.) to its customers. A customer of the insurance company can include an employer that has employees. The system can enable the employees that participate in the insurance company plans to initiate and receive a report indicating predicted expenses and a suggested contribution scheme to healthcare and non-healthcare benefits accounts for the employee. The suggestions presented to the employee are based on the health and financial data personal to the employee, and on the vast financial and health data of the various employees that are provided with the electronic benefits accounts from the multiple insurance companies.

Figure 14:
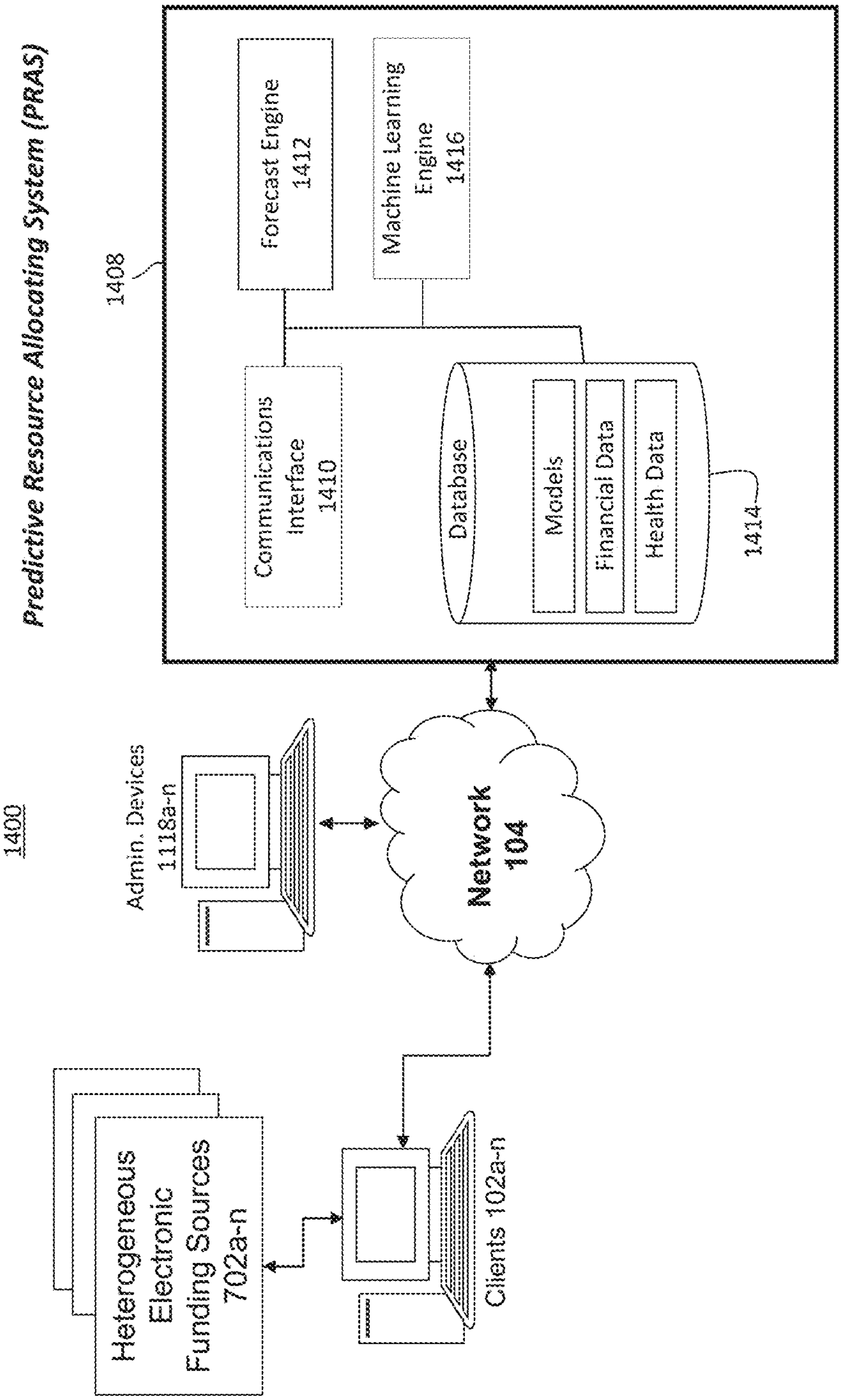
FIG. 14 is a block diagram depicting an embodiment of a system for allocating resources using an information technology infrastructure.

Referring now to FIG. 14, a block diagram depicting an embodiment of a system 1400 comprising a predictive resource allocating system is shown. In brief overview, the system 1400 includes a predictive resource allocating system 1408 ("PRAS"). The PRAS 1408 can include the MPTS 120 depicted in FIG. 2, the MPTS 408 depicted in FIG. 4, the TEPS 708 depicted in FIG. 7, or the AMRGS 1108 depicted in FIG. 11, or one or more components or modules depicted in FIG. 2, 4, 7, or 11, and can perform the functions of the MPTS 120, MPTS 408, TEPS 708, or the AMRGS 1108. The PRAS 1408 can receive or transmit data via a network 104 with clients 102*a-n*. The system 1400 can include or interact with one or more clients 102*a-n* (or client device 102).

The PRAS 1408 can include a communications interface 1410. The communications interface 1410 can include the communications interface 210 depicted in FIG. 2, the communications interface 410 depicted in FIG. 4, the communications interface 710 depicted in FIG. 7, or the communications interface 1110 depicted in FIG. 11, or one or more components or modules depicted in FIG. 2, 4, 7, or 11, and can perform the functions of the communications interfaces 210, 410, 710, or 1110. The communications interface 1410 is configured with one or more communications ports, application programming interfaces, network protocols (e.g., TCP/IP), authentication protocols, or security protocols (e.g., SSL). The communications interface 1410 can receive financial data and health data of a participant of a client device 102 or a request to perform predictive resource allocation for the participant. In some aspects, the communications interface 1410 is implemented to address the technical problems and challenges of prior systems not deploying the present solution. In some aspects, the communications interface 1410 is implemented to make or cause more effective and efficient use of computing and networking resources. For example, the communications interface 1410 can cause more effective and efficient use of computing and network resources by reducing the number of processing cycles, memory or network bandwidth used to determine resource allocations to reduce resource consumption. The communications interface 1410 can provide a reduction in resource consumption by integrating with a forecast engine 1412, machine learning engine 1416, database 1414, clients 102*a-n*, admin devices 1118*a-n*, or heterogeneous electronic funding sources 702*a-n* to allocate resources or reduce resource consumption.

The PRAS 1408 can include a forecast engine 1412. The forecast engine 1412 determines, responsive to the communications interface 1410 receiving the financial and health data, an amount of funds a participant should allocate to healthcare tax benefit accounts and an amount of funds the participant should allocate to non-healthcare tax benefits accounts. In some aspects, the forecast engine 1412 is implemented to make or cause more effective and efficient use of computing and networking resources. For example, the forecast engine 1412 can cause more effective and efficient use of computing and network resources by reducing the number of processing cycles, memory or network bandwidth used to determine resource allocations to reduce resource consumption. The forecast engine 1412 can provide a reduction in resource consumption by integrating with the communications interface 1410, machine learning engine 1416, database 1414, clients 102*a-n*, admin devices 1118*a-n*, or heterogeneous electronic funding sources 702*a-n* to allocate resources or reduce resource consumption.

The PRAS 1408 can include a machine learning engine 1416. The machine learning engine 1416 generates and trains on an ongoing basis healthcare expense prediction models based on stored and aggregated health and financial data of a plurality of account participants. In some aspects, the machine learning engine 1416 is implemented to make or cause more effective and efficient use of computing and networking resources. For example, the machine learning engine 1416 can cause more effective and efficient use of computing and network resources by reducing the number of processing cycles, memory or network bandwidth used to determine resource allocations to reduce resource consumption. The machine learning engine 1416 can provide a reduction in resource consumption by integrating with the communications interface 1410, forecast engine 1412, database 1414, clients 102*a-n*, admin devices 1118*a-n*, or heterogeneous electronic funding sources 702*a-n* to allocate resources or reduce resource consumption.

The PRAS 1408 can include one or more databases or data structures that store information to facilitate the systems and methods of the present solution, such as database 1414. The database 1414 can include the database 216, the databases 418 and 420 depicted in FIG. 4, the databases 714 and 716 depicted in FIG. 7, or the database 1116 depicted in FIG. 11, or one or more components or modules depicted in FIG. 2, 4, 7, or 11, and can perform the functions of the databases 216, 418, 420, 714, 716, or 1116. The database 1414 can include a financials database including financial information corresponding to a plurality of participants. The database 1414 can include a health database including health information corresponding to a plurality of participants. In some embodiments, the health and financial data stored in the database 1414 can be stored securely and can also be encrypted. In some embodiments, participants may be required to opt-in or volunteer to allow the PRAS 1408 to store their health and financial data. The database 1414 can include a models database including a plurality of healthcare expense prediction models. The financial and health data can include biographical information associated with users, identifiers for clients 102 or other devices associated with users, security credentials associated with users, transaction histories, etc. In some embodiments, the financial and health data can include contact information such as an electronic mail protocol address or identifier, a mobile telephone number, an SMS protocol, a landline telephone number, or a postal address associated with users.

In some embodiments, the data maintained at the database 1414 includes various pieces of aggregated information from a plurality of participants across various administrators of electronic benefits accounts. The administrators may correspond to the administrator devices 1118*a-n* at which the administrators may perform operations for caretaking, monitoring, or modifying electronic benefits accounts with which participants (e.g., those at client devices 102*a-n*) corresponding to a particular administrator are associated. As such, because the PRAS 1408 is connected to the one or more administrator devices 1118*a-n*, the PRAS 1408 may access and accumulate information and data of the various participants across various administrators, and maintain the information at the database 1414 for future use.

In some embodiments, the database 1414 may aggregate financial data, health data, and personal data based on a plurality of participants. The financial information may include data such as, but not limited to, amount spent on healthcare per a given time period, household income, amount of contribution to healthcare benefits accounts, amount of contribution to non-healthcare benefits account, amount an employer of a participant matches contributions to electronic benefits accounts, amount a participant has saved for retirement (e.g., amount of funds saved in a healthcare benefits account or a non-healthcare benefits account), or the like. The health data may include data such as, but not limited to, diet information, fitness and exercise information, health insurance information, medical care information, or the like. The personal information may include data such as, but not limited to, age, gender, marital status, target retirement age, or the like.

In some embodiments, the health data, the financial data, and the personal information of the plurality of participants may be obtained by the administrator devices 1118 sending such data to the PRAS 1408, since the administrator devices 1118 directly interface with the participants at the client devices 102. For example, in some embodiments, the administrator at the administrator device 1118 is an employer and the participants are employees of the employer, and in such a case the administrator device 1118 may have information regarding personal and financial information pertaining to its employees that may be accessible by the PRAS 1408. In some embodiments, the administrator may be an electronic benefits account (healthcare and non-healthcare accounts) provider to the participants, and thus may have health, financial, and personal information regarding the participants. In some embodiments, the PRAS 1408 may require or request the participants to fill out electronic surveys containing questions regarding their health, personal, and financial information, and the completed surveys may be sent to the PRAS 1408 for storing. In some embodiments, the health data may be determined by the PRAS 1408 by identifying and parsing electronic transactions by participants (e.g., buying medication with the multipurse debit card, paying for medical procedures or visits, transaction codes and the transaction code mapping).

The healthcare benefits account may include, but not be limited to, a health savings account, a medical savings account, a flexible savings account, or the like. The non-healthcare benefits account may include, but not be limited to, a 401k account, a 403b account, a 457b account, an individual retirement account (IRA), or the like. In some embodiments, the aggregated health data and financial data may be stored in database 1414 such that the participant information corresponding to a set of data is maintained anonymously. In other embodiments, the participant information corresponding to a set of health or financial data is identifiable. In some embodiments, the database 1414 may also maintain healthcare expense prediction models based on the aggregated financial and health data.

The PRAS 1408, communications interface 1410, forecast engine 1412, and machine learning engine 1416 can each include one or more processing units or other logic devices such as programmable logic array engines, modules, or circuitry designed and constructed to facilitate managing security on a network infrastructure. The PRAS 1408 can include the components 100 shown in FIG. 1C or FIG. 1D, or be configured to operate as a service in cloud 108. The PRAS 1408 can include or interact with one or more servers 106*a-n* and clients 102*a-n*.

In some embodiments, the PRAS 1408 can employ a multitier architecture such as a client-server architecture in which presentation, application processing, and data management functions are logically or physically separated. The presentation tier, or front-end, can include the communications interface 1410 that serves static content or dynamic content to be rendered by the client 102 (e.g., by a web browser executing on client 102). The presentation tier or web server can interact or communicate with the application tier to obtain data to provide to the client 102. The application tier can include the forecast engine 1412 that controls the system's functionality and performs additional processing or analysis on data. The application tier can interact with the data tier to obtain the transaction data. The data tier can include data persistence mechanisms (database servers, file shares, etc.) and the data access layer that encapsulates the persistence mechanisms and exposes the data. The data tier can include database 1414. The data tier can include an application programming interface (API) to the application tier. The database 1414 can include stored procedures (e.g., SQL statements) that perform tasks with respect the stored data.

In further detail, and in some embodiments, the PRAS 1408 includes a communications interface 1410. The communications interface 1410 can execute on one or more processors of a server. The communications interface 1410 can include one or more communications ports and be configured with one or more network protocols. Communications ports can include, e.g., network ports, Ethernet ports, WAN ports, I/O ports, or software ports. The communication port can be configured with a network protocol such as Transport Layer Protocols such as TCP/IP or UDP that are configured to receive and process data packets received via a computer network. The port can include or be associated with an IP address of a host and a protocol type of the communication.

In some embodiments, the communication interface 1410 can receive data packets. The data packets can be generated by client device 102 or by administrator device 1118. The client device 102 may be a device at which a participant of an electronic benefits account may access their account. In some embodiments, the client device 102 is the place at which a participant enters financial and health data personal to the participant to be sent to the PRAS 1408. The client device 102 may be any device for entering information and sending the information to the PRAS 1408, such as, but not limited to a laptop, a desktop, a smartphone, a tablet, or the like. In some embodiments, the client device 102 can interact with one or more heterogeneous electronic funding sources 702*a-n*. The heterogeneous electronic funding sources 702*a-n* can include at least one of an ACH, an electronic checking account, an electronic bill pay account, an electronic savings account, an electronic credit card account, or an electronic employer payroll account. The heterogeneous electronic funding sources 702*a-n* are accessed to fund the electronic benefits accounts of a participant, and the PRAS 1408 can calculate amounts of funds, to be taken from one or more of the heterogeneous electronic funding sources 702*a-n*, that a participant should transfer to one or more electronic benefits accounts based on the participant's health and financial information.

The administrator device 1118 may be a device at which an administrator of an electronic benefits account that is associated with a plurality of participants may access the account. In some embodiments, the administrator device 1118 is the place at which an administrator maintains personal, financial, and health information of a plurality of participants corresponding to that administrator device 1118. The administrator device 1118 may be any device for storing information or for entering information and sending the information to the PRAS 1408, such as, but not limited to a laptop, a desktop, a smartphone, a tablet, a server, or the like. In some embodiments, the administrator device 1118 can interact with the client device 102 for providing services related to the electronic benefits accounts in which a participant of the client device 102 contributes funds. For example, the administrator device 1118 may provide to the client device 102 troubleshooting support, investment advice, modifications to accounts, or the like.

The communications interface 1410 can receive data packets generated by the client device 102 or by the administrator device 1118 (e.g., financial or health information of a participant or a plurality of participants). In some embodiments, the communication interface 1410 receives data packets corresponding only to financial information, only to health information, or to both financial and health information. The data packets can include header information and payload information. Multiple data packets can be strung together in a sequence. The header information can refer to TCP/IP headers that include fields such as source port, destination port, sequence number, acknowledge number, window size, etc. The payload information of the data packet can include information related to the health or financial data or related to the participant associated with the health or financial data. The PRAS 1408 can receive the data packet with header information and payload information and process the packets to obtain information for further processing. The payload can include data identifying the client device 102 at which the financial and health data was entered, the customer associated with the health and data information, the financial and health data, personal information of the customer, and other information for predicting amounts of funds the customer should be investing into electronic benefits accounts. The data packets (e.g., via the payload) can include a request to provide a report displaying the calculated amounts of funds the customer should be investing into electronic benefits accounts. The request can specify the types of electronic benefits account for funding. The request can specify information for identifying a healthcare expense prediction model for estimating future healthcare expenses of the customer.

The data packets (e.g., payload of the data packets) can further identify an electronic account maintained and configured on the server. The electronic account can be maintained and configured in a database 1414. The electronic account can correspond to a user and have a unique identifier. The unique identifier can include numbers, letters, characters, symbols, etc. The electronic account can be associated with the customer entering financial and health data or making the request for resource allocation calculations. The client device 102 can receive or determine the electronic account identifier via data saved at the client device 102, data entered into the client device 102, or the like, which the client device 102 can then convey to the PRAS 1408.

In some embodiments, the client device 102 or administrator device 1118 can generate multiple data packets for the financial and health information being sent to the PRAS 1408. The multiple data packets can each include a header and a payload. The header can indicate that the multiple data packets are to be grouped together for routing, transmission or processing purposes.

The PRAS 1408 can be configured to authenticate communications. In some embodiments, the communications interface 1410 receives communications such as the financial and health data of a participant. The data can include security credential such as a security certificate or security token. The security credential can be associated with a participant. The PRAS 1408 can be configured to extract the security credential from the data, and authenticate the data by comparing the security credential against a known or verified security credential. For example, user profiles stored in database 1414 can include known or verified security credentials for comparison with the security credential of the request. In some embodiments, the PRAS 1408 receives the financial and health data via the communications interface 1410, extracts a security credential from the data, analyzes the extracted security credential to identify a user, queries the database 1414 for a verified security credential stored with a user profile corresponding to the identified user, compares the extracted security credential to the verified security credential, and authenticates the data based on the extracted security credential matching the verified security credential.

In some embodiments, the PRAS 1408 includes a forecast engine 1412. The forecast engine 1412 can execute on one or more processors of a server, such as a server of the PRAS 1408. The forecast engine 1412 can receive, retrieve, or otherwise obtain or access some or all of the data carried by the data packets. The forecast engine 1412 can receive, retrieve, or otherwise obtain or access healthcare expense prediction models, such as models maintained in database 1414. The forecast engine 1412 can determine, responsive to the communications interface 1410 receiving the financial and health data of a participant, a lifetime of health care expenses particular to the participant and an amount of funds the participant should allocate to healthcare tax benefit accounts, based on the determined lifetime healthcare expenses, and an amount of funds the participant should allocate to non-healthcare tax benefits accounts.

A healthcare expense may include any expense related to the health of an individual. In some embodiments, a healthcare expense may be more restricted and pertain to medical expenses, such as, but not limited to optometry expenses, dental expenses, physical checkups, or the like. In some embodiments, a health care expense may be more inclusive and include personal well-being expenses related to health, such as, but not limited to, gym memberships, nutritional supplements, or the like. Non-healthcare expenses may correspond to any expense that isn't categorized as a healthcare expense. For example, procedures related to enhancing the looks of an individual, such as, hair transplants, cosmetic surgery, or the like. In addition, expenses that have little correlation with health may correspond to non-healthcare expenses, such as, but not limited to, home purchase, car purchase, clothing, or the like.

The PRAS 1408 can initiate a resource allocation process responsive to receiving the data packets, such as by causing the forecast engine 1412 to access healthcare expense prediction models maintained in the database 1414. The healthcare expense prediction models may include a plurality of models stored in the database 1414, and each model may dictate a lifetime of healthcare expenses. Each model may identify or indicate a different amount of lifetime healthcare expenses. Each model can be associated with a plurality of parameters having values. For example, each model can include a parameter for age, annual gross income, overall health, geographic location, contributions to tax deferred accounts, amount of savings, gender, marital status, and so on. In some embodiments, the values for the parameters for a given model may be discrete values (e.g., a participant age of 36). In other embodiments, the values for the parameters for a given model may be a range of values (e.g., a participant age in the range from 31-39). With each model indicating an amount of lifetime healthcare expenses based on a plurality of parameters having respective values, each model can be compared to the received financial and health data of a participant to identify a healthcare expense prediction model having values of parameters similar to those of the participant, and to determine the predicted lifetime healthcare expenses of the participant associated with the identified similar model.

The PRAS 1408 can cause the forecast engine 1412 to identify a healthcare expense predication model maintained in the database 1414 to perform resource allocation based on the information extracted from the received data packets (e.g., the financial and health data corresponding to a participant). The PRAS 1408 can cause the forecast engine 1412 to determine that a remote healthcare expense prediction model is required based on information extracted from the received data packets, and the PRAS 1408 can request the remote model by transmitting one or more data packets carrying a model request to a remote server, such as a server of an insurance administrator or an employer. The model request can cause the remote server to transmit the requested remote policy to the PRAS 1408. For example, the forecast engine 1412 can determine that the received data packets indicate a new insurance administrator or employer for which models are not yet maintained in the database 1408.

The forecast engine 1412 can identify a healthcare expense prediction model by specifying, or can otherwise determine, an ordered list of account destinations for allocating resources to benefits account. The ordered list of account destinations can include or refer to a set of electronic account identifiers or electronic account types that are in a sequence of priority. For example, each electronic account identifier or electronic account type can be associated with, correspond to, or configured with an allocation priority. The priority can include a numeric value, score, text, symbol, or other indicator of a rank, preference, selection technique, selection protocol, or sequence. In some embodiments, the ordered list of account destinations may include an electronic benefits account maintained in a server by an entity remote from the PRAS 1408 (e.g., at administrator device 1118), such as, but not limited to, a server of a financial institution, of an insurance administrator, or of an employer. The electronic benefits account can include, but not be limited to, a tax benefit account, an HSA, an FSA, a 401k account, a checking account, a savings account, an investment account provided by a financial institution, or other electronic accounts. For example, the ordered list can prioritize for resource allocation the healthcare benefits account first, and the non-healthcare benefits account second. Any other combinations of account allocation priorities are contemplated. In some embodiments, the PRAS 1408 specifies a default ordered list. In some embodiments, the PRAS 1408 can receive data specifying the ordered list, for example, from the client device 102 or the administrator device 1118.

In some embodiments, the PRAS 1408 determines the prioritization of the accounts based on characteristics of the different accounts. For example, The PRAS 1408 can determine different rate of returns associated with different types of tax benefit accounts to determine how to optimally allocate funds. The PRAS 1408 may also utilize rules or policies associated with the accounts. For example, the PRAS 1408 may lookup rules for an HSA and determine that it can be used only for qualifying expenses, but the funds of the account can be used immediately. The PRAS 1408 may also determine that a 401k account cannot be used until the age of 65 without a penalty, but can be used for anything (not just qualifying expenses). As such, the PRAS 1408 can score the different accounts and prioritize allocation based on the situation and needs of the individual participants. For example, if a participant typically spends a high amount of funds on f prescriptions, but is relatively young (e.g., 35), the PRAS 1408 may prioritize the HAS over the 401k so that the participant can utilize the funds immediately on the prescription drugs (a qualifying expense). The rules regarding various accounts may be stores at the PRAS 1408, or the PRAS 1408 may access the rules remotely.

The forecast engine 1412 can parse the received request for performance of resource allocation or the received financial and health data to determine amounts of funds a participant should contribute to a healthcare benefits account and a non-healthcare benefits account. From the received financial and health data of the participant, the forecast engine 1412 can generate a multi-dimensional feature vector or array corresponding to the data. In some embodiments, the forecast engine 1412 can parse the received financial and health data and organize the data into a multi-dimensional feature vector. The multi-dimensional feature array may be a data structure including a collection of elements, values, or variables that can be identified an index or key. The multi-dimensional feature vectors may be implemented as hash tables, linked lists, search trees, or as any other suitable data structure. The multi-dimensional feature vectors may include any suitable number of dimensions for organizing the received financial and health data, such as, but not limited, to two dimensions, three dimensions, and so on. For example, the multi-dimensional vector may include a feature indicating demographic information of the participant, a feature indicating healthcare spending amount, a feature indicating a health savings account contribution amount, and a feature indicating a health preference.

The forecast engine 1412 can identify a healthcare expense prediction model to predict the future healthcare expenses of the participant. The forecast engine 1412 may utilize the received financial and health data to identify a relevant healthcare expense prediction model. In some embodiments, the forecast engine 1412 identifies the healthcare expense prediction model based on how similar the model is to the values of the received financial and health data. The forecast engine 1412 may therefore perform a similarity analysis between the values of parameters of the received financial and health data to the values of the parameters of the models stored in database 1414 to determine which model is most similar to the received data. The forecast engine 1412 may determine a similarity metric between the received data and each of the healthcare expense prediction models or a subset of the models. After determining a value of a similarity metric for one or more of the healthcare expense prediction models, the forecast engine 1412 may rank the models and select the model having the highest rank.

In some embodiments, the forecast engine 1412 may determine the similarity metric based on the respective similarities of individual parameters included in the information of the models and the received financial and health data of a participant. The forecast engine 1412 may determine how similar the individual parameters are, and from these similarities, calculate an overall similarity value for a model. For example, the received data may include a first portion of information indicating that the participant has a gross annual income of $70,000 per year. The forecast engine 1412 can determine a difference between the received gross annual income and each gross annual income parameters associated with respective models stored in database 1414, and rank the models based on difference or an absolute value of the difference. Accordingly, the forecast engine 1412 may calculate a higher similarity score for a model including a gross income of $67,000 than for a model including a gross income of $110,000 because the absolute difference between $70,000 and $67,000 is less than the absolute difference between $110,000 and $70,000.

In some embodiments, the forecast engine 1412 may allocate predetermined weightings to certain parameters of the healthcare expense models based on how important some parameters are compared to others for the similarity analysis. For example, the parameter of annual income may be weighted heavier than the parameter of geographic location proximity. In some embodiments, the respective weightings associated with individual parameters may be modified at the administrator device 1118, at the client device 102, or at the PRAS 1408.

In some embodiments, the forecast engine 1412 performs the similarity analysis for each healthcare expense model in the database 1414 to determine the model most similar to the received financial, health, and personal data. In some embodiments, the forecast engine 1412 performs the similarity analysis on a subset of the total healthcare expense models. For example, in a first step, the forecast engine 1412 may perform a first pass filter to remove or exclude models in the database 1414 that are not yet reliable due to lack of information for that particular model. In some cases, certain models may be flagged as being inactive in the database 1414. In some embodiments, a participant at the client device 102 may input a filter, and in response to the received filter information (e.g., via data packets), the forecast engine 1412 may exclude healthcare expense models from similarity analysis that are excluded due to the filter. For example, a user may input a filter indicating a desire to target models that are within a certain territory of a country (e.g., a state), in which case the forecast engine 1412 may perform the similarity analysis only on those models that satisfy the filter criteria.

The healthcare expense models can be retrieved from a variety of entities, such as client devices 102 or servers (e.g., administrator device 1118) associated with an insurance administrator, an employer, a financial institution (e.g., a bank administering or otherwise maintaining an electronic reimbursement account or a payroll account configured for direct deposit). The insurance administrator can establish or otherwise maintain the electronic benefits account.

In some embodiments, the forecast engine 1412 may identify non-healthcare expenses of the participant over the participant's lifetime. The non-healthcare expense model may also be dictated by the selected healthcare expense model that includes parameters similar to the parameters associated with the participant. In other embodiments, the non-healthcare expenses may be calculated based on the data received by the PRAS 1408 instead of, or in addition to, being based on the healthcare expense model.

In some embodiments, the forecast engine 1412 may perform a lookup in the database 1414 to identify a healthcare benefits account of the participant associated with the received financial, health, and personal data to provide funds towards the predicted lifetime healthcare expenses of the participant, and a non-healthcare benefits account of the participant to provide funds towards lifetime non-healthcare expenses of the participant. The healthcare account and the non-healthcare account may already be established and associated with the participant, and this information may be stored in the database 1414. In some embodiments, the PRAS 1408 may remotely access the administrator device 1118 for the participant's accounts information. In some embodiments, the participant may not currently be enrolled in a healthcare benefits account, a non-healthcare benefits account, or both, and thus the forecast engine 1412 may identify a default one or more benefits account. In some embodiments, the participant may identify one or more accounts that are received by the PRAS 1408. In some embodiments, the PRAS 1408 may identify one or more accounts that would provide the maximum tax advantage to the participant over a lifetime. For example, the PRAS 1408 may identify that an HSA account may be most beneficial to the participant, or the PRAS 1408 may identify that the participant is already enrolled in both an HSA account and a 401k account with a particular administrator.

In some embodiments, based on the predicted lifetime healthcare expenses of the participant, the forecast engine 1412 may determine an amount of funds to allocate per a time period to the identified healthcare tax benefit account. The amount may also be based on the received financial, personal, and health data of the participant. In some embodiments, the PRAS 1412 may determine the amount of funds to allocate to the healthcare tax benefit account based on the allocation priorities associated with each of the electronic benefits accounts (e.g., the health account and the non-health account), in addition to the identified healthcare expense prediction model.

For example, the forecast engine 1412 may determine that a healthy (e.g., health indicators such as blood pressure, weight, or cholesterol are within predetermined ranges) and young (e.g., less than 40 years old) participant will incur less lifetime health expenses (e.g., $50,000) as compared to someone who is unhealthy (e.g., health indicators such as blood pressure, weight, or cholesterol that exceed predetermined maximum limits) and young. Because the participant is young and may be able to contribute funds to an account for several years, and because the participant is relatively healthy, the forecast engine 1412 may determine that a lower amount of funds may need to be allocated to the healthcare tax benefit account on an annual basis as compared to a young participant that is unhealthy. The forecast engine 1412 can match the healthy and unhealthy participants with corresponding models to determine or predict the total lifetime healthcare expenses. The forecast engine 1412 can further determine the annual amount to contribute to the account based on configuration parameters. If the participant is middle-aged and particularly unhealthy (e.g., has a number of health complications), and may thus incur a relatively high amount of lifetime health expenses, the forecast engine 1412 can determine that the participant should allocate a relatively large amount of funds to their health benefits account. As another example, the forecast engine 1412 may determine the amount of funds to allocate per time period to the healthcare tax benefit account using a feature indicating demographic information, a feature indicating a healthcare spending amount, a feature indicating a health savings account contribution amount, and a feature indicating a health preference.

In some embodiments, based on the predicted lifetime non-healthcare expenses of the participant, the forecast engine 1412 may determine an amount of funds to allocate based on a time interval or period to the identified non-healthcare tax benefit account. The amount may also be based on the received financial, personal, and health data of the participant. The amount may further be based on the lifetime healthcare expenses amount determined by the forecast engine 1412. The non-healthcare expenses may include, for example, costs or fees associated with everyday living, mortgage payments, rent payments, utility bills, gas, car payments, transportation, food, entertainment, cell phone, or costs associated with vacations. For example, the forecast engine 1412 may determine the amount of funds to allocate per time period to the non-healthcare tax benefit account using one or more features including a feature indicating demographic information, a feature indicating a geographic area or location, a feature indicating a non-healthcare spending amount, and a feature indicating a non-health retirement account contribution amount.

In some embodiments, the communication interface 1410 may provide, for presentation via an interactive user interface (UI) at the client device 102 associated with the participant, the amount of funds to allocate to the healthcare tax benefit account and the amount of funds to allocate to the non-healthcare tax benefit account. The interactive user interface may include a control object that receives an input to adjust the amount allocated to the healthcare tax benefit account. In addition, responsive to receiving the input to adjust the amount allocated to the healthcare tax account, the forecast engine 1412 may update a total amount of funds projected to be allocated to the healthcare tax benefit account. The interactive user interface may be sent to the client device 102 for interaction with the participant that initially transmitted the health, profile, and financial data. The interactive user interface may be sent as data packets including header and payload information, and the adjustments of control features at the interactive user interface may be transmitted as data packets including header and payload information. The data packets can include instructions that instruct central processing unit or a dedicated graphics processor of the client device to render the interactive user interface for display via a display device communicatively coupled to the client device and processor.

The PRAS 1408 may also generate the interactive UI with an electronic survey including one or more input elements. The interactive UI may receive the financial and health data of the participant. In some embodiments, the interactive UI is sent in response to a request from the client device 102. The interactive UI may have a plurality of blank fields corresponding to information to be filled pertaining to the participant, and the participant may interact with the UI to fill out the requested information. After completing the electronic survey, the client device 102 may transmit the information entered into the UI to the PRAS 1408, the information including the financial and health data of the participant.

In some embodiments, the PRAS 1408 may generate the interactive UI with a countdown timer set to a predetermined time interval. The predetermined time interval may be an interval set at the PRAS 1408, at the administrator device 1118, or at the client device 102. The time interval may be set to a suitable amount of time for allowing a participant to enter information into the interactive UI, but also not too much time for security purposes. For example, the timer may be short enough such that if a participant were to leave the client device 102 for a period a time, another unauthorized user may access the interactive UI while the authorized participant is away. The PRAS 1408 may initiate the countdown timer responsive to enabling the interactive UI to receive the financial and health data. In some embodiments, once the PRAS 1408 sends the interactive UI to the client device 102 and enables a participant at the client device 102 to enter health and financial information, the PRAS 1408 may initiate the timer. The PRAS 1408 may disable input via the interactive UI responsive to expiration of the countdown timer. In some embodiments, the PRAS 1408 may transmit a time out notification to the client device 102 upon expiration of the timer.

In some embodiments, the forecast engine 1412 can update the UI sent to the client device 102 in real-time in response to the adjusted amount triggered at the client device 102 and received at the PRAS 1408 via the communications interface 1410. The communications interface 1410 can be configured to provide the UI via an application package executed or rendered by a web browser of the client device. The communications interface 1410 can be configured to provide the UI via an application executed by the client device. The communications interface 1410 can be configured to provide the UI via an electronic mail protocol, SMS protocol, transport layer protocol, notification or prompt on a mobile telecommunications devices (e.g., a smartphone, tablet, smartwatch, wearable telecommunications device, laptop computer, desktop computer, etc.). A participant profile maintained in the database 1414 can include other contact information corresponding to the participant associated with the client device 102, and the PRAS 1408 can be configured to transmit the one or more data packets including the UI to the participant using the contact information via the communications interface 1410. In some embodiments, the participant profile can include a priority order associated with multiple contact information, a preferred contact information, or an indication of multiple contact information for receiving the UI. For example, the participant profile can indicate an electronic mail protocol as a preferred contact information, and the PRAS 1408 can be configured to identify the electronic mail protocol as the preferred contact information, and transmit the one or more data packets to the participant using the electronic mail protocol via the communications interface 1410.

In some embodiments, the PRAS 1408 can retrieve an electronic UI template configured for the delivering of the results of the operations of the forecast engine 1412. The forecast engine 1412 can generate the UI using the electronic UI template. The forecast engine 1412 can transmit the one or more data packets carrying the results generated using the electronic UI template to the client device 102 via the communications interface 1410. For example, the communications interface 1410 can transmit the one or more data packets via at least one of an SMS protocol or an electronic mail protocol.

In some embodiments, the PRAS 1408 is configured to retrieve an electronic UI template configured for transmission via a particular transmission protocol. For example, the PRAS 1408 can retrieve an SMS-compatible electronic UI template configured to be compatible with SMS protocol, such as an electronic UI template having a particular character limit and an organization configured to use plain text. The PRAS 1408 can retrieve an electronic mail-compatible electronic UI template configured to be compatible with electronic mail protocol, such as an electronic UI template using rich text or HTML. In some embodiments, the PRAS 1408 can retrieve multiple electronic UI templates compatible with multiple transmission protocols, generate multiple UIs using the multiple transmission protocols, and transmit the multiple UIs via the multiple transmission protocols via the communications interface 1410.

In some embodiments, the PRAS 1408 may include a machine learning engine 1416 executed by the server and configured to train the healthcare expense prediction model with the financial data and the health data of the plurality of participants. The PRAS 1408 may utilize the constantly updated profiles of the stored participant profiles to extrapolate data and to formulate the models based on similar profiles. The PRAS 1408 may constantly receive data regarding the various profiles of the various participants, and may constantly update and refine healthcare expense prediction models based on the newly received data. For example, the PRAS 1408 may store a healthcare expense prediction model corresponding to a middle-aged individual who is relatively healthy and who has an annual income of over $100,000. The PRAS 1408 may monitor the health care tendencies and outcome of this demographic and those who used to be in this demographic to refine the prediction model associated with this demographic. For instance, if an overwhelming majority of elderly people that used to be in this demographic when they were middle-aged do not have many health complications, the prediction model can adjust its predicted health care expenses associated with this middle-aged demographic to account for the likelihood that they will need minimal medical care in their future. The more indications that this demographic will realize good health, as ascertained by the various profiles accessible to the PRAS 1408, the stronger this correlation becomes and the machine learning engine 1416 may update the healthy middle-aged demographic accordingly.

The machine learning engine 1416 can access the information maintained by the PRAS 1408, due to the PRAS 1408 being connected to the various administrator devices 1118, with each administrator device 1118 servicing various participants. In some embodiments, the machine learning engine 1416 may access the health-related spending habits of participants to deduce their health status and to directly identify how much and on what health-related costs they are spending on. In addition, the machine learning engine 1416 may parse survey data associated with participants (e.g., health surveys given to the participants by an insurance administrator to determine the participants' level of health). Furthermore, because insurance administrators may require health records from their participants, the PRAS 1408 may access those health records of the participants (e.g., at the administrator devices 1118) for use in conjunction with the expense prediction models. In addition, the PRAS 1408 may utilize any other suitable and available information to use with the health expense prediction models for better predicting lifetime health-related expenses for various and diverse participants, such as, but not limited to, participant contribution to health benefits accounts, frequency of physical examinations, amount of exercise, diet, blood pressure, history of disease, family disease history, and so on.

In machine learning engine 1416 may access the wealth of information at the disposal of the PRAS 1408 and execute a machine learning technique or algorithm for generating and refining the health expense prediction models stored on the database 1414. A machine learning algorithm operates by building a model from example inputs in order to make data-driven predictions or decisions, rather than following strictly static program instructions. In some embodiments, the machine learning engine 1416 may employ supervised learning in which a computer is presented with example inputs and their desired outputs, and the goal is to learn a general rule that maps inputs to outputs. In some embodiments, the machine learning engine 1416 may employ unsupervised learning in which no labels are given to the learning algorithm, leaving it alone to find structure in its input.

In some embodiments, the machine learning engine 1416 may employ decision tree learning, using a decisions tree as a predictive model, which maps observations out an item to conclusions about the item's target value. In some embodiments, the machine learning engine 1416 may employ association rule learning, which is a method for discovering interesting relations between variables in large databases. In some embodiments, the machine learning engine 1416 may employ support vector machines (SVM), which are a set of supervised learning methods used for classification and regression. Given a set of training examples, each marked belonging to one of two categories, an SVM training algorithm builds a model that predicts whether a new example falls into one category or the other. In other embodiments, the machine learning engine 1416 may employ any other suitable algorithm for generating and refining the healthcare expense models, such as, but not limited to, clustering, reinforcement learning, representation learning, Bayesian networks, or the like.

For example, the machine learning engine 1416 can receive healthcare information as sets of inputs or profiles of participants and divide the sets of inputs into groups using a clustering technique or a classification technique. In some cases, the machine learning engine 1416 can utilize a clustering technique in which the groups are not predetermined. In some cases, the machine learning engine 1416 can use a classification technique in which the groups are predetermined. The cluster generated by the machine learning engine 1416 can include sets of input data or profiles of participants that are more similar to profiles within the cluster as compared to profiles in a different cluster or adjacent cluster. The clustering technique can include generating vectors using multi-dimensional features associated with each profile, and determining a distance between vectors to identify a set of vectors within a threshold distance from one another. The identified set of vectors within the threshold distance from one another can form a cluster.

To generate a healthcare expense model, the machine learning engine 1412 can obtain healthcare information and expense data associated with profiles or participants, and train the healthcare model using the feature data and corresponding expense data of each of the participants. The healthcare information and expense data can be input into the PRAS 1408 by a participant or administrator via an interface. The PRAS 1408 can be configured to determine or identify various healthcare information or expense data of a participant or administrator via parsing electronic healthcare transaction processed or received by the PRAS 1408. For example, the machine learning engine 1416 can be configured with a regression analysis technique that uses a statistical process to estimate the relationship between a feature (e.g., healthy or not healthy) determined from healthcare information (e.g., received from an electronic survey presented by an interactive user interface or determined from a healthcare transactions for purchasing a prescription medication for high cholesterol) and an expense signal (e.g., cost of the prescription medication or healthcare visits or expenses related to complications). The feature (e.g., healthy) can be a predictor or independent variable, and the signal (e.g., expense) can be a dependent variable or a criterion variable that can change as the features are varied. In some cases, the machine learning engine 1416 can estimate, determine or predict a conditional expectation of the dependent variable given the independent variables (e.g., an average value of the dependent variable when the independent variables are fixed; or other parameter or metric of the conditional distribution of the dependent variable or signal given the independent variable or feature). The predicted signal (e.g., expense) can be a function of the independent variables and can be referred to as a regression function. The machine learning engine 1416 can further identify, determine or characterize a variation of the dependent variable around the regression function which can be described by a probability distribution. The machine learning engine 1416 can use the probability distribution to generate a confidence score in the predicted signal value, or use the probability distribution as the confidence score. For a given feature or feature combination, the machine learning engine 1416 can identify the expense corresponding to the highest confidence score, and use this expense to predict an amount of resources or funds a participant should allocate to a tax benefit account based on a time interval in order to have sufficient resources to pay for the predicted healthcare expenses.

In some aspects, the system of the present solutions implements a combination of the communications interface 1410, forecast engine 1412, machine learning engine 1416, database 1414, clients 102*a-n*, admin devices 1118*a-n*, or heterogeneous electronic funding sources 702*a-n* in an innovative, non-conventional and/or non-routine manner. In some aspects, the system of the present solutions integrates communications interface 1410, forecast engine 1412, machine learning engine 1416, database 1414, clients 102*a-n*, admin devices 1118*a-n*, or heterogeneous electronic funding sources 702*a-n* in an innovative, non-conventional and/or non-routine manner to implement the improved functionality, performance and operation of the present solution. In some aspects, the system of the present solutions integrates communications interface 1410, forecast engine 1412, machine learning engine 1416, database 1414, clients 102*a-n*, admin devices 1118*a-n*, or heterogeneous electronic funding sources 702*a-n* in an innovative, non-conventional and/or non-routine manner to more efficiently and effectively use computing and networking resources. The communications interface 1410, forecast engine 1412, machine learning engine 1416, database 1414, clients 102*a-n*, admin devices 1118*a-n*, or heterogeneous electronic funding sources 702*a-n* are integrated in an innovative, nonconventional manner to mitigate, reduce, prevent, or resolve the technical problems of resource allocation in an electronic transaction based technology platform. The communications interface 1410, forecast engine 1412, machine learning engine 1416, database 1414, clients 102*a-n*, admin devices 1118*a-n*, or heterogeneous electronic funding sources 702*a-n* integrated in the innovative, non-conventional manner address at least these technical problems by, for example, receiving financial data indicating a financial snapshot of a participant of a client device and health data of the participant to predict lifetime healthcare expenses of the participant; generating a multi-dimensional feature vector of the participant based on the received financial data and the health data of the participant; identifying a healthcare expense prediction model to predict the future healthcare expenses of the participant; determining from the identified healthcare expense prediction model using the multi-dimensional feature vector of the participant, the predicted lifetime healthcare expenses of the participant; identifying lifetime non-healthcare expenses of the participant; performing a lookup in a database to identify a healthcare tax benefit account of the participant to provide funds towards the predicted lifetime healthcare expenses of the participant and a non-healthcare tax benefit account of the participant to provide funds towards lifetime non-healthcare expenses of the participant; determining, based on the predicted lifetime healthcare expenses of the participant, a first amount of funds to allocate per time period to the healthcare tax benefit account; determining, based on the lifetime non-healthcare expenses of the participant, a second amount of funds to allocate per time period to the non-healthcare tax benefit account; and providing, for presentation via an interactive user interface, the first amount of funds to allocate to the healthcare tax benefit account and the second amount of funds to allocate to the non-healthcare tax benefit account, the interactive user interface including a control object configured to i) receive an input to adjust the first amount, and ii) responsive to receiving the input to adjust the first amount, updating a total amount of funds projected to be allocated to the healthcare tax benefit account.

Figure 15A:
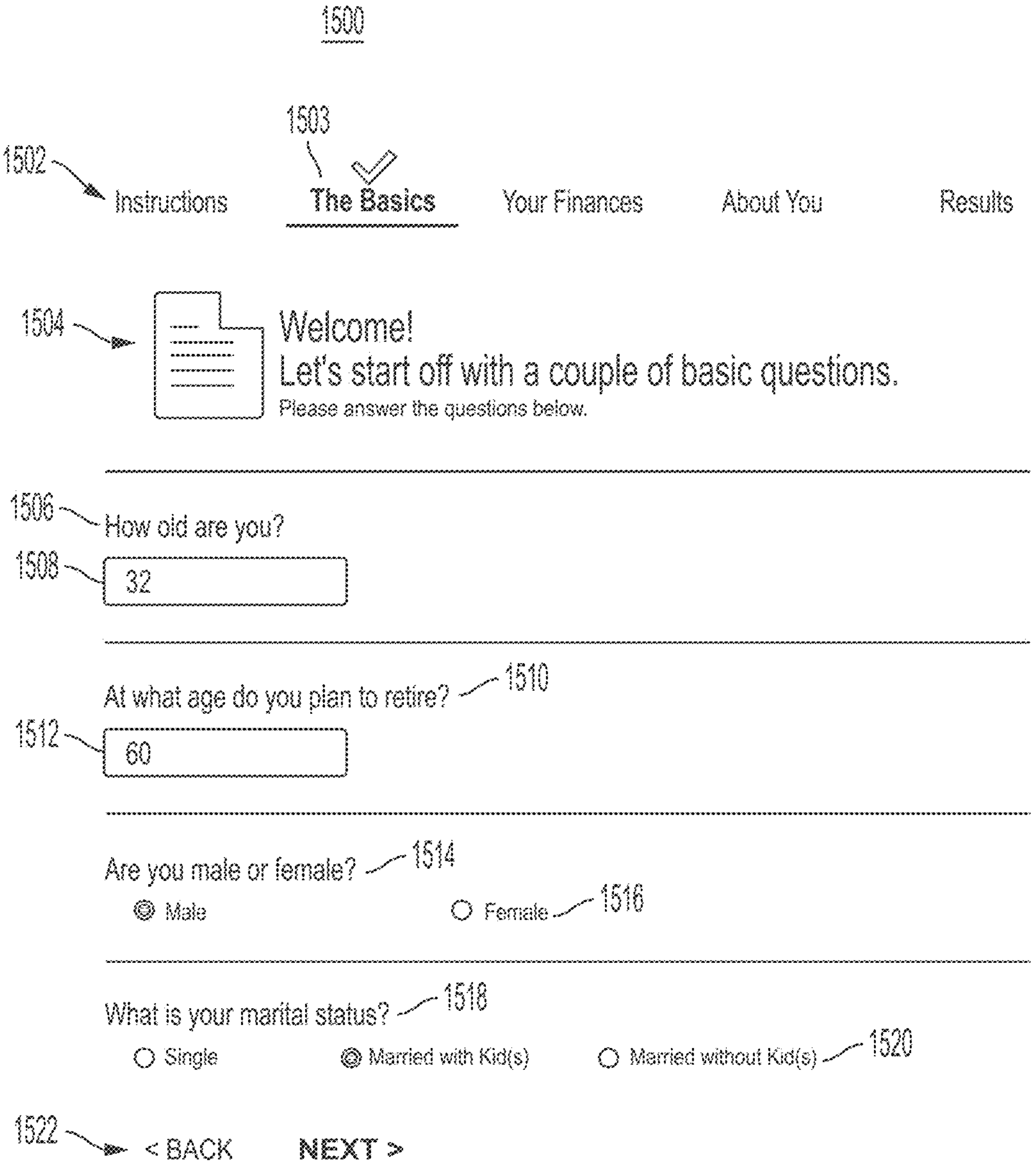
FIG. 15A-15D are diagrams depicting an interactive user interface associated with a predictive resource allocating system.

Referring now to FIG. 15A, a diagram of an interactive user interface 1500 is depicted. In some embodiments, the UI 1500 may be displayed at the client device 102 for interaction with a participant of an electronic benefits account. The interactive UI 1500 includes a navigation pane 1502, an instructive prompt 1504, an inquiry field 1506 (and 1510, 1514, and 1518), a value field 1508 (and 1512, 1516, and 1520) corresponding to the inquiry field 1506 (and 1510, 1514, and 1518, respectively), and a navigator 1522.

In some embodiments, the interactive UI 1500 is a page (e.g., a web page) for entering information relevant to the PRAS 1408 for sending to the PRAS 1408. The navigation pane 1502 includes a highlight indicator 1503 for indicating to a user the page that the UI currently displays. For example, the indicator 1503 indicates to a user that they are currently viewing a page for inputting "The Basics." In addition, for further guidance, the UI 1500 includes the instructive prompt 1504 for further guiding the user as to what to do on this page. For example, the instructive prompt 1504 may welcome the user and guide the user by stating: "Let's start off with a couple of basic questions. Please answer the questions below."

In some embodiments, the interactive UI 1500 may display one or more basic questions for the participant to answer. The questions may be general questions the answers to which will be transmitted to the PRAS 1408 and will enable the PRAS 1408 to perform its calculations. For example, inquiry field 1506 states: "How old are you?" In response to this question, the field 1508 has been filled with the number "32." Inquiry field 1510 states: "At what age do you plan to retire?" In response to this question, the field 1512 has been filled with the number "60." Inquiry field 1514 states: "Are you male or female?" In response to this question, an option of the field 1516 has been selected, the selection corresponding to "Male." Inquiry field 1518 states:

"What is your marital status?" In response to this question, an option of the field 1520 has been selected, the selection corresponding to "Married with Kid(s)." In some embodiments, the value fields 1508, 1512, 1516, and 1520 may be a text box for entering in text by a participant. In other embodiments, the value field 1508 may provide a list of possible values that the participant may select (e.g., "male" or "female"). Once a participant has entered responses to the questions, the participant may interact with the navigator 1522 to continue to the next page, or to a previous page, as desired.

The PRAS 1408 can receive inputs corresponding to questions 1506, 1510, 1514, and 1518 and can identify features for the participant and determine values for the features. For example, the PRAS 1408 can generate a first feature indicative of age, with values of young, middle-aged, and elderly. The PRAS 1408 can determine a first value of the first feature based on a first mapping that maps the input to the first feature value. For example, the input of 32 years (1508) can map to a first feature value of young. The PRAS 1408 can determine a second value for a second feature corresponding to retirement age (question 1510). The PRAS 1408 can include a second mapping different from the first mapping. For example, a second input 1512 of 60 years can map to a second value of young for the second feature because retiring at age 60 may be determined to be a young retirement age. The PRAS 1408 can determine a third value for a third feature corresponding to gender (question 1514). The PRAS 1408 can include a third mapping different from the first and second mappings. For example, a third input 1516 of "male" can map to a third value of male for the third feature. The PRAS 1408 can determine a fourth value for a fourth feature corresponding to marital status (question 1518). The PRAS 1408 can include a fourth mapping different from the first, second, and third mapping. For example, a fourth input 1520 of "married with kid(s)" can map to a fourth value of married with kid(s) for the fourth feature. In some embodiments, PRAS 1408 can combine two or more of the determined features to perform a fifth mapping different from the first, second, third, and fourth mappings to determine a fifth value for a fifth feature. For example, the first input 1506 and the fourth input 1518 can map to a fifth value of "young family."

Figure 15B:
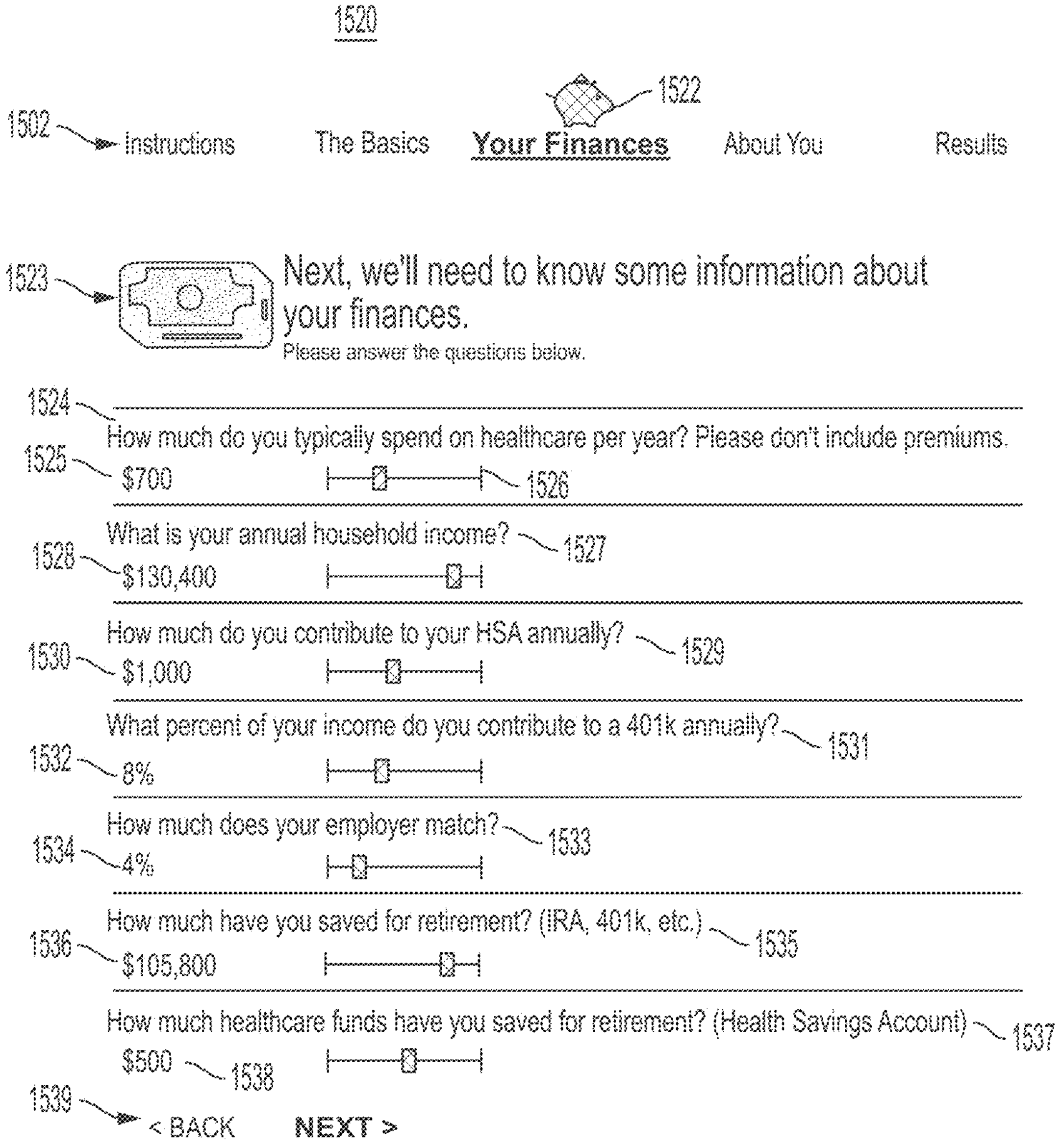

Referring now to FIG. 15B, a diagram of an interactive user interface 1520 is depicted. In some embodiments, the UI 1520 may be displayed at the client device 102 for interaction with a participant of an electronic benefits account. The interactive UI 1520 includes the navigation pane 1502, an instructive prompt 1524, an inquiry field 1525 (and 1527, 1529, 1531, 1533, 1535, and 1537), a value field 1525 (and 1528, 1530, 1532, 1534, 1536, and 1538) corresponding to the inquiry field 1524 (and 1527, 1529, 1531, 1533, 1535, and 1537, respectively), a control feature 1526, and a navigator 1539.

In some embodiments, the interactive UI 1520 is a page (e.g., a web page) for entering information relevant to the PRAS 1408 for sending to the PRAS 1408. The navigation pane 1502 includes a highlight indicator 1522 for indicating to a user the page that the UI currently displays. For example, the indicator 1522 indicates to a user that they are currently viewing a page for inputting "Your Finances." In addition, for further guidance, the UI 1520 includes the instructive prompt 1523 for further guiding the user as to what to do on this page. For example, the instructive prompt 1523 may guide the user by stating: "Next, we'll need to know some information about your finances. Please answer the questions below."

In some embodiments, the interactive UI 1520 may display one or more questions for the participant to answer. The questions may be financial-related questions the answers to which will be transmitted to the PRAS 1408 and will enable the PRAS 1408 to perform its calculations. For example, inquiry field 1524 states: "How much do you typically spend on healthcare per year? Please don't include premiums." In response to this question, the field 1525 has been filled with the value "$700." The value entered into the value field may be increased or decrease, or otherwise controlled, by the control feature 1526. The control feature 1526 is an interactive element embedded in the UI 1520 such that a user may interact with the control feature 1526 to control the value in the value field 1525.

In addition, inquiry field 1527 states: "What is your annual household income?" In response to this question, the field 1528 has been filled with the value "$130,400." Inquiry field 1529 states: "How much do you contribute to your HAS annually?" In response to this question, the field 1530 has been filled with the value "$1000." Inquiry field 1531 states: "What percent of your income do you contribute to a 401k annually?" In response to this question, the field 1531 has been filled with the value "8%." Inquiry field 1533 states: "How much does your employer match?" In response to this question, the field 1534 has been filled with the value "4%". Inquiry field 1535 states: "How much have you saved for retirement?" In response to this question, the field 1536 has been filled with the value "$105,800." Inquiry field 1537 states: "How much healthcare funds have you saved for retirement? (Health Savings Account)." In response to this question, the field 1538 has been filled with the value "$500." In some embodiments, each, some, or none of the values in the respective value fields may include a slider for controlling a corresponding value.

The PRAS 1408 can receive inputs corresponding to questions 1524, 1527, 1529, 1531, 1533, 1535, and 1537 and can identify features for the participant and determine values for the features. For example, the PRAS 1408 can generate a first feature indicative of healthcare expenditures, with values of high, medium, and low. The PRAS 1408 can determine a first value of the first feature based on a first mapping that maps the input to the first feature value. For example, the input of $700 (1525) can map to a first feature value of medium. The PRAS 1408 can determine a second value for a second feature corresponding to income (question 1527). The PRAS 1408 can include a second mapping different from the first mapping. For example, a second input 1528 of $130,400 can map to a second value of rich for the second feature because an annual income of over $120,000 may be considered rich by the PRAS 1408. The PRAS 1408 can determine other feature values based on the inputs of FIG. 15B to map certain feature values of features associated with the participant. In some embodiments, PRAS 1408 can combine two or more of the determined features to perform a third mapping different from the first and second mappings to determine a third value for a third feature. In some embodiments, as an example, the predictive expense models can use these features to predict that people with incomes in a certain range may have higher or lower healthcare expenses, and may extrapolate other deductions from other features of the participants.

In some embodiments, the value field 1528 may be a text box for entering in text by a participant or a slider controller. In other embodiments, the value field 1528 may provide a list of possible values that the participant may select. Once a participant has entered responses to the questions, the participant may interact with the navigator 1532 to continue to the next page, or to the previous page (e.g., "The Basics" page), as desired. In various embodiments, the information entered into the interactive UI 1520 may correspond to the financial data that is sent to the PRAS 1408, for use by the forecast engine 1412.

Figure 15C:
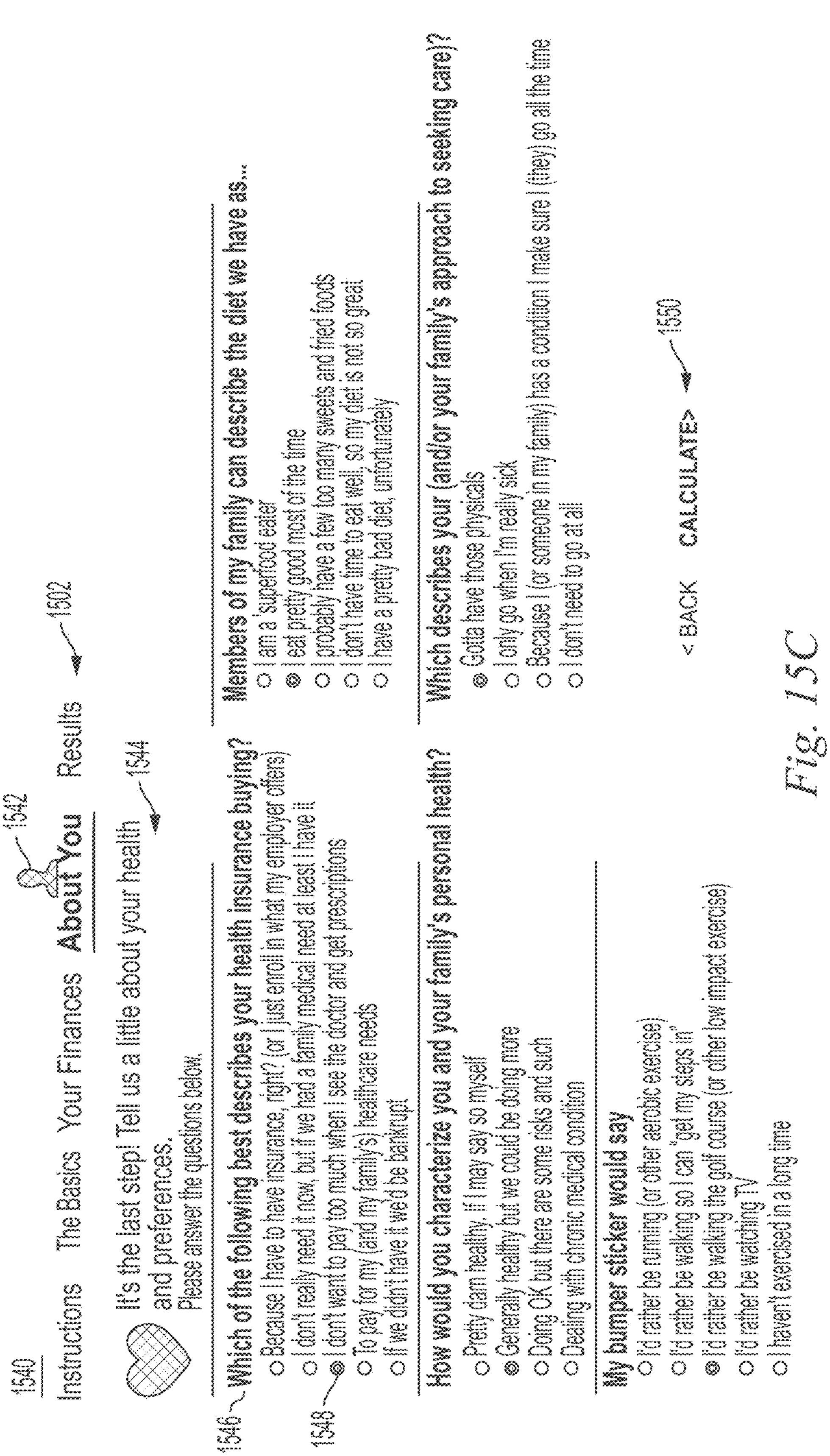

Referring now to FIG. 15C, a diagram of an interactive user interface 1540 is depicted. In some embodiments, the UI 1540 may be displayed at the client device 102 for interaction with a participant of an electronic benefits account. The interactive UI 1540 includes the navigation pane 1502, an instructive prompt 1544, an inquiry field 1546, and a value field 1548 corresponding to the inquiry field 1546.

In some embodiments, the interactive UI 1540 is a page (e.g., a web page) for entering information relevant to the PRAS 1408 for sending to the PRAS 1408. The navigation pane 1502 includes a highlight indicator 1542 for indicating to a user the page that the UI currently displays. For example, the indicator 1542 indicates to a user that they are currently viewing a page for inputting "About You." In addition, for further guidance, the UI 1540 includes the instructive prompt 1544 for further guiding the user as to what to do on this page. For example, the instructive prompt 1544 may guide the user by stating: "It's the last step! Tell us a little about your health and preferences. Please answer the questions below."

In some embodiments, the interactive UI 1540 may display one or more questions for the participant to answer. The questions may be health-related questions the answers to which will be transmitted to the PRAS 1408 and will enable the PRAS 1408 to perform its calculations. In some embodiments, the inputs to these queries enable the PRAS 1408 to identify features corresponding to the participant and generate values for the features. Accordingly, the values of the features corresponding to the participant can be input into the expense prediction model generated by the machine learning engine 1416 to determine an output for the participant corresponding to predicted expenses of the participant.

Inquiry field 1546 states: "Which of the following best describes your health insurance buying?" In response to this question, the field 1548 has been selected corresponding to the value "I don't want to pay too much when I see the doctor and get prescriptions." In some embodiments, the value field 1548 may be a text box for entering in text by a participant or a slider controller. In other embodiments, the value field 1548 may provide a list of possible values that the participant may select. Once a participant has entered or selected responses to the questions, the participant may interact with the navigator 1550 to continue to the next page (e.g., to calculate the results), or revert to the previous page (e.g., "Your Finances" page), as desired.

In various embodiments, the information entered into the interactive UI 1540 may correspond to the health data that is sent to the PRAS 1408, for use by the forecast engine 1412. In response to selecting the "Calculate" feature in the navigator 1550, the client 102 may send the entered information to the PRAS 1408, including the information entered in the UIs 1500, 1520, and 1540. Accordingly, by clicking the "Calculate" button, the client device 102 can transmit the personal, financial, and health data of the participant so that the forecast engine 1412 may perform operations on the entered data.

Figure 15D:
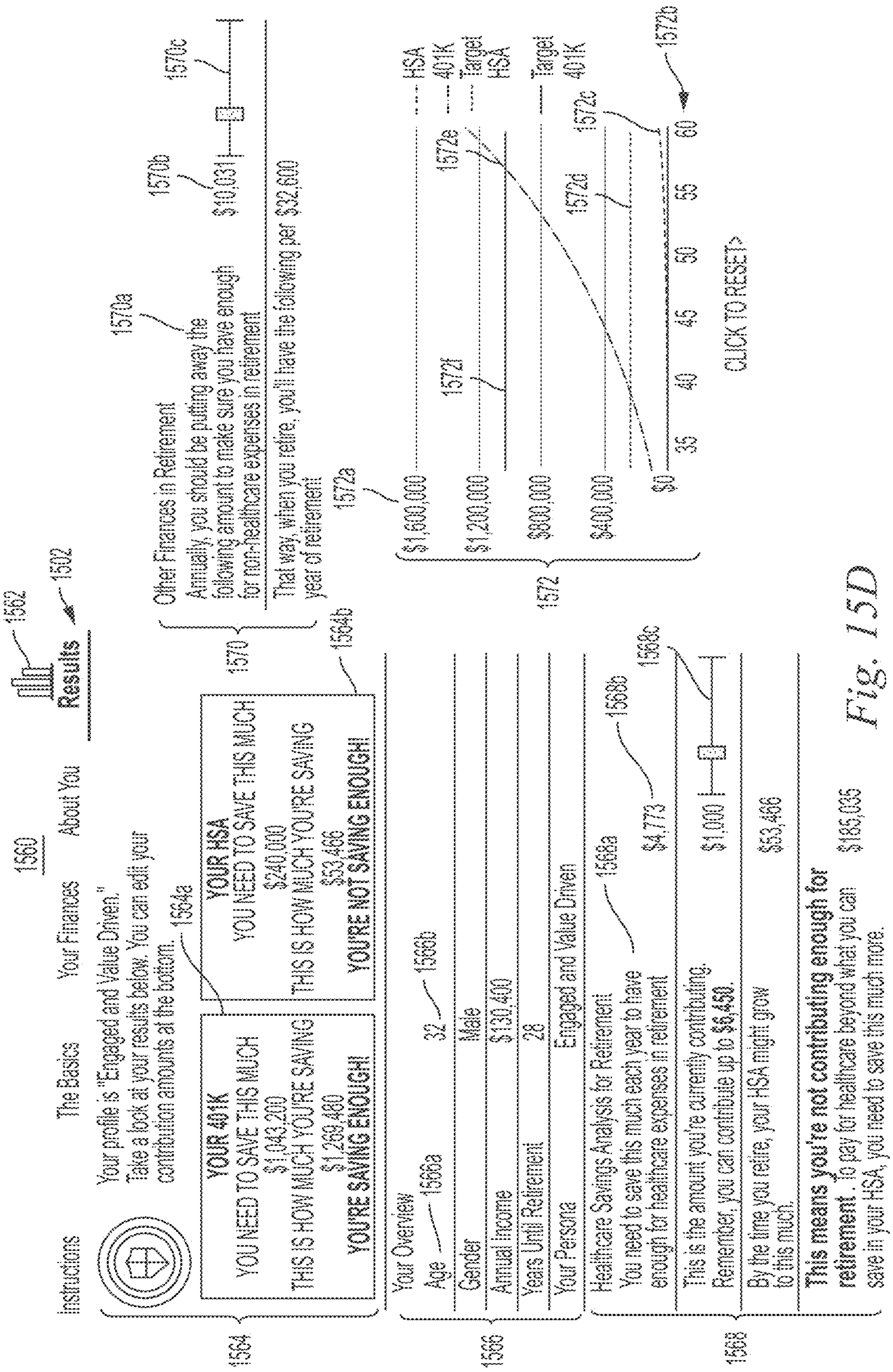

Referring now to FIG. 15D, a diagram of an interactive user interface 1560 is depicted. In some embodiments, the UI 1560 may be displayed at the client device 102 for interaction with a participant of an electronic benefits account. The interactive UI 1560 includes the navigation pane 1502, a results field 1564, an overview field 1566, a healthcare analysis field 1568, a financial analysis field 1570, and a graphical result 1572.

In some embodiments, after the financial, personal, and health data is entered in UIs 1500, 1520, and 1540 and are submitted to the PRAS 1408, the forecast engine 1412 may perform a resource allocation process on the received data. Upon completing the resource allocation process with respect to the received participant data, the PRAS 1408 may send the results of the operations of the forecast engine 1412 to the client device 102 for displaying the results via the interactive UI 1560.

In some embodiments, the interactive UI 1560 is a page (e.g., a web page) for viewing information received from the PRAS 1408. The navigation pane 1502 includes a highlight indicator 1562 for indicating to a user the page that the UI currently displays. For example, the indicator 1562 indicates to a user that they are currently viewing the "Results" page. Accordingly, the interactive UI 1560 may display the results determined, based on the entered personal, health, and financial data, by the forecast engine 1412.

The results UI 1560 may include a results field 1566. The results field 1566 includes a non-healthcare account result field 1564*a* and a healthcare account results field 1564*b*. Each of the results fields 1564*a* and 1564*b* may indicate a total amount of savings that a participant should save in each account over the participant's lifetime, as determined by the forecast engine 1412. In some embodiments, the results fields 1564*a* and 1564*b* may also indicate the amount that the participant will save during the participant's lifetime. This piece of information may be based on the participant's current contribution habits, current balances in the accounts, gross income, expected income raises, or the like. This information may be accessed by the PRAS 1408 from the database 1414 or from the administrator device 1118 associated with the participant's account. In some embodiments, the results field 1506 may also indicate whether the participant is saving enough or not with respect to each of the non-healthcare account (1564*a*) and the healthcare account (1564*b*).

In some embodiments, the overview field 1566 includes a plurality of parameter fields 1566*a* and a plurality of corresponding value fields 1566*b*. The overview field 1566 can include basic information pertaining to the participant. The values 1566*b* of the overview field 1566 may be populated based on the participant's responses to questions in the previous UI pages. In some embodiments, the values 1566*b* of the overview field 1566 may be populated based on information contained in the participant's profile stored in the administrator device 1118 or the PRAS 1408. For example, the overview field 1566 may include such parameters as age, gender, annual income, or the like.

In some embodiments, the healthcare analysis field 1568 includes a plurality of prompts 1568*a*, a plurality of values 1568*b* corresponding to the prompts 1568*a*, and a control feature 1568*c*. The plurality of prompt 1568*a* indicate various financial attributes associated with the participant's health savings account, such as, but not limited to, amount needed to save in the healthcare account each year for retirement, amount the participant is currently contributing to the healthcare account, how much the participant should be contributing, or the like. The values 1568*b* correspond to the prompts 1568*a* (e.g., the participant needs to save $4,773 in the health benefits account each year for retirement).

In addition, the healthcare analysis field 1568 may include a control feature 1568*c*, which may be a slider, or any other feature suitable for adjusting a value of the value fields 1568*b*. In some embodiments, the control feature 1568*c* may increase or decrease a value corresponding to the prompt of how much the participant is currently contributing to the health benefits account. As such, a participant may adjust this value, as desired. In response to adjusting the value via the control feature 1568*c*, one or more values displayed in the UI 1560 may also change. For example, in response to increasing the value associated with the control feature 1568*c* (e.g., the value of amount currently contributed to HSA), the value associated with the prompt "By the time you retire your HSA might grow to this much" may increase, since the value associated with current yearly contributions increased. This change in the UI 1560 may occur in real-time or responsive to an adjustment to the control feature 1568*c*. The adjusted value may be sent to the PRAS 1408 in real-time as updated financial data or health data of the participant, and the PRAS 1408 may calculate the updated values of the UI 1560 in response to the new data and send the updated results to the client device 102 in real-time. Other input features from previous features can also be adjusted to generate an updated value at the UI 1560. For example, a participant can change the answer to the question "Members of my family can describe the diet we have as . . . " displayed in FIG. 15C, and depending on the adjusted input responsive to the question, the PRAS 1408 may update the values at the UI 1560.

As such, the present solution provides an interactive report to a participant that can reduce the number of requests and processing required because the PRAS 1408 can adjust a single field to update the prediction of expenses. Because the PRAS 1408 includes predictive models trained with data from a plurality of participants over time, the PRAS 1408 can efficiently identify the change in the feature and identify a new predictive model to determine a new prediction. Also, the system can update the healthcare prediction if the change in feature is a healthcare-related feature. Thus, the PRAS 1408 reduces data communications, bandwidth, and processing because it can focus on updating the healthcare expense and savings and efficiently allocate resources for healthcare expenses without re-processing non-healthcare expense. This is especially beneficial for mobile devices where battery and data usage is an issue. In addition, battery life may be saved because the present system updates or renders the screen because with only one field. The system also saves time as a user does not need to re-enter all other inputs, and only need change one input for a new result.

Similar to the health analysis field, the UI 1560 may include the financial analysis field 1570 including a plurality of prompts 1570*a*, a plurality of values 1570*b* corresponding to the prompts 1570*a*, and a control feature 1570*c*. The plurality of prompt 1570*a* indicate various financial attributes associated with the participant's non-healthcare savings account, such as, but not limited to, amount needed to save in the non-healthcare account each year for retirement, amount the participant is currently contributing to the non-healthcare account, how much the participant should be contributing, or the like. The values 1570*b* correspond to the prompts 1570*a*. The financial analysis field 1570 may also include the a control feature 1570*c* for adjusting one or more of the values in the value field 1570*b*. For example, the control feature 1570*c* may adjust a value corresponding to an amount saved annually in the non-healthcare savings account. Similar to the function of control feature 1568*c*, the control feature 1570*c* may cause one or more of the values of the UI 1560 to update based on the changed value.

The UI 1560 may further include a graphical result 1572, which may display the results of the UI 1560 in graphical form. The graphical result 1572 may include an x-axis corresponding to the participant's age in year and a y-axis corresponding to amounts of money. Accordingly, the graphical result 1572 indicates the amount of savings over time in accordance with the results determined and shown in the UI 1560. In particular, the graphical result 1572 displays the amount saved in the participant's HSA account over time as represented by line 1572*c*, and the amount saved in the participant's 401k account over time as represented by line 1572*e*. The graphical result 1572 may also indicate target savings in each of the accounts, as illustrated by lines 1572*d* and 1572*f*. In other embodiments, other forms of data representation may be depicted in the UI 1560, such as, but not limited to, a pie chart, a bar chart, or the like.

Figure 16:
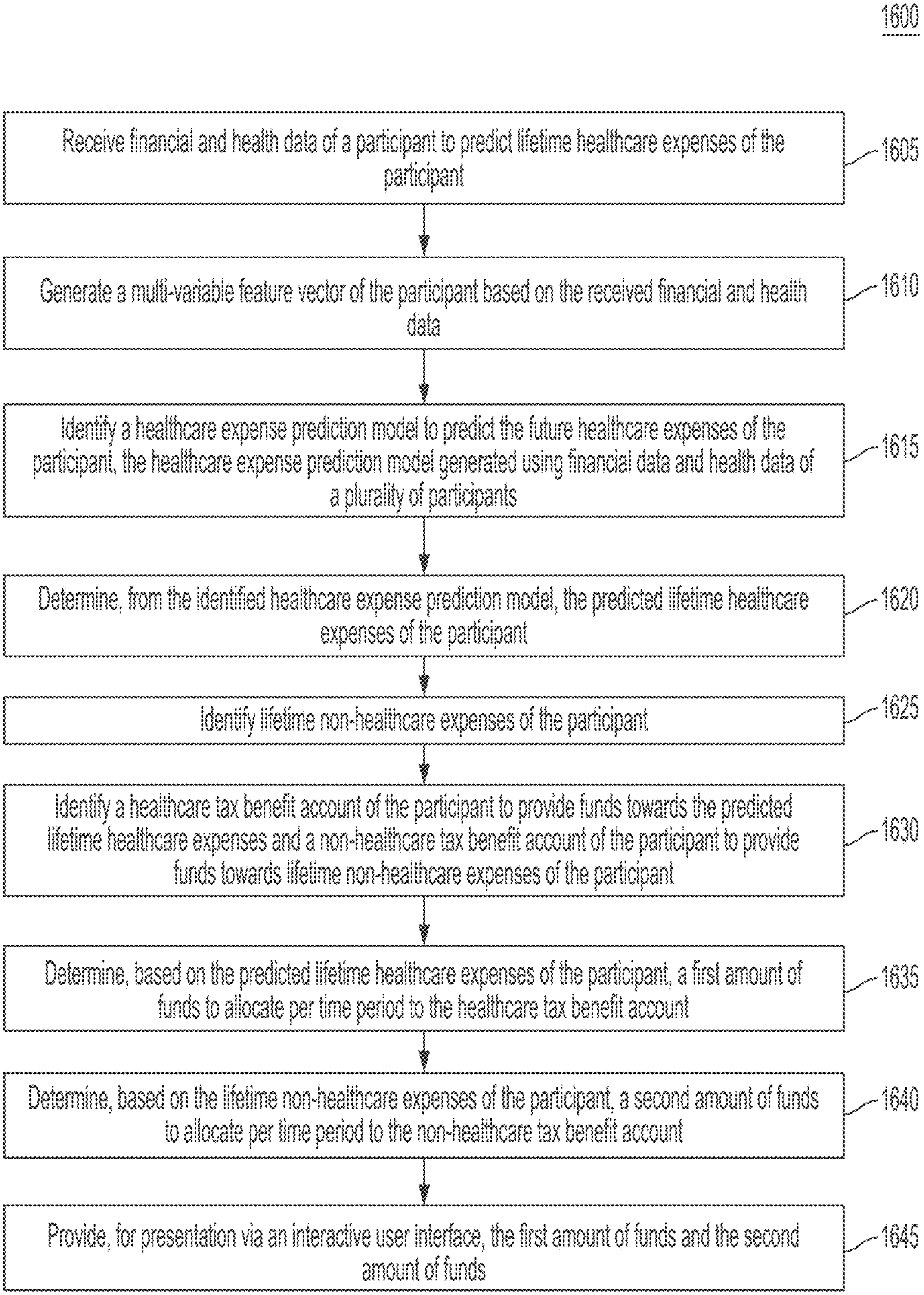
FIG. 16 is a flow diagram depicting an embodiment of a method of allocating resources using an information technology infrastructure.

Referring now to FIG. 16, a flow diagram depicting an embodiment of a method 1600 of allocating resources using an information technology infrastructure is shown. The method can be performed by one or more component or module of system 1400, the PRAS 1408, or one or more component or module depicted in FIGS. 1A-1D. In brief overview, at step 1605, a server of a predictive resource allocating system receives financial data indicating a financial snapshot of a participant of a client device and health data of the participant to predict lifetime healthcare expenses of the participant. At step 1610, the server generates a multi-dimensional feature vector of the participant based on the received financial data and the health data of the participant. At step 1615, the server identifies a healthcare expense prediction model to predict the future healthcare expenses of the participant, the healthcare expense prediction model generated by the server using financial data and health data of a plurality of participants. At step 1620, the server determines from the identified healthcare expense prediction model using the multi-dimensional feature vector of the participant, the predicted lifetime healthcare expenses of the participant. At step 1625, the server identifies lifetime non-healthcare expenses of the participant. At step 1630, the server performs a lookup in a database to identify a healthcare tax benefit account of the participant to provide funds towards the predicted lifetime healthcare expenses of the participant and a non-healthcare tax benefit account of the participant to provide funds towards lifetime non-healthcare expenses of the participant. At step 1635, the server determines based on the predicted lifetime healthcare expenses of the participant, a first amount of funds to allocate per time period to the healthcare tax benefit account. At step 1640, the server determines based on the lifetime non-healthcare expenses of the participant, a second amount of funds to allocate per time period to the non-healthcare tax benefit account. At step 1645, the server provides, for presentation via an interactive user interface, the first amount of funds to allocate to the healthcare tax benefit account and the second amount of funds to allocate to the non-healthcare tax benefit account, the interactive user interface including a control object configured to i) receive an input to adjust the first amount, and ii) responsive to receiving the input to adjust the first amount, updating a total amount of funds projected to be allocated to the healthcare tax benefit account.

Still referring to FIG. 16, and in further detail, at step 1605, a server of a predictive resource allocating system receives financial data indicating a financial snapshot of a participant of a client device and health data of the participant to predict lifetime healthcare expenses of the participant. The server can include one or more processors. The server can include a communications interface for receiving the data. One or more data packets carrying data indicating the request can be received. In some aspects, step 1605 comprises an innovative, non-conventional or non-routine way to operate or perform the functionality of the present solution. In some aspects, step 1605 is implemented to address the technical problems and challenges of prior systems not deploying the present solution. In some aspects, step 1605 is implemented to make or cause more effective and efficient use of computing and networking resources.

The data can be received via a computer network using a networking protocol. The data can be generated by a client device of a participant. The data packets can include header information and payload information. The header information can include, e.g., TCP header information that can facilitate the routing and transmission of the data packet. The payload information can include data related to, describing, defining, associated with or otherwise about the financial and health data. The one or more data packets can include data identifying the client device or participant sending the data. The client device can generate or obtain information that allows the server to conduct the resource allocation, encapsulate or process the information using a protocol to generate data packets, and transmit the data packets in a secure manner over a network to the server for further processing. The server can initiate a resource allocation process responsive to receiving the one or more data packets.

At step 1610, the server generates a multi-dimensional feature vector of the participant based on the received financial data and the health data of the participant. In some aspects, step 1610 comprises an innovative, non-conventional or non-routine way to operate or perform the functionality of the present solution. In some aspects, step 1610 is implemented to address the technical problems and challenges of prior systems not deploying the present solution. In some aspects, step 1610 is implemented to make or cause more effective and efficient use of computing and networking resources.

The server can parse the received data and organize the data in the multi-dimensional vector. The server can perform the generating of the vector responsive to receiving the health and financial data. In some embodiments, the server parses the one or more data packets to identify the participant profile, and performs a lookup in an administrator profile database maintained by the server using the identifier to retrieve the participant's information. The server may generate the multi-dimensional feature vector comprising a first feature indicating demographic information, a second feature indicating a healthcare spend amount, a third feature indicating a health savings account contribution amount, and a fourth feature indicating a health preference.

At step 1615, the server identifies a healthcare expense prediction model to predict the future healthcare expenses of the participant, the healthcare expense prediction model generated by the server using financial data and health data of a plurality of participants. In some aspects, step 1615 comprises an innovative, non-conventional or non-routine way to operate or perform the functionality of the present solution. In some aspects, step 1615 is implemented to address the technical problems and challenges of prior systems not deploying the present solution. In some aspects, step 1615 is implemented to make or cause more effective and efficient use of computing and networking resources.

The server can access the database to access or identify a relevant predictive model. The server can perform the identifying responsive to the generating of the multi-dimensional vector. The server can perform a similarity analysis between the received financial and health data and each of the stored healthcare expense prediction model, and identify the model that is the most similar to the received financial and health data. The healthcare expense prediction models may be refined and updated as more data of various participants across various administrators is received by the server. The server may include a machine learning engine executed by the server configured to train the healthcare expense prediction model with the financial data and the health data of the plurality of participants. The serve can input the multi-dimensional feature vector into the healthcare expense prediction model to output the predicted lifetime healthcare expenses of the participant, the predicted lifetime healthcare expenses of the participant based on data associated with similar participants used to generate the healthcare expense prediction model.

At step 1620, the server determines from the identified healthcare expense prediction model using the multi-dimensional feature vector of the participant, the predicted lifetime healthcare expenses of the participant. The server can perform the determining responsive to the identifying of the healthcare expense prediction model. The healthcare expenses may include doctor visits, medicine, surgeries, or the like. In some aspects, step 1620 comprises an innovative, non-conventional or non-routine way to operate or perform the functionality of the present solution. In some aspects, step 1620 is implemented to address the technical problems and challenges of prior systems not deploying the present solution. In some aspects, step 1620 is implemented to make or cause more effective and efficient use of computing and networking resources.

At step 1625, the server identifies lifetime non-healthcare expenses of the participant. The identifying may be performed responsive to the determining the predicted lifetime healthcare expenses. The non-healthcare expenses may include day-to-day expense, such as, groceries, bills, insurance, or the like. In some aspects, step 1625 comprises an innovative, non-conventional or non-routine way to operate or perform the functionality of the present solution. In some aspects, step 1625 is implemented to address the technical problems and challenges of prior systems not deploying the present solution. In some aspects, step 1625 is implemented to make or cause more effective and efficient use of computing and networking resources.

At step 1630, the server performs a lookup in a database to identify a healthcare tax benefit account of the participant to provide funds towards the predicted lifetime healthcare expenses of the participant and a non-healthcare tax benefit account of the participant to provide funds towards lifetime non-healthcare expenses of the participant. The performing may be performed responsive to the identifying of the non-healthcare expenses. The benefit accounts may be those that the participant is enrolled in. The participant's account information may be accessed from the database of the server or may be accessed remotely, for example, at an administrator of the participant's accounts. In some aspects, step 1630 comprises an innovative, non-conventional or non-routine way to operate or perform the functionality of the present solution. In some aspects, step 1630 is implemented to address the technical problems and challenges of prior systems not deploying the present solution. In some aspects, step 1630 is implemented to make or cause more effective and efficient use of computing and networking resources.

At step 1635, the server determines based on the predicted lifetime healthcare expenses of the participant, a first amount of funds to allocate per time period to the healthcare tax benefit account. In some aspects, step 1635 comprises an innovative, non-conventional or non-routine way to operate or perform the functionality of the present solution. In some aspects, step 1635 is implemented to address the technical problems and challenges of prior systems not deploying the present solution. In some aspects, step 1635 is implemented to make or cause more effective and efficient use of computing and networking resources. The first amount may be an amount the participant should contribute to the participant's healthcare account on a yearly basis to cover the predicted healthcare expenses of the participant. The healthcare tax benefit account may be an HSA account. The server can determine the first amount of funds to allocate per time period to the healthcare tax benefit account using a first feature indicating demographic information, a second feature indicating a healthcare spend amount, a third feature indicating a health savings account contribution amount, and a fourth feature indicating a health preference.

At step 1640, the server determines based on the lifetime non-healthcare expenses of the participant, a second amount of funds to allocate per time period to the non-healthcare tax benefit account. The second amount may be an amount the participant should contribute to the participant's non-healthcare account on a yearly basis to cover the predicted non-healthcare expenses of the participant. The non-healthcare tax benefit account may be a 401k account. In some aspects, step 1640 comprises an innovative, non-conventional or non-routine way to operate or perform the functionality of the present solution. In some aspects, step 1640 is implemented to address the technical problems and challenges of prior systems not deploying the present solution. In some aspects, step 1640 is implemented to make or cause more effective and efficient use of computing and networking resources.

The server can determine the second amount of funds to allocate per time period to the non-healthcare tax benefit account using a first feature indicating demographic information, a second feature indicating a non-healthcare spend amount, and a third feature indicating a non-health retirement account contribution amount. The server can determine a first allocation priority associated with the healthcare tax benefit account, and determine a second allocation priority associated with the non-healthcare tax benefit account, the second allocation priority less than the first allocation priority. The server can determine the first amount of funds to allocate to the healthcare tax benefit account based on the first allocation priority, the second allocation priority, and the healthcare expense prediction model.

At step 1645, the server provides, for presentation via an interactive user interface, the first amount of funds to allocate to the healthcare tax benefit account and the second amount of funds to allocate to the non-healthcare tax benefit account, the interactive user interface including a control object configured to i) receive an input to adjust the first amount, and ii) responsive to receiving the input to adjust the first amount, updating a total amount of funds projected to be allocated to the healthcare tax benefit account. In some aspects, step 1645 comprises an innovative, non-conventional or non-routine way to operate or perform the functionality of the present solution. In some aspects, step 1645 is implemented to address the technical problems and challenges of prior systems not deploying the present solution. In some aspects, step 1645 is implemented to make or cause more effective and efficient use of computing and networking resources.

The server can send the data to be presented via the communications interface of the server. The data sent by the communications interface may be received at the client device of the participant. The interactive user interface displayed to the participant may be adjusted using control features embedded in the UI to adjust input values and to adjust the results based on the adjusted values. The result values may be adjusted in real time in response to the adjusted input values. The server may generate the interactive user interface with an electronic survey comprising one or more input elements, the interactive user interface configured to receive the financial data and the health data. The server may generate the interactive user interface with a countdown timer set to a predetermined time interval. The server may initiate the countdown timer responsive to enabling the interactive user interface to receive the financial data and the health data. The server may disable input via the interactive user interface responsive to expiration of the countdown timer.

In some aspects, the methods of the present solutions implements a combination of steps in an innovative, non-conventional and/or non-routine manner. In some aspects, the method 1600 of the present solution combines the steps of FIG. 16 in an innovative, non-conventional and/or non-routine combination to implement the improved functionality, performance and operation of the present solution. In some aspects, the method of the present solution combines the steps of FIG. 16 in in an innovative, non-conventional and/or non-routine manner to more efficiently and effectively use computing and networking resources. In some aspects, the method of the present solution provides innovative, non-conventional and/or non-routine ordered combination of steps.

G. Reducing Resource Consumption

The systems and methods of the present solution are directed to the technical problems and challenges of implementing the functionality of reducing resource consumption via information technology in an electronic transaction based technology and platform. Existing electronic transaction based technologies and platforms do not effectively and efficiently make use of the computing and network resources deployed for electronic transaction based technologies and platforms to include such functionality. Without implementing such functionality, existing electronic transaction based technologies and platforms have the problems of excessive server-client requests and responses, processing delays, increase bandwidth usage, or increased or inefficient resource consumption.

The systems and methods of the present solution are directed to the improvement of the performance and operation of the electronic transaction based technology and platform and computing and networking resource used by such electronic transaction based technology and platform. In some aspects, the present solution improves and enhances the implemented functionality of the electronic transaction based technology and platform implemented on, integrated with and inherently tied to the processor, memory, network and computing resources of one or more computing devices. In some aspects, the present solution more effectively performs the functionality of the electronic transaction based technology and platform thereby making and causing more effective use of the computing and networking resources to achieve the improved functionality of the present solution. The same computing and network resources used by such electronic transaction based technology and platform will provide increased and improved functionality with implementation of the present solution.

In some aspects, the present solution more efficiently uses the computing and networking resources to implement the improved functionality of the electronic transaction based technology and platform. For example, systems and methods of the present solution are directed to reducing resource consumption via information technology infrastructure. The present solution can determine resource consumption trends and configure an engine to generate a notification based on an event correlation coefficient.

Administrators, such as companies or health insurance providers, can establish electronic benefits accounts such as flexible spending accounts or healthcare tax benefit accounts (e.g., health savings accounts) for participants such as employees, subscribers, or customers. These electronic benefits accounts can provide a tax advantage for the participants. Administrators that establish or provide electronic tax benefits accounts for various participants of those accounts can utilize backend information technology infrastructure to process, analyze, monitor or manage the electronic tax benefits accounts. The tax benefit management information technology infrastructure can be configured with processing rules that are applied to electronic transactions. Electronic transactions can include allocating funds to the tax benefit account, withdrawing funds from the tax benefit account, making a purchase with funds from the tax benefit account, modifying a profile of the tax benefit account, or submitting a claim. The management information technology infrastructure can apply one or more rules to each type of transaction to determine an event. As the types of transactions and rules increase in number and complexity, the types and events can also increase in number and complexity, thereby consuming an increasing amount of resources of the information technology infrastructure. For example, events such as a card denial increases the number of transaction attempts, communications with the server, account resets, profile corruption, or resources consumed by a point-of-sale device initiating the transaction.

Systems and methods of the present solution can reduce resource consumption of tax benefit information technology infrastructure. For example, a system of the present solution can reduce resource consumption by determining a resource consumption trend. The resource consumption trend can refer to a trend of events such as card denials. The system can then select a recommendation based on the event trend. The system can select the recommendation from a plurality of recommendations by determine or computing an event correlation coefficient between the trend and the recommendation. The event correlation coefficient can refer to a level of correlation between the event or event trend and the recommendation. For example, card transactions may be denied because the cards were being used to make non-qualifying purchases. A highly correlated recommendation may be to provide participants with information on the types of qualifying and non-qualifying purchases so they can avoid attempting to conduct a transaction for a non-qualifying item using funds allocated in an electronic tax benefit account.

Upon identifying a recommendation based on the event correlation coefficient, the system can generate a notification. To generate the notification, the system can select a notification template corresponding to the identified recommendation. The system can configure a notification engine with the notification template, and the notification engine can generate a notification. In some cases, the notification engine can automatically generate campaigns based on the trends. The system can provide proactive, client customized communications via email and text messages to participants based on events processed by the system, such as claim paid, card denied, password changed, or deposit received. The system provides a trend based proactive communication plan using data with the administrator, employer or participant data sets. Marketing campaigns can be automatically triggered based on the need identified in the trended data to communicate through various media to educate, promote or advance programs to reduce costs, increase revenue, and/or drive consumer, employer and administrator satisfaction. By automatically identifying transaction event trends and generating notifications based on the trends, the present solution can reduce resource consumption by causing an increase in resource efficient electronic transactions and a decrease in resource intensive electronic transactions. By shifting the types of transactions from resource intensive to resource light, the present solution can improve the functioning of both the tax benefit information technology infrastructure as well as the functioning of associated point of sale devices and computing devices by reducing the number of processing errors or transaction attempts.

For example, the system can identify an increase in card denials. The system can identify additional features associated with the card denial and select a trend model that matches the event. The trend model can be further associated with recommendations or transaction modifications that are configured to reduce the type of event. For example, to reduce an increase in card denials, the system can generate a notification that includes processing instructions for the card (e.g., a type of electronic configuration to use for electronic transactions with the card). In another example, the system can generate a notification based on a denial code associated with the event.

Figure 17:
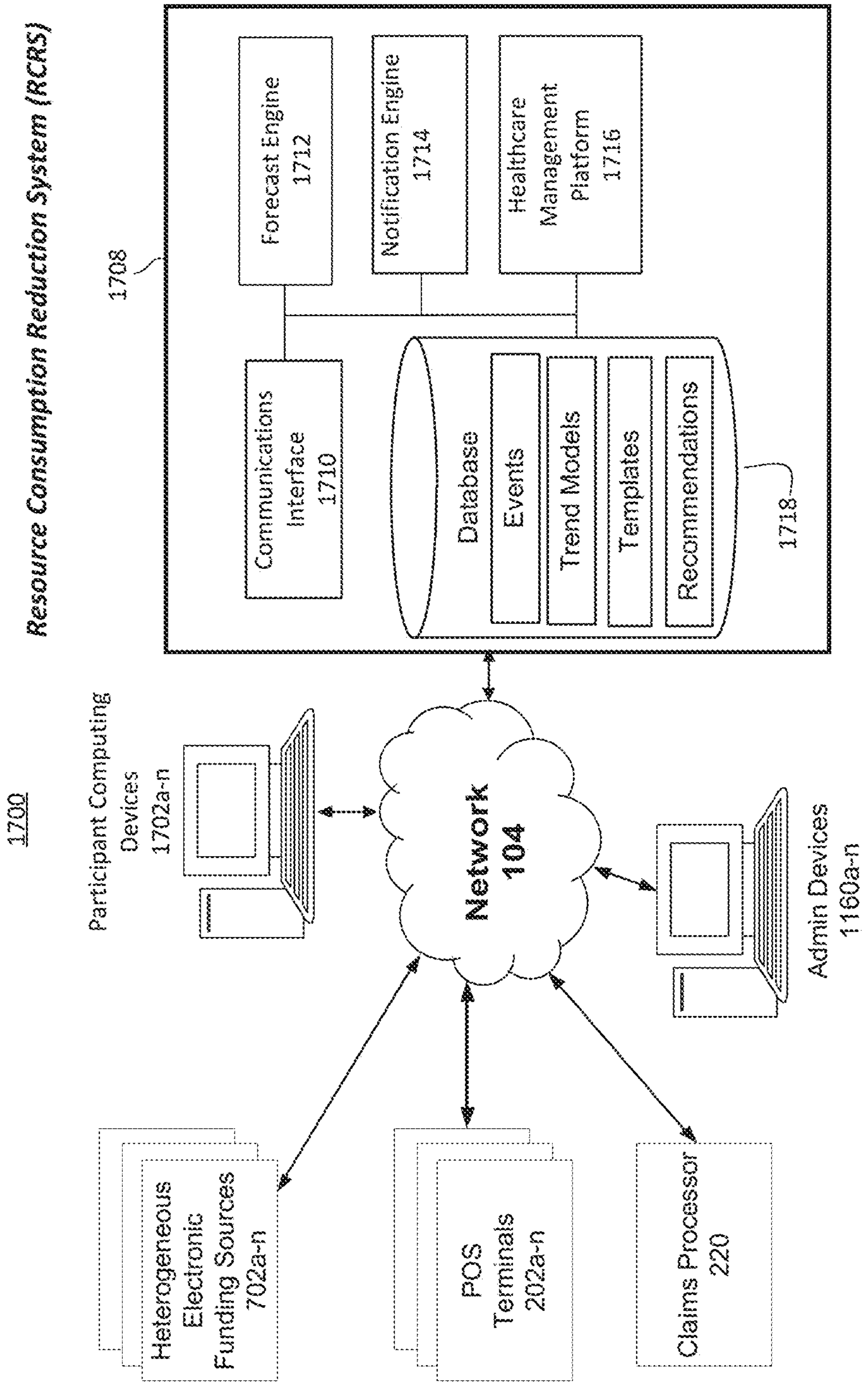
FIG. 17 is a block diagram depicting an embodiment of a system to reduce resource consumption via information technology infrastructure.

Referring now to FIG. 17, a block diagram depicting an embodiment of a system 1700 that includes a resource consumption reduction system is shown. In brief overview, and in some embodiments, the system 1700 includes a resource consumption reduction system ("RCRS") 1708. The RCRS 1708 can include one or more servers 106*a-n*. In some embodiments, the RCRS 1708 can include the MPTS 120 depicted in FIG. 2, the MPTS 408 depicted in FIG. 4, the TEPS 708 depicted in FIG. 7, the AMRGS 1108 depicted in FIG. 11, the PRAS 1408 depicted in FIG. 14, or one or more components or modules depicted in FIG. 2, 4, 7, 11, or 14, and can perform the functions of the MPTS 120, MPTS 408, TEPS 708, the AMRGS 1108, or the PRAS 1408. The RCRS 1708 can receive or transmit data via a network 104 with computing devices participant computing device 1702*a-n*, administrator devices 1160*a-n*, heterogeneous funding sources 702*a-n*, POS terminals 202*a-n*, or a claims processor 220. The participant computing devices 1702*a-n* can include one or more component or functionality of client computing devices 102*a-n*.

In some embodiments, the RCRS 1708 includes a communications interface 1710 designed and constructed to receive and transmit data packets for tax benefit electronic transactions. The RCRS 1708 can include a forecast engine 1712 designed and constructed to use the received data packets to identify a corresponding transaction trend model. The RCRS 1708 can include a notification engine 1714 designed and constructed to select a resource consumption reduction recommendation corresponding to the identified transaction trend model, generate a notification for the recommendation, and provide the notification to the communications interface 1710 for transmission to a participant computing device 1702*a*. The RCRS 1708 can include a database 1718 stored in storage device or memory accessible to the RCRS 1708. The database 1708 can include, store, or maintain event information, trend models, templates, or recommendations. The database 1708 can communicate or interface with one or more of the communications interface 1710, forecast engine 1712, notification engine 1714 and healthcare management platform 1716.

Still referring to FIG. 17, and in further detail, the communications interface 1710 can include the communications interface 210 depicted in FIG. 2, the communications interface 410 depicted in FIG. 4, the communications interface 710 depicted in FIG. 7, the communications interface 1110 depicted in FIG. 11, or the communications interface 1410 depicted in FIG. 14, or one or more components or modules depicted in FIG. 2, 4, 7, 11, or 14 and can perform the functions of the communications interfaces 210, 410, 710, 1110, or 1410. The communications interface 1710 is configured with one or more communications ports, application programming interfaces, network protocols (e.g., TCP/IP), authentication protocols, or security protocols (e.g., SSL). The communications interface 1710 can receive data associated with tax benefit electronic transactions for one or more participant devices 1702*a-n*. In some aspects, the communications interface 1710 is implemented to address the technical problems and challenges of prior systems not deploying the present solution. In some aspects, the communications interface 1710 is implemented to make or cause more effective and efficient use of computing and networking resources. For example, the communications interface 1710 can cause more effective and efficient use of computing and network resources by reducing the number of processing cycles, memory or network bandwidth used to determine resource allocations to reduce resource consumption. The communications interface 1710 can provide a reduction in resource consumption by integrating with a forecast engine 1712, notification engine 1714, healthcare management platform 1716, database 1718, participant computing devices 1702*a-n*, admin devices 1160*a-n*, claims processor 220, POS terminals 202*a-n*, or heterogeneous electronic funding sources 702*a-n* to allocate resources or reduce resource consumption.

The communications interface 1710 can receive one or more data packets including data indicating a healthcare transaction event corresponding to a participant of a plurality of participants of a healthcare management platform. The communications interface 1710 can receive the data packets via network 104 from one or more devices. In some cases, the communications interface 1710 receives data packets indicative of an electronic transaction, and then the RCRS 1708 processes the data packets to determine, generate or identify the healthcare transaction event. In some cases, the communications interface 1710 receives the data packets from a healthcare management platform or one or more system or depicted or described in FIGS. 1-16.

In some embodiments, the RCRS 1708 can receive data packets from a device of an administrator remote from the server and use these data packets to generate or train a trend model. The data packets used to train the trend model can be referred to as previously received data packets because they may be received prior to the current transaction event that triggers the generation of a notification. For example, the RCRS 1708 can cause an administrator interface (e.g., an interface including a graphical user interface including text input, fields, drop down menus, a batch upload mechanism, or a file browser) to be rendered on the device of the administrator. The administrator can input a file or data indicative of the transaction via the administrator interface, and the administrator interface can convert the file or data into data packets suitable for transmission over network 104 to communications interface 1710. Conversion of the data into a suitable for transmission form can include converting the data into network packets such as TCP/IP packets or encapsulating the packets using a security protocol or encryption protocol.

For example, the communications interface 1710 can receive data packets that indicate a claim payment, a card denial, a password change, or a received deposit. The data packets can include network data packets such as TCP/IP data packets. The data packets can be encrypted with a data encryption technique. The data packets can be sent via a secure communication channel established with another server or computing device. The data packets can include a header and payload data.

A claim payment can refer to a payment by an insurance provider based on terms of an insurance policy. For example, the claims processor 220 can process a request for a claim payment and then generate an event indicating a claim payment to an electronic account of the participant. The claims processor 220 can transmit the indication to the RCRS 1708.

A card denial can refer to a denial to withdraw or use funds from an electronic tax benefit account. The term card can also include other types of transaction mechanisms, including, e.g., wireless mobile device-based payment mechanisms such as NFC or Bluetooth enabled payment techniques, or inputting an identifier of the electronic tax benefit account into an interface. The denial can refer to a denial to allocate funds towards the transaction. The denial can be associated with a denial code that indicates a reason for the denial. The denial code can indicate, for example, a lack of sufficient funds in the account, incorrect processing parameter or configuration (e.g., transaction cannot be processed as a debit transaction or a credit transaction; incorrect pin number), the transaction includes non-qualifying items, the transaction is occurring at a non-qualifying merchant, or the card has expired.

A received deposit can refer to allocating funds to an electronic tax benefit account of the participant. For example, funds can be allocated to the electronic tax benefit account from one or more heterogeneous electronic funding sources 702*a-n* using one or more allocation techniques, such as direct deposit, pay roll, wire transfer, or ACH. The RCRS 1708 can process the deposit or the RCRS 1708 can receive an indication of the deposit.

The RCRS 1708 can include a forecast engine 1712 designed and constructed to select a healthcare trend model used to identify healthcare related recommendations to provide to participants of the healthcare management platform. In some aspects, the forecast engine 1712 is implemented to address the technical problems and challenges of prior systems not deploying the present solution. In some aspects, the forecast engine 1712 is implemented to make or cause more effective and efficient use of computing and networking resources. For example, the forecast engine 1712 can cause more effective and efficient use of computing and network resources by reducing the number of processing cycles, memory or network bandwidth used to determine resource allocations to reduce resource consumption. The forecast engine 1712 can provide a reduction in resource consumption by integrating with the communications interface 1710, notification engine 1714, healthcare management platform 1716, database 1718, participant computing devices 1702*a-n*, admin devices 1160*a-n*, claims processor 220, POS terminals 202*a-n*, or heterogeneous electronic funding sources 702*a-n* to allocate resources or reduce resource consumption.

In some embodiments, the forecast engine 1712 can include one or more component or functionality of forecast engine 1412. In some embodiments, the forecast engine 1712 can train one or more healthcare trend models using previously received data packets that indicate healthcare transaction events corresponding to participants of the healthcare management platform. To train the healthcare trend model, the forecast engine 1712 can obtain electronic tax benefit account transaction information, and electronic tax benefit account transaction event information associated with profiles or participants. The forecast engine 1712 can maintain historical transaction and event data and monitor transactions occurring in real-time or data received from one or more component of the system 1700 in real-time. The forecast engine 1712 can be configured with one or more trend detection techniques to identify an increase or spike in a type of event, or to identify a decrease or lull in a type of an event. The forecast engine 1712 can identify or determine additional characteristics associated with the increase or decrease in types of events, such as the rate of increase or decrease, features associated with the events (e.g., geographic area associated with the increase or decrease, type of transaction, transaction method, type of merchant, time of day, or portion of month or year).

In some embodiments, the forecast engine 1712 can be configured with a trend detection technique that uses historical transaction and event data to generate a baseline model. The baseline model can indicate a baseline threshold, for example, a number of card denials for a type of transaction during a time interval. The forecast engine 1712 can monitor transactions occurring in real-time, or transaction data received via communications interface 1710. The forecast engine 1712 can generate a metric for the transactions and compare the metric with the baseline threshold of the trend model. If the metric meets or exceeds the baseline threshold, the RCRS 1708 can determine that there is an increase or spike in the type of event. If the metric falls below the baseline threshold, the RCRS 1708 can determine that there is decrease or lull in the type of event.

In some embodiments, the forecast engine 1712 can categorize healthcare transaction events into a first category selected from a plurality of categories. For example, the categories of health care transaction events can include denial, claim payment, deposit, password change, stolen card number, disputed transaction, or insufficient funds. The forecast engine 1712 may generate a separate healthcare trend model for each category, where each healthcare trend model includes a baseline model or baseline threshold. In some cases, each healthcare trend model can further includes sub-models for sub-categories for features such as geographic area, temporal values (e.g., time of day, time of year), or demographic indicators. For a given transaction, the forecast engine can determine one or more features, and then select a healthcare trend model matching the determined features. If the RCRS 1708 identify only one feature, such as event type, then the RCRS 1708 can select the broadest healthcare trend model matching the identified feature. If the RCRS 1708 can identify multiple features associated with the event, such as type of event, geographic area, and time of year (e.g., $4^{th}$ quarter), then the RCRS 1708 can select a healthcare trend model that matches this combination of features. For example, if the event is a denial that occurred in Boston, Massachusetts during the fourth quarter of the year, the forecast engine 1708 can select a healthcare trend model that includes a baseline model for historical denials that occurred in Boston, Massachusetts during a fourth quarter.

In some embodiments, the RCRS 1708 can generate vectors in a multidimensional graph for features associated with an event and trends to select the trend having a minimum vector distance to the event. For example, the RCRS 1708 can generate a first vector based on the healthcare transaction event and one or more healthcare transaction events of the participants. The vector can include features of the event and historical events such as geographic area, type of event, or time of day. The RCRS 1708 can identify a second vector for each of a plurality of healthcare transaction trend models. The second vectors can each be based on feature values corresponding to the healthcare transaction trend models. The RCRS 1708 can determine distance between the first vector and each of the second vectors. The distance can refer to a vector or a magnitude of the distance. For example, the RCRS 1708 can determine a distance vector between an endpoint of the first vector and an end point of the second vector, and then determine the distance as a magnitude of the distance vector. The RCRS 1708 can identify a minimum distance vector from the determined distance vector for each of the plurality of healthcare transaction events, and select the healthcare trend model corresponding to the minimum distance vector.

In some embodiments, the forecast engine 1712 can be configured with one or more of a smoothing filter, a significant change detection algorithm, a threshold selector or a dynamic threshold. The smoothing filter can be configured to smooth a data set to create an approximating function that indicates patterns in the data, while leaving out noise or other fine-scale structures. For example, the forecast engine 1712 can use a smoothing filter such as a moving average to determine a baseline curve that fits a data set including a type of event over a time interval. The moving average can capture trends in the event data by creating a series of averages of different subsets of the full data set. The forecast engine 1712 can determine an event trend above a threshold and, responsive to determining the event trend above the threshold, trigger the notification engine 1714 to initiate.

In some embodiments, the forecast engine 1712 can determine whether a recommendation is correlated with a reduction in a number of events or a desired event trend. The forecast engine 1712 can correlate a reduction in events with one or more features of transactions to determine which features resulted in the reduction. The forecast engine 1712 can correlate a reduction in events with one or more recommendations or notification that were previously transmitted to participants to determine whether features associated with the recommendation or notification are correlated with the desired event trend.

For example, the forecast engine 1712 can receive data indicating that a type of notification was sent to participants. The forecast engine 1712 can monitor event trends before and after the notification was transmitted to participants to identify a change in the trend. If the forecast engine 1712 determines that the notification resulted in a reduction of resource consumption of the RCRS 1708 (e.g., fewer computing resources were used to process denials), then the forecast engine 1712 can link the notification with the reduction of the event. If the forecast engine 1712 at a later time identifies an increase in the type of event, the RCRS 1708 can automatically determine the type of event and corresponding features, identify the type of recommendation correlated with a reduction of the event, and transmit the notification. Types of recommendations can include informational, warning, alert, advertisement, descriptive, customized, or general.

The forecast engine 1712 can use a machine learning engine or technique to correlate notifications including recommendations with a change in an event trend. For example, the forecast engine 1712 can be configured with one or more techniques of the machine learning engine 1416. The forecast engine 1712 can generate a feature indicative of the notification and use the trend data as signals that are dependent on the features. The forecast engine 1712 can be configured with a regression analysis technique that uses a statistical process to estimate the relationship between a feature (e.g., type of recommendation; time of day notification was sent out; geographic area notification was sent; communication medium of notification such as text, email, print, direct mail, television or radio advertisement) and an event trend signal (e.g., increase or decrease in number of events, increase or decrease in number of events in one or more geographic areas or across a demographic). The feature (e.g., type of recommendation) can be a predictor or independent variable, and the signal (e.g., event trend) can be a dependent variable or a criterion variable that can change as the features are varied. In some cases, the forecast engine 1712 can estimate, determine or predict a conditional expectation of the dependent variable given the independent variables (e.g., an average value of the dependent variable when the independent variables are fixed; or other parameter or metric of the conditional distribution of the dependent variable or signal given the independent variable or feature). The predicted signal (e.g., event trend) can be a function of the independent variables and can be referred to as a regression function. The forecast engine 1712 can further identify, determine or characterize a variation of the dependent variable around the regression function which can be described by a probability distribution. The forecast engine 1712 can use the probability distribution to generate a correlation coefficient or confidence score in the predicted signal value, or use the probability distribution as the correlation coefficient or confidence score. For a given feature or feature combination, the forecast engine 1712 can identify the event trend corresponding to the highest confidence score to the recommendation, and select this recommendation to generate and transmit a new notification.

The RCRS 1708 can include a notification engine 1714 designed and constructed to identify a notification template based on an event or event trend, and transmit the notification to one or more participants. In some aspects, the notification engine 1714 is implemented to make or cause more effective and efficient use of computing and networking resources. For example, the notification engine 1714 can cause more effective and efficient use of computing and network resources by reducing the number of processing cycles, memory or network bandwidth used to determine resource allocations to reduce resource consumption. The notification engine 1714 can provide a reduction in resource consumption by integrating with the communications interface 1710, forecast engine 1712, healthcare management platform 1716, database 1718, participant computing devices 1702*a-n*, admin devices 1160*a-n*, claims processor 220, POS terminals 202*a-n*, or heterogeneous electronic funding sources 702*a-n* to allocate resources or reduce resource consumption.

The notification template can include or identify text, fields, images, multimedia, data format, or a communication medium. In some cases, the notification template includes predetermined text in a predetermined format. The notification template can include fields that can be customized to a type of event, time of day, geographic area, or other feature associated with an event or participant. The notification engine 1714 can determine, identify or select a notification template using one or more techniques. For example, the notification engine 1714 can select the notification template from a predetermined recommendation data structure that assigns recommendations to event trends. In another example, the notification engine 1714 can select a random notification template. In yet another example, the notification engine 1714 can determine a notification template for a recommendation that satisfies a correlation coefficient with a corresponding trend model.

The notification engine 1714 can perform a lookup in the recommendation data structure stored in database 1718 using an identifier of the selected healthcare trend model to identify a healthcare related recommendation. In some cases, the notification engine 1714 can identify multiple healthcare related recommendations linked with the selected healthcare trend model. The RCRS 1708 can determine a correlation coefficient between each of the plurality of healthcare related recommendations and the selected healthcare trend model. The RCRS 1708 can rank the healthcare related recommendations based on the correlation coefficient. For example, a recommendation with a high correlation coefficient can be ranked higher than a low correlation coefficient because a high correlation coefficient can indicate a high level of correlation. Correlation coefficient can be a numeric value in the range of 0 to 1, 1 to 10, 1 to 100, a percentage or any other indicator of a level of correlation. The RCRS 1708 can select a highest ranking healthcare related recommendation of the plurality of healthcare related recommendations.

The RCRS 1708 can determine the correlation coefficient between recommendations, notification templates, and event trends. For example, a first type of recommendation can be highly correlated with a reduction in event trend if the first type of recommendation resulted in a reduction in the number of events below a threshold amount during a predetermined time interval (e.g., 5% reduction within 2 weeks). A higher reduction percentage and shorter time interval can indicate a higher correlation coefficient. If a recommendation does not affect the event trend, then it may correspond to a low correlation coefficient.

Similar to recommendations, notification templates can be correlated with event trends. For example, the same recommendation can be made using one or more notification templates. A notification template can refer to a communication medium for the notification, font, text size, image, format, color, multimedia, time of day notification, or day of week of notification. The RCRS 1708 can cycle through various notification templates or recommendations to identify notification templates or recommendations that are highly correlated with a desired event trend. The RCRS 1708 can use a machine learning technique to determine the notification template or recommendation that is highly correlated with an event trend or change in event trend.

In some cases, the notification engine 1714 can select a notification template from a predetermined recommendation data structure stored in database 1718. For example, the RCRS 1708 can receive a configuration file from a user that maps event trends to notification templates or recommendations. When the RCRS 1708 identifies an event trend, the RCRS 1708 can select the corresponding notification template and recommendation, generate the notification, and transmit the notification.

In some embodiments, the notification engine 1714 can select a default notification template that is not correlated or tied to the event trend. For example, the RCRS 1708 can determine that a particular event is not correlated to a recommendation or notification template. For example, there may be an absence of a notification template for an event trend. The RCRS 1708 can then select a default notification template for the event trend and update the recommendation data structure in database 1718 to include the selected default notification template. The RCRS 1708 can monitor the event trend responsive to transmitting the default notification to determine whether the notification causes a reduction in resource consumption. In the event the selected default notification did not cause an improvement in the event trend or reduction in resource consumption, the RCRS 1708 can select a different notification template. The RCRS 1708 can continue to cycle through different notification templates or recommendations until the RCRS 1708 identifies a notification template and recommendation that causes a reduction in resource consumption or event trend that satisfies a threshold.

Upon identifying a recommendation, the RCRS 1708 can retrieve a notification template from a notification template data structure that maps to the healthcare related recommendation. The RCRS 1708 can use the notification template to generate a notification corresponding to the highest ranking healthcare related recommendation. For example, the RCRS 1708 can populate one or more fields in the notification template with recommendation information. The RCRS 1708 can populate one or more fields in the notification template with data customized for a participant. The notification engine 1714 can generate a request to deliver the notification corresponding to the highest ranking healthcare related recommendation at a destination address of a computing device 1702*a* of the participant. The RCRS 1708 can transmit the notification to the computing device 1702*a* via a communication channel established between the server and the computing device. For example, the communication interface 1710 can establish a communication channel between the computing device and the server using a TCP/IP protocol. In some cases, establishing a communication channel can include transmitting a text message such as a SMS message over a network provided by a cellular service provider and network 104. In some cases, establishing a communication channel can include transmitting an electronic mail message via an email service provider and data network 104.

In one example, the healthcare transaction event can include a denial of a transaction. A denial of the transaction can refer to a participant swiping card linked to the participant's electronic tax benefit account at a POS terminal 202*a*. The RCRS 1708 can receive data packets from the POS terminal 202*a* indicating the denial of the transaction. In some cases, the RCRS 1708 can receive data packets indicating the transaction from the POS 202*a*, and the RCRS 1708 can determine to deny the transaction. In some cases, a healthcare management platform 1716 processes the transaction, determines to deny the transaction, and transmits the data packets indicating denial to the RCRS 1708. For example, the RCRS 1708 can include the healthcare management platform 1716. The healthcare management platform 1716 can include one or more component or functionality depicted in FIGS. 1A-16.

The RCRS 1708 can determine that there has been an increase in transaction denials above a threshold that may cause or result in an unsatisfactory increase in resource consumption of the information technology infrastructure. The RCRS 1708 can select a denial recommendation that is correlated with the denial event. The denial recommendation can be correlated with a reduction in the event rend. For example, the RCRS 1708 can determine, based on historical trend data and a machine learning technique, that the denial recommendation reduces denial events by 5% over two weeks. The denial recommendation can include instructions on how to properly process a transaction such as a recommended processing configuration. For example, a card transaction can be processed as a debit card transaction or a credit card transaction. In some cases, a POS terminal 202 at a merchant may be configured to only process credit card transactions. Thus, an attempt at a debit card transaction can result in a denial of the transaction. To reduce the spike in denial events, the RCRS 1708 can generate a recommendation that instructs participants to configure the transaction as a credit card transaction. In some cases, the recommendation may identify types of merchants that only process transactions as credit transactions.

In some cases, the RCRS 1708 can determine the denial event based on a denial reason or code, and select a denial recommendation corresponding to the denial reason or code. Denial reasons can include incorrect processing configuration (e.g., credit verses debit card), insufficient funds, non-qualifying purchase, or invalid card. If the denial reason maps to insufficient funds, and there is an increased trend of denials due to this reason, the RCRS 1708 can generate a denial recommendation that recommends a resource allocation amount. For example, the RCRS 1708 can indicate to maintain a minimum balance of funds in the tax benefit electronic account to avoid denials.

In some embodiments, the denial event trend can be a trend of partial denials of transactions. For example, a transaction can be denied because the transaction includes both qualifying and non-qualifying items. In some embodiments, a partial denial can refer to the entire transaction being denied because the transaction includes both qualifying and non-qualifying items. In some embodiments, a partial denial can refer to only the non-qualifying items being denied. The RCRS 1708 can select a denial recommendation that includes an ordered list of qualifying items and non-qualifying items responsive to determining that the denial healthcare transaction event resulted from a transaction including one or more qualifying items and one or more non-qualifying items. The RCRS 1708 can retrieve the ordered list from the recommendation data structure stored in database 1718. Qualifying items can include, e.g., prescription medications or doctor co-payments. Non-qualifying items can include chips or soda.

In some embodiments, the notification engine 1714 can identify participant computing devices to transmit the notification to using a targeting criteria. Targeting criteria can include, for example, location, type of computing device, or type of event or transaction associated with the participant computing device 1702. For example, if a set of multiple participant computing devices as associated with the event and the event trend that triggered the generation of the notification, the RCRS 1708 can automatically generate a marketing campaign to send the notification with the recommendation to the corresponding participant devices. The server can, in some embodiments, customize the notification for each participant computing device 1702*a-n* by using different notification templates based on device type (e.g., screen size or communication medium). The notification engine 1714 can automatically update the marketing campaign by monitoring event trends and triggering the generation of new notifications with new recommendations responsive to the determined event trend that falls outside threshold.

In some aspects, the system of the present solutions implements a combination of one or more of the communications interface 1710, forecast engine 1712, notification engine 1714, database 1718, or healthcare management platform 1716 in an innovative, non-conventional and/or non-routine manner. In some aspects, the system of the present solutions integrates the communications interface 1710, forecast engine 1712, notification engine 1714, database 1718, or healthcare management platform 1716 in an innovative, non-conventional and/or non-routine manner to implement the improved functionality, performance and operation of the present solution. In some aspects, the system of the present solutions integrates the communications interface 1710, forecast engine 1712, notification engine 1714, database 1718, or healthcare management platform 1716 in an innovative, non-conventional and/or non-routine manner to more efficiently and effectively use computing and networking resources. The communications interface 1710, forecast engine 1712, notification engine 1714, database 1718, or healthcare management platform 1716 are integrated in an innovative, nonconventional manner to mitigate, reduce, prevent, or resolve the technical problems of excessive resource consumption. The communications interface 1710, forecast engine 1712, notification engine 1714, database 1718, or healthcare management platform 1716 integrated in the innovative, non-conventional manner address at least these technical problems by receiving one or more data packets including data indicating a healthcare transaction event corresponding to a participant of a plurality of participants of a healthcare management platform; selecting a healthcare trend model to provide healthcare related recommendations to the plurality of participants of the healthcare management platform maintained by the server, the healthcare trend model trained by the server using previously received data packets including data indicating healthcare transaction events corresponding to the plurality of participants of the healthcare management platform; performing a lookup in a recommendation data structure using an identifier of the selected healthcare trend model to identify a plurality of healthcare related recommendations linked with the selected healthcare trend model; determining a correlation coefficient between each of the plurality of healthcare related recommendations and the selected healthcare trend model; selecting, based on a rank of each correlation coefficient, a highest ranking healthcare related recommendation of the plurality of healthcare related recommendations; retrieving, responsive to the selection of the highest ranking healthcare related recommendation, a notification template from a notification template data structure that maps to the highest ranking healthcare related recommendation; generating, using the notification template, a notification corresponding to the highest ranking healthcare related recommendation; generating a request to deliver the notification corresponding to the highest ranking healthcare related recommendation at a destination address of a computing device of the participant; and transmitting, to the computing device via a communication channel established between the server and the computing device, responsive to the request, the notification to the computing device of the participant.

Figure 18:
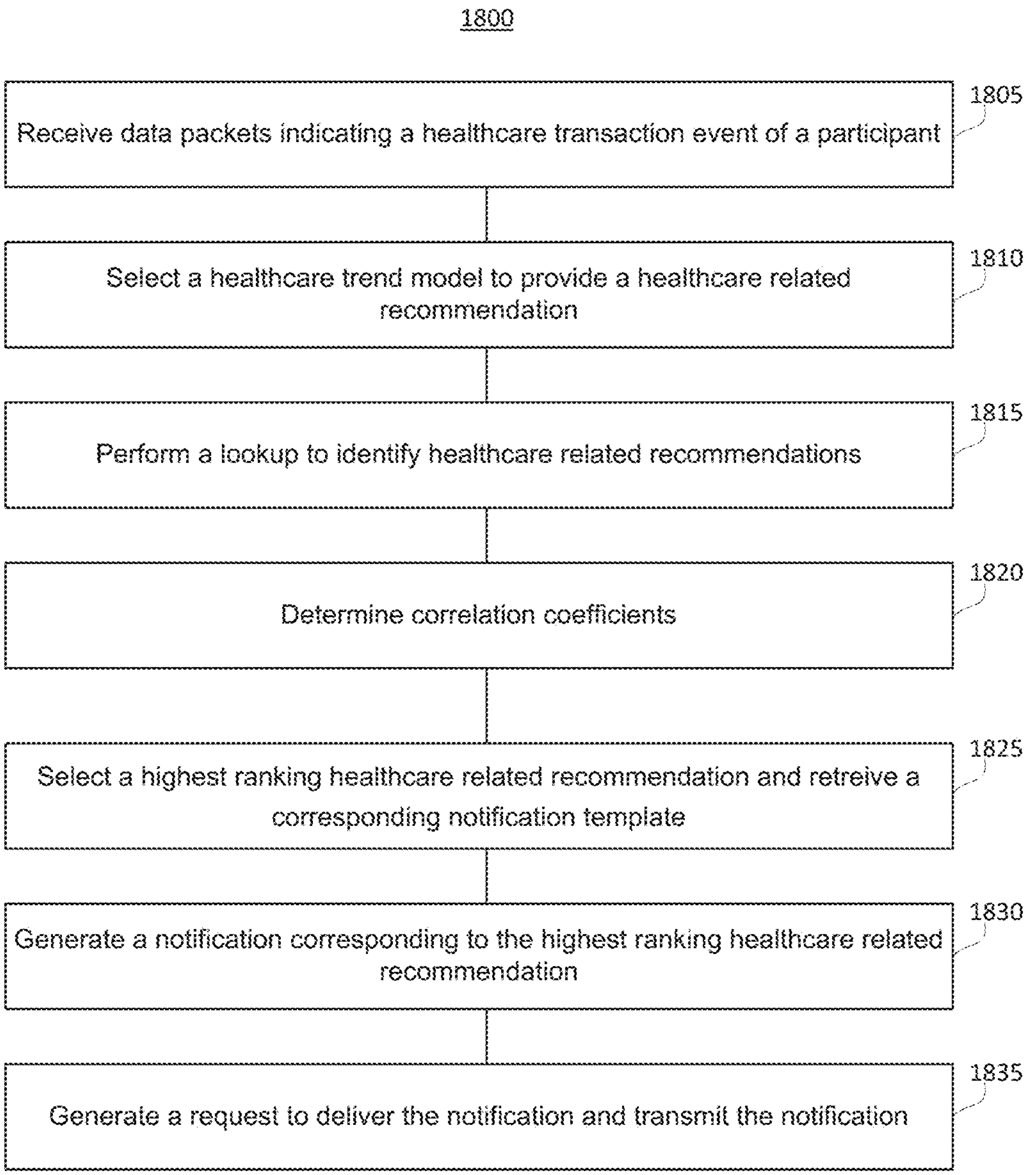
FIG. 18 is a block diagram depicting an embodiment of a method for reducing resource consumption via information technology infrastructure.

Referring now to FIG. 18, a flow diagram depicting an embodiment of a method 1800 of reducing resource consumption via information technology infrastructure is shown. The method can be performed by one or more component or module of system 1700, the RCRS 1708, or one or more component or module depicted in FIGS. 1A-1D. In brief overview, and in some embodiments, the method 1800 includes a server receiving data packets indicating a healthcare transaction event of a participant at step 1805. At step 1810, the server selects a healthcare trend model to provide a healthcare related recommendation. At 1815, the server performs a lookup to identify healthcare related recommendations. At 1820, the server determines correlation coefficients for the recommendations. At 1825, the server selects a highest ranking healthcare related recommendation and retrieves a corresponding notification template. At 1830, the server generates a notification corresponding to the highest ranking healthcare related recommendation. At 1835, the server generates a request to deliver the notification and transmit the notification.

In further detail, the server receives data packets indicating a healthcare transaction event of a participant at step 1805. In some aspects, step 1805 comprises an innovative, non-conventional or non-routine way to operate or perform the functionality of the present solution. In some aspects, step 1805 is implemented to address the technical problems and challenges of prior systems not deploying the present solution. In some aspects, step 1805 is implemented to make or cause more effective and efficient use of computing and networking resources.

The server can receive the data packets via a communications interface. The data packets can indicate a transaction event such as a denial, password change, claim deposit, or detected fraudulent card use. The server can parse the payload data of the data packets to identify the event. For example, the server can parse one or more received data packets and determine a type of event. In some cases, the data packets can include an event data structure that defines or describes the transaction event. The event data structure provided via the data packets can include one or more of an event type (e.g., denial, password change, claim payment), participant identifier (e.g., a unique identifier, an alphanumeric identifier), a tax benefit account identifier, time stamp, geographic area or location, or merchant identifier. In some cases, the communications interface 1710 can perform pre-processing on the data packets and then route or forward the pre-processed data packets to a component or module of the RCRS 1708. For example, the communications interface 1710 can de-encapsulate or decrypt the data packets and forward them to one or more of the forecast engine, notification engine, or healthcare management platform. In some cases, the communications interface 1710 can store the data of the data packets in database 1718. The communication interface 1710 may create an event data structure from the data packets and store the event data structure in the database 1718. The communication interface 1710 may provide a pointer or identifier of the stored event data structure to one or more component or module of the RCRS 1708.

At step 1810, the server selects a healthcare trend model to provide a healthcare related recommendation. The healthcare trend model can be trained by the server using previously received data packets including data indicating healthcare transaction events corresponding to the plurality of participants of the healthcare management platform. In some aspects, step 1810 comprises an innovative, non-conventional or non-routine way to operate or perform the functionality of the present solution. In some aspects, step 1810 is implemented to address the technical problems and challenges of prior systems not deploying the present solution. In some aspects, step 1810 is implemented to make or cause more effective and efficient use of computing and networking resources.

The trend model can include a baseline trend for an event. The server can update the trend model as the server receives data packets indicating tax benefit account transaction events. The server can monitor the continuously updated trend model to determine whether the trend of events is exceeding a maximum threshold (e.g., a first threshold) or falling below a minimum threshold (e.g., a second threshold). The server can poll the trend model for an update regarding the current trend relative to the first and second thresholds. The trend model can be configured to provide a binary value responsive to a polling request or query. For example, the trend model can be configured with one or more scripts, API's, or libraries. The trend model can be configured to compare a current trend value with the first and second threshold and respond to the polling request or query with an indication as to whether the current trend satisfies the desired range by falling within the first and second thresholds, or does not satisfy the desired range by fallout outside the first and second thresholds. If the current trend falls below the threshold or exceeds the threshold, the trend model may further indicate, in the response, that the current trend is below the minimum threshold, or above the maximum threshold.

The server can train the trend model by computing a moving average over a time period. The server can determine a moving average of a value associated with the trend, such as a number of denials, rate of denials, amount of denial, number of password changes, or amount of payment deposits. The trend model can include a unique identifier. The unique identifier can include an alpha numeric identifier or one or more of strings, characters, or symbols. Thus, in some cases, training the trend model can include determining a moving average to set a baseline trend. In some cases, training the trend model can further include computing or determining a dynamic first and second threshold (or dynamic maximum and minimum thresholds). The server can determine a dynamic threshold as a function of a baseline trend. For example, the threshold can be a function of a statistical value of the baseline trend, such as a standard deviation, variance, percentage, or logarithm or exponential function. For example, the threshold range can be plus or minus one or more standard deviations from the baseline trend or average.

At 1815, the server performs a lookup to identify tax benefit account related recommendations. In some aspects, step 1815 comprises an innovative, non-conventional or non-routine way to operate or perform the functionality of the present solution. In some aspects, step 1815 is implemented to address the technical problems and challenges of prior systems not deploying the present solution. In some aspects, step 1815 is implemented to make or cause more effective and efficient use of computing and networking resources. The server can perform the lookup in a recommendation data structure using an identifier of the selected trend model. The server can perform the lookup to identify one or more tax benefit account related recommendations linked with the selected trend model.

In some cases, the server may determine that there are no recommendations linked to the trend model. For example, recommendations may not have been previously transmitted for the event type of the trend model. For situations in which recommendations are not linked to the trend model in the recommendation data structure, the server can select a random one or more recommendations from a pool of available recommendations. In some cases, the server can retrieve a default recommendation. In these cases, the server can be configured to cycle through one or more recommendations to obtain data on how the recommendation might affect the event trend. If the recommendation has no or minimal impact on the event trend (e.g., decreases or increases the event trend by less than 2%, 1%, 0.5%, 0.3%, or some other deminimis amount), then the server can determine that the recommendation has a zero or low correlation coefficient with respect to affecting the event trend. By cycling through different recommendations based on a time interval and monitoring the recommendation's effect on the event trend, the server can determine a correlation coefficient between the recommendation and the event trend. The server can link the event trend to the recommendation and store the link along with the correlation coefficient in the recommendation data structure for future use.

At 1820, the server determines correlation coefficients for the one or more recommendations. The server can determine the correlation coefficient between each of the plurality of healthcare related recommendations and the selected healthcare trend model. In some cases, the correlation coefficient between a recommendation and an event trend model can be stored in a recommendation data structure. In some aspects, step 1820 comprises an innovative, non-conventional or non-routine way to operate or perform the functionality of the present solution. In some aspects, step 1820 is implemented to address the technical problems and challenges of prior systems not deploying the present solution. In some aspects, step 1820 is implemented to make or cause more effective and efficient use of computing and networking resources.

In some cases, the server can input the recommendation (or features of the recommendation) and features of the event trend into a machine learning model for the trend that is trained by the server. The output of the machine learning model can include a correlation coefficient that indicates a level of correlation between the recommendation and the event trend or an increase or decrease in the event trend. This correlation coefficient can indicate a likelihood that the recommendation can affect the event trend.

For example, providing a notification with a recommendation to change an account password (or other security recommendation) can be correlated with a decrease in fraudulent transaction reported to the RCRS. A decrease in fraudulent transactions reduces resource consumption and processing of the system.

At 1825, the server selects a highest ranking healthcare related recommendation and retrieves a corresponding notification template. In some cases, a recommendation is linked to a notification template that is predetermined to most effectively convey the recommendation. For example, the recommendation data structure can map recommendations to notification templates stored in the notification template data structure. In some cases, the server may determine an additional correlation coefficient between each of a plurality of notification templates and the selected recommendation to identify a highest ranking notification template. In some aspects, step 1825 comprises an innovative, non-conventional or non-routine way to operate or perform the functionality of the present solution. In some aspects, step 1825 is implemented to address the technical problems and challenges of prior systems not deploying the present solution. In some aspects, step 1825 is implemented to make or cause more effective and efficient use of computing and networking resources.

In some embodiments, the server can be configured to select a notification template for a recommendation using one or more criteria. For example, if recommendation includes text and an image, the server can select a notification template that includes a field for text and an image slot. The server can further select the notification template that includes sufficient space for the recommendation, such as sufficient space for a certain number of characters. In some embodiments, the recommendation can include criteria specifying a communication medium. In some embodiments, the server can determine that a type of communication medium is correlated with a desired event trend adjustment. For example, sending a list of qualifying and non-qualifying items may be more effective in improving an event trend if the list is sent via email as opposed to physical mail or text message. Thus, in some embodiments, the server can select a notification template based on criteria of a recommendation or based on the notification template being correlated with an desired trend adjustment. The server can determine the correlation coefficient between the notification template and event trend adjustment using a machine learning technique.

At 1830, the server generates a notification corresponding to the highest ranking healthcare related recommendation. For example, the server can configure a notification engine with the notification template to cause the notification engine to generate a notification corresponding to the highest ranking healthcare related recommendation. The notification engine can be configured to populate the selected notification template with the recommendation data. The notification engine can be further configured to customize the notification with participant data, temporal data, event type data, or geographic data. In some aspects, step 1830 comprises an innovative, non-conventional or non-routine way to operate or perform the functionality of the present solution. In some aspects, step 1830 is implemented to address the technical problems and challenges of prior systems not deploying the present solution. In some aspects, step 1830 is implemented to make or cause more effective and efficient use of computing and networking resources.

Configuring the notification engine to generate a notification can include providing the notification template to the notification engine. For example, the notification template can include a data file, a script, or HTML fields. In some embodiments, providing the notification template can include inputting or providing an identifier corresponding to the notification template to the notification engine. For example, the server can generate a function call where the function input includes an identifier for the notification template. The identifier can include an alphanumeric identifier. The identifier can include a path to a data file comprising the notification template.

In some embodiments, generating the notification for the recommendation using the notification template can include populating one or more fields of the notification template, calling a scripting function, or assembling one or objects identified by the template or the recommendation. For example, the recommendation can include a data file with instructions that include text or bitmap to be printed or rendered on a display. Example notifications can include a text message to one or more participants that states, for example: "Remember: only use your card for qualifying purchases such as prescription medications and do not conduct a transaction that includes both qualifying and non-qualifying items"; "Check your balance before you swipe by clicking here"; or "Merchant <X> is only configured for credit transactions, so do not use your tax benefit card in debit mode", where <X> can include a merchant name such as a local pharmacy. The server can determine the local pharmacy based on location information received from the mobile device. For example, the server can receive latitude and longitude information from the participant's mobile computing device and map this location information to merchant location information by performing a lookup in a merchant location database.

At 1835, the notification engine generates a request to deliver the notification and transmit the notification. In some aspects, step 1835 comprises an innovative, non-conventional or non-routine way to operate or perform the functionality of the present solution. In some aspects, step 1835 is implemented to address the technical problems and challenges of prior systems not deploying the present solution. In some aspects, step 1835 is implemented to make or cause more effective and efficient use of computing and networking resources.

The notification engine can generate the request to deliver the notification to a destination address of a computing device of the participant. The destination address can correspond to a phone number, email address, physical address, username, identifier of an application, or other identifier of communication medium of the participant computing device.

In some embodiments, the notification engine can store the generated or assembled notification in database. The notification engine can generate a request to deliver the notification. The request can include an identifier, pointer, or file path of the notification stored in the database. The server can, responsive to the generated request, retrieve the stored notification and transmit the notification. The request can include instructions regarding when to transmit the notification, a time interval for repeating transmission of the notification, and to which computing device to transmit the notification. The notification engine can identify participant computing devices to receive the notification using a targeting criteria such as location, type of computing device, or type of event or transaction associated with the computing device. For example, if a set of multiple participant computing devices as associated with the event and the event trend that triggered the generation of the notification, the RCRS can automatically generate a marketing campaign to send the notification with the recommendation to the corresponding participant devices. The server can, in some embodiments, customize the notification for each devices by using different notification templates based on device type (e.g., screen size or communication medium).

In some aspects, the methods of the present solutions implements a combination of steps in an innovative, non-conventional and/or non-routine manner. In some aspects, the method 1800 of the present solution combines the steps of FIG. 18 in an innovative, non-conventional and/or non-routine combination to implement the improved functionality, performance and operation of the present solution. In some aspects, the method of the present solution combines the steps of FIG. 18 in in an innovative, non-conventional and/or non-routine manner to more efficiently and effectively use computing and networking resources. In some aspects, the method of the present solution provides innovative, non-conventional and/or non-routine ordered combination of steps.

It should be understood that the systems described above can provide multiple ones of any or each of those components and these components can be provided on either a standalone machine or, in some embodiments, on multiple machines in a distributed system. The systems and methods described above can be implemented as a method, apparatus or article of manufacture using programming or engineering techniques to produce software, firmware, hardware, or any combination thereof. In addition, the systems and methods described above can be provided as one or more computer-readable programs embodied on or in one or more articles of manufacture. The term "article of manufacture" as used herein is intended to encompass code or logic accessible from and embedded in one or more computer-readable devices, firmware, programmable logic, memory devices (e.g., EEPROMs, ROMs, PROMs, RAMs, SRAMs, etc.), hardware (e.g., integrated circuit chip, Field Programmable Gate Array (FPGA), Application Specific Integrated Circuit (ASIC), etc.), electronic devices, a computer readable non-volatile storage unit (e.g., CD-ROM, floppy disk, hard disk drive, etc.). The article of manufacture can be accessible from a file server providing access to the computer-readable programs via a network transmission line, wireless transmission media, signals propagating through space, radio waves, infrared signals, etc. The article of manufacture can be a flash memory card or a magnetic tape. The article of manufacture includes hardware logic as well as software or programmable code embedded in a computer readable medium that is executed by a processor. In general, the computer-readable programs can be implemented in any programming language, such as LISP, PERL, C, C++, C#, PROLOG, or in any byte code language such as JAVA. The software programs can be stored on or in one or more articles of manufacture as object code.

References to “or” may be construed as inclusive so that any terms described using “or” may indicate any of a single, more than one, and all of the described terms.

While various embodiments of the methods and systems have been described, these embodiments are exemplary and in no way limit the scope of the described methods or systems. Those having skill in the relevant art can effect changes to form and details of the described methods and systems without departing from the broadest scope of the described methods and systems. Thus, the scope of the methods and systems described herein should not be limited by any of the exemplary embodiments and should be defined in accordance with the accompanying claims and their equivalents.

What is claimed is:

1. A system comprising:

a server-side platform of a network environment comprising one or more engines configured to process electronic requests and transmit electronic notifications as a real-time transaction comprising a real-time adjudication to generate and transmit instructions for reimbursement and one or more electronic notifications during transaction processing, the server-side platform configured with a communications interface to interact with a plurality of heterogeneous devices using a plurality of application programming interfaces (APIs), wherein the server-side platform comprises one or more processors, coupled with memory, configured to:

store, in a database of the server-side platform, an electronic account data structure comprising one or more account-level policies and a plurality of sub-structures, each sub-structure defining a purse of a different type and including one or more purse-level policies corresponding to the respective purse, wherein at least one of the plurality of sub-structures defines a benefits purse;

receive, via the communications interface, from one or more servers remote from the server-side platform, an indication of eligibility of an electronic transaction conducted at a terminal device at a merchant to obtain funds from the benefits purse of the plurality of sub-structures stored in the database;

maintain, based on receipt of the indication, the sub-structure of the benefits purse in accordance with the funds obtained to conduct the electronic transaction at the terminal device;

receive, by the communications interface from a mobile device of the plurality of heterogeneous devices, via a first API of the plurality of APIs, a request for a reimbursement, wherein the server-side platform processes the reimbursement in real-time relative to the request for the reimbursement, different from processing the reimbursement in a batch mode that relates to one or more temporary memo-posts of one or more amounts that cause one or more occurrences of one or more erroneous transactions that exceed current amounts in electronic accounts;

retrieve, as input to the one or more engines, responsive to receipt of the request for the reimbursement, the one or more account-level policies for the electronic account data structure and the one or more purse-level policies for at least one sub-structure of the plurality of sub-structures;

generate, in real-time relative to the request for the reimbursement, by the one or more engines using the input of the one or more account-level policies and the one or more purse-level policies, a result related to adjudication of the request;

determine, responsive to the result related to the adjudication of the request, by the one or more engines, in real-time relative to receipt of the request for the reimbursement, to authorize a reimbursement amount related to the request for the reimbursement;

select, based on the result related to the adjudication of the request, by the one or more engines, one of the plurality of sub-structures stored in the database of the server-side platform from which to obtain funds for the reimbursement amount;

identify, using a configuration associated with the electronic account data structure, an electronic identifier of a user specified account destination to which to provide the reimbursement amount, the user specified account destination configured to allow transactions other than for qualifying benefits accounts expenditures;

provide, in real-time relative to receipt of the request for the reimbursement, by the communications interface via a second API of the plurality of APIs configured for reimbursement transactions, first data packets carrying data and the electronic identifier used to update the user specified account destination with the reimbursement amount from the selected one of the plurality of sub-structures, the user specified account destination configured to allow transactions other than for qualifying benefits accounts expenditures; and transmit, in real-time relative to providing the first data packets, via the communications interface to the mobile device, one or more second data packets carrying payload data indicating notification of the reimbursement amount.

2. The system of claim 1, wherein a profile database includes an entry corresponding to the mobile device configured to receive the notification of the reimbursement amount, the entry including (i) a unique identifier for the mobile device, and (ii) a notification mode, wherein the communications interface configures the one or more second data packets carrying the payload data indicating the notification of the reimbursement amount based on the notification mode.

3. The system of claim 1, wherein one of the plurality of sub-structures defining purses stored in the database corresponds to a benefits purse of a predefined account type comprising one of a flexible spending account, a health savings account, or a health reimbursement account.

4. The system of claim 1, wherein the server-side platform is further configured to:

determine, via the communications interface, in real-time while processing the reimbursement, to transmit a request for more information to the mobile device; and transmit, via the communications interface, one or more third data packets to the mobile device responsive to the determination to request more information, via the communications interface.

5. The system of claim 4, wherein the server-side platform is further configured to:

receive further information from the mobile device.

6. The system of claim 5, wherein the server-side platform is further configured to:

determine, responsive to receipt of the further information from the mobile device, to approve the reimbursement amount.

7. The system of claim 4, wherein the server-side platform is further configured to:

provide, in real-time relative to receipt of the request for the reimbursement, without intermediate memo-posting or batch reconciliation, the one or more third data packets with the request for more information.

8. The system of claim 4, wherein the server-side platform is further configured to:

provide, in real-time relative to receipt of the request for the reimbursement and prior to posting the transaction to an electronic ledger and a determination on whether to approve the request for the reimbursement, the one or more third data packets with the request for more information.

9. The system of claim 1, wherein the server-side platform is further configured to:

identify, via a configuration maintained by the server-side platform, the user specified account destination from a list of one or more user specified account destinations for an electronic reimbursement account, each user specified account destination of the one or more user specified account destinations comprising an electronic identifier of a type of electronic account and being configured to allow transactions for non-qualifying benefits account expenditures.

10. The system of claim 1, wherein the user specified account destination is a default destination identified by a reimbursement policy among an ordered list of account destinations for reimbursements.

11. The system of claim 1, wherein the user specified account destination comprises one of a checking account, a deposit account or an account of a financial institution maintained by a server by an entity remote from the one or more processors.

12. A system, comprising:

a server-side platform of a network environment comprising a transaction system including a communications interface configured with one or more communications ports and one or more network protocols to receive and process data packets via a computer network and using one or more application programming interfaces (APIs), the data packets including header information and payload information, and the server-side platform further including one or more engines comprising at least a policy engine and a transaction engine to process the payload information and generate instructions for reimbursement and to transmit, via the one or more APIs, electronic notifications in real-time relative to the received data packets, wherein the server-side platform comprises one or more processors, coupled with memory, configured to:

store, in one or more non-transitory databases of the server-side platform, a plurality of structured electronic account records comprising an electronic benefits account record, at least one of the plurality of structured electronic account records including an account-level parameter, a purse-level sub-structure, and in-process transaction data maintained separately from posted ledger balances, wherein the server-side platform accesses and causes an update to the structured electronic account records during a real-time claim adjudication session;

receive, via the communications interface, from one or more servers remote from the server-side platform, one or more response packets indicating whether an item corresponding to an electronic transaction conducted at a terminal device at a merchant is approved for an amount of expenditures qualifying under an electronic benefits account associated with the electronic benefits account record;

maintain, responsive to receipt of the one or more response packets indicating whether the item is approved for an amount of expenditures qualifying under the electronic benefits account, an in-process transaction data structure in a non-transitory database of the server-side platform, the in-process transaction data structure comprising a real-time representation of a benefits purse sub-structure of the electronic benefits account record, wherein the in-process transaction data structure is updated in accordance with the approved amount and is maintained separately from posted ledger balances to reflect a real-time adjudication status of the benefits purse sub-structure;

receive, via the communications interface and a first application programming interface (API) configured for mobile reimbursement interactions, one or more data packets transmitted from a mobile device, the one or more data packets carrying a reimbursement request comprising a structured request payload including at least an identifier of the electronic benefits account represented by the electronic benefits account record and an indication of a reimbursement amount, wherein the server-side platform processes the structured request payload as part of the real-time claim adjudication session, different from processing the reimbursement request in a batch mode that relates to one or more temporary memo-posts of one or more amounts that cause one or more occurrences of one or more erroneous transactions that exceed current amounts in electronic accounts;

access, as input to the one or more engines and responsive to receipt of the reimbursement request, configuration data associated with the identifier of the electronic benefits account record and the purse-level sub-structure of the electronic benefits account record, the configuration data including one or more of a rule, a parameter, or a policy associated with the electronic benefits account record;

execute, responsive to receipt of the reimbursement request and during the real-time claim adjudication session, the one or more engines using at least the configuration data as input and further using the in-process transaction data structure to process the reimbursement request comprising the structured request payload and generate output indicating an adjudication result indicating authorization or denial of the reimbursement request;

determine, based on the execution of the one or more engines to process the reimbursement request comprising the structured request payload and in real-time relative to receipt of the reimbursement request, an authorized reimbursement amount;

select, responsive to the adjudication result indicating authorization of the reimbursement request by the one or more engines and based on at least the configuration data, a selected purse-level sub-structure from which to obtain funds for the reimbursement amount, wherein the selected purse-level sub-structure is selected from the electronic benefits account record;

identify, responsive to the adjudication result indicating authorization of the reimbursement request, an electronic identifier of an account destination to which to transfer the authorized reimbursement amount, wherein the account destination is identified from an electronic reimbursement account record associated with the electronic benefits account, and the account destination is configured to allow transactions for non-qualifying benefits account expenditures;

provide, in real-time relative to receipt of the reimbursement request and responsive to the authorized reimbursement amount, via the communications interface via a second application programming interface (API) of the one or more APIs configured for reimbursement transactions, one or more instruction data packets comprising header information and payload information, the payload information including at least (i) the electronic identifier of the account destination and (ii) the authorized reimbursement amount, wherein the one or more instruction data packets include one or more instructions that cause an update of the account destination with the authorized reimbursement amount based on funds obtained from the selected purse-level sub-structure; and transmit, in real-time relative to providing the one or more instruction data packets that cause the update of the account destination, via the communications interface to the mobile device, one or more notification data packets comprising header information and payload information, the payload information including at least (i) the authorized reimbursement amount and (ii) an indication related to the provision of the instruction data packets to cause the update of the account destination with the authorized reimbursement amount using the funds obtained from the selected purse-level sub-structure.

13. The system of claim 12, wherein the server-side platform is further configured to:

parse the electronic benefits account record to identify the one or more of the rule, the parameter, or the policy associated with the electronic benefits account record.

14. The system of claim 12, wherein the server-side platform is further configured to:

obtain, via a lookup using the identifier, the one or more of the rule, the parameter, or the policy associated with the electronic benefits account record.

15. The system of claim 12, wherein the server-side platform is further configured to:

determine, during the real-time claim adjudication session and via the communications interface, to request further information to complete the execution of the adjudication of the reimbursement request;

transmit, responsive to the determination and prior to provision of the one or more instruction data packets, one or more additional data packets to the mobile device, the one or more additional data packets carrying payload information comprising a request for the further information; and prevent, responsive to the determination to request the further information, the one or more engines from performing further actions to cause the update of the account destination until the further information is received.

16. The system of claim 15, wherein the real-time claim adjudication session comprises a TCP/IP communication session between the server-side platform and the mobile device, and the server-side platform is further configured to:

receive, via the communications interface and during the real-time claim adjudication session, one or more response data packets transmitted from the mobile device, the one or more response data packets comprising header information and payload information, the payload information including the further information, wherein the further information is received in response to the request for the further information carried by the one or more additional data packets.

17. The system of claim 16, wherein the server-side platform is further configured to:

determine, responsive to receiving the further information in the one or more response data packets and during the real-time claim adjudication session, that the reimbursement request is approved; and cause, responsive to the determination that the reimbursement request is approved, performance of the one or more instructions to update the account destination with the authorized reimbursement amount.

18. The system of claim 15, wherein the server-side platform is further configured to:

provide, in real-time relative to receipt of the reimbursement request and prior to provision of the one or more instruction data packets, the one or more additional data packets carrying the request for the further information, without intermediate memo-posting or batch reconciliation.

19. The system of claim 15, wherein the server-side platform is further configured to:

provide, in real-time relative to receipt of the reimbursement request and during the real-time claim adjudication session, the one or more additional data packets carrying the request for the further information, prior to (i) causing posting of a transaction corresponding to the reimbursement request to posted ledger balances, and (ii) generating the output indicating the adjudication result indicating authorization or denial of the reimbursement request.

20. The system of claim 12, wherein the account destination comprises a default account destination identified by a reimbursement policy associated with the electronic benefits account represented by the electronic benefits account record, the reimbursement policy specifying one or more account destinations for benefits account reimbursements.

21. The system of claim 12, wherein the account destination comprises one of (i) a checking account, (ii) a deposit account, or (iii) an account of a financial institution maintained by a server remote from the server-side platform.

22. A system comprising:

a server-side platform of a network environment comprising one or more engines configured to process electronic requests and transmit electronic notifications as a real-time transaction comprising a real-time adjudication to generate and transmit instructions for reimbursement and one or more electronic notifications during transaction processing, the server-side platform configured with a communications interface to interact with a plurality of heterogeneous devices using a plurality of application programming interfaces (APIs), wherein the server-side platform comprises one or more processors, coupled with memory, configured to:

store, in a database of the server-side platform, a plurality of electronic account data structures, wherein each of the plurality of electronic account data structures comprises one or more account-level policies and a plurality of sub-structures, each sub-structure of the plurality of sub-structures defining a purse of a different type and including one or more purse-level policies corresponding to the respective purse, wherein at least one of the plurality of sub-structures defines a benefits purse;

receive, via the communications interface, from one or more servers remote from the server-side platform, a plurality of indications of eligibility, each indication of the plurality of indications of eligibility corresponding to a respective electronic transaction conducted at a respective terminal device at a respective merchant to obtain funds from a respective benefits purse of a respective sub-structure of a respective electronic account data structure of the plurality of electronic account data structures stored in the database;

maintain, responsive to receipt of each indication of the plurality of indications of eligibility, in the database, the respective sub-structure that defines the respective benefits purse of the respective electronic account data structure, in accordance with the funds obtained to conduct the respective electronic transaction at the respective terminal device;

receive, by the communications interface from a plurality of mobile devices of the plurality of heterogeneous devices, via a first API of the plurality of APIs, a plurality of requests for reimbursement, wherein the server-side platform processes a reimbursement for each of the plurality of requests in real-time relative to the respective request, different from processing the plurality of requests for reimbursement in a batch mode that relates to one or more temporary memo-posts of one or more amounts that cause one or more occurrences of one or more erroneous transactions that exceed current amounts in electronic accounts, and wherein for each of the plurality of requests for reimbursement, the server-side platform is further configured to:

retrieve, as input to the one or more engines, responsive to receipt of the request for reimbursement, a respective one or more account-level policies for a respective electronic account data structure of the plurality of electronic account data structures and a respective one or more purse-level policies corresponding to a respective purse of the plurality of sub-structures;

generate, in real-time relative to the request for reimbursement, by the one or more engines using the input of the respective one or more account-level policies and the respective one or more purse-level policies, an output related to adjudication of the request;

determine, responsive to the output related to the adjudication of the request for reimbursement, by the one or more engines, in real-time relative to receipt of the request for reimbursement, to authorize a reimbursement amount related to the request for reimbursement;

select, based on the output related to the adjudication of the request by the one or more engines, a respective one of the plurality of sub-structures stored in the database of the server-side platform from which to obtain funds for the reimbursement amount;

identify, using a configuration associated with the respective electronic account data structure, a respective electronic identifier of a respective user specified account destination to which to provide the reimbursement amount, the respective user specified account destination configured to allow transactions other than for qualifying benefits accounts expenditures;

provide, in real-time relative to receipt of the request for reimbursement, by the communications interface via a second API of the plurality of APIs configured for reimbursement transactions, first data packets carrying data and the respective electronic identifier used to update the respective user specified account destination with the reimbursement amount from the selected respective one of the plurality of sub-structures, the respective user specified account destination configured to allow transactions other than for qualifying benefits accounts expenditures; and transmit, in real-time relative to providing the first data packets, via the communications interface to a respective mobile device of the plurality of mobile devices, one or more second data packets carrying payload data indicating notification of the reimbursement amount, wherein the one or more second data packets cause the respective mobile device to display the notification of the reimbursement amount.

23. The system of claim 22, wherein:

a first benefits purse of a first electronic account data structure of the plurality of electronic account data structures comprises a first configuration provided by a first administrator device; and a second benefits purse of a second electronic account data structure of the plurality of electronic account data structures comprises a second configuration provided by a second administrator device that is different from the first administrator device.

24. The system of claim 23, wherein:

for a first request for reimbursement of the plurality of requests for reimbursement, the selected respective one of the plurality of sub-structures corresponds to the first benefits purse; and for a second request for reimbursement of the plurality of requests for reimbursement, the selected respective one of the plurality of sub-structures corresponds to the second benefits purse.

25. The system of claim 22, wherein:

a first benefits purse of a first electronic account data structure of the plurality of electronic account data structures comprises a first configuration provided by a first administrator device; and a second benefits purse of the first electronic account data structure of the plurality of electronic account data structures comprises a second configuration provided by a second administrator device that is different from the first administrator device.

26. The system of claim 25, wherein:

for a first request for reimbursement of the plurality of requests for reimbursement, the selected respective one of the plurality of sub-structures from which to obtain the funds for reimbursement corresponds to the first benefits purse; and for a second request for reimbursement of the plurality of requests for reimbursement, the selected respective one of the plurality of sub-structures from which to obtain the funds for reimbursement corresponds to the second benefits purse.

27. The system of claim 26, wherein:

the respective user specified account destination is a same account destination for the first request for reimbursement and the second request for reimbursement.

28. The system of claim 22, wherein the server-side platform is further configured to:

store, in the database, a plurality of purse-level policies provided by a plurality of administrator devices.

29. The system of claim 22, wherein:

a first indication of eligibility of the plurality of indications of eligibility corresponds to a first benefits purse of a first electronic account data structure, and the first benefits purse comprises a first purse-level policy provided by a first administrator device; and a second indication of eligibility of the plurality of indications of eligibility corresponds to a second benefits purse of a second electronic account data structure, and the second benefits purse comprises a second purse-level policy provided by a second administrator device.

30. The system of claim 22, wherein:

a first indication of eligibility of the plurality of indications of eligibility corresponds to a first benefits purse of a first electronic account data structure, and the first benefits purse comprises a first purse-level policy provided by a first administrator device; and a second indication of eligibility of the plurality of indications of eligibility corresponds to a second benefits purse of the first electronic account data structure, and the second benefits purse comprises a second purse-level policy provided by a second administrator device.

31. The system of claim 22, wherein to process each of the plurality of requests for reimbursement in real-time relative to the respective request, the server-side platform is further configured to:

for a first request for reimbursement of the plurality of requests for reimbursement, provide third data packets with a first one or more instructions to obtain first funds from a first benefits purse configured via a first administrator device; and for a second request for reimbursement of the plurality of requests for reimbursement, provide fourth data packets with a second one or more instructions to obtain second funds from a second benefits purse configured via a second administrator device.

32. The system of claim 22, wherein for each of the plurality of requests for reimbursement, the server-side platform is further configured to:

determine, during processing of the request for reimbursement, to request further information to process the request for reimbursement; and transmit, responsive to the determination to request further information, via the communications interface to the respective mobile device of the plurality of mobile devices, one or more data packets carrying a request for the further information.

33. The system of claim 32, wherein for each of the plurality of requests for reimbursement, the server-side platform is further configured to:

receive, via the communications interface from the respective mobile device, the further information.

34. The system of claim 33, wherein for each of the plurality of requests for reimbursement, the server-side platform is further configured to:

determine, responsive to receipt of the further information and during real-time adjudication of the request for reimbursement, that the reimbursement amount is approved.

35. The system of claim 32, wherein for each of the plurality of requests for reimbursement, the server-side platform is further configured to:

provide, in real-time relative to receipt of the request for reimbursement, the one or more data packets carrying the request for the further information, without intermediate memo-posting or batch reconciliation.

36. A system, comprising:

a server-side platform of a network environment comprising a transaction system including a communications interface configured with one or more communications ports and one or more network protocols to receive and process data packets via a computer network and using one or more application programming interfaces (APIs), the data packets including header information and payload information, and the server-side platform further including one or more engines comprising at least a policy engine and a transaction engine to process the payload information to generate instructions to transmit, via the one or more APIs, one or more electronic notifications in real-time relative to the received data packets, wherein the server-side platform comprises one or more processors, coupled with memory, configured to:

store, in one or more non-transitory databases of the server-side platform, a plurality of structured electronic account records comprising an electronic account record of a first type and a second electronic account record of a second type, at least one of the plurality of structured electronic account records including a parameter, a sub-structure, and in-process transaction data maintained separately from posted ledger balances, wherein the server-side platform accesses and causes an update to the plurality of structured electronic account records during a real-time session;

receive, via the communications interface, from one or more servers remote from the server-side platform, one or more response packets indicating whether an item corresponding to an electronic transaction conducted at a terminal device is approved for an amount of expenditures qualifying under an electronic account associated with the electronic account record of the first type;

maintain, responsive to receipt of the one or more response packets indicating whether the item is approved for an amount of expenditures qualifying under the electronic account, an in-process transaction data structure in a non-transitory database of the server-side platform, the in-process transaction data structure comprising a real-time representation of the sub-structure, wherein the in-process transaction data structure is updated in accordance with the approved amount and is maintained separately from posted ledger balances to reflect a real-time status;

receive, via the communications interface and a first application programming interface (API) configured for mobile interactions, one or more data packets transmitted from a mobile device, the one or more data packets carrying a request comprising a structured request payload including at least an identifier associated with the electronic account and an indication of an amount, wherein the server-side platform processes the structured request payload as part of a real-time session, different from processing the request in a batch mode that relates to one or more temporary memo-posts of one or more amounts that cause one or more occurrences of one or more erroneous transactions that exceed current amounts in electronic accounts;

access, to provide as input to the one or more engines and responsive to receipt of the request, configuration data associated with the electronic account record of the first type and one or more sub-structures of the electronic account record of the first type, the configuration data including one or more of a rule, a parameter, or a policy associated with the electronic account record of the first type;

execute, responsive to receipt of the request and during the real-time session, the one or more engines using at least the configuration data as input and further using the in-process transaction data structure to process the request of the structured request payload and to generate an output indicating a result of authorization or denial of the request;

determine, based on the execution of the one or more engines to process the request and in real-time relative to receipt of the request, an authorized amount;

select, responsive to the result indicating authorization of the request by the one or more engines and based on at least the configuration data, a selected sub-structure from which to obtain funds for the amount, wherein the selected sub-structure is selected from the one or more sub-structures of the electronic account record of the first type;

identify, responsive to the result indicating authorization of the request, an electronic identifier of an account destination to which to transfer the authorized amount, wherein the account destination is identified from the second electronic account record of the second type associated with the electronic account, and the account destination is configured to allow transactions other than for qualifying benefits account expenditures;

provide, in real-time relative to receipt of the request and responsive to the authorized amount, via the communications interface via a second application programming interface (API) of the one or more APIs configured for transactions, first data packets comprising header information and payload information, the payload information including at least (i) the electronic identifier of the account destination and (ii) the authorized amount, wherein the first data packets include one or more instructions that cause an update of the account destination with the authorized amount based on funds obtained from the selected sub-structure; and transmit, in real-time relative to providing the first data packets, via the communications interface to the mobile device, one or more notification data packets comprising header information and payload information, the payload information including at least (i) the authorized amount and (ii) an indication related to the provision of the first data packets to cause the update of the account destination with the authorized amount using the funds obtained from the selected sub-structure.

37. The system of claim 36, wherein the server-side platform is further configured to:

parse the electronic account record of the first type to identify the one or more of the rule, the parameter, or the policy associated with the electronic account record of the first type.

38. The system of claim 36, wherein the server-side platform is further configured to:

determine, during the real-time session and via the communications interface, to request further information to complete execution responsive to the request;

transmit, responsive to the determination and prior to providing the first data packets, one or more additional data packets to the mobile device, the one or more additional data packets carrying payload information comprising a request for the further information; and prevent, responsive to the determination to request the further information, the one or more engines from performing further actions to cause the update of the account destination until the further information is received.

39. The system of claim 38, wherein the real-time session comprises a TCP/IP communication session between the server-side platform and the mobile device, and the server-side platform is further configured to:

receive, via the communications interface and during the real-time session, one or more response data packets transmitted from the mobile device, the one or more response data packets comprising header information and payload information, the payload information including the further information, wherein the further information is received in response to the request for the further information carried by the one or more additional data packets.

40. The system of claim 39, wherein the server-side platform is further configured to:

determine, responsive to receiving the further information in the one or more response data packets and during the real-time session, that the request is approved; and cause, responsive to the determination that the request is approved, performance of the one or more instructions to update the account destination with the authorized amount.

41. The system of claim 38, wherein the server-side platform is further configured to:

provide, in real-time relative to receipt of the request from the mobile device and prior to providing the first data packets, the one or more additional data packets carrying the request for the further information, without intermediate memo-posting or batch reconciliation.

42. The system of claim 36, wherein the server-side platform is further configured to:

receive, via the communications interface and the first API, from a plurality of mobile devices, one or more second data packets carrying a plurality of requests, each request of the plurality of requests comprising a respective structured request payload including:

(i) a respective identifier of the electronic account represented by the electronic account record of the first type, and (ii) a respective indication of an amount, wherein the server-side platform processes each request of the plurality of requests in real-time relative to receipt of the respective request as part of a respective real-time session, different from processing the plurality of requests in a batch mode.

43. The system of claim 42, wherein the server-side platform is further configured to:

for a first request of the plurality of requests, provide second data packets including a first one or more instructions to obtain first funds from a first sub-structure of the electronic account record of the first type, the first sub-structure configured based on a first configuration provided by a first administrator device; and for a second request of the plurality of requests, provide third data packets including a second one or more instructions to obtain second funds from a second sub-structure of the electronic account record of the first type, the second sub-structure configured based on a second configuration provided by a second administrator device that is different from the first administrator device.

* * * * *